US007270811B2

(12) United States Patent
Bout et al.

(10) Patent No.: US 7,270,811 B2
(45) Date of Patent: *Sep. 18, 2007

(54) SEROTYPE OF ADENOVIRUS AND USES THEREOF

(75) Inventors: Abraham Bout, Moerkapelle (NL); Menzo Havenga, Alphen aan den Rijn (NL); Ronald Vogels, Linschoten (NL)

(73) Assignee: Crucell Holland B.V., Leiden (NL)

(*) Notice: Subject to any disclaimer, the term of this patent is extended or adjusted under 35 U.S.C. 154(b) by 116 days.

This patent is subject to a terminal disclaimer.

(21) Appl. No.: 10/951,102

(22) Filed: Sep. 27, 2004

(65) Prior Publication Data

US 2005/0084480 A1    Apr. 21, 2005

Related U.S. Application Data

(63) Continuation of application No. 09/573,740, filed on May 18, 2000, now Pat. No. 6,913,922.

(60) Provisional application No. 60/134,764, filed on May 18, 1999.

(51) Int. Cl.
*A01N 63/00* (2006.01)
*A61K 48/00* (2006.01)
*C12N 15/00* (2006.01)

(52) U.S. Cl. .................. 424/93.2; 435/320.1
(58) Field of Classification Search ............. 435/320.1; 424/93.2
See application file for complete search history.

(56) References Cited

U.S. PATENT DOCUMENTS

| | | |
|---|---|---|
| 4,487,829 A | 12/1984 | Sharp et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |
| 4,792,525 A | 12/1988 | Ruoslahti et al. |
| 4,797,368 A | 1/1989 | Carter et al. |
| 4,956,281 A | 9/1990 | Wallner et al. |
| 5,024,939 A | 6/1991 | Gorman |
| 5,096,815 A | 3/1992 | Ladner et al. |
| 5,166,320 A | 11/1992 | Wu et al. |
| 5,198,346 A | 3/1993 | Ladner et al. |
| 5,204,445 A | 4/1993 | Plow et al. |
| 5,223,394 A | 6/1993 | Wallner |
| 5,223,409 A | 6/1993 | Ladner et al. |
| 5,240,846 A | 8/1993 | Collins et al. |
| 5,246,921 A | 9/1993 | Reddy et al. |
| 5,332,567 A | 7/1994 | Goldenberg |
| 5,349,053 A | 9/1994 | Landolfi |
| 5,403,484 A | 4/1995 | Ladner et al. |
| 5,436,146 A | 7/1995 | Shenk et al. |
| 5,443,953 A | 8/1995 | Hansen et al. |
| 5,474,935 A | 12/1995 | Chatterjee et al. |
| 5,521,291 A | 5/1996 | Curiel et al. |
| 5,534,423 A | 7/1996 | Plasson et al. |
| 5,543,328 A | 8/1996 | Mcclelland et al. |
| 5,547,932 A | 8/1996 | Curiel et al. |
| 5,552,311 A | 9/1996 | Sorscher et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,712,136 A | 1/1998 | Wickham et al. |
| 5,731,190 A | 3/1998 | Wickham et al. |
| 5,756,086 A | 5/1998 | Mcclelland et al. |
| 5,770,442 A | 6/1998 | Wickham et al. |
| 5,837,511 A | 11/1998 | Falck-Pedersen et al. |
| 5,846,782 A | 12/1998 | Wickham et al. |
| 5,849,561 A | 12/1998 | Falck-Pedersen |
| 5,856,152 A | 1/1999 | Wilson et al. |
| 5,871,727 A | 2/1999 | Curiel |
| 5,871,982 A | 2/1999 | Wilson et al. |
| 5,877,011 A | 3/1999 | Armentano et al. |
| 5,922,315 A | 7/1999 | Roy |
| 5,994,128 A | 11/1999 | Fallaux et al. |
| 6,033,908 A | 3/2000 | Bout et al. |
| 6,057,155 A | 5/2000 | Wickham et al. |
| 6,100,086 A | 8/2000 | Kaplan et al. |

(Continued)

FOREIGN PATENT DOCUMENTS

EP    259212    8/1987

(Continued)

OTHER PUBLICATIONS

Flomenberg et al., "Sequence and genetic Organization of Adenovirus Type 35 Early Region 3," Journal of Virology, Nov. 1988, pp. 4431-4437, vol. 62, No. 11.

(Continued)

Primary Examiner—Brian Whiteman
(74) Attorney, Agent, or Firm—TraskBritt

(57) ABSTRACT

The invention provides a gene delivery vehicle and a gene of interest comprising at least one Ad35 element or a functional equivalent thereof, responsible for avoiding or diminishing neutralizing activity against adenoviral elements by the host to which the gene is to be delivered. A functional equivalent/homologue of an Ad35 (element) includes an adenovirus (element) which, like adenovirus 35, encounters pre-existing immunity in less than about 10% of the hosts to which it is administered for the first time, or which is capable in more than about 90% of the hosts to which it is administered of avoiding or diminishing the immune response.

17 Claims, 44 Drawing Sheets

U.S. PATENT DOCUMENTS

| | | | |
|---|---|---|---|
| 6,127,525 | A | 10/2000 | Crystal et al. |
| 6,287,857 | B1 | 9/2001 | O'riordan et al. |
| 6,306,652 | B1 | 10/2001 | Fallaux et al. |
| 6,486,133 | B1 | 11/2002 | Herlyn et al. |
| 6,492,169 | B1 | 12/2002 | Vogels et al. |
| 6,669,942 | B2 | 12/2003 | Perricaudet et al. |
| 6,913,922 | B1 * | 7/2005 | Bout et al. ............ 435/320.1 |

FOREIGN PATENT DOCUMENTS

| | | |
|---|---|---|
| EP | 1016726 | 12/1998 |
| EP | 99201545.3 | 5/1999 |
| EP | 1067188 | 7/1999 |
| EP | 1020529 | 11/1999 |
| EP | 0 978 566 A2 | 2/2000 |
| EP | 1 054 064 A1 | 11/2000 |
| WO | WO91/00360 | 1/1991 |
| WO | WO91/05805 | 5/1991 |
| WO | WO91/05871 | 5/1991 |
| WO | WO92/02553 | 2/1992 |
| WO | WO92/13081 | 8/1992 |
| WO | WO93/03769 | 3/1993 |
| WO | WO93/06223 | 4/1993 |
| WO | WO93/07282 | 4/1993 |
| WO | WO93/07283 | 4/1993 |
| WO | WO94/08026 | 4/1994 |
| WO | WO94/10323 | 5/1994 |
| WO | WO94/11506 | 5/1994 |
| WO | WO94/15644 | 7/1994 |
| WO | WO94/17832 | 8/1994 |
| WO | WO94/24299 | 10/1994 |
| WO | WO94/26915 | 11/1994 |
| WO | WO95/05201 | 2/1995 |
| WO | WO95/06745 | 3/1995 |
| WO | WO95/14785 | 6/1995 |
| WO | WO95/16037 | 6/1995 |
| WO | WO95/21259 | 8/1995 |
| WO | WO95/26412 | 10/1995 |
| WO | WO95/27071 | 10/1995 |
| WO | WO96/13598 | 10/1995 |
| WO | WO95/31187 | 11/1995 |
| WO | WO95/31566 | 11/1995 |
| WO | WO96/00326 | 1/1996 |
| WO | WO96/00790 | 1/1996 |
| WO | WO96/07739 | 3/1996 |
| WO | WO96/10087 | 4/1996 |
| WO | WO96/12030 | 4/1996 |
| WO | WO96/13597 | 5/1996 |
| WO | WO96/14837 | 5/1996 |
| WO | WO97/12986 | 5/1996 |
| WO | WO96/17073 | 6/1996 |
| WO | WO96/18740 | 6/1996 |
| WO | WO96/24553 | 8/1996 |
| WO | WO96/26281 | 8/1996 |
| WO | WO96/35798 | 11/1996 |
| WO | WO97/00326 | 1/1997 |
| WO | WO98/22609 | 4/1997 |
| WO | WO97/20575 | 6/1997 |
| WO | WO97/38723 | 10/1997 |
| WO | WO98/07865 | 2/1998 |
| WO | WO98/11221 | 3/1998 |
| WO | WO98/13499 | 4/1998 |
| WO | WO98/32842 | 7/1998 |
| WO | WO98/40509 | 9/1998 |
| WO | WO98/49300 | 11/1998 |
| WO | WO98/50053 A1 | 11/1998 |
| WO | WO99/32647 | 7/1999 |
| WO | WO99/47180 A1 | 9/1999 |
| WO | WO99/55132 | 11/1999 |
| WO | WO99/58646 | 11/1999 |
| WO | WO 00/03029 | 1/2000 |
| WO | WO 00/24730 A2 | 5/2000 |
| WO | WO 00/31285 | 6/2000 |
| WO | WO 00/52186 | 9/2000 |
| WO | WO 00/70071 A1 | 11/2000 |
| WO | WO 01/04334 | 1/2001 |
| WO | WO 01/90158 A1 | 11/2001 |
| WO | WO 02/24730 | 3/2002 |
| WO | WO 02/27006 | 4/2002 |

OTHER PUBLICATIONS

Gahery-Segard et al., "Immune response to recombinant Capsid Proteins of Adenovirus in Humans: Antifiber and Anti-Penton Base Antibodies Have a Synergistic Effect on Neutralizing Activity," Journal of Virology, Mar. 1998, pp. 2388-2397, vol. 72, No. 3.

Notice of Opposition to a European Patent, Patent No. 1054064, by Cell Genesys Inc., dated Jul. 5, 2005.

Rosenfeld et al., Adenovirus-Mediated Transfer of a recombinant alpha-1-Antitrypsin Gene to the Lung Epithelium in Vivo, Science, Apr. 19, 1991, pp. 431-434, vol. 252.

Roy et al., "Circumvention of Immunity to the Adenovirus major Cost Protein Hexon," Journal of Virology, Aug. 1998, pp. 6875-6879, vol. 72, No. 8.

Stevenson et al., "Human Adenovirus Serotypes 3 and 5 Bind to Two Different Cellular receptors via the Fiber Head Domain," Journal of Virology, May 1995, pp. 2850-2857, vol. 69, No. 5.

Stratford-Perricaudet et al., "Evaluation of the Transfer and Expression in Mice of an Enzyme-Encoding Gene Using a Human Adenovirus Vector," Human Gene Therapy, 1990, pp. 241-256, vol. 1.

Abrahamsen et al., "Construction of an Adenovirus Tpe 7a E1A Vector," Journal of Virology, Nov. 1997, p. 8946-8951 vol. 71, No. 11.

Albiges-Rizo et al., "Human Adenovirus Serotype 3 Fiber Protein," Journal of Biological Chemistry, 266(6), 3961-3967 (1991).

Athappilly et al., "The Refined Crystal Structure of Hexon, the Major Coat Protein of Adenovirus Type 2, at 2·9 A Resolution," J. Mol. Biol. (1994) 242, 430-455.

Bai et al., "Mutations That Alter an Arg-Gly-Asp (RGD) Sequence in the Adenovirus Type 2 Penton Base Protein Abolish Its Cell-Rounding Activity and Delay Virus Reproduction in Flat Cells," Journal of Virology, 67(9), 5198-5205 (1993).

Bailey et al., "Phylogenetic Relationships among Adenovirus Serotypes," Virology, 205, 439-452 (1994).

Ball-Goodrich et al., "Parvoviral Target Cell Specificity: Acquisition of Fibrotropism by a Mutant of the Lymphotropic Strain of Minute Virus of Mice Involves Multiple Amino Acid Substitutions within the Capsid," Virology, 184, 175-186 (1991).

Basler et al., "Subgroup B Adenovirus Type 35 Early Region 3 mRNAs Differ from Those of the Subgroup C Adenoviruses," Virology 215, 165-177 (1996).

Batra et al., "Receptor-mediated gene delivery employing lectin-binding specificity," Gene Therapy, 1, 255-260 (1994).

Berendsen, Herman J.C., A Glimpse of the Holy Grail, Science, 1998, vol. 282, pp. 642-643.

Boursnell et al., "In vitro construction of a recombinant adenovirus Ad2:Ad5," Gene, 13, 311-317 (1981).

Bridge et al., "Adenovirus Early Region 4 and Viral DNA Synthesis," Virology 193, 794-801 (1993).

Brody et al., "Adenovirus-Mediated in Vivo Gene Transfer," Annals of New York Academy of Sciences pp. 90-100.

Caillet-Boudin et al., "Functional and Structural Effects of an Ala to Val Mutation in the Adenovirus Serotype 2 Fibre," J. Mol. Biol., 217, 477-486 (1991).

Chroboczek et al., "The Sequence of the Genome of Adenovirus Type 5 and Its Comparison with the Genome of Adenovirus Type 2," Virology, 186, 280-285 (1992).

Chroboczek et al., Adenovirus Fiber, Current Topics in Microbiology and Immunology 1995,199 (Pt 1) pp. 163-200.

Chu et al., "Cell targeting with retroviral vector particles containing antibodyBenvelope fusion proteins," Gene Therapy, 1, 292-299 (1994).

Cotten et al., "TransferrinBpolycation-mediated introduction of DNA into human leukemic cells: Stimulation by agents that affect the survival of transfected DNA or modulate transferrin receptor levels," Proc. Natl. Acad. Sci. USA, 87, 4033-4037 (1990).

Cotten et al., "High-efficiency receptor-mediated delivery of small and large (48 kilobase gene constructs using the endosome-disruption activity of defective or chemically inactivated adenovirus particles," Proc. Natl. Acad. Sci. USA, 89, 6094-6098 (1992).

Crawford-Miksza et al., "Analysis of 15 Adenovirus Hexon Proteins Reveals the Location and Structure of Seven Hypervariable Regions Containing Serotype-Specific Residues," Journal of Virology, Mar. 1996, p. 1836-1844.

Crompton et al., "Expression of a foreign epitope on the surface of the adenovirus hexon," J. Gen. Virol., 75(1), 133-139 (1994).

Crystal, Ronald G., "Transfer of Genes to Humans: Early Lessons and Obstacles to Success," Science, 270, 404-410 (1995).

Curiel et al., "High-Efficiency Gene Transfer Mediated by Adenovirus Coupled to DNABPolylysine Complexes," Human Gene Therapy, 3, 147-154 (1992).

Curiel et al., "Adenovirus enhancement of transferrinBpolylysine-mediated gene delivery," Proc. Natl. Acad. Sci. USA, 88, 8850-8854 (1991).

De Jong et al., "Adenovirus Isolates From Urine of Patients with Acquired Immunodeficiency Syndrome," The Lancet, Jun. 11, 1983 pp. 1293-1296.

De Jong et al., Adenoviruses from Human Immunodeficiency Virus-Infected Individuals, Including Two Strains That Represent New Candidate Serotypes Ad50 and Ad51 of Species B1 and D, Respectively, Journal of Clinical Microbiology, Dec. 1999, p. 3940-45, vol. 37, No. 12, American Society for Microbiology.

Defer et al., "Human Adenovirus-Host Cell Interactions: Comparative Study with Members of Subgroups B and C," Journal of Virology, 64(8), 3661-3673 (1990).

Deonarain, "Ligand-targeted receptor-mediated vectors for gene delivery," (1998) Expert Opin. Ther. Pat. 8: 53-69.

Dukema et al., "Transformation of Primary Rat Kidney Cells by DNA Fragments of Weakly Oncogenic Adenoviruses," Journal of Virology, Dec. 1979, p. 943-950.

Douglas J T et al.: "Strategies to accomplish targeted gene delivery to muscle cells employing tropism-modified adenoviral vectors" Neuromusclar Disorders, Pergamon Press, GB, vol. 7, Jul. 1997, pp. 284-298, XP002079944 ISSN: 0960-8966.

Dupuit et al., "Regenerating Cells in Human Airway Surface Epithelium Represent Preferential Targets for Recombinant Adenovirus," Human Gene Therapy, 6, 1185-1193 (1995).

Eck et al., "Gene-Based Therapy," (1996) Goodman & Gillman's The Pharmacological Basis of Therapeutics, Mc-Graw-Hill, New York, N.Y., pp. 77-101.

Etienne-Julan et al., "The efficiency of cell targeting by recombinant retroviruses depends on the nature of the receptor and the composition of the artificial cellBvirus linker," Journal of General Virology, 73, 3251-3255 (1992).

Falgout et al., "Characterization of Adenovirus Particles Made by Deletion Mutants Lacking the Fiber Gene," Journal of Virology, 62(2), 622-625 (1988).

Flomenberg et al., "Molecular Epidemiology of Adenovirus Type 35 Infections in Immunocompromised Hosts," The Journal Of Infectious Diseases vol. 155, No. 6, Jun. 1987.

Francki et al., "Classification and Nomenclature of Viruses," Fifth Report of the International Committee on Taxonomy of Viruses; Virology Division of the International Union of Microbiology Societies pp. 140-143.

Gall et al., "Construction and characterization of Hexon-Chimeric Adenoviruses: Specification of adenovirus serotype," 72(12) Journal of Virology 10260-64 (1998).

Gall et al., "Adenovirus Type 5 and 7 Capsid Chimera: Fiber Replacement Alters Receptor Tropism without Affecting Primary Immune Neutralization Epitopes," Journal Of Virology, Apr. 1996, p. 2116-2123.

George et al., "Gene therapy progress and prospects: adenoviral vectors," Gene Therapy (2003) 10, 1135-1141.

Gorecki, "Prospects and problems of gene therapy: an update," (2001) Expert Opin. Emerging Drugs 6(2): 187-98.

Greber et al., "Stepwise Dismantling of Adenovirus 2 during Entry into Cells," Cell, 75, 477-486 (1993).

Green et al., "Evidence for a repeating cross: sheet structure in the adenovirus fibre," EMBO Journal, 2(8), 1357-1365 (1983).

Grubb et al., Inefficient gene transfer by adenovirus vector to cystic fibrosis airway epithelia of mice and humans, Nature, 371, 802-806 (1994).

Han et al., "Ligand-directed retroviral targeting of human breast cancer cells," Proc. Natl. Acad. Sci. USA, 92, 9747-9751 (1995).

He et al., "A simplified system for generating recombinant adenoviruses," Proc. Natl. Acad. Sci. USA vol. 95, pp. 2509-2514, Mar. 1998.

Henry et al., "Characterization of the Knob Domain of the Adenovirus Type 5 Fiber Protein Expressed in *Escherichia coli*," Journal of Virology, 68(8), 5239-5246 (1994).

Hidaka, Chisa, et al., "CAR-dependent and CAR-independent pathways of adenovirus vector-mediated gene transfer and expression in human fibroblasts," 103(4) The Journal of Clinical Investigations 579-87 (Feb. 1999).

Hierholzer et al., "Adenoviruses from Patients with AIDS: A Plethora of Serotypes and A Description of Five New Serotypes of Subgenus D (Types 43-47)," The Journal Of Infectious Diseases vol. 158, No. 4 Oct. 1988.

Hong et al., "The Amino Terminus of the Adenovirus Fiber Protein Encodes the Nuclear Localization Signal," Virology, 185(2), 758-767 (1991).

Horvath et al., "Nonpermissivity of Human Peripheral Blood Lymphocytes to Adenovirus Type 2 Infection," Journal of Virology, 62(1), 341-345 (1988).

Huang et al., "Upregulation of Integrins $\gamma3$ and $\gamma5$ on Human Monocytes and T Lymphocytes Facilitates Adenovirus-Mediated Gene Delivery," Journal of Virology, 69(4), 2257-2263 (1995).

Imler et al., "Novel complementation cell lines derived from human lung carcinoma A549 cells support the growth of E1-deleted adenovirus vectors," Gene Therapy, vol. 3: p. 75-84, 1996.

Kang et al., "Molecular Cloning And Physical Mapping Of The Dna Of Human Adenovirus Type 35," Acta Microbiologica Hungarica 36 (1), pp. 67-75 (1989).

Kang et al., "Relationship Of E1 And E3 Regions Of Human Adenovirus 35 To Those Of Human Adenovirus Subgroups A, C And D," Acta Microbiologica Hungarica 36 (4), pp. 445-457 (1989).

Karayan et al., "Oligomerization of Recombinant Penton Base of Adenovirus Type 2 and Its Assembly with Fiber in Baculovirus-Infected Cells," Virology, 202, 782-795 (1994).

Kass-Eisler et al., "Quantitative determination of adenovirus-mediated gene delivery to rat cardiac myocytes in vitro and in vivo," Proc. Natl. Acad. Sci. USA, 90, 11498-11502 (1993).

Kmiec, "Gene Therapy," American Scientist, vol. 87, pp. 240.

Komoriya et al., The Minimal Essential Sequence for a Major Cell Type-specific Adhesion Site (CS1) within the Alternatively Spliced Type III Connecting Segment Domain of Fibronectin Is Leucine-Aspartic Acid-Valine,: Journal of Biological Chemistry, 266(23), 15075-15079 (1991).

Krasnykh et al.: "Generation Of Recombinant Adenovirus Vectors With Modified Fibers For Altering Viral Tropism" Journal Of Virology, The American Society For Microbiology, US, vol. 70, No. 10, Oct. 1, 1996, pp. 6839-6846, XP002067518 ISSN: 0022-538X.

Lattanzi, Laura, et al., "High Efficiency Myogenic Conversion of Human Fibroblasts by Adenoviral Vector-mediated *MyoD* Gene Transfer," 101(10) J. Clin. Invest. 2119-28 (May 1998).

Lee et al., "The constitutive expression of the immunomodulatory gp 19k protein in E1', E3' adenoviral vectors strongly reduces the host cytotoxic T cell response against the vector," Gene Therapy (1995) 2, 256-262.

Levrero et al., "Defective and nondefective adenovirus vectors for expressing foreign genes in vitro and in vivo," Gene, 101 (1991) 195-202.

Li et al., "Genetic Relationship between Thirteen Genome Types of Adenovirus 11, 34, and 35 with Different Tropisms," Intervirology 1991;32:338-350.

Liu et al., Molecular Basis of the inflammatory response to adenovirus vectors. Gene Therapy (2003 10, 935-40.

Maraveyas et al., "Targeted Immunotherapy B An update with special emphasis on ovarian cancer," Acta Oncologica, 32(7/8), 741-746 (1993).

Mastrangeli et al., "ASero-Switch@ Adenovirus-Mediated In Vivo Gene Transfer: Circumvention of Anti-Adenovirus Humoral Immune Defenses Against Repeat Adenovirus Vector Administration by Changing the Adenovirus Serotype," Human Gene Therapy, 7, 79-87 (1996).

Mathias et al., "Multiple Adenovirus Serotypes Use v Integrins for Infection," Journal of Virology, 68(10), 6811-6814 (1994).

Mautner et al., "Recombination in Adenovirus: DNA Sequence Analysis of Crossover Sites in Intertypic Recombinants," Virology, 131, 1-10 (1983).

Mautner et al., "Recombination in Adenovirus: Analysis of Crossover Sites in Intertypic Overlap Recombinants," Virology, 139, 43-52, (1984).

Merriam-Webster Dictionary (on line) retrieved from the internet<URL:htpp://www. m-w.com/cgi-bin/dictionary, "derive," 2002.

Michael et al., "Addition of a short peptide ligand to the adenovirus fiber protein," Gene Therapy, 2, 660-668 (1995).

Michael et al., "Binding-incompetent Adenovirus Facilitates Molecular Conjugate-mediated Gene Transfer by the Receptor-mediated Endocytosis Pathway," Journal of Biological Chemistry, 268(10), 6866-6869 (1993).

Miller et al., "Targeted vectors for gene therapy," FASEB Journal, 9, 190-199 (1995).

Neda et al., "Chemical Modification of an Ecotropic Murine Leukemia Virus Results in Redirection of Its Target Cell Specificity," Journal of Biological Chemistry, 266(22), 14143-14146 (1991).

Nemerow et al., "The Role of v Integrins in Adenovirus Infection," Biology of Vitronectins and their Receptors, 177-184 (1993).

Nemerow et al., "Adenovirus entry into host cells: a role for $_v$ integrins," Trends In Cell Biology, 4, 52-55 (1994).

Novelli et al., "Deletion Analysis of Functional Domains in Baculovirus-Expressed Adenovirus Type 2 Fiber," Virology, 185, 365-376 (1991).

Orkin et al., "Report and Recommendations of the Panel to Assess the NIH Investment in Research on Gene Therapy," (1995), file:///F/NIHrec.htm 1/4/01 1:37pm.

Peteranderl et al., "Trimerization of the Heat Shock Transcription Factor by a Triple-Stranded -Helical Coiled-Coil," Biochemistry, 31, 12272-12276 (1992).

Prince, "Gene Transfer: A Review Of Methods And Applications," Pathology (1998), 30, pp. 335-347.

Pring-Åkerblom et al., "Sequence Characterization and Comparison of Human Adenovirus Subgenus B and E Hexons," Virology, 212, 232-36 (1995).

Ragot et al.,: "Efficient adenovirus-mediated transfer of a human minidystrophin gene to skeletal muscle of mdx mice" Nature, Macmillan Journals of Ltd. London, GB, vol. 361, No. 6413, 1993, pp. 647-650, XP002162515 ISSN: 0028-0836.

Rea et al., "Highly efficient transduction of human monocyte-derived dendritic cells with subgroup B fiber-modified adenovirus vectors enhances transgene-encoded antigen presentation to cytotoxic T cells." Journal Of Immunology, (Apr. 15, 2000) 166 (8) 5236-44.,—Apr. 15, 2001 XP002192775.

Robbins et al., "Viral Vectors for Gene Therapy," Pharmacol. Ther. vol. 80, No. 1, pp. 35-47, 1998.

Roberts et al., "Three-Dimensional Structure of the Adenovirus Major Coat Protein Hexon," Science, 232, 1148-51 (1986).

Roelvink et al., The Coxsackievirus-Adenovirus Receptor Protein Can Function as a Cellular Attachment Protein for Adenovirus Serotypes from Subgroups, A, C, D, E, and F, Journal Of Virology, Oct. 1998, p. 7909-7915, vol. 72, No. 10.

Romano, "Gene Transfer in Experimental Medicine," Drug & News Perspectives, vol. 16, No. 5, 2003, 13 pages.

Russell et al., "Retroviral vectors displaying functional antibody fragments," Nucleic Acids Research, 21(5), 1081-1085 (1993).

Russell, "Replicating Vectors for Gene Therapy of Cancer: Risks, Limitations and Prospects," European Journal of Cancer, vol. 30A, No. 8, pp. 1165.

Sabourin et al., "The molecular regulation of myogenesis," (2000) Clin.' Genet. 57(1): 16-25.

Schnurr et al., "Two New Candidate Adenovirus Serotypes," Intervirology 1993;36:79-83.

Schulick et al., "Established Immunity Precludes Adenovirus-mediated Gene Transfer in Rat Carotid Arteries," The Journal of Clinical Investigation vol. 99, No. 2, Jan. 1997, 209-219.

Segerman et al.: "Adenovirus types 11p and 35p show high binding efficiencies for committed hematopoietic cell lines and are infective to these cell lines" Journal of Virology, The American Society for Microbiology, US, vol. 74, No. 3, Feb. 2000, pp. 1457-1467, XP002161682 ISSN: 0022-538X.

Shayakhmetov et al., "Efficient Gene Transfer into Human CD34$^+$ Cells by a Retargeted Adenovirus Vector," Journal Of Virology, Mar. 2000, p. 2567-2583.

Signäs et al., "Adenovirus 3 Fiber Polypeptide Gene: Implications for the Structure of the Fiber Protein," Journal of Virology, 53(2), 672-678 (1985).

Silver et al., "Interaction of Human Adenovirus Serotype 2 with Human Lymphoid Cells," Virology, 165, 377-387 (1988).

Stewart et al., "Difference imaging of adenovirus: bridging the resolution gap between X-ray crystallography and electron microscopy," EMBO Journal, 12(7), 2589-2599 (1993).

Stratford-Perricaudet LD et al.: "Widespread Long-Term Gene Transfer To Mouse Skeletal Muscles And Heart" Journal Of Clinical Investigation, New York, NY, US, vol. 90 No. 2, Aug. 1992, ISSN: 0021-9738.

Toogood et al., "The Adenovirus Type 40 Hexon: Sequence, Predicted Structure and Relationship to Other Adenovirus Hexons," J. gen. Virol (1989), 70, 3203-3214.

Valderrama-Leon et al., "Restriction Endonuclease Mapping of Adenovirus 35, a Type Isolated from Immunocompromised Hosts," Journal Of Virology, Nov. 1985, p. 647-650.

Verma et al., Nature, "Gene therapy-promises, problems and prospects," Sep. 1997, vol. 389, pp. 239-242.

Wadell, "Molecular Epidemiology of Human Adenoviruses," Microbiology and Immunology, vol. 110 pp. 191-220.

Wagner et al., "Coupling of adenovirus to transferrinBpolylysine/DNA complexes greatly enhances receptor-mediated gene delivery and expression of transfected genes," Proc. Natl. Acad. Sci. USA, 89, 6099-6103 (1992).

Watson et al., "An Antigenic Analysis of the Adenovirus Type 2 Fibre Polypeptide," Journal of Virology, 69, 525-535 (1988).

Wickham et al., "Integrins $_{v3}$ and $_{v5}$ Promote Adenovirus Internalization but Not Virus Attachment," Cell, 73, 309-319 (1993).

Wickham et al., "Integrin γ5 Selectively Promotes Adenovirus Mediated Cell Membrane Permeabilization," Journal of Cell Biology, 127(1), 257-264 (1994).

Wickham et al.: "Increased In Vitro and In Vivo Gene Transfer by Adenovirus Vectors Containing Chimeric Fiber Proteins," Journal of Virology, Nov. 1997, p. 8221-8229.

Zhong et al.: "Recombinant Adenovirus Is An Efficient And Non-Pertubing Genetic Vector For Human Dendritic Cells" European Journal Of Immunology, Weinheim, DE, vol. 29, No. 3, 1999, pp. 964-972 , XP000938797 ISSN: 0014-2980.

Basler et al., Sequence of the immunoregulatory early region 3 and flanking sequences of adenovirus type 35, 1996, pp. 249-254, Gene, vol. 170.

Jolly, Viral vector systems for gene therapy, 1994, Cancer Gene Therapy, pp. 51-64, vol. 1, No. 1.

Stevenson et al., Selective Targeting of Human Cells by a Chimeric Adenovirus Vector Containing a Modified Fiber Protein, 1997, Journal of Virology, pp. 4782-4790, vol. 71.

Gurunathan et al., American Association of Immunologists, "CD40 Ligand/Trimer DNA Enhances Both Humoral and Cellular Immune Responses and Induces Protective Immunity to Infectious and Tumor Challenge," 1998, pp. 4563-4571, vol. 161.

Chiu et al., Folding & Design, "Optimizing energy potentials for success in protein tertiary structure prediction," May 1998, pp. 223-228, vol. 3.

Ngo et al., The Protein Folding Problem and Tertiary Structure Prediction, "Computational Complexity, Protein Structure Prediction, and the Levinthal Paradox," 1994, Merz et al. (editors), Birkhauser, Boston, MA, pp. 433 and 492-495.

Anderson, Nature, "Human gene therapy," Apr. 1998, pp. 25-30, vol. 392.

PCT International Search Report, PCT/NL00/00325 dated Sep. 7, 2000.

* cited by examiner

% of human sera with neutralising capacity for human adenovirus (n=100)

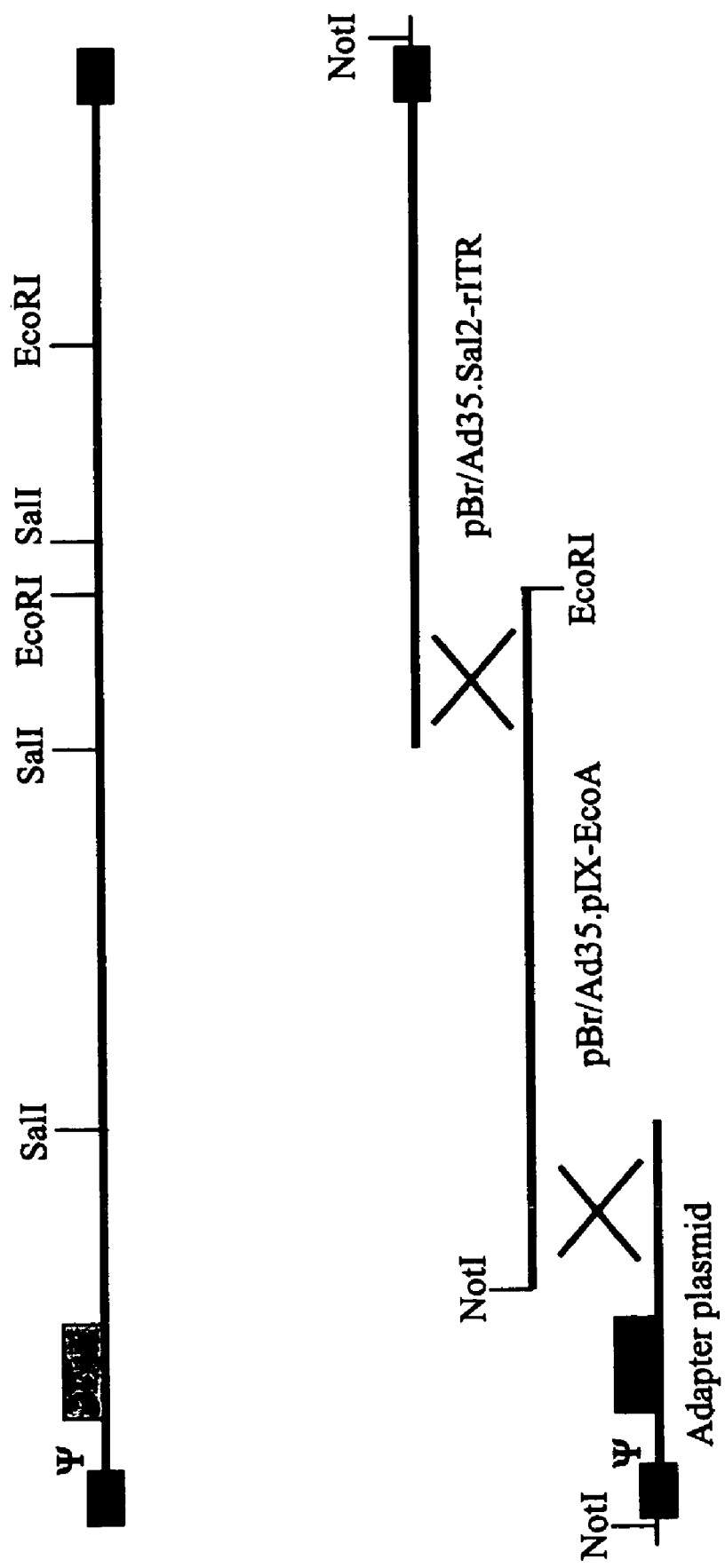
Figure 3: Ad35 plasmid-based system for virus generation

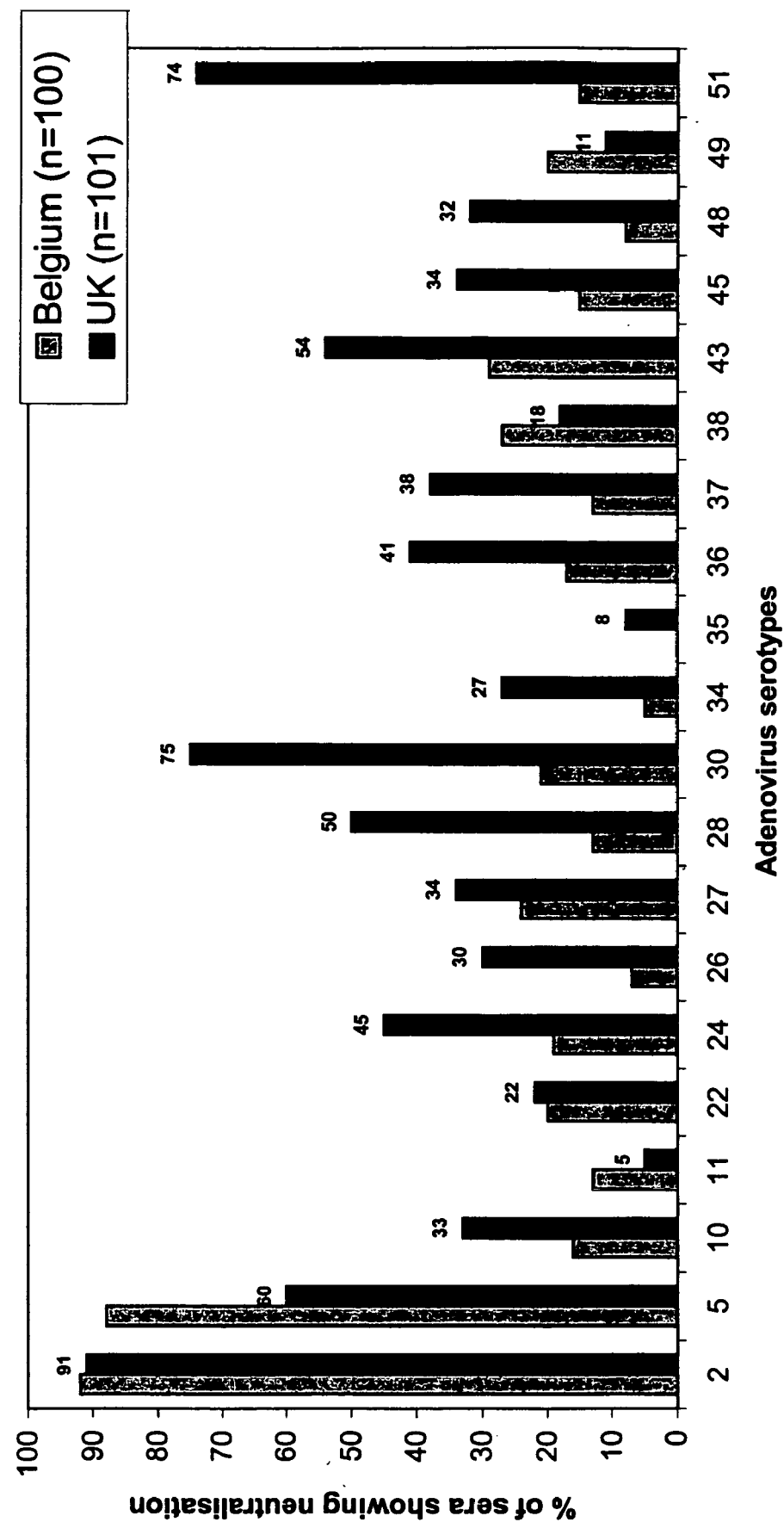

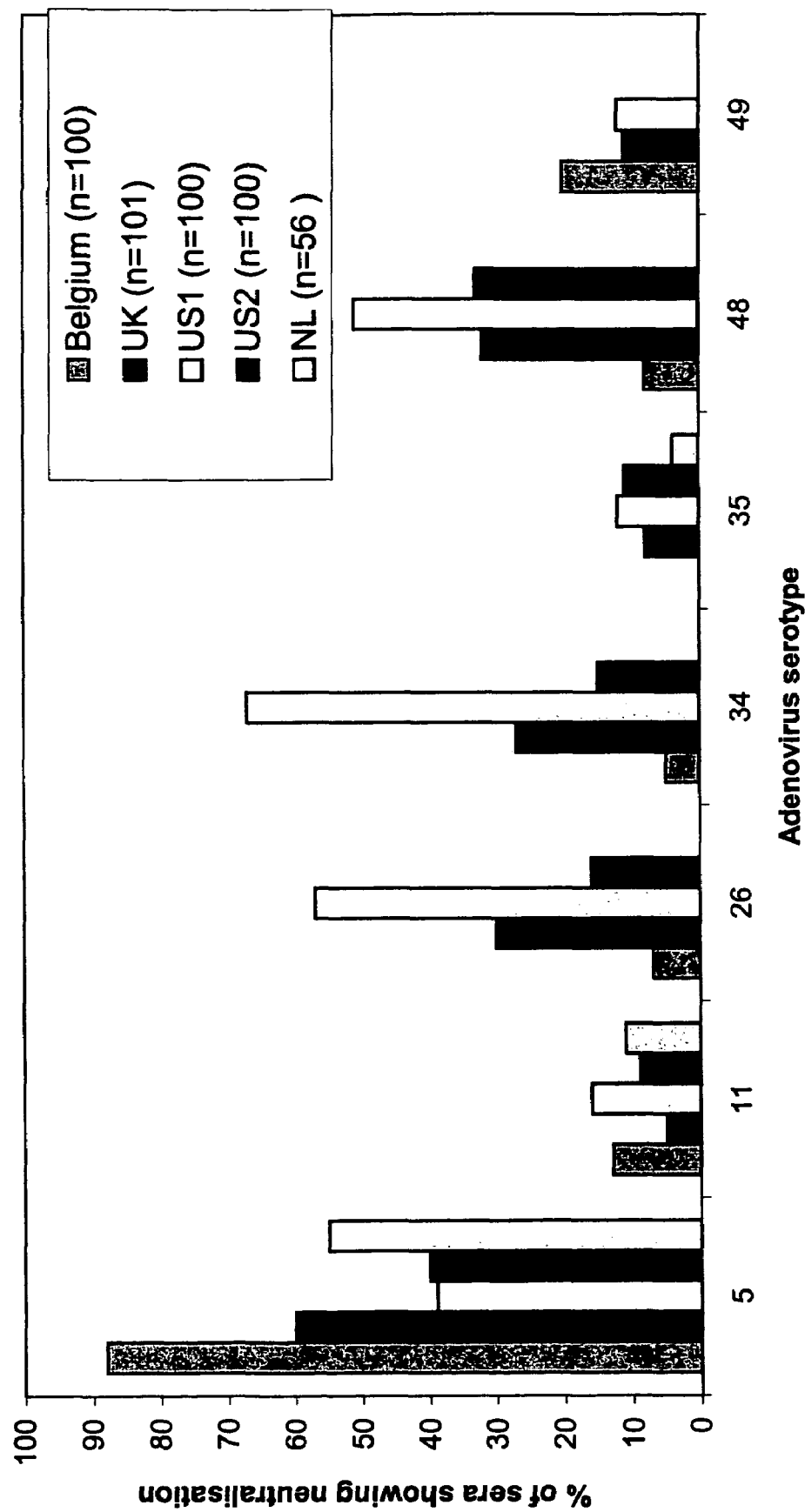

Figure 6A: Total sequence of Ad35.

```
   1 CATCATCAAT AATATACCTT ATAGATGGAA TGGTGCCAAT ATGTAAATGA GGTGATTTTA AAAAGTGTGG
  71 GCCGTGTGGT GATTGGCTGT GGGGTTAACG GTTAAAAGGG GCGGCGCGGC CGTGGGAAAA TGACGTTTTA
 141 TGGGGGTGGA GTTTTTTTGC AAGTTGTCGC GGGAAATGTT ACGCATAAAA AGGCTTCTTT TCTCACGGAA
 211 CTACTTAGTT TTCCCACGGT ATTTAACAGG AAATGAGGTA GTTTTGACCG GATGCAAGTG AAAATTGCTG
 281 ATTTTCGCGC GAAAACTGAA TGAGGAAGTG TTTTTCTGAA TAATGTGGTA TTTATGGCAG GGTGGAGTAT
 351 TTGTTCAGGG CCAGGTAGAC TTTGACCCAT TACGTGGAGG TTTCGATTAC CGTGTTTTTT ACCTGAATTT
 421 CCGCGTACCG TGTCAAAGTC TTCTGTTTTT ACGTAGGTGT CAGCTGATCG CTAGGGTATT TATACCTCAG
 491 GGTTTGTGTC AAGAGGCCAC TCTTGAGTGC CAGCGAGAAG AGTTTTCTCC TCTGCGCCGG CAGTTTAATA
 561 ATAAAAAAAT GAGAGATTTG CGATTTCTGC CTCAGGAAAT AATCTCTGCT GAGACTGAAA ATGAAATATT
 631 GGAGCTTGTG GTGCACGCCC TGATGGGAGA CGATCCGGAG CCACCTGTGC AGCTTTTTGA GCCTCCTACG
 701 CTTCAGGAAC TGTATGATTT AGAGGTAGAG GGATCGGAGG ATTCTAATGA GGAAGCTGTG AATGGCTTTT
 771 TTACCGATTC TATGCTTTTA GCTGCTAATG AAGGATTAGA ATTAGATCCG CCTTTGGACA CTTTCAATAC
 841 TCCAGGGGTG ATTGTGGAAA GCGGTACAGG TGTAAGAAAA TTACCTGATT TGAGTTCCGT GGACTGTGAT
 911 TTGCACTGCT ATGAAGACGG GTTTCCTCCG AGTGATGAGG AGGACCATGA AAAGGAGCAG TCCATGCAGA
 981 CTGCAGCGGG TGAGGGAGTG AAGGCTGCCA ATGTTGGTTT TCAGTTGGAT TGCCCGGAGC TTCCTGGACA
1051 TGGCTGTAAG TCTTGTGAAT TCACAGGAA AAATACTGGA GTAAAGGAAC TGTTATGTTC GCTTTGTTAT
1121 ATGAGAACGC ACTGCCACTT TATTTACAGT AAGTGTGTTT AAGTTAAAAT TTAAAGGAAT ATGCTGTTTT
1191 TCACATGTAT ATTGAGTGTG AGTTTTGTGC TTCTTATTAT AGGTCCTGTG TCTGATGCTG ATGAATCACC
1261 ATCTCCTGAT TCTACTACCT CACCTCCTGA TATTCAAGCA CCTGTTCCTG TGGACGTGCG CAAGCCCATT
1331 CCTGTGAAGC TTAAGCCTGG GAAACGTCCA GCAGTGGAGA AACTTGAGGA CTTGTTACAG GGTGGGGACG
1401 GACCTTTGGA CTTGAGTACA CGGAAACGTC CAAGACAATA AGTGTTCCAT ATCCGTGTTT ACTTAAGGTG
1471 ACGTCAATAT TTGTGTGAGA GTGCAATGTA ATAAAATAT GTTAACTGTT CACTGGTTTT TATTGCTTTT
1541 TGGGCGGGGA CTCAGGTATA TAAGTAGAAG CAGACCTGTG TGGTTAGCTC ATAGGAGCTG GCTTTCATCC
1611 ATGGAGGTTT GGGCCATTTT GGAAGACCTT AGGAAGACTA GGCAACTGTT AGAGAGCGCT TCGGACGGAG
1681 TCTCCGGTTT TTGGAGATTC TGGTTCGCTA GTGAATTAGC TAGGGTAGTT TTTAGGATAA AACAGGACTA
1751 TAAACAAGAA TTTGAAAAGT TGTTGGTAGA TTGCCCAGGA CTTTTTGAAG CTCTTAATTT GGGCCATCAG
1821 GTTCACTTTA AAGAAAAAGT TTTATCAGTT TTAACCCCAGG TAGAACTGCT GCTGCTGTGG
1891 CTTTTCTTAC TTTTATATTA GATAAATGGA TCCCGCAGAC TCATTTCAGC AGGGGATACG TTTTGGATTT
1961 CATAGCCACA GCATTGTGGA GAACATGAAG GGTTCGCAAG ATGAGGACAA TCTTAGGTTA CTGGCCAGTG
2031 CAGCCTTTGG GTGTAGCGGG AATCCTGAGG CATCCACCGG TCATGCCAGC GGTTCTGGAG GAGGAACAGC
2101 AAGAGGACAA CCCGAGAGCC GGCCTGGACC CTCCAGTGGA GGAGGCGGAG TAGCTGACTT GTCTCCTGAA
2171 CTGCAACGGG TGCTTACTGG ATCTACGTCC ACTGGACGGG ATAGGGGCGT TAAGAGGGAG AGGGCATCCA
2241 GTGGTACTGA TGCTAGATCT GAGTTGGCTT TAAGTTTAAT GAGTCGCAGA CGTCCTGAAA CCATTTGGTG
2311 GCATGAGGTT CAGAAAGAGG GAAGGGATGA AGTTTCTGTA TTGCAGGAGA AATATTCACT GGAACAGGTG
2381 AAAACATGTT GGTTGGAGCC AGAGGATGAT TGGGCGGTGG CCATTAAAAA TTATGCCAAG ATAGCTTTGA
2451 GGCCTGATAA ACAGTATAAG ATCAGTAGAC GGATTAATAT CCGGAATGCT TGTTACATAT CTGGAAATGG
2521 GGCTGAGGTG GTAATAGATA CTCAAGACAA GACAGTTATT AGATGCTGCA TGATGGATAT GTGGCCTGGA
2591 GTAGTCGGTA TGGAAGCAGT CACTTTTGTA AATGTTAAGT TTAGGGGAGA TGGTTATAAT GGAATAGTGT
2661 TTATGGCCAA TACCAAACTT ATATTGCGTA GTTGAGCTCT TTTTGGTTTC AACAATACCT GTGTAGATGC
2731 CTGGGGACAG GTTAGTGTAC GGGGGTGTAG TTTCTATGCG TGTTGGATTG CCACAGCTGG CAGAACCAAG
2801 AGTCAATTGT CTCTGAAGAA ATGCATATTC CAAAGATGTA ACCTGGGCAT TCTGAATGAA GGCGAAGCAA
2871 GGGTCCGTCA CTGCGCTTCT ACAGATACTG GATGTTTTAT TTTAATTAAG GAAATGCCA GCGTAAAGCA
2941 TAACATGATT TGTGGTGCTT CCGATGAGAG GCCTTATCAA ATGCTCACTT GTGCTGGTGG GCATTGTAAT
3011 ATGCTGGCTA CTGTGCATAT TGTTTCCCAT CAACGCAAAA AATGGCCTGT TTTTGATCAC AATGTGTTGA
3081 CCAAGTGCAC CATGCATGCA GGTGGGCGTA GAGGAATGTT TATGCCTTAC CAGTGTAACA TGAATCATGT
3151 GAAAGTGTTG TTGGAACCAG ATGCCTTTTC CAGAATGAGC CTAACAGGAA TCTTTGACAT GAACACGCAA
3221 ATCTGGAAGA TCCTGAGGTA TGATGATACG AGATCGAGGG TGCGCGCATG CGAATGCGGA GGCAAGCATG
3291 CCAGGTTCCA GCCGGTGTGT GTAGATGTGA CCGAAGATCT CAGACCGGAT CATTTGGTTA TTGCCCGCAC
3361 TGGAGCAGAG TTCGGATCCA GTGGAGAAGA AACTGACTAA GGTGAGTATT GGGAAAACTT TGGGGTGGGA
3431 TTTTCAGATG GACAGATTGA GTAAAAATTT GTTTTTCTG TCTTGCAGCT GACATGAGTG GAAATGCTTC
3501 TTTTAAGGGG GGAGTCTTCA GCCCTTATCT GACAGGGCGT CTCCCATCCT GGGCAGGAGT TCGTCAGAAT
3571 GTTATGGGAT CTACTGTGGA TGGAAGACCC GTTCAACCCG CCAATTCTTC AACGCTGACC TATGCTACTT
3641 TAAGTTCTTC ACCTTTGGAC GCAGCTGCAG CCGCTGCCGC CGCCTCTGTC GCCGCTAACA CTGTGCTTGG
3711 AATGGGTTAC TATGGAAGCA TCGTGCTAAC ATTCACTTCC TCTAATAACC CTTCTACACT GACTCAGGAC
3781 AAGTTACTTG TCCTTTTGGC CCAGCTGGAG GCTTTGACCC AACGTCTGGG TGAACTTTCT CAGCAGGTGG
3851 CCGAGTTGCG AGTACAAACT GAGTCTGCTC TCGGCACGGC AAAGTCTAAA TAAAAAAAAT TCCAGAATCA
3921 ATGAATAAAT AAACGAGCTT GTTGTTGATT TAAAATCAAG TGTTTTATT TCATTTTTCG CGCACGGTAT
3991 GCCCTGGACC ACCGATCTCG ATCATTGAGA ACTCGGTGGA TTTTTTCCAG AATCCTATAG AGGTGGGATT
4061 GAATGTTTAG ATACATGGGC ATTAGGCCGT CTTTGGGGTG GAGATAGCTC CATTGAAGGG ATTCATGCTC
4131 CGGGGTAGTG TTGTAAATCA CCCAGTCATA ACAAGGTCGC AGTGCATGGT GTTGCACAAT ATCTTTTAGA
4201 AGTAGGCTGA TTGCCACAGA TAAGCCCTTG GTGTAGGTGT TTACAAACCG GTTGAGCTGG GAGGGGTGCA
4271 TTCGAGGTGA AATTATGTGC ATTTTGGATT GGATTTTTAA GTTGGCAATA TTGCCGCCAA GATCCCGTCT
```

Figure 6B

```
4341 TGGGTTCATG TTATGAAGGA CTACCAAGAC GGTGTATCCG GTACATTTAG GAAATTTATC GTGCAGCTTG
4411 GATGGAAAAG CGTGGAAAAA TTTGGAGACA CCCTTGTGTC CTCCGAGATT TTCCATGCAC TCATCCATGA
4481 TAATAGCAAT GGGGCCGTGG GCAGCGGCGC GGGCAAACAC GTTCCGTGGG TCTGACACAT CATAGTTATG
4551 TTCCTGAGTT AAATCATCAT AAGCCATTTT AATGAATTTG GGGCGGAGCG TACCAGATTG GGTATGAAT
4621 GTTCCTTCGG GCCCCGGAGC ATAGTTCCCC TCACAGATTT GCATTTCCCA AGCTTTCAGT TCTGAGGGTG
4691 GAATCATGTC CACCTGGGGG GCTATGAAGA ACACCGTTTC GGGGGCGGGG GTGATTAGTT GGGATGATAG
4761 CAAGTTTCTG AGCAATTGAG ATTTGCCACA TCCGGTGGGG CCATAAATAA TTCCGATTAC AGGTTGCAGG
4831 TGGTAGTTTA GGGAACGGCA ACTGCCGTCT TCTCGAAGCA AGGGGGCCAC CTCGTTCATC ATTTCCCTTA
4901 CATGCATATT TTCCCGCACC AAATCCATTA GGAGGCGCTC TCCTCCTAGT GATAGAAGTT CTTGTAGTGA
4971 GGAAAAGTTT TTCAGCGGTT TTAGACCGTC AGCCATGGGC ATTTTGGAAA GAGTTTGCTG CAAAAGTTCT
5041 AGTCTGTTCC ACAGTTCAGT GATGTGTTCT ATGGCATCTC GATCCAGCAG ACCTCCTCGT TTCGCGGGTT
5111 TGGACGGCTC CTGGAGTAGG GTATGAGACG ATGGGCGTCC AGCGCTGCCA GGGTTCGGTC CTTCCAGGGT
5181 CTCAGTGTTC GAGTCAGGGT TGTTTCCGTC ACAGTGAAGG GGTGTGCGCC TGCTTGGGCG CTTGCCAGGG
5251 TGCGCTTCAG ACTCATTCTG CTGGTGGAGA ACTTCTGTCG CTTGGCGCCC TGTATGTCGG CCAAGTAGCA
5321 GTTTACCATG AGTTCGTAGT TGAGCGCCTC GGCTGCGTGG CCTTTGGCGC GGAGCTTACC TTTGAAGTT
5391 TTCTTGCATA CCGGGCAGTA TAGGCATTTC AGCGCATACA GCTTGGGCGC AAGGAAAATG GATTCTGGGG
5461 AGTATGCATC CGCGCCGCAG GAGGCGCAAA CAGTTTCACA TTCCACCAGC CAGGTTAAAT CCGGTTCATT
5531 GGGGTCAAAA ACAAGTTTTC CGCCATATTT TTTGATGCGT TTCTTACCTT TGGTCTCCAT AAGTTCGTGT
5601 CCTCGTTGAG TGACAAACAG GCTGTCCGTA TCTCCGTAGA CTGATTTTAC AGGCCTCTTC TCCAGTGGAG
5671 TGCCTCGGTC TTCTTCGTAC AGGAACTCTG ACCACTCTGA TACAAAGGCG CGCGTCCAGG CCAGCACAAA
5741 GGAGGCTATG TGGGAGGGGT AGCGATCGTT GTCAACCAGG GGGTCCACCT TTTCCAAAGT ATGCAAACAC
5811 ATGTCACCCT CTTCAACATC CAGGAATGTG ATTGGCTTGT AGGTGTATTT CACGTGACCT GGGGTCCCCG
5881 CTGGGGGGGT ATAAAAGGGG GCGGTTCTTT GCTCTTCCTC ACTGTCTTCC GGATCGCTGT CCAGGAACGT
5951 CAGCTGTTGG GGTAGGTATT CCCTCTCGAA GGCGGGCATG ACCTCTGCAC TCAGGTTGTC AGTTTCTAAG
6021 AACGAGGAGG ATTTGATATT GACAGTGCCG GTTGAGATGC CTTTCATGAG GTTTTCGTCC ATTTGGTCAG
6091 AAAACACAAT TTTTTATTG TCAAGTTTGG TGGCAAATGA TCCATACAGG GCGTTGGATA AAAGTTTGGC
6161 AATGGATCGC ATGGTTTGGT TCTTTTCCTT GTCCGCGCGC TCTTTGGCGG CGATGTTGAG TTGGACATAC
6231 TCGCGTGCCA GGCACTTCCA TTCGGGGAAG ATAGTTGTTA ATTCATCTGG CACGATTCTC ACTTGCCACC
6301 CTCGATTATG CAAGGTAATT AAATCCACAC TGGTGGCCAC CTCGCCTCGA AGGGGTTCAT TGGTCCAACA
6371 GAGCCTACCT CCTTTCCTAG AACAGAAAGG GGGAAGTGGG TCTAGCATAA GTTCATCGGG AGGGTCTGCA
6441 TCCATGGTAA AGATTCCCGG AAGTAAATCC TTATCAAAAT AGCTGATGGG AGTGGGGTCA TCTAAGGCCA
6511 TTTGCCATTC TCGAGCTGCC AGTGCGCGCT CATATGGGTT AAGGGGACTG CCCCAGGGCA TGGGATGGGT
6581 GAGAGCAGAG GCATACATGC CACAGATGTC ATAGACGTAG ATGGGATCCT CAAAGATGCC TATGTAGGTT
6651 GGATAGCATC GCCCCCCTCT GATACTTGCT CGCACATAGT CATATAGTTC ATGTGATGGC GCTAGCAGCC
6721 CCGGACCCAA GTTGGTGCGA TTGGGTTTTT CTGTTCTGTA GACGATCTGG CGAAAGATGG CGTGAGAATT
6791 GGAAGAGATG GTGGGTCTTT GAAAAATGTT GAAATGGGCA TGAGGTAGAC CTACAGAGTC TCTGACAAAG
6861 TGGGCATAAG ATTCTTGAAG CTTGGTTACC AGTTCGGCGG TGACAAGTAC GTCTAGGGCG CAGTAGTCAA
6931 GTGTTTCTTG AATGATGTCA TAACCTGGTT GGTTTTCTT TTCCCACAGT TCGCGGTTGA GAAGGTATTC
7001 TTCGCGATCC TTCCAGTACT CTTCTAGCGG AAACCCGTCT TTGTCTGCAC GGTAAGATCC TAGCATGTAG
7071 AACTGATTAA CTGCCTTGTA AGGGCAGCAG CCCTTCTCTA CGGGTAGAGA GTATGCTTGA GCAGCTTTTC
7141 GTAGCGAAGC GTGAGTAAGG GCAAAGGTGT CTCTGACCAT GACTTTGAGA AATTGGTATT TGAAGTCCAT
7211 GTCGTCACAG GCTCCCTGTT CCCAGAGTTG GAAGTCTACC CGTTTCTTGT AGGCGGGGTT GGGCAAAGCG
7281 AAAGTAACAT CATTGAAGAG AATCTTACCG GCTCTGGGCA TAAAATTGCG AGTGATGCGG AAAGGCTGTG
7351 GTACTTCCGC TCGATTGTTG ATCACCTGGG CAGCTAGGAC GATTTCGTCG AAACCGTTGA TGTTGTGTCC
7421 TACGATGTAT AATTCTATGA AACGCGGCGT GCCTCTGACG TGAGGTAGCT TACTGAGCTC ATCAAAGGTT
7491 AGGTCTGTGG GGTCAGATAA GGCGTAGTGT TCGAGAGCCC ATTCGTGCAG GTGAGGATTT GCATGTAGGA
7561 ATGATGACCA AAGATCTACC GCCAGTGCTG TTTGTAACTG GTCCCGATAC TGACGAAAAT GCCGGCCAAT
7631 TGCCATTTTT TCTGGAGTGA CACAGTAGAA GGTTCTGGGG TCTTGTTGCC ATCGATCCCA CTTGAGTTTA
7701 ATGGCTAGAT CGTGGGCCAT GTTGACGAGA CGCTCTTCTC CTGAGAGTTT CATGACCAGC ATGAAAGGAA
7771 CTAGTTGTTT GCCAAAGGAT CCCATCCAGG TGTAAGTTTC CACATCGTAG GTCAGGAAGA GTCTTTCTGT
7841 GCGAGGATGA GAGCCGATCG GAAGAACTG GATTTCCTGC CACCAGTTGG AGGATTGGCT GTTGATGTGA
7911 TGGAAGTAGA AGTTTCTGCG GCGCGCCGAG CATTCGTGTT TGTGCTTGTA CAGACGGCCG CAGTAGTCGC
7981 AGCGTTGCAC GGGTTGTATC TCGTGAATGA GCTGTACCTG GCTTCCCTTG ACAGAGAATT TCAGTGGGAA
8051 GCCGAGGCCT GGCGATTGTA TCTCGTGCTC TTCTATATTC GCTGTATCGG CCTGTTCATC TTCTGTTTCG
8121 ATGGTGGTCA TGCTGACGAG CCCCCGCGGG AGGCAAGTCC AGACCTCGGC GCGGGAGGGG CGGAGCTGAA
8191 GGACGAGAGC GCGCAGGCTG GAGCTGTCCA GAGTCCTGAG ACGCTGCGGA CTCAGGTTAG TAGGTAGGGA
8261 CAGAAGATTA ACTTGCATGA TCTTTTCCAG GGCGTGCGGG AGGTTCAGAT GGTACTTGAT TTCCACAGGT
8331 TCGTTTGTAG AGACGTCAAT GGCTTGCAGG GTTCCGTGTC CTTTGGGCGC CACTACCGTA CCTTTGTTTT
8401 TTCTTTTGAT CGGTGGTGGC TCTCTTGCTT CTTGCATGCT CAGAAGCGGT GACGGGACG CGCGCCGGGC
8471 GGCAGCGGTT GTTCCGGACC CGGGGGCATG GCTGGTAGTG GCACGTCGGC GCCGCGCACG GCAGGTTCT
8541 GGTATTGCGC TCTGAGAAGA CTTGCGTGCG CCACCACGCG TCGATTGACG TCTTGTATCT GACGTCTCTG
8611 GGTGAAAGCT ACCGGCCCCG TGAGCTTGAA CCTGAAAGAG AGTTAACAG AATCAATTTC GGTATCGTTA
8681 ACGGCAGCTT GTCTCAGTAT TTCTTGTACG TCACCAGAGT TGTCCTGGTA GGCGATCTCC GCCATGAACT
8751 GCTCGATTTC TTCCTCCTGA AGATCTCCGC GACCCGCTCT TTCGACGGTG GCCGCGAGGT CATTGGAGAT
```

Figure 6C

```
8821  ACGGCCCATG AGTTGGGAGA ATGCATTCAT GCCCGCCTCG TTCCAGACGC GGCTGTAAAC CACGGCCCCC
8891  TCGGAGTCTC TTGCGCGCAT CACCACCTGA GCGAGGTTAA GCTCCACGTG TCTGGTGAAG ACCGCATAGT
8961  TGCATAGGCG CTGAAAAAGG TAGTTGAGTG TGGTGGCAAT GTGTTCGGCG ACGAAGAAAT ACATGATCCA
9031  TCGTCTCAGC GGCATTTCGC TAACATCGCC CAGAGCTTCC AAGCGCTCCA TGGCCTCGTA GAAGTCCACG
9101  GCAAAATTAA AAAACTGGGA GTTTCGCGCG GACACGGTCA ATTCCTCCTC GAGAAGACGG ATGAGTTCGG
9171  CTATGGTGGC CCGTACTTCG CGTTCGAAGG CTCCCGGGAT CTCTTCTTCC TCTTCTATCT CTTCTTCCAC
9241  TAACATCTCT TCTTCGTCTT CAGGCGGGGG CGGAGGGGGC ACGCGGCGAC GTCGACGGCG CACGGGCAAA
9311  CGGTCGATGA ATCGTTCAAT GACCTCTCCG CGGCGGCGGC GCATGGTTTC AGTGACGGCG CGGCCGTTCT
9381  CGCGCGGTCG CAGAGTAAAA ACACCGCCGC GCATCTCCTT AAAGTGGTGA CTGGGAGGTT CTCCGTTTGG
9451  GAGGGAGAGG GCGCTGATTA TACATTTTAT TAATTGGCCC GTAGGGACTG CGCGCAGAGA TCTGATCGTG
9521  TCAAGATCCA CGGGATCTGA AAACCTTTCG ACGAAAGCGT CTAACCAGTC ACAGTCACAA GGTAGGCTGA
9591  GTACGGCTTC TTGTGGGCGG GGGTGGTTAT GTGTTCGGTC TGGGTCTTCT GTTTCTTCTT CATCTCGGGA
9661  AGGTGAGACG ATGCTGCTGG TGATGAAATT AAAGTAGGCA GTTCTAAGAC GGCGGATGGT GGCGAGGAGC
9731  ACCAGGTCTT TGGGTCCGGC TTGCTGGATA CGCAGGCGAT TGGCCATTCC CCAAGCATTA TCCTGACATC
9801  TAGCAAGATC TTTGTAGTAG TCTTGCATGA GCCGTTCTAC GGGCACTTCT TCCTCACCCG TTCTGCCATG
9871  CATACGTGTG AGTCCAAATC CGCGCATTGG TTGTACCAGT GCCAAGTCAG CTACGACTCT TTCGGCGAGG
9941  ATGGCTTGCT GTACTTGGGT AAGGGTGGCT TGAAAGTCAT CAAAATCCAC AAAGCGGTGG TAAGCCCCTG
10011 TATTAATGGT GTAAGCACAG TTGGCCATGA CTGACCAGTT AACTGTCTGG TGACCAGGGC GCACGAGCTC
10081 GGTGTATTTA AGGCGCGAAT AGGCGCGGGT GTCAAAGATG TAATCGTTGC AGGTGCGCAC CAGATACTGG
10151 TACCCTATAA GAAAATGCGG CGGTGGTTGG CGGTAGAGAG GCCATCGTTC TGTAGCTGGA GCGCCAGGGG
10221 CGAGGTCTTC CAACATAAGG CGGTGATAGC CGTAGATGTA CCTGGACATC CAGGTGATTC CTGCGGCGGT
10291 AGTAGAAGCC CGAGGAAACT CGCGTACGCG GTTCCAAATG TTGCGTAGCG GCATGAAGTA GTTCATTGTA
10361 GGCACGGTTT GACCAGTGAG GCGCGCGCAG TCATTGATGC TCTATAGACA CGGAGAAAAT GAAAGCGTTC
10431 AGCGACTCGA CTCCGTAGCC TGGAGGAACG TGAACGGGTT GGGTCGCGGT GTACCCCGGT TCGAGACTTG
10501 TACTCGAGCC GGCCGGAGCC GCGGCTAACG TGGTATTGGC ACTCCGTCT CGACCCAGCC TACAAAAATC
10571 CAGGATACGG AATCGAGTCG TTTTGCTGGT TTCCGAATGG CAGGGAAGTG AGTCCTATTT TTTTTTTTT
10641 TTTGCCGCTC AGATGCATCC CGTGCTGCGA CAGATGCGCC CCCAACAACA GCCCCCCTCG CAGCAGCAGC
10711 AGCAGCAACC ACAAAAGGCT GTCCCTGCAA CTACTGCAAC TGCCGCCGTG AGCGGTGCGG GACAGCCCGC
10781 CTATGATCTG GACTTGGAAG AGGGCGAAGG ACTGGCACGT CTAGGTGCGC CTTCGCCCGA GCGGCATCCG
10851 CGAGTTCAAC TGAAAAAGA TTCTCGCGAG GCGTATGTGC CCCAACAGAA CCTATTTAGA GACAGAAGCG
10921 GCGAGGAGCC GGAGGAGATG CGAGCTTCCC GCTTTAACGC GGGTCGTGAG CTGCGTCACG GTTTGGACCG
10991 AAGACGAGTG TTGCGAGACG AGGATTTCGA AGTTGATGAA GTGACAGGGA TCAGTCCTGC CAGGGCACAC
11061 GTGGCTGCAG CCAACCTTGT ATCGGCTTAC GAGCAGACAG TAAAGGAAGA GCGTAACTTC CAAAAGTCTT
11131 TTAATAATCA TGTGCGAACC CTGATTGCCC GCGAAGAAGT TACCCTTGGT TTGATGCATT TGTGGGATTT
11201 GATGGAAGCT ATCATTCAGA ACCCTACTAG CAAACCTCTG ACCGCCCAGC TGTTTCTGGT GGTGCAACAC
11271 AGCAGAGACA ATGAGGCTTT CAGAGAGGCG CTGCTGAACA TCACCGAACC CGAGGGGAGA TGGTTGTATG
11341 ATCTTATCAA CATTCTACAG AGTATCATAG TGCAGGAGCG GAGCCTGGGC CTGGCCGAGA AGGTAGCTGC
11411 CATCAATTAC TCGGTTTTGA GCTTGGGAAA ATATTACGCT CGCAAAATCT ACAAGACTCC ATACGTTCCC
11481 ATAGACAAGG AGGTGAAGAT AGATGGGTTC TACATGCGCA TGACGCTCAA GGTCTTGACC CTGAGCGATG
11551 ATCTTGGGGT GTATCGCAAT GACAGAATGC ATCGCGCGGT TAGCGCCAGC AGGAGGCGCG AGTTAAGCGA
11621 CAGGGAACTG ATGCACAGTT TGCAAAGAGC TCTGACTGGA GCTGGAACCG AGGGTGAGAA TTACTTCGAC
11691 ATGGGAGCTG ACTTGCAGTG GCAGCCTAGT CGCAGGGCTC TGAGCGCCGC GACGGCAGGA TGTGAGCTTC
11761 CTTACATAGA AGAGGCGGAT GAAGGCGAGG AGGAAGAGGG CGAGTACTTG GAAGACTGAT GGCACAACCC
11831 GTGTTTTTTG CTAGATGGAA CAGCAAGCAC CGGATCCGC AATGCGGGCG GCGCTGCAGA GCCAGCCGTC
11901 CGGCATTAAC TCCTCGGACG ATTGGACCCA GGCCATGCAA CGTATCATGG CGTTGACGAC TCGCAACCCC
11971 GAAGCCTTTA GACAGCAACC CCAGGCCAAC CGTCTATCGG CCATCATGGA AGCTGTAGTG CCTTCCCGAT
12041 CTAATCCCAC TCATGAGAAG GTCCTGACCA TCGTGGACGG GTTGGTGGAG AACAAAGCTA TTCGTCCAGA
12111 TGAGGCCGGA CTGGTATACA ACGCTCTCTT AGAACGCGTG GCTCGCTACA ACAGTAGCAA TGTGCAAACC
12181 AATTTGGACC GTATGATAAC AGATGTACGC GAAGCCGTGT CTCAGCGCGA AAGGTTCCAG CGTGATGCCA
12251 ACCTGGGTTC GCTGGTGGCG TTAAATGCTT TCTTGAGTAC TCAGCCTGCT AATGTGCCGC GTGGTCAACA
12321 GGATTATACT AACTTTTTAA GTGCTTTGAG ACTGATGGTA TCAGAAGTAC CTCAGAGCGA AGTGTATCAG
12391 TCCGGTCCTG ATTACTTCTT TCAGACTAGC AGACAGGGCT TGCAGACGGT AAATCTGAGC CAAGCTTTTA
12461 AAAACCTTAA AGGTTTGTGG GGAGTGCATG CCCCGGTAGG AGAAAGAGCA ACCGTGTCTA GCTTGTTAAC
12531 TCCGAACTCC CGCCTGTTAT TACTGTTGGT AGCTCCTTTC ACCGACAGCG GTAGCATCGA CCGTAATTCC
12601 TATTTGGGTT ACCTACTAAA CCTGTATCGC GAAGCCATAG GCAAAGTCA GGTGGACGAG CAGACCTATC
12671 AAGAAATTAC CAAGTCAGT CGCGCTTTGG GACAGGAAGA CACTGGCAGT TTGAAGCCA CTCTGAACTT
12741 CTTGCTTACC AATCGGTCTC AAAAGATCCC TCCTCAATAT GCTCTTACTG CGGAGGAGGA GAGGATCCTT
12811 AGATATGTGC AGCAGAGCGT GGGATTGTTT CTGATGCAAG AGGGGGCAAC TCCGACTGCA GCACTGGACA
12881 TGACAGCGCG AAATATGGAG CCCAGCATGT ATGCCAGTAA CCGACCTTTC ATTAACAAAC TGCTGGACTA
12951 CTTGCACAGA GCTGCCGCTA TGAACTCTGA TTATTTCACC AATGCCATCT TAAACCCGCA CTGGCTGCCC
13021 CCACCTGGTT TCTACACGGG CGAATATGAC ATGCCCGACC CTAATGACGG ATTTCTGTGG GACGACGTGG
13091 ACAGCGATGT TTTTTCACCT CTTTCTGATC ATCGCACGTG GAAAAGGAA GGCGGTGATA GAATGCATTC
13161 TTCTGCATCG CTGTCCGGGG TCATGGGTGC TACCGCGGCT GAGCCCGAGT CTGCAAGTCC TTTTCCTAGT
13231 CTACCCTTTT CTCTACACAG TGTACGTAGC AGCGAAGTGG GTAGAATAAG TCGCCCGAGT TTAATGGGCG
```

Figure 6D

```
13301 AAGAGGAGTA CCTAAACGAT TCCTTGCTCA GACCGGCAAG AGAAAAAAAT TTCCCAAACA ATGGAATAGA
13371 AAGTTTGGTG GATAAAATGA GTAGATGGAA GACTTATGCT CAGGATCACA GAGACGAGCC TGGGATCATG
13441 GGGACTACAA GTAGAGCGAG CCGTAGACGC CAGCGCCATG ACAGACGGAG GGGTCTTGTG TGGGACGATG
13511 AGGATTCGGC CGATGATAGC AGCGTGTTGG ACTTGGGTGG GAGAGGAAGG GGCAACCCGT TTGCTCATTT
13581 GCGCCCTCGC TTGGGTGGTA TGTTGTGAAA AAAAATAAAA AAGAAAAACT CACCAAGGCC ATGGCGACGA
13651 GCGTACGTTC GTTCTTCTTT ATTATCTGTG TCTAGTATAA TGAGGCGAGT CGTGCTAGGC GGAGCGGTGG
13721 TGTATCCGGA GGGTCCTCCT CCTTCGTACG AGAGCGTGAT GCAGCAGCAG CAGGCGACGG CGGTGATGCA
13791 ATCCCCACTG GAGGCTCCCT TTGTGCCTCC GCGATACCTG GCACCTACGG AGGGCAGAAA CAGCATTCGT
13861 TACTCGGAAC TGGCACCTCA GTACGATACC ACCAGGTTGT ATCTGGTGGA CAACAAGTCG GCGGACATTG
13931 CTTCTCTGAA CTATCAGAAT GACCACAGCA ACTTCTTGAC CACGGTGGTG CAGAACAATG ACTTTACCCC
14001 TACGGAAGCC AGCACCCAGA CCATTAACTT TGATGAACGA TCGCGGTGGG GCGGTCAGCT AAAGACCATC
14071 ATGCATACTA ACATGCCAAA CGTGAACGAG TATATGTTTA GTAACAAGTT CAAAGCGCGT GTGATGGTGT
14141 CCAGAAAACC TCCCGACGGT GCTGCAGTTG GGGATACTTA TGATCACAAG CAGGATATTT TGGAATATGA
14211 GTGGTTCGAG TTTACTTTGC CAGAAGGCAA CTTTTCAGTT ACTATGACTA TTGATTTGAT GAACAATGCC
14281 ATCATAGATA ATTACTTGAA AGTGGGTAGA CAGAATGGAG TGCTTGAAAG TGACATTGGT GTTAAGTTCG
14351 ACACCAGGAA CTTCAAGCTG GGATGGGATC CCGAAACCAA GTTGATCATG CCTGGAGTGT ATACGTATGA
14421 AGCCTTCCAT CCTGACATTG TCTTACTGCC TGGCTGCGGA GTGGATTTTA CCGAGAGTCG TTTGAGCAAC
14491 CTTCTTGGTA TCAGAAAAAA ACAGCCATTT CAAGAGGGTT TTAAGATTTT GTATGAAGAT TTAGAAGGTG
14561 GTAATATTCC GGCCCTCTTG GATGTAGATG CCTATGAGAA CAGTAAGAAA GAACAAAAAG CCAAAATAGA
14631 AGCTGCTACA GCTGCTGCAG AAGCTAGGCC AAACATAGTT GCCAGCGACT CTACAAGGGT TGCTAACGCT
14701 GGAGAGGTCA GAGGAGACAA TTTTGCGCCA ACACCTGTTC CGACTGCAGA ATCATTATTG GCCGATGTGT
14771 CTGAAGGAAC GGACGTGAAA CTCACTATTC AACCTGTAGA AAAAGATAGT AAGAATAGAA GCTATAATGT
14841 GTTGGAAGAC AAAATCAACA CAGCCTATCG CAGTTGGTAT CTTTCGTACA ATTATGGCGA TCCCGAAAAA
14911 GGAGTGCGTT CCTGGACATT GCTCACCACC TCAGATGTCA CCTGCGGAGC AGAGCAGGTT TACTGGTCGC
14981 TTCCAGACAT GATGAAGGAT CCTGTCACTT TCCGCTCCAC TAGACAAGTC AGTAACTACC CTGTGGTGGG
15051 TGCAGAGCTT ATGCCCGTCT TCTCAAAGAG CTTCTACAAC GAACAAGCTG TGTACTCCCA GCAGCTCCGC
15121 CAGTCCACCT CGCTTACGCA CGTCTTCAAC CGCTTTCCTG AGAACCAGAT TTTAATCCGT CCGCGGCGC
15191 CCACCATTAC CACCGTCAGT GAAAACGTTC CTGCTCTCAC AGATCGGG ACCCTGCCGT TGCGCAGCAG
15261 TATCCGGGGA GTCCAACGTG TGACCGTTAC TGACGCCAGA CGCCGCACCT GTCCCTACGT GTACAAGGCA
15331 CTGGGCATAG TCGCACCGCG CGTCCTTTCA AGCCGCACTT TCTAAAAAAA AAAAATGTCC ATTCTTATCT
15401 CGCCCAGTAA TAACACCGGT TGGGGTCTGC GCGCTCCAAG CAAGATGTAC GGAGGCGCAC GCAAACGTTC
15471 TACCCAACAT CCCGTGCGTG TTCGCGGACA TTTTCGCGCT CCATGGGGTG CCCTCAAGGG CCGCACTCGC
15541 GTTCGAACCA CCGTCGATGA TGTAATCGAT CAGGTGGTTG CCGACGCCCG TAATTATACT CCTACTGCGC
15611 CTACATCTAC TGTGGATGCA GTTATTGCA GTGTAGTGGC TGACGCTCGC AACTACTGCTC GACGTAAGAG
15681 CCGGCGAAGG CGCATTGCCA GACGCCACCG AGCTACCACT GCCATGCGAG CCGCAAGAGC TCTGCTACGA
15751 AGAGCTAGAC GCGTGGGGCG AAGAGCCATG CTTAGGGCGG CCAGACGTGC AGCTTCGGGC GCCAGCGCCG
15821 GCAGGTCCCG CAGGCAAGCA GCCGCTGTCG CAGCGGCGAC TATTGCCGAC ATGGCCCAAT CGCGAAGAGG
15891 CAATGTATAC TGGGTGCGTG ACGCTGCCAC CGGTCAACGT GTACCCGTGC GCACCCGTCC CCCTCGCACT
15961 TAGAAGATAC TGAGCAGTCT CCGATGTTGT GTCCCAGCGG CGAGGATGTC CAAGCGCAAA TACAAGGAAG
16031 AAATGCTGCA GGTTATCGCA CCTGAAGTCT ACGGCCAACC GTTGAAGGAT GAAAAAAAAC CCCGCAAAAT
16101 CAAGCGGGTT AAAAAGGACA AAAAAGAAGA GGAAGATGGC GATGATGGAC TGGCGGAGTT TGTGCGCGAG
16171 TTTGCCCCAC GGCGACGCGT GCAATGGCGT GGGCGACAGA TTCGACATGT GTTGAGACCT GGAACTTCGG
16241 TGGTCTTTAC ACCCGGCGAG CGTTCAAGCG CTACTTTTAA GCGTTCCTAT GATGAGGTGT ACGGGGATGA
16311 TGATATTCTT GAGCAGGCGG CTGACCGATT AGGCGAGTTT GCTTATGGCA AGCGTAGTAG AATAACTTCC
16381 AAGGATGAGA CAGTGTCAAT ACCCTTGGAT CATGGAAATC CCACCCCTAG TCTTAAACCG GTCACTTTGC
16451 AGCAAGTGTT ACCCGTAACT CCGCGAACAG GTGTTAAACG CGAAGGTGAA GATTTGTATC CCACTATGCA
16521 ACTGATGGTA CCCAAACGCC AGAAGTTGGA GGACGTTTTG GAGAAAGTAA AAGTGGATCC AGATATTCAA
16591 CCTGAGGTTA AAGTGAGACC CATTAAGCAG GTAGCGCCTG GTCTGGGGGT ACAAACTGTA GACATTAAGA
16661 TTCCCACTGA AAGTATGGAA GTGCAAACTG AACCCGCAAA GCCTACTGCC ACCTCCACTG AAGTGCAAAC
16731 GGATCCATGG ATGCCCATGC CTATTACAAC TGACGCCGCC GGTCCACTC GAAGATCCCG ACGAAAGTAC
16801 GGTCCAGCAA GTCTGTTGAT GCCCAATTAT GTTGTACACC CATCTATTAT TCCTACTCCT GGTTACCGAG
16871 GCACTCGCTA CTATCGCAGC CGAAACAGTA CCTCCCGCCG TCGCCGCAAG ACACCTGCAA ATCGCAGTCG
16941 TCGCCGTAGA CGCACAAGCA AACCGACTCC CGGCGCCCTG GTGCGGCAAG TGTACCGCAA TGGTAGTGCG
17011 GAACCTTTGA CACTGCCGCG TGCGCGTTAC CATCCGAGTA TCATCACTTA ATCAATGTTG CCGCTGCCTC
17081 CTTGCAGATA TGGCCCTCAC TTGTCGCCTT CGCGTTCCCA TCACTGGTTA CCGAGGAAGA AACTCGCGCC
17151 GTAGAAGAGG GATGTTGGGA CGCGGAATGC GACGCTACAG GCGACGGCGT GCTATCCGCA AGCAATTGCG
17221 GGGTGGTTTT TTACCAGCCT TAATTCCAAT TATCGCTGCT GCAATTGGCG CGATACCAGG CATAGCTTCC
17291 GTGGCGGTTC AGGCCTCGCA ACGACATTGA CATTGACAGA AAAACGTATA AATAAAAAAA AATACAATGG
17361 ACTCTGACAC TCCTGGTCCT GTGACTATGT TTTCTTAGAG ATGGAAGACA TCAATTTTC ATCCTTGGCT
17431 CCGCGACACG GCACGAAGCC GTACATGGGC ACCTGAGCG ACATCGGCAC GAGCCAACTG AACGGGGCG
17501 CCTTCAATTG GAGCAGTATC TGGAGCGGGC TTAAAATTT TGGCTCAACC ATAAAAACAT ACGGGAACAA
17571 AGCTTGGAAC AGCAGTACAG GACAGGCGCT TAGAAATAAA CTTAAAGACC AGAACTTCCA ACAAAAAGTA
17641 GTCGATGGGA TAGCTTCCGG CATCAATGGA GTGGTAGATT TGGCTAACCA GGCTGTGCAG AAAAAGATAA
17711 ACAGTCGTTT GGACCCGCCG CCAGCAACCC CAGGTGAAAT GCAAGTGGAG GAAGAAATTC CTCCGCCAGA
```

Figure 6E

```
17781 AAAACGAGGC GACAAGCGTC CGCGTCCCGA TTTGGAAGAG ACGCTGGTGA CGCGCGTAGA TGAACCGCCT
17851 TCTTATGAGG AAGCAACGAA GCTTGGAATG CCCACCACTA GACCGATAGC CCCAATGGCC ACCGGGGTGA
17921 TGAAACCTTC TCAGTTGCAT CGACCCGTCA CCTTGGATTT GCCCCCTCCC CCTGCTGCTA CTGCTGTACC
17991 CGCTTCTAAG CCTGTCGCTG CCCCGAAACC AGTCGCCGTA GCCAGGTCAC GTCCCGGGGG CGCTCCTCGT
18061 CCAAATGCGC ACTGGCAAAA TACTCTGAAC AGCATCGTGG GTCTAGGCGT GCAAAGTGTA AAACGCCGTC
18131 GCTGCTTTTA ATTAAATATG GAGTAGCGCT TAACTTGCCT ATCTGTGTAT ATGTGTCATT ACACGCCGTC
18201 ACAGCAGCAG AGGAAAAAAG GAAGAGGTCG TGCGTCGACG CTGAGTTACT TTCAAGATGG CCACCCCATC
18271 GATGCTGCCC CAATGGGCAT ACATGCACAT CGCCGGACAG GATGCTTCGG AGTACCTGAG TCCGGGTCTG
18341 GTGCAGTTCG CCCGCGCCAC AGACACCTAC TTCAATCTGG GAAATAAGTT TAGAAATCCC ACCGTAGCGC
18411 CGACCCACGA TGTGACCACC GACCGTAGCC AGCGGCTCAT GTTGCGCTTC GTGCCCGTTG ACCGGGAGGA
18481 CAATACATAC TCTTACAAAG TGCGGTACAC CCTGGCCGTG GGCGACAACA GAGTGCTGGA TATGGCCAGC
18551 ACGTTCTTTG ACATTAGGGG CGTGTTGGAC AGAGGTCCCA GTTTCAAACC CTATTCTGGT ACGGCTTACA
18621 ACTCTCTGGC TCCTAAAGGC GCTCCAAATG CATCTCAATG GATTGCAAAA GGCGTACCAA CTGCAGCAGC
18691 CGCAGGCAAT GGTGAAGAAG AACATGAAAC AGAGGAGAAA ACTGCTACTT ACACTTTTGC CAATGCTCCT
18761 GTAAAAGCCG AGGCTCAAAT TACAAAAGAG GGCTTACCAA TAGGTTTGGA GATTTCAGCT GAAAACGAAT
18831 CTAAACCCAT CTATGCAGAT AAACTTTATC AGCCAGAACC TCAAGTGGGA GATGAAACTT GGACTGACCT
18901 AGACGGAAAA ACCGAAGAGT ATGGAGGCAG GGCTCTAAAG CCTACTACTA ACATGAAACC CTGTTACGGG
18971 TCCTATGCGA AGCCTACTAA TTTAAAAGGT GGTCAGGCAA AACCGAAAAA CTCGGAACCG TCGAGTGAAA
19041 AAATTGAATA TGATATTGAC ATGGAATTTT TTGATAACTC ATCGCAAAGA ACAAACTTCA GTCCTAAAAT
19111 TGTCATGTAT GCAGAAAATG TAGGTTTGGA AACGCCAGAC ACTCATGTAG TGTACAAACC TGGAACAGAA
19181 GACACAAGTT CCGAAGCTAA TTTGGGACAA CAGTCTATGC CCAACAGACC CAACTACATT GGCTTCAGAG
19251 ATAACTTTAT TGGACTCATG TACTATAACA GTACTGGTAA CATGGGGGTG CTGGCTGGTC AAGCGTCTCA
19321 GTTAAATGCA GTGGTTGACT TGCAGGACAG AAACACAGAA CTTTCTTACC AACTCTTGCT TGACTCTCTG
19391 GGCGACAGAA CCAGATACTT TAGCATGTGG AATCAGGCTG TGGACAGTTA TGATCCTGAT GTACGTGTTA
19461 TTGAAAATCA TGGTGTGGAA GATGAACTTC CCAACTATTG TTTTCCACTG GACGGCATAG GTGTTCCAAC
19531 AACCAGTTAC AAATCAATAG TTCCAAATGG AGAAGATAAT AATAATTGGA AAGAACCTGA AGTAAATGGA
19601 ACAAGTGAGA TCGGACAGGG TAATTTGTTT GCCATGGAAA TTAACCTTCA AGCCAATCTA TGGCGAAGTT
19671 TCCTTTATTC CAATGTGGCT CTGTATCTCC CAGACTCGTA CAAATACACC CCGTCCAATG TCACTCTTCC
19741 AGAAAACAAA AACACCTACG ACTACATGAA CGGGCGGGTG GTGCCGCCAT CTCCTAGTAGA CACCTATGTG
19811 AACATTGGTG CCAGGTGGTC TCTGGATGCC ATGGACAATG TCAACCCATT CAACCACCAC CGTAACGCTG
19881 GCTTGCGTTA CCGATCTATG CTTCTGGGTA ACGGACGTTA TGTGCCTTTC CACATACAAG TGCCTCAAAA
19951 ATTCTTCGCT GTTAAAAACC TGCTGCTTCT CCCAGGCTCC TACACTTATG AGTGGAACTT TAGGAAGGAT
20021 GTGAACATGG TTCTACAGAG TTCCCTCGGT AACGACCTGC GGGTAGATGG CGCCAGCATC AGTTTCACGA
20091 GCATCAACCT CTATGCTACT TTTTTCCCCA TGGCTCACAA CACCGCTTCC ACCCTTGAAG CCATGCTGCG
20161 GAATGACACC AATGATCAGT CATTCAACGA CTACCTATCT GCAGCTAACA TGCTCTACCC CATTCCTGCC
20231 AATGCAACCA ATATTCCCAT TTCCATTCCT TCTCGCAACT GGGCGGCTTT CAGAGGCTGG TCATTTACCA
20301 GACTGAAAAC CAAAGAAACT CCCTCTTTGG GGTCTGGATT TGACCCCTAC TTTGTCTATT CTGGTTCTAT
20371 TCCCTACCTG GATGGTACCT TCTACCTGAA CCACACTTTT AAGAAGGTTT CCATCATGTT TGACTCTTCA
20441 GTGAAATGA CTGGAAATGA CAGGTTACTA TCTCCTAACG AATTTGAAAT AAAGCGCACT GTGGATGGCG
20511 AAGGCTACAA CGTAGCCCAA TGCAACATGA CCAAAGACTG GTTCTTGGTA CAGATGCTCG CCAACTACAA
20581 CATCGGCTAT CAGGGCTTCT ACATTCCAGA AGGATACAAA GATCGCATGT ATTCATTTTT CAGAAACTTC
20651 CAGCCCATGA GCAGGCAGGT GGTTGATGAG GTCAATTACA AAGACTTCAA GGCCGTCGCC ATACCCTACC
20721 AACACAACAA CTCTGGCTTT GTGGGTTACA TGGCTCCGAC CATGCGCCAA GGTCAACCCT ATCCCGCTAA
20791 CTATCCCTAT CCACTCATTG AACAACTGC CGTAAATAGT GTTACGCAGA AAAGTTCTT GTGTGACAGA
20861 ACCATGTGGC GCATACCGTT CTCGAGCAAC TTCATGTCTA TGGGGGCCCT TACAGACTTG GGACAGAATA
20931 TGCTCTATGC CAACTCAGCT CATGCTCTGG ACATGACTTT TGAGGTGGAT CCCATGGATG AGCCCACCCT
21001 GCTTTATCTT CTCTTCGAAG TTTTCGACGT GGTCAGAGTG CATCAGCCAC ACCGCGGCAT CATCGAGGCA
21071 GTCTACCTGC GTACACCGTT CTCGGCCGGT AACGCTACCA CGTAAGAAGC TTCTTGCTTC TTGCAAATAG
21141 CAGCTGCAAC CATGGCCTGC GGATCCCAAA ACGGCTCCAG CGAGCAAGAG CTCAGAGCCA TTGTCCAAGA
21211 CCTGGGTTGC GGACCCTATT TTTTGGGAAC CTACGATAAG CGCTTCCCGG GGTTCATGGC CCCCGATAAG
21281 CTCGCCTGTG CCATTGTAAA TACGGCCGGA CGTGAGACGG GGGAGAGCA CTGGTTGGCT TTCGGTTGGA
21351 ACCCACGTTC TAACACCTGC TACCTTTTTG ATCCTTTTGG ATTCTCGGAT GATCGTCTCA AACAGATTTA
21421 CCAGTTTGAA TATGAGGGTC TCCTGCGCCG CAGCGCTCTT GCTACCAAGG ACCGCTGTAT TACGCTGGAA
21491 AAATCTACCC AGACCGTGCA GGGCCCCGT TCTGCCGCCT GCGGACTTTT CTGCTGCATG TTCCTTCACG
21561 CCTTTGTGCA CTGGCCTGAC CGTCCCATGG ACGGAAACCC CACCATGAAA TTGCTAACTG GAGTGCCAAA
21631 CAACATGCTT CATTCTCCTA AAGTCCAGCC CACCGTGTGT GACAATCAAA AAGCACTCTA CCATTTTCTT
21701 AATACCCATT CGCCTTATTT TCGCTCTCAT CGTACACACA TCGAAAGGGC CACTGCGTTC GACCGTATGG
21771 ATGTTCAATA ATGACTCATG TAAACAACGT GTTCAATAAA CATCACTTTA TTTTTTTACA TGTATCAAGG
21841 CTCTGGATTA CTTATTTATT TACAAGTCGA ATGGGTTCTG ACGAGAATCA GAATGACCCG CAGGCAGTGA
21911 TACGTTGCGG AACTGATACT TGGGTTGCCA CTTGAATTCG GAATCACCA ACTTGGGAAC CGGTATATCG
21981 GGCAGGATGT CACTCCACAG CTTTCTGGTC AGCTGCAAAG CTCCAAGCAG GTCAGGAGCC GAAATCTTGA
22051 AATCACAATT AGGACCAGTG CTCTGAGCGC GAGAGTTGCG GTACACCGGA TTGCAGCACT GAAACACCAT
22121 CAGCGACGGA TGTCTCACGC TTGCCAGCAC GGTGGGATCT GCAATCATGC CCACATCCAG ATCTTCAGCA
22191 TTGGCAATGC TGAACGGGGT CATCTTGCAG GTCTGCCTAC CCATGGCGGG CACCCAATTA GGCTTGTGGT
```

Figure 6F

```
22261 TGCAATCGCA GTGCAGGGGG ATCAGTATCA TCTTGGCCTG ATCCTGTCTG ATTCCTGGAT ACACGGCTCT
22331 CATGAAAGCA TCATATTGCT TGAAAGCCTG CTGGGCTTTA CTACCCTCGG TATAAAACAT CCCGCAGGAC
22401 CTGCTCGAAA ACTGGTTAGC TGCACAGCCG GCATCATTCA CACAGCAGCG GGCGTCATTG TTGGCTATTT
22471 GCACCACACT TCTGCCCCAG CGGTTTTGGG TGATTTTGGT TCGCTCGGGA TTCTCCTTTA AGGCTCGTTG
22541 TCCGTTCTCG CTGGCCACAT CCATCTCGAT AATCTGCTCC TTCTGAATCA TAATATTGCC ATGCAGGCAC
22611 TTCAGCTTGC CCTCATAATC ATTGCAGCCA TGAGGCCACA ACGCACAGCC TGTACATTCC CAATTATGGT
22681 GGGCGATCTG AGAAAAAGAA TGTATCATTC CCTGCAGAAA TCTTCCCATC ATCGTGCTCA GTGTCTTGTG
22751 ACTAGTGAAA GTTAACTGGA TGCCTCGGTG CTCTTCGTTT ACGTACTGGT GACAGATGCG CTTGTATTGT
22821 TCGTGTTGCT CAGGCATTAG TTTAAAACAG GTTCTAAGTT CGTTATCCAG CCTGTACTTC TCCATCAGCA
22891 GACACATCAC TTCCATGCCT TTCTCCCAAG CAGACACCAG GGGCAAGCTA ATCGGATTCT TAACAGTGCA
22961 GGCAGCAGCT CCTTTAGCCA GAGGGTCATC TTTAGCGATC TTCTCAATGC TTCTTTTGCC ATCCTTCTCA
23031 ACGATGCGCA CGGGCGGGTA GCTGAAACCC ACTGCTACAA GTTGCGCCTC TTCTCTTTCT TCTTCGCTGT
23101 CTTGACTGAT GTCTTGCATG GGATATGTT TGGTCTTCCT TGGCTTCTTT TTGGGGGGTA TCGGAGGAGG
23171 AGGACTGTCG CTCCGTTCCG GAGACAGGGA GGATTGTGAC GTTTCGCTCA CCATTACCAA CTGACTGTCG
23241 GTAGAAGAAC CTGACCCCAC ACGGCGACAG GTGTTTTTCT TCGGGGGCAG AGGTGGAGGC GATTGCGAAG
23311 GGCTGCGGTC CGACCTGGAA GGCGGATGAC TGGCAGAACC CCTTCCGCGT TCGGGGTGT GCTCCCTGTG
23381 GCGGTCGCTT AACTGATTTC CTTCGCGGCT GGCCATTGTG TTCTCCTAGG CAGAGAAACA ACAGACATGG
23451 AAACTCAGCC ATTGCTGTCA ACATCGCCAC GAGTGCCATC ACATCTCGTC CTCAGCGACG AGGAAAAGGA
23521 GCAGAGCTTA AGCATTCCAC CGCCCAGTCC TGCCACCACC TCTACCCTAG AAGATAAGGA GGTCGACGCA
23591 TCTCATGACA TGCAGAATAA AAAAGCGAAA GAGTCTGAGA CAGACATCGA GCAAGACCCG GGCTATGTGA
23661 CACCGGTGGA ACACGAGGAA GAGTTGAAAC GCTTTCTAGA GAGAGAGGAT GAAAACTGCC CAAAACAGCG
23731 AGCAGATAAC TATCACCAAG ATGCTGGAAA TAGGGATCAG AACACCGACT ACCTCATAGG GCTTGACGGG
23801 GAAGCAGCGC TCCTTAAACA TCTAGCAAGA CAGTCGCTCA TAGTCAAGGA TGCATTATTG GACAGAACTG
23871 AAGTGCCCAT CAGTGTGGAA GAGCTCAGCT GCGCCTACGA GCTTAACCTT TTTTCACCTC GTACTCCCCC
23941 CAAACGTCAG CCAAACGGCA CCTGCGAGCC AAATCCTCGC TTAAACTTTT ATCCAGCTTT TGCTGTGCCA
24011 GAAGTACTGG CTACCTATCA CATCTTTTTT AAAAATCAAA AAATTCCAGT CTCCTGCCGC GCTAATCGCA
24081 CCCGCGCCGA TGCCCTACTC AATCTGGGAC CTGGTTCACG CTTACCTGAT ATAGCTTCCT TGGAAGAGGT
24151 TCCAAAGATC TTCGAGGGTC TGGGCAATAA TGAGACTCGG GCCGCAAATG CTCTGCAAAA GGGAGAAAAT
24221 GGCATGGATG AGCATCACAG CGTTCTGGTG GAATTGGAAG GCGATAATGC CAGACTCGCA GTACTCAAGC
24291 GAAGCGTCGA GGTCACACAC TTCGCATATC CCGCTGTCAA CCTGCCCCCT AAAGTCATGA CGGCGGTCAT
24361 GGACCAGTTA CTCATTAAGC GCGCAAGTCC CCTTTCAGAA GACATGCATG ACCCAGATGC CTGTGATGAG
24431 GGTAAACCAG TGGTCAGTGA TGAGCAGCTA ACCCGATGGC TGGGCACCGA CTCTCCCCGG GATTTGGAAG
24501 AGCGTCGCAA GCTTATGATG GCCGTGGTGC TGGTTACCGT AGAACTAGAG TGTCTCCGAC GTTTCTTTAC
24571 CGATTCAGAA ACCTTGCGCA AACTCGAAGA GAATCTGCAC TACACTTTTA GACACGGCTT TGTGCGGCAG
24641 GCATGCAAGA TATCTAACGT GGAACTCACC AACCTGGTTT CCTACATGGG TATTCTGCAT GAGAATCGCC
24711 TAGGACAAAG CGTGCTGCAC AGCACCCTTA AGGGGAAGC CCGCCGTGAT TACATCCGCG ATTGTGTCTA
24781 TCTCTACCTG TGCCACACAG GGCAAACCGG CATGGTGTCA TGGCAGCAAT GTTTAGAAGA ACAGAACTTG
24851 AAAGAGCTTG ACAAGCTCTT ACAGAAATCT CTTAAGGTTC TGTGGACAGG GTTCGACGAG CGCACCGTCG
24921 CTTCCGACCT GGCAGACCTC ATCTTCCCAG AGCGTCTCAG GGTTACTTTG CGAAACGGAT TGCCTGACTT
24991 TATGAGCCAG AGCATGCTTA ACAATTTTCG CTCTTTCATC CTGGAACGCT CCGGTATCCT GCCCGCCACC
25061 TGCTGCGCAC TGCCCTCCGA CTTTGTGCCT CTCACCTACC GCGAGTGCCC CCCGCCGCTA TGGAGTCACT
25131 GCTACCTGTT CCGTCTGGCC AACTATCTCT CCTACCACTC GGATGTGATC GAGGATGTGA GCGGAGACGG
25201 CTTGCTGGAG TGCCACTGCC GCTGCAATCT GTGCACGCCC CACCGGTCCC TAGCTTGCAA CCCCCAGTTG
25271 ATGAGCGAAA CCCAGATAAT AGGCACCTTT GAATTGCAAG GCCCCAGCAG CCAAGGCGAT GGGTCTTCTC
25341 CTGGGCAAAG TTTAAAACTG ACCCCGGGAC TGTGGACCTC CGCCTACTTG CGCAAGTTTG CTCCGGAAGA
25411 TTACCACCCC TATGAAATCA AGTTCTATGA GGACCAATCA CAGCCTCCAA AGGCCGAACT TTCGGCTTGC
25481 GTCATCACCC AGGGGGCAAT TCTGGCCCAA TTGCAAGCCA TCCAAAAATC CCGCCAAGAA TTTCTACTGA
25551 AAAAGGGTAA GGGGGTCTAC CTTGACCCCC AGACCGGCGA GGAACTCAAC ACAAGGTTCC CTCAGGATGT
25621 CCCAACGACG AGAAAACAAG AAGTTGAAGG TGCAGCCGCC GCCCCCAGAA GATATGGAGG AAGATTGGGA
25691 CAGTCAGGCA GAGGAGGCGG AGGAGGACAG TCTGGAGGAC AGTCTGGAGG AAGACAGTTT GGAGGAGGAA
25761 AACGAGGAGG CAGAGGAGGT GGAAGAAGTA ACCGCCGACA AACAGTTATC CTCGGCTGCG GAGACAAGCA
25831 ACAGCGCTAC CATCTCCGCT CCGAGTCGAG GCGTCCCAGC GGTAGATGGG ACGAGACCGG
25901 ACGCTTCCCG AACCCAACCA GCGCTTCCAA GACCGGTAAG AAGGATCGGC AGGGATACAA GTCCTGGCGG
25971 GGGCATAAGA ATGCCATCAT CTCCTGCTTG CATGAGTGCG GGGCAACAT ATCCTTCACG CGGCGCTACT
26041 TGCTATTCCA CCATGGGGTG AACTTTCCGC GCAATGTTTT GCATTACTAC GTCACCTCC ACAGCCCCTA
26111 CTATAGCCAG CAAATCCCGA CAGTCTGACA AGATAAAGAC AGCGGCGGCG ACCTCCAACA GAAAACCAGC
26181 AGCGGCAGTT AGAAAATACA CAACAAGTGC AGCAACAGGA GGATTAAAGA TTACAGCCAA CGAGCCAGCG
26251 CAAACCCGAG AGTTAAGAAA TCGGATCTTT CCAACCCTGT ATGCCATCTT CCAGCAGAGT CGGGGTCAAG
26321 AGCAGGAACT GAAAATAAAA AACCGATCTC TGCGTTCGCT CACCAGAAGT TGTTTGTATC ACAAGAGCGA
26391 AGATCAACTT CAGCGCACTC TCGAGGACGC CGAGGCTCTC TTCAACAAGT ACTGCGCTTC GACTCTTAAA
26461 GAGTAGGCAG CGACCGCGCT TATTCAAAAA AGGCGGGAAT TACATCATCC TCGACATGAG TAAAGAAATT
26531 CCCACGCCTT ACATGTGGAG TTATCAACCC CAAATGGGAT TGGCAGCAGG CGCCTCCCAG GACTACTCCA
26601 CCCGCATGAA TTGGCTCAGC GCCGGGCCTT CTATGATTTC TCGAGTTAAT GATATACGCG CCTACCGAAA
26671 CCAAATACTT TTGGAACAGT CAGCTCTTAC CACCACGCCC CGCCAACACC TTAATCCCAG AAATTGGCCC
```

Figure 6G

```
26741 GCCGCCCTAG TGTACCAGGA AAGTCCCGCT CCCACCACTG TATTACTTCC TCGAGACGCC CAGGCCGAAG
26811 TCCAAATGAC TAATGCAGGT GCGCAGTTAG CTGGCGGCTC CACCCTATGT CGTCACAGGC CTCGGCATAA
26881 TATAAAACGC CTGATGATCA GAGGCCGAGG TATCCAGCTC AACGACGAGT CGGTGAGCTC TCCGCTTGGT
26951 CTACGACCAG ACGGAATCTT TCAGATTGCC GGCTGCGGGA GATCTTCCTT CACCCCTCGT CAGGCTGTTC
27021 TGACTTTGGA AAGTTCGTCT TCGCAACCCC GCTCGGGCGG AATCGGGACC GTTCAATTTG TAGAGGAGTT
27091 TACTCCCTCT GTCTACTTCA ACCCCTTCTC CGGATCTCCT GGGCACTACC CGGACGAGTT CATACCGAAC
27161 TTCGACGCGA TTAGCGAGTC AGTGGACGGC TACGATTGAT GTCTGGTGAC GCGGCTGAGC TATCTCGGCT
27231 GCGACATCTA GACCACTGCC GCCGCTTTCG CTGCTTTGCC CGGGAACTTA TTGAGTTCAT CTACTTCGAA
27301 CTCCCCAAGG ATCACCCTCA AGGTCCGGCC CACGGAGTGC GGATTACTAT CGAAGGCAAA ATAGACTCTC
27371 GCCTGCAACG AATTTTCTCC CAGCGGCCCG TGCTGATCGA GCGAGACCAG GGAAACACCA CGGTTTCCAT
27441 CTACTGCATT TGTAATCACC CCGGATTGCA TGAAAGCCTT TGCTGTCTTA TGTGTACTGA GTTAATAAA
27511 AACTGAATTA AGACTCTCCT ACGGACTGCC GCTTCTTCAA CCCGGATTTT ACAACCAGAA GAACAAAACT
27581 TTTCCTGTCG TCCAGGACTC TGTTAACTTC ACCTTTCTCA CTCACAAACT AGAAGCTCAA CGACTACACC
27651 GCTTTTCCAG AAGCATTTTC CCTACTAATA CTACTTTCAA AACCGGAGGT GAGCTCCACG GTCTCCCTAC
27721 AGAAAACCCT TGGGTGGAAG CGGGCCTTGT AGTACTAGGA ATTCTTGCGG GTGGGCTTGT GATTATTCTT
27791 TGCTACCTAT ACACACCTTG CTTCACTTTC CTAGTGGTGT TGTGGTATTG GTTTAAAAAA TGGGGCCCAT
27861 ACTAGTCTTG CTTGTTTTAC TTTCGCTTTT GGAACCGGGT TCTGCCAATT ACGATCCATG TCTAGACTTT
27931 GACCCAGAAA ACTGCACACT TACTTTTGCA CCCGACACAA GCCGCATCTG TGGAGTTCTT ATTAAGTGCG
28001 GATGGGAATG CAGGTCCGTT GAAATTACAC ACAATAACAA AACCTGGAAC AATACCTTAT CCACCACATG
28071 GGAGCCAGGA GTTCCGAGT GGTACACTGT CTCTGTCCGA GGTCCTGACG GTTCCATCCG CATTAGTAAC
28141 AACACTTTCA TTTTTCTGA AATGTGCGAT CTGGCCATGT TCATGAGCAA ACAGTATTCT CTATGGCCTC
28211 CTAGCAAGGA CAACATCGTA ACGTTCTCCA TTGCTTATTG CTTGTGCGCT TGCCTTCTTA CTGCTTTACT
28281 GTGCGTATGC ATACACCTGC TTGTAACCAC TCGCATCAAA AACGCCAATA ACAAAGAAAA AATGCCTTAA
28351 CCTCTTTCTG TTTACAGACA TGGCTTCTCT TACATCTCTC ATATTTGTCA GCATTGTCAC TGCCGCTCAC
28421 GGACAAACAG TCGTCTCTAT CCCACTAGGA CATAATTACA CTCTCATAGG ACCCCAATC ACTTCAGAGG
28491 TCATCTGGAC CAAACTGGGA AGCGTTGATT ACTTTGATAT AATCTGTAAC AAAACAAAAC CAATAATAGT
28561 AACTTGCAAC ATACAAAATC TTACATTGAT TAATGTTAGC AAAGTTTACA GCGGTTACTA TTATGGTTAT
28631 GACAGATACA GTAGTCAATA TAGAAATTAC TTGGTTCGTG TTACCCAGTT GAAAACCACG AAAATGCCAA
28701 ATATGGCAAA GATTCGATCC GATGACAATT CTCTAGAAAC TTTTACATCT CCCACCACAC CCGACGAAAA
28771 AAACATCCCA GATTCAATGA TTGCAATTGT TGCAGCGGTG GCAGTGGTGA TGGCACTAAT AATAATATGC
28841 ATGCTTTTAT ATGCTTGTCG CTACAAAAAG TTTCATCCTA AAAAACAAGA TCTCCTACTA AGGCTTAACA
28911 TTTAATTTCT TTTTATACAG CCATGGTTTC CACTACCACA TTCCTTATGC TTACTAGTCT CGCAACTCTG
28981 ACTTCTGCTC GCTCACACCT CACTGTAACT ATAGGCTCAA ACTGCACACT AAAAGGACCT CAAGGTGGTC
29051 ATGTCTTTTG GTGGAGAATA TATGACAATG GATGGTTTAC AAAACCATGT GACCAACCTG GTAGATTTTT
29121 CTGCAACGGC AGAGACCTAA CCATTATCAA CGTGACAGCA AATGACAAAG GCTTCTATTA TGGAACCGAC
29191 TATAAAAGTA GTTTAGATTA TAACATTATT GTACTGCCAT CTACCACTCC AGCACCCGC ACAACTACTT
29261 TCTCTAGCAG CAGTGTCGCT AACAATACAA TTTCCAATCC AACCTTTGCC GCGCTTTTAA AACGCACTGT
29331 GAATAATTCT ACAACTTCAC ATACAACAAT TTCCACTTCA ACAATCAGCA TCATCGCTGC AGTGACAATT
29401 GGAATATCTA TTCTTGTTTT TACCATAACC TACTACGCCT GCTGCTATAG AAAAGACAAA CATAAAGGTG
29471 ATCCATTACT TAGATTTGAT ATTTAATTTG TTCTTTTTTT TTATTTACAG TATGGTGAAC ACCAATCATG
29541 GTACCTAGAA ATTTCTTCTT CACCCATACTC ATCTGTGCTT TTAATGTTTG CGCTACTTTC ACAGCAGTAG
29611 CCACAGCAAC CCCAGACTGT ATAGGAGCAT TTGCTTCCTA TGCACTTTTT GCTTTTGTTA CTTGCATCTG
29681 CGTATGTAGC ATAGTCTGCC TGGTTATTAA TTTTTTCCAA CTTCTAGACT GGATCCTTGT GCGAATTGCC
29751 TACCTGCGCC ACCATCCCGA ATACCGCAAC CAAAATATCG CGGCACTTCT TAGACTCATC TAAAACCATG
29821 CAGGCTATAC TACCAATATT TTTGCTTCTA TTGCTTCCCT ACGCTGTCTC AACCCCAGCT GCCTATAGTA
29891 CTCCACCAGA ACACCTTAGA AAATGCAAAT TCCAACAACC GTGGTCATTT CTTGCTTGCT ATCGAGAAAA
29961 ATCAGAAATC CCCCCAAATT TAATAATGAT TGCTGGAATA ATTAATATAA TCTGTTGCAC CATAATTTCA
30031 TTTTTGATAT ACCCCCTATT TGATTTTGGC TGGAATGCTC CCAATGCACA TGATCATCCA CAAGACCCAG
30101 AGGAACACAT TCCCCACAA AACATGCAAC ATCCAATAGC GCTAATAGAT TACGAAAGTG AACCACAACC
30171 CCCACTACTC CCTGCTATTA GTTACTTCAA CCTAACCGGC GGAGATGACT GAAACACTCA CCACCTCCAA
30241 TTCCGCCGAG GATCTGCTCG ATATGGACGG CCGCGTCTCA GAACAACGAC TTGCCCAACT ACGCATCCGC
30311 CAGCAGCAGG AACGCGTGGC CAAAGAGCTC AGAGATGTCA TCCAAATTCA CCAATGCAAA AAAGGCATAT
30381 TCTGTTTGGT AAAACAAGCC AAGATATCCT ACGAGATCAC CGCTACTGAC CATCGCCTCT CTTACGAACT
30451 TGGCCCCCAA CGACAAAAAT TTACCTGCAT GGTGGGAATC AACCCCATAG TTATCACCCA ACAAAGTGGA
30521 GATACTAAGG GTTGCATTCA CTGCTCCTGC GATTCCATCC AGTGCACCTA CACCCTGCTG AAGACCCTAT
30591 GCGGCCTAAG AGACCTGCTA CCAATGAATT AAAAAAAAAT GATTAATAAA AAATCACTTA CTTGAAATCA
30661 GCAATAAGGT CTCTGTTGAA ATTTTCTCCC AGCAGCACCT CACTTCCCTC TTCCCAACTC TGGTATTCTA
30731 AACCCCGTTC AGCGGCATAC TTTCTCCATA CTTTAAAGGG GATGTCAAAT TTTAGCTCCT CTCCTGTACC
30801 CACAATCTTC ATGTCTTTCT TCCCAGATGA CCAAGAGAGT CCGGCTCAGT GACTCCTTCA ACCCTGTCTA
30871 CCCCTATGAA GATGAAAGCA CCTCCCAACA CCCCTTTATA AACCCAGGGT TTATTTCCCC AAATGGCTTC
30941 ACACAAAGCC CAGACGGAGT TCTTACTTTA AATGTTTAA CCCCACTAAC AACCACAGGC GGATCTCTAC
31011 AGCTAAAAGT GGGAGGGGGA CTTACAGTGG ATGACACTGA TGGTACCTTA CAAGAAAACA TACGTGCTAC
31081 AGCACCCATT ACTAAAAATA ATCACTCTGT AGAACTATCC ATTGGAAATG GATTAGAAAC TCAAAACAAT
31151 AAACTATGTG CCAAATTGGG AAATGGGTTA AAATTTAACA ACGGTGACAT TTGTATAAAG GATAGTATTA
```

Figure 6H

```
31221 ACACCTTATG GACTGGAATA AACCCTCCAC CTAACTGTCA AATTGTGGAA ACACTAATA CAAATGATGG
31291 CAAACTTACT TTAGTATTAG TAAAAAATGG AGGGCTTGTT AATGGCTACG TGTCTCTAGT TGGTGTATCA
31361 GACACTGTGA ACCAAATGTT CACACAAAAG ACAGCAAACA TCCAATTAAG ATTATATTTT GACTCTTCTG
31431 GAAATCTATT AACTGAGGAA TCAGACTTAA AAATTCCACT TAAAAATAAA TCTTCTACAG CGACCAGTGA
31501 AACTGTAGCC AGCAGCAAAG CCTTTATGCC AAGTACTACA GCTTATCCCT TCAACACCAC TACTAGGGAT
31571 AGTGAAAACT ACATTCATGG AATATGTTAC TACATGACTA GTTATGATAG AAGTCTATTT CCCTTGAACA
31641 TTTCTATAAT GCTAAACAGC CGTATGATTT CTTCCAATGT TGCCTATGCC ATACAATTTG AATGGAATCT
31711 AAATGCAAGT GAATCTCCAG AAAGCAACAT AGCTACGCTG ACCACATCCC CCTTTTTCTT TTCTTACATT
31781 ACAGAAGACG ACAACTAAAA TAAAGTTTAA GTGTTTTTAT TTAAAATCAC AAAATTCGAG TAGTTATTTT
31851 GCCTCCACCT TCCCATTTGA CAGAATACAC CAATCTCTCC CCACGCACAG CTTTAAACAT TTGGATACCA
31921 TTAGAGATAG ACATTGTTTT AGATTCCACA TTCCAAACAG TTTCAGAGCG AGCCAATCTG GGGTCAGTGA
31991 TAGATAAAAA TCCATCGCGA TAGTCTTTTA AAGCGCTTTC ACAGTCCAAC TGCTGCGGAT GCGACTCCGG
32061 AGTTTGGATC ACGGTCATCT GGAAGAAGAA CGATGGGAAT CATAATCCGA AAACGGTATC GGACGATTGT
32131 GTCTCATCAA ACCCACAAGC AGCCGCTGTC TGCGTCGCTC CGTGCGACTG CTGTTTATGG GATCAGGGTC
32201 CACAGTTTCC TGAAGCATGA TTTTAATAGC CCTTAACATC AACTTTCTGG TGCGATGCGC GCAGCAACGC
32271 ATTCTGATTT CACTCAAATC TTTGCAGTAG GTACAACACA TTATTACAAT ATTGTTTAAT AAACCATAAT
32341 TAAAAGCGCT CCAGCCAAAA CTCATATCTG ATATAATCGC CCCTGCATGA CCATCATACC AAAGTTTAAT
32411 ATAAATTAAA TGACGTTCCC TCAAAACAC ACTACCCACA TACATGATCT CTTTTGGCAT GTGCATATTA
32481 ACAATCTGTC TGTACCATGG ACAACGTTGG TTAATCATGC AACCCAATAT AACCTTCCGG AACCACACTG
32551 CCAACACCGC TCCCCCAGCC ATGCATTGAA GTGAACCCTG CTGATTACAA TGACAATGAA GAACCCAATT
32621 CTCTCGACCG TGAATCACTT GAGAATGAAA AATATCTATA GTGGCACAAC ATAGACATAA ATGCATGCAT
32691 CTTCTCATAA TTTTTAACTC CTCAGGATTT AGAAACATAT CCCAGGGAAT AGGAAGCTCT TGCAGAACAG
32761 TAAAGCTGGC AGAACAAGGA AGACCACGAA CACAACTTAC ACTATGCATA GTCATAGTAT CACAATCTGG
32831 CAACAGCGGG TGGTCTTCAG TCATAGAAGC TCGGGTTTCA TTTTCCTCAC AACGTGGTAA CTGGGCTCTG
32901 GTGTAAGGGT GATGTCTGGC GCATGATGTC GAGCGTGCGC GCAACCTTGT CATAATGGAG TTGCTTCCTG
32971 ACATTCTCGT ATTTTGTATA GCAAAACGCG GCCCTGGCAG AACACACTCT TCTTCGCCTT CTATCCTGCC
33041 GCTTAGCGTG TTCCGTGTGA TAGTTCAAGT ACAGCCACAC TCTTAAGTTG GTCAAAGAA TGCTGGCTTC
33111 AGTTGTAATC AAAACTCCAT CGCATCTAAT TGTTCTGAGG AAATCATCCA CGGTAGCATA TGCAAATCCC
33181 AACCAAGCAA TGCAACTGGA TTGCGTTTCA AGCAGGAGAG GAGAGGGAAG AGACGGAAGA ACCATGTTAA
33251 TTTTTATTCC AAACGATCTC GCAGTACTTC AAATTGTAGA TCGCGCAGAT GGCATCTCTC GCCCCCACTG
33321 TGTTGGTGAA AAAGCACAGC TAAATCAAAA GAAATGCGAT TTTCAAGGTG CTCAACGGTG GCTTCCAACA
33391 AAGCCTCCAC GCGCACATCC AAGAACAAAA GAATACCAAA AGAAGGAGCA TTTTCTAACT CCTCAATCAT
33461 CATATTACAT TCCTGCACCA TTCCCAGATA ATTTTGACTT TTCCAGCCTT GAATTATTCG TGTCAGTTCT
33531 TGTGGTAAAT CCAATCCACA CATTACAAAC AGGTCCCGGA GGGCGCCCTC CACCACCATT CTTAAACACA
33601 CCCTCATAAT GACAAAATAT CTTGCTCCTG TGTCACCTGT AGCGAATTGA GAATGGCAAC ATCAATTGAC
33671 ATGCCCTTGG CTCTAAGTTC TTCTTTAAGT TCTAGTTGTA AAAACTCTCT CATATTATCA CCAAACTGCT
33741 TAGCCAGAAG CCCCCCGGGA ACAAGAGCAG GGGACGCTAC AGTGCAGTAC AAGCGCAGAC CTCCCCAATT
33811 GGCTCCAGCA AAAACAAGAT TGGAATAAGC ATATTGGGAA CCACCAGTAA TATCATCGAA GTTGCTGGAA
33881 ATATAATCAG GCAGAGTTTC TTGTAGAAAT TGAATAAAAG AAAAATTTGC CAAAAAAACA TTCAAAACCT
33951 CTGGGATGCA AATGCAATAG GTTACCGCGC TGCGCTCCAA CATTGTTAGT TTTGAATTAG TCTGCAAAAA
34021 TAAAAAAAAA ACAAGCGTCA TATCATAGTA GCCTGACGAA CAGGTGGATA AATCAGTCTT TCCATCACAA
34091 GACAAGCCAC AGGGTCTCCA GCTCGACCCT CGTAAAACCT GTCATCGTGA TTAAACAACA GCACCGAAAG
34161 TTCCTCGCGG TGACCAGCAT GAATAAGTCT TGATGAAGCA TACAATCCAG ACATGTTAGC ATCAGTTAAG
34231 GAGAAAAAAC AGCCAACATA GCCTTTGGGT ATAATTATGC TTAATCGTAA GTATAGCAAA GCCACCCCTC
34301 GCGGATACAA AGTAAAAGGC ACAGGAGAAT AAAAAATATA ATTATTTCTC TGCTGCTGTT TAGGCAACGT
34371 CGCCCCCGGT CCCTCTAAAT ACACATACAA AGCCTCATCA GCCATGGCTT ACCAGAGAAA GTACAGCGGG
34441 CACACAAACC ACAAGCTCTA AAGTCACTCT CCAACCTSTC CACAATATAT ATACACAAGC CCTAAACTGA
34511 CGTAATGGGA CTAAAGTGTA AAAAATCCCG CCAAACCCAA CACACACCCC GAAACTGCGT CACCAGGGAA
34581 AAGTACAGTT TCACTTCCGC AATCCCAACA AGCGTCACTT CCTCTTTCTC ACGGTACGTC ACATCCCATT
34651 AACTTACAAC GTCATTTTCC CACGGCCGCG CCGCCCCTTT TAACCGTTAA CCCCACAGCC AATCACCACA
34721 CGGCCCACAC TTTTTAAAAT CACCTCATTT ACATATTGGC ACCATTCCAT CTATAAGGTA TATTATTGAT
34791 GATG
```

Figure 23

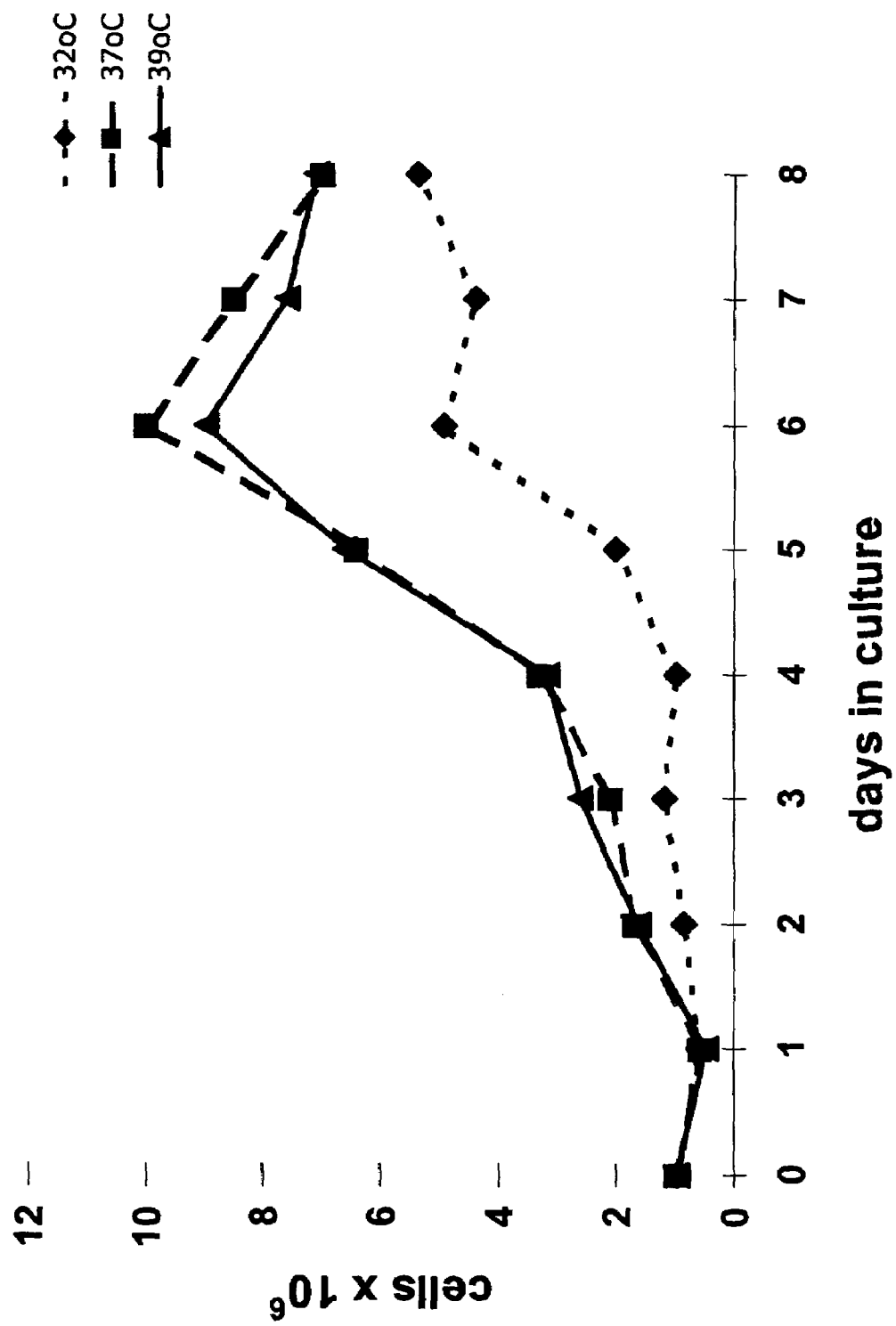
Figure 30 Temperature dependent growth of PER.C6

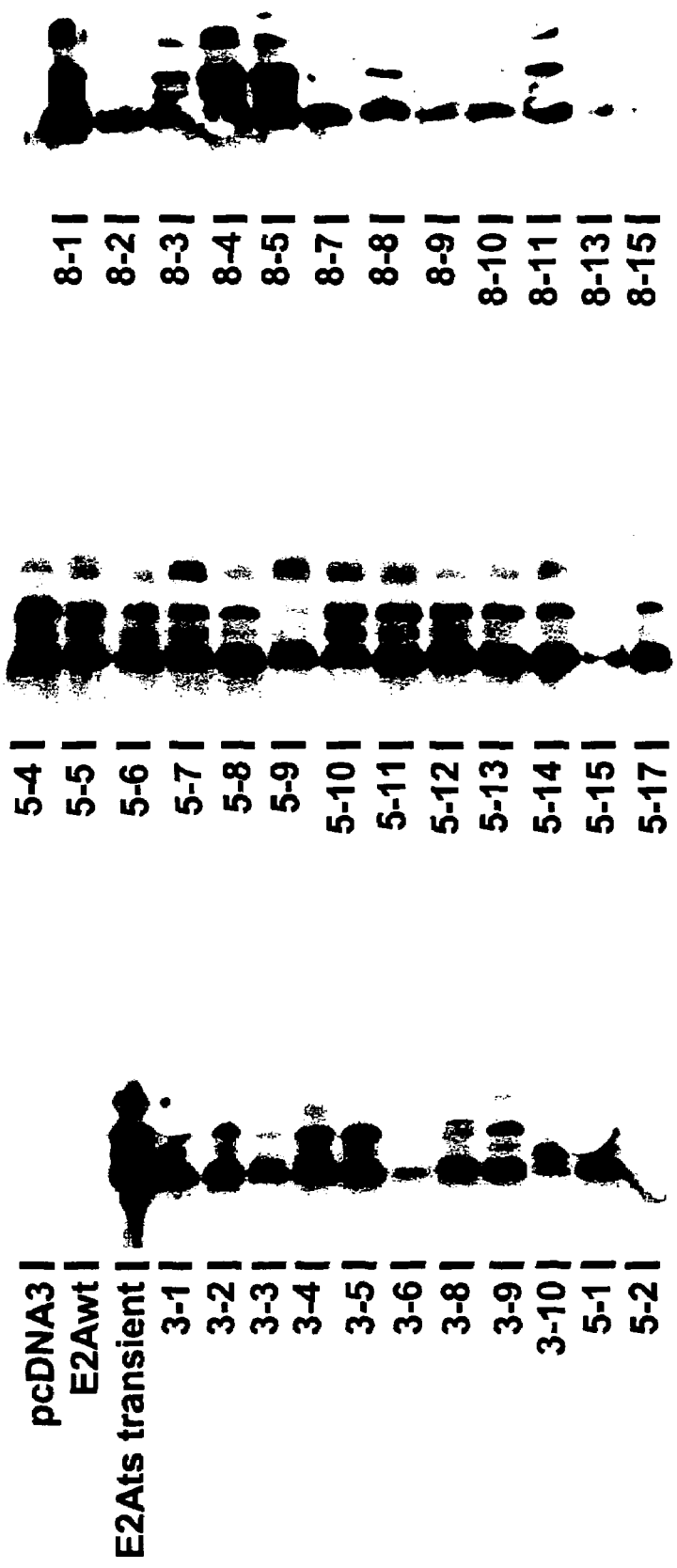
Figure 31  DBP levels in PER.C6 cells transfected with pcDNA3, pcDNA3wtE2A or pcDNA3ts125E2A

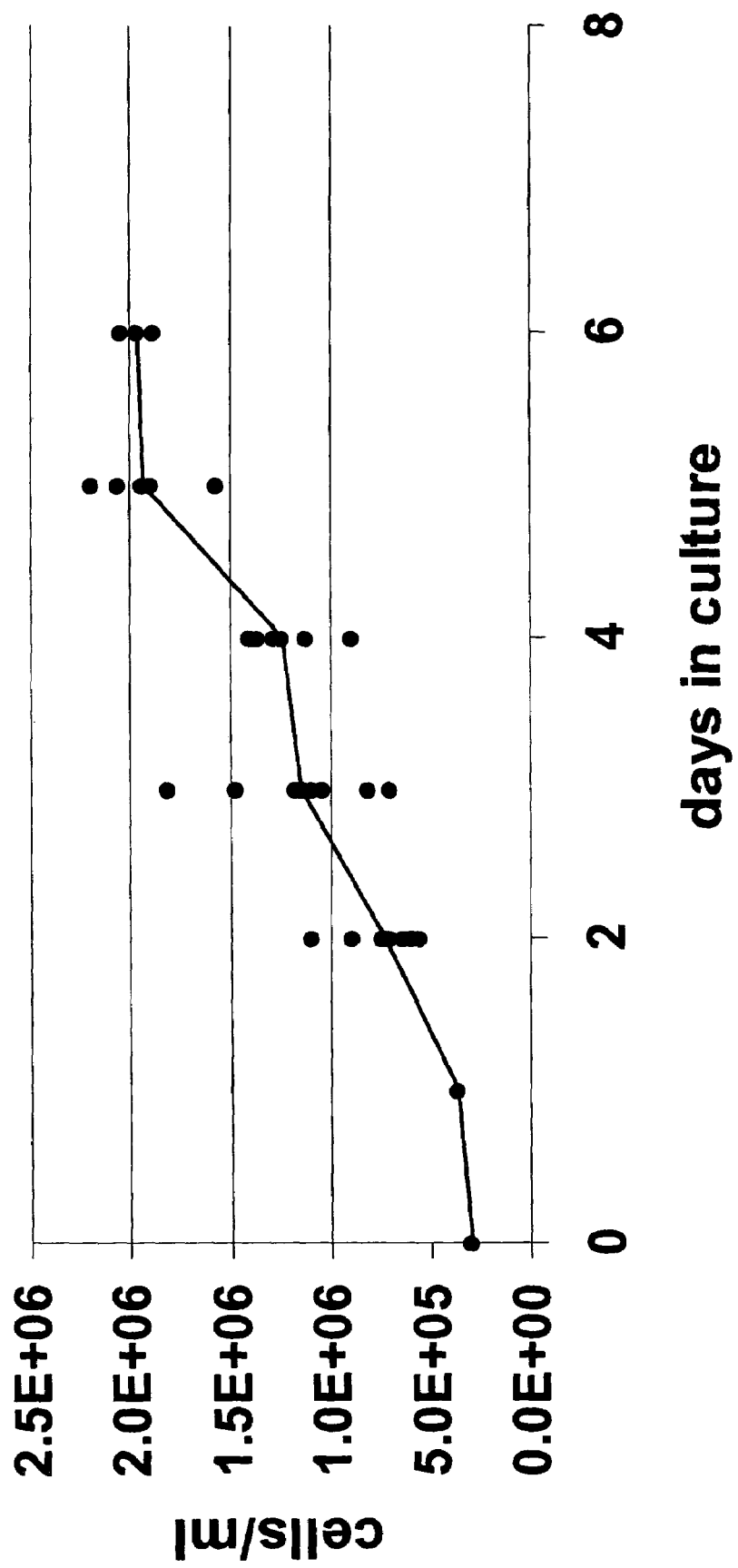
Figure 32  Suspension growth of PER.C6ts125E2A C5-9

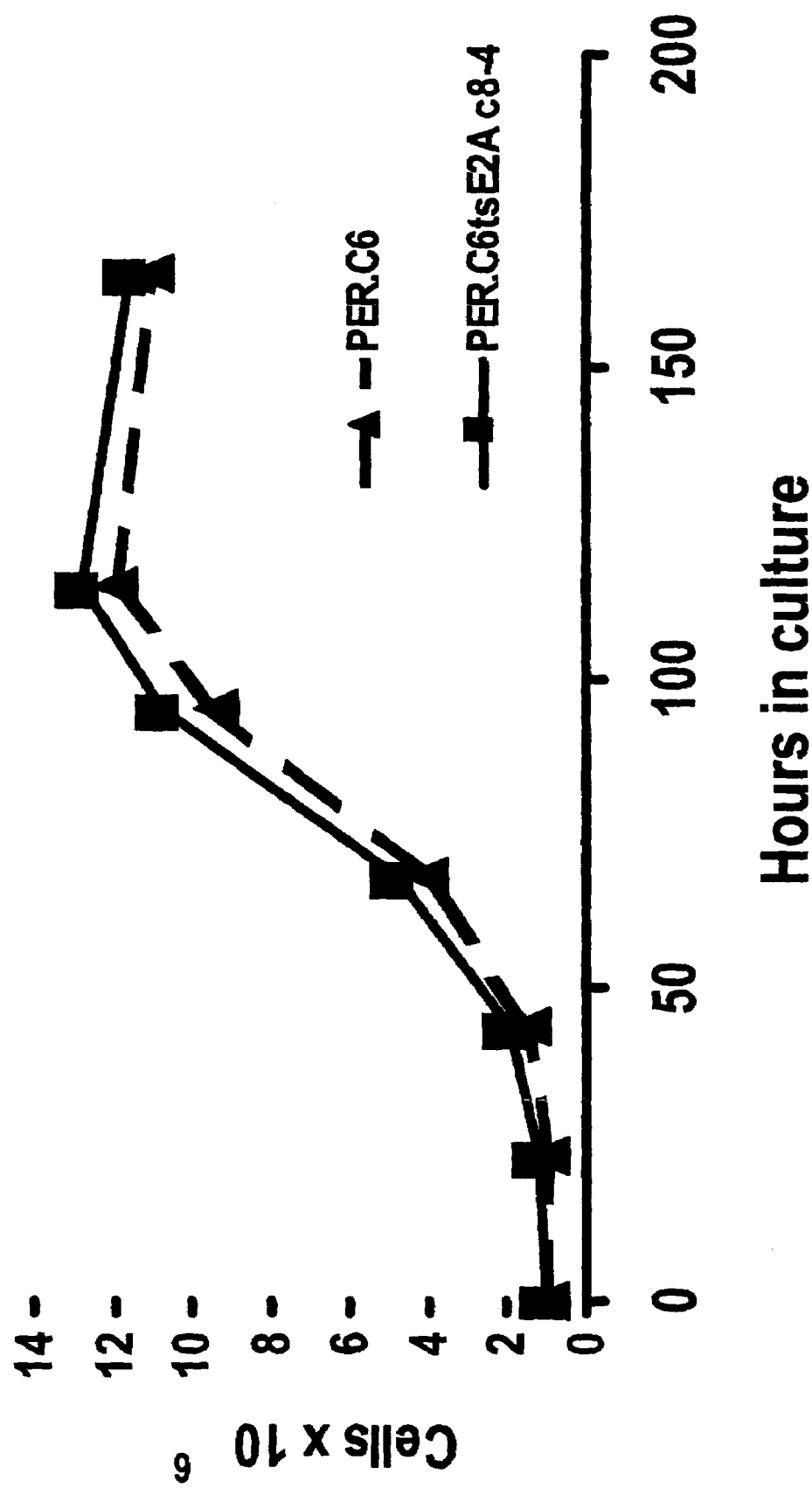

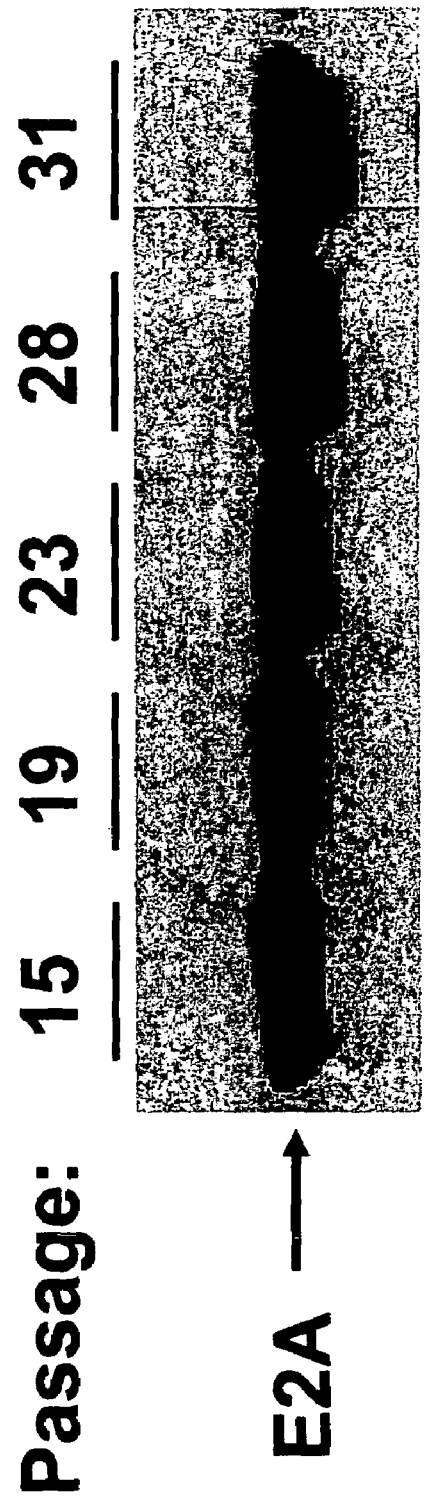
Figure 34 Stability of PER.C6ts125E2A

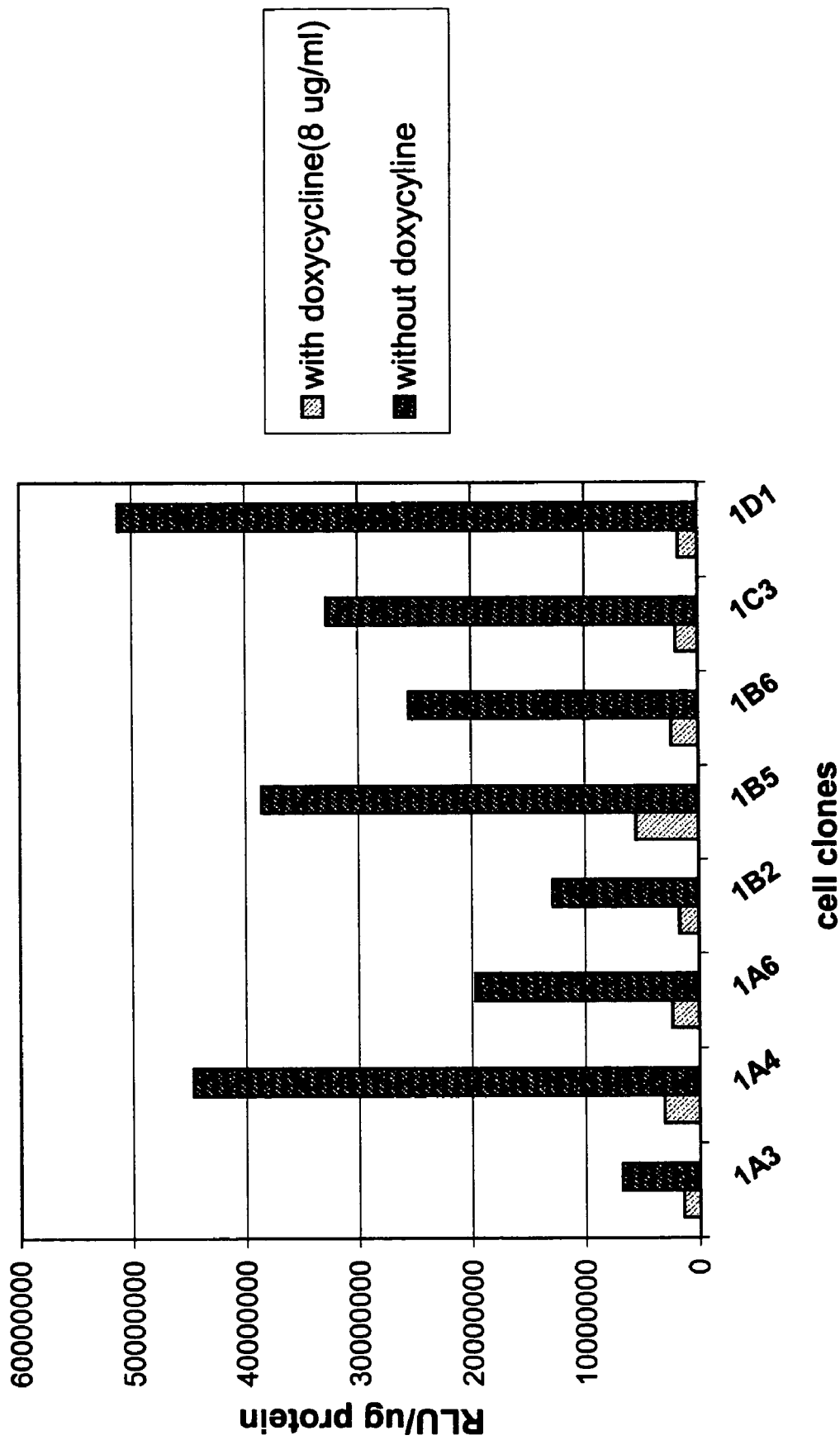

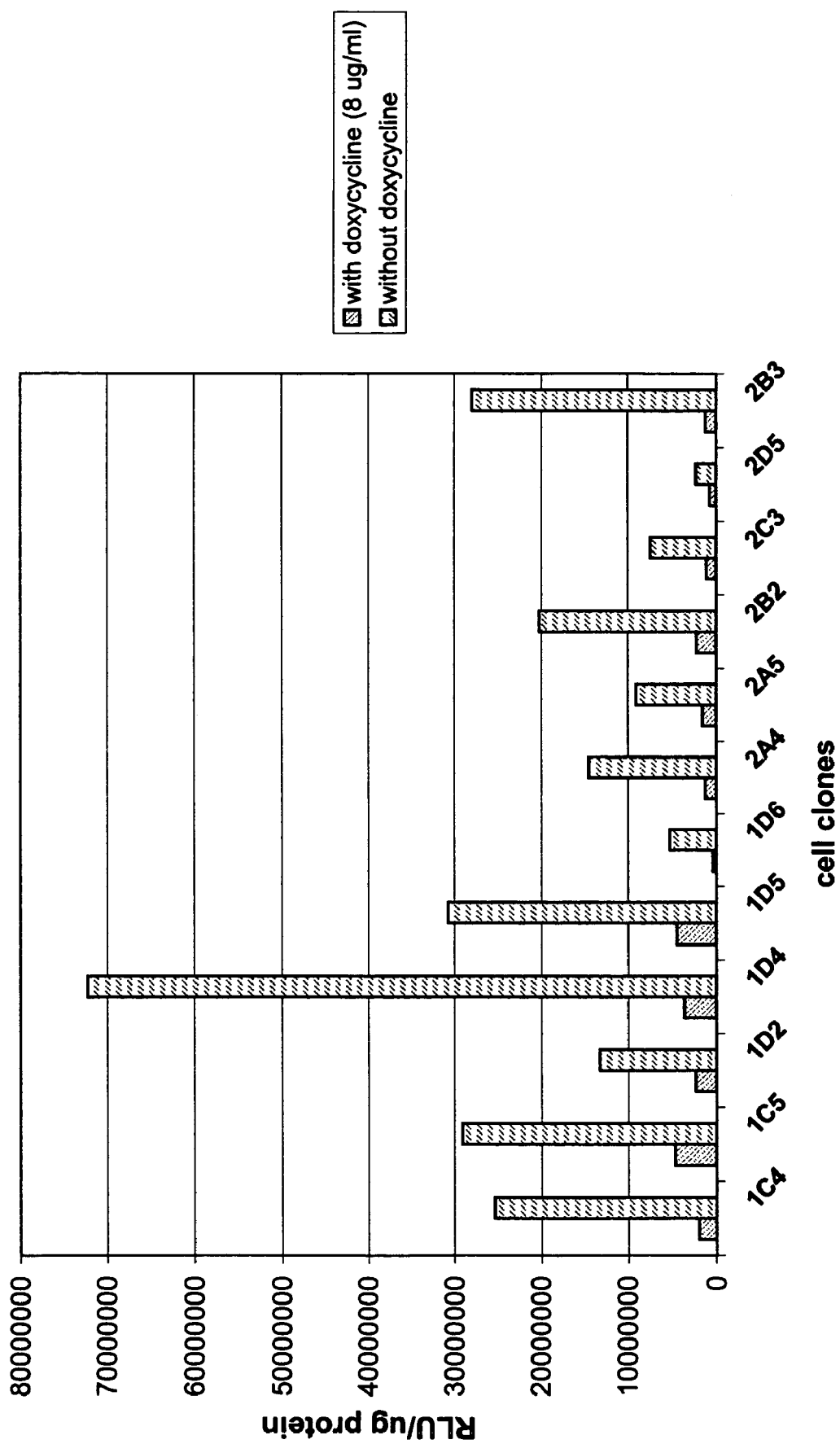

SEQUENCE LISTING

```
<160> NUMBER OF SEQ ID NOS: 86

<210> SEQ ID NO 1
<211> LENGTH: 23
<212> TYPE: DNA
<213> ORGANISM: Adenovirus

<400> SEQUENCE: 1
aattgtctta attaaccgct taa                                          23

<210> SEQ ID NO 2
<211> LENGTH: 19
<212> TYPE: DNA
<213> ORGANISM: Adenovirus

<400> SEQUENCE: 2
aattgtctta attaaccgc                                               19

<210> SEQ ID NO 3
<211> LENGTH: 19
<212> TYPE: DNA
<213> ORGANISM: Adenovirus

<400> SEQUENCE: 3
aattgcggtt aattaagac                                               19

<210> SEQ ID NO 4
<211> LENGTH: 39
<212> TYPE: DNA
<213> ORGANISM: Adenovirus

<400> SEQUENCE: 4
cggaattctt aattaagtta acatcatcaa taatatacc                         39

<210> SEQ ID NO 5
<211> LENGTH: 20
<212> TYPE: DNA
<213> ORGANISM: Adenovirus

<400> SEQUENCE: 5
tgattcacat cggtcagtgc                                              20

<210> SEQ ID NO 6
<211> LENGTH: 23
<212> TYPE: DNA
<213> ORGANISM: Adenovirus

<400> SEQUENCE: 6
ggcgtacgta gccctgtcga aag                                          23

<210> SEQ ID NO 7
<211> LENGTH: 35
<212> TYPE: DNA
```

<213> ORGANISM: Adenovirus

<400> SEQUENCE: 7
ccaatgcatt cgaagtactt ccttctccta taggc          35

<210> SEQ ID NO 8
<211> LENGTH: 22
<212> TYPE: DNA
<213> ORGANISM: Adenovirus

<400> SEQUENCE: 8
ccaatgcata cggcgcagac gg          22

<210> SEQ ID NO 9
<211> LENGTH: 21
<212> TYPE: DNA
<213> ORGANISM: Adenovirus

<400> SEQUENCE: 9
gaggtggatc ccatggacga g          21

<210> SEQ ID NO 10
<211> LENGTH: 47
<212> TYPE: DNA
<213> ORGANISM: Adenovirus

<400> SEQUENCE: 10
ctgtacgtac cagtgcactg gcctaggcat ggaaaaatac ataactg          47

<210> SEQ ID NO 11
<211> LENGTH: 63
<212> TYPE: DNA
<213> ORGANISM: Adenovirus

<400> SEQUENCE: 11
gcggatcctt cgaaccatgg taagcttggt accgctagcg ttaaccgggc gactcagtca          60
atc          63

<210> SEQ ID NO 12
<211> LENGTH: 27
<212> TYPE: DNA
<213> ORGANISM: Adenovirus

<400> SEQUENCE: 12
gcgccaccat gggcagagcg atggtgg          27

<210> SEQ ID NO 13
<211> LENGTH: 50
<212> TYPE: DNA
<213> ORGANISM: Adenovirus

<400> SEQUENCE: 13
gttagatcta agcttgtcga catcgatcta ctaacagtag agatgtagaa          50

<210> SEQ ID NO 14
<211> LENGTH: 10
<212> TYPE: DNA
<213> ORGANISM: Adenovirus

<400> SEQUENCE: 14
ttaagtcgac          10

```
<210> SEQ ID NO 15
<211> LENGTH: 23
<212> TYPE: DNA
<213> ORGANISM: Adenovirus

<400> SEQUENCE: 15
aattgtctta attaaccgca att                                          23

<210> SEQ ID NO 16
<211> LENGTH: 67
<212> TYPE: DNA
<213> ORGANISM: Adenovirus

<400> SEQUENCE: 16
gccatcccta ggaagcttgg taccggtgaa ttcgctagcg ttaacggatc ctctagacga   60
gatctgg                                                            67

<210> SEQ ID NO 17
<211> LENGTH: 67
<212> TYPE: DNA
<213> ORGANISM: Adenovirus

<400> SEQUENCE: 17
ccagatctcg tctagaggat ccgttaacgc tagcgaattc accggtacca agcttcctag   60
ggatggc                                                            67

<210> SEQ ID NO 18
<211> LENGTH: 39
<212> TYPE: DNA
<213> ORGANISM: Adenovirus

<400> SEQUENCE: 18
gatcggtacc actgcagtgg tcaatattgg ccattagcc                         39

<210> SEQ ID NO 19
<211> LENGTH: 29
<212> TYPE: DNA
<213> ORGANISM: Adenovirus

<400> SEQUENCE: 19
gatcaagctt ccaatgcacc gttcccggc                                    29

<210> SEQ ID NO 20
<211> LENGTH: 32
<212> TYPE: DNA
<213> ORGANISM: Adenovirus

<400> SEQUENCE: 20
ggggtggcca gggtacctct aggcttttgc aa                                32

<210> SEQ ID NO 21
<211> LENGTH: 29
<212> TYPE: DNA
<213> ORGANISM: Adenovirus

<400> SEQUENCE: 21 gggggggatcc ataaacaagt tcagaatcc                                   29

<210> SEQ ID NO 22
<211> LENGTH: 18
<212> TYPE: DNA
<213> ORGANISM: Adenovirus
```

```
<400> SEQUENCE: 22
cctggtgctg ccaacagc                                                    18

<210> SEQ ID NO 23
<211> LENGTH: 30
<212> TYPE: DNA
<213> ORGANISM: Adenovirus

<400> SEQUENCE: 23
ccggatccac tagtggaaag cgggcgcgcg                                        30

<210> SEQ ID NO 24
<211> LENGTH: 35
<212> TYPE: DNA
<213> ORGANISM: Adenovirus

<400> SEQUENCE: 24
ccggatccaa ttgagaagca agcaacatca acaac                                 35

<210> SEQ ID NO 25
<211> LENGTH: 19
<212> TYPE: DNA
<213> ORGANISM: Adenovirus

<400> SEQUENCE: 25
gagaagggca tggaggctg                                                   19

<210> SEQ ID NO 26
<211> LENGTH: 32
<212> TYPE: DNA
<213> ORGANISM: Adenovirus
<220> FEATURE:
<221> NAME/KEY: variation
<222> LOCATION: (17)
<223> OTHER INFORMATION: Y: Can be C or T -- Degenerate oligo sequence
<220> FEATURE:
<221> NAME/KEY: variation
<222> LOCATION: (23)
<223> OTHER INFORMATION: H: Can be A, T or C -- Degenerate oligo
      sequence

<400> SEQUENCE: 26
gactagtcaa gatggcyacc cchtcgatga tg                                    32

<210> SEQ ID NO 27
<211> LENGTH: 33
<212> TYPE: DNA
<213> ORGANISM: Adenovirus
<220> FEATURE:
<221> NAME/KEY: variation
<222> LOCATION: (19)
<223> OTHER INFORMATION: K: Can be T or G -- Degenerate oligo sequence
<220> FEATURE:
<221> NAME/KEY: variation
<222> LOCATION: (22)
<223> OTHER INFORMATION: K: Can be T or G -- Degenerate oligo sequence
<220> FEATURE:
<221> NAME/KEY: variation
<222> LOCATION: (28)
<223> OTHER INFORMATION: R: Can be A or G -- Degenerate oligo sequence

<400> SEQUENCE: 27
gctggccaat tgttatgtkg tkgcgttrcc ggc                                   33

<210> SEQ ID NO 28
<211> LENGTH: 20
<212> TYPE: DNA
```

<213> ORGANISM: Adenovirus

<400> SEQUENCE: 28
ctgttgctgc tgctaatagc                                               20

<210> SEQ ID NO 29
<211> LENGTH: 32
<212> TYPE: DNA
<213> ORGANISM: Adenovirus

<400> SEQUENCE: 29
cgcggatcct gtacaactaa ggggaataca ag                                 32

<210> SEQ ID NO 30
<211> LENGTH: 33
<212> TYPE: DNA
<213> ORGANISM: Adenovirus

<400> SEQUENCE: 30
cgcggatccc ttaaggcaag catgtccatc ctt                                33

<210> SEQ ID NO 31
<211> LENGTH: 27
<212> TYPE: DNA
<213> ORGANISM: Adenovirus

<400> SEQUENCE: 31
aaaacacgtt ttacgcgtcg acctttc                                       27

<210> SEQ ID NO 32
<211> LENGTH: 33
<212> TYPE: DNA
<213> ORGANISM: Adenovirus

<400> SEQUENCE: 32
gctcgatgta caatgaggag acgagccgtg cta                                33

<210> SEQ ID NO 33
<211> LENGTH: 33
<212> TYPE: DNA
<213> ORGANISM: Adenovirus

<400> SEQUENCE: 33
gctcgactta agttagaaag tgcggcttga aag                                33

<210> SEQ ID NO 34
<211> LENGTH: 35
<212> TYPE: DNA
<213> ORGANISM: Adenovirus

<400> SEQUENCE: 34
gctcgatgta caatgaggcg tgcggtggtg tcttc                              35

<210> SEQ ID NO 35
<211> LENGTH: 34
<212> TYPE: DNA
<213> ORGANISM: Adenovirus

<400> SEQUENCE: 35
gctcgactta agttagaagg tgcgactgga aagc                               34

<210> SEQ ID NO 36
<211> LENGTH: 42

-continued

```
<212> TYPE: DNA
<213> ORGANISM: Adenovirus

<400> SEQUENCE: 36
cgacatatgt agatgcatta gtttgtgtta tgtttcaacg tg                         42

<210> SEQ ID NO 37
<211> LENGTH: 18
<212> TYPE: DNA
<213> ORGANISM: Adenovirus

<400> SEQUENCE: 37
ggagaccact gccatgtt                                                    18

<210> SEQ ID NO 38
<211> LENGTH: 14
<212> TYPE: DNA
<213> ORGANISM: Adenovirus

<400> SEQUENCE: 38
ccaataatat acct                                                        14

<210> SEQ ID NO 39
<211> LENGTH: 21
<212> TYPE: DNA
<213> ORGANISM: Adenovirus

<400> SEQUENCE: 39
aggtatatta ttgatgatgg g                                                21

<210> SEQ ID NO 40
<211> LENGTH: 18
<212> TYPE: DNA
<213> ORGANISM: Adenovirus

<400> SEQUENCE: 40
catcatcaat aatatacc                                                    18

<210> SEQ ID NO 41
<211> LENGTH: 47
<212> TYPE: DNA
<213> ORGANISM: Adenovirus

<400> SEQUENCE: 41
tcgatggcaa acagctatta tgggtattat gggttcgaat taattaa                    47

<210> SEQ ID NO 42
<211> LENGTH: 47
<212> TYPE: DNA
<213> ORGANISM: Adenovirus

<400> SEQUENCE: 42
tcgattaatt aattcgaacc cataataccc ataatagctg tttgcca                    47

<210> SEQ ID NO 43
<211> LENGTH: 42
<212> TYPE: DNA
<213> ORGANISM: Adenovirus

<400> SEQUENCE: 43
ccccaattgg tcgaccatca tcaataatat accttatttt gg                         42

<210> SEQ ID NO 44
```

```
<211> LENGTH: 22
<212> TYPE: DNA
<213> ORGANISM: Adenovirus

<400> SEQUENCE: 44
gcgaaaattg tcacttcctg tg                                              22

<210> SEQ ID NO 45
<211> LENGTH: 37
<212> TYPE: DNA
<213> ORGANISM: Adenovirus

<400> SEQUENCE: 45
aattcggcgc gccgtcgacg atatcgatag cggccgc                              37

<210> SEQ ID NO 46
<211> LENGTH: 37
<212> TYPE: DNA
<213> ORGANISM: Adenovirus

<400> SEQUENCE: 46
aattgcggcc gctatcgata tcgtcgacgg cgcgccg                              37

<210> SEQ ID NO 47
<211> LENGTH: 49
<212> TYPE: DNA
<213> ORGANISM: Adenovirus

<400> SEQUENCE: 47
agctctagag gatccgttaa cgctagcgaa ttcaccggta ccaagctta                 49

<210> SEQ ID NO 48
<211> LENGTH: 49
<212> TYPE: DNA
<213> ORGANISM: Adenovirus

<400> SEQUENCE: 48
ctagtaagct tggtaccggt gaattcgcta gcgttaacgg atcctctag                 49

<210> SEQ ID NO 49
<211> LENGTH: 44
<212> TYPE: DNA
<213> ORGANISM: Adenovirus

<400> SEQUENCE: 49
cggaattctt aattaatcga catcatcaat aatatacctt atag                      44

<210> SEQ ID NO 50
<211> LENGTH: 33
<212> TYPE: DNA
<213> ORGANISM: Adenovirus

<400> SEQUENCE: 50
ggtggtccta ggctgacacc tacgtaaaaa cag                                  33

<210> SEQ ID NO 51
<211> LENGTH: 30
<212> TYPE: DNA
<213> ORGANISM: Adenovirus

<400> SEQUENCE: 51
tggtggagat ctggtgagta ttgggaaaac                                      30
```

-continued

```
<210> SEQ ID NO 52
<211> LENGTH: 37
<212> TYPE: DNA
<213> ORGANISM: Adenovirus

<400> SEQUENCE: 52
cggaattctt aattaaggga aatgcaaatc tgtgagg                              37

<210> SEQ ID NO 53
<211> LENGTH: 34
<212> TYPE: DNA
<213> ORGANISM: Adenovirus

<400> SEQUENCE: 53
cggaattcgc ggccgcggtg agtattggga aaac                                34

<210> SEQ ID NO 54
<211> LENGTH: 22
<212> TYPE: DNA
<213> ORGANISM: Adenovirus

<400> SEQUENCE: 54
cgccagatcg tctacagaac ag                                             22

<210> SEQ ID NO 55
<211> LENGTH: 23
<212> TYPE: DNA
<213> ORGANISM: Adenovirus

<400> SEQUENCE: 55
gaatgctggc ttcagttgta atc                                            23

<210> SEQ ID NO 56
<211> LENGTH: 42
<212> TYPE: DNA
<213> ORGANISM: Adenovirus

<400> SEQUENCE: 56
cggaattcgc ggccgcattt aaatcatcat caataatata cc                       42

<210> SEQ ID NO 57
<211> LENGTH: 33
<212> TYPE: DNA
<213> ORGANISM: Adenovirus

<400> SEQUENCE: 57
ggggtaccga attctcgcta gggtatttat acc                                 33

<210> SEQ ID NO 58
<211> LENGTH: 38
<212> TYPE: DNA
<213> ORGANISM: Adenovirus

<400> SEQUENCE: 58
gctctagacc tgcaggttag tcagtttctt ctccactg                            38

<210> SEQ ID NO 59
<211> LENGTH: 27
<212> TYPE: DNA
<213> ORGANISM: Adenovirus

<400> SEQUENCE: 59
ggctctagag atccttcgcg ggacgtc                                        27
```

<210> SEQ ID NO 60
<211> LENGTH: 26
<212> TYPE: DNA
<213> ORGANISM: Adenovirus

<400> SEQUENCE: 60
ggcgaattca ctgccttcca ccaagc                                          26

<210> SEQ ID NO 61
<211> LENGTH: 12
<212> TYPE: DNA
<213> ORGANISM: Adenovirus

<400> SEQUENCE: 61
ctggtggtta at                                                         12

<210> SEQ ID NO 62
<211> LENGTH: 14
<212> TYPE: DNA
<213> ORGANISM: Adenovirus

<400> SEQUENCE: 62
taaccaccag acgt                                                       14

<210> SEQ ID NO 63
<211> LENGTH: 20
<212> TYPE: DNA
<213> ORGANISM: Adenovirus

<400> SEQUENCE: 63
cactcaccac ctccaattcc                                                 20

<210> SEQ ID NO 64
<211> LENGTH: 32
<212> TYPE: DNA
<213> ORGANISM: Adenovirus

<400> SEQUENCE: 64
cgggatcccg tacgggtaga cagggttgaa gg                                   32

<210> SEQ ID NO 65
<211> LENGTH: 49
<212> TYPE: DNA
<213> ORGANISM: Adenovirus

<400> SEQUENCE: 65
cgggatccgc tagctgaaat aaagtttaag tgttttatt taaaatcac                  49

<210> SEQ ID NO 66
<211> LENGTH: 21
<212> TYPE: DNA
<213> ORGANISM: Adenovirus

<400> SEQUENCE: 66
ccagttgcat tgcttggttg g                                               21

<210> SEQ ID NO 67
<211> LENGTH: 27
<212> TYPE: DNA
<213> ORGANISM: Adenovirus
<220> FEATURE:
<221> NAME/KEY: variation
<222> LOCATION: (3)
<223> OTHER INFORMATION: K: Can be T or G -- Degenerate oligo sequence

```
<220> FEATURE:
<221> NAME/KEY: variation
<222> LOCATION: (6)
<223> OTHER INFORMATION: S: Can be C or G -- Degenerate oligo sequence

<400> SEQUENCE: 67
cckgtstacc cgtacgaaga tgaaagc                                          27

<210> SEQ ID NO 68
<211> LENGTH: 30
<212> TYPE: DNA
<213> ORGANISM: Adenovirus

<400> SEQUENCE: 68
ccggctagct cagtcatctt ctctgatata                                       30

<210> SEQ ID NO 69
<211> LENGTH: 31
<212> TYPE: DNA
<213> ORGANISM: Adenovirus

<400> SEQUENCE: 69
gatccggagc tcacaacgtc attttcccac g                                     31

<210> SEQ ID NO 70
<211> LENGTH: 25
<212> TYPE: DNA
<213> ORGANISM: Adenovirus

<400> SEQUENCE: 70
cggaattcgc ggccgcattt aaatc                                            25

<210> SEQ ID NO 71
<211> LENGTH: 30
<212> TYPE: DNA
<213> ORGANISM: Adenovirus

<400> SEQUENCE: 71
cccaagcttg cttgtgtata tatattgtgg                                       30

<210> SEQ ID NO 72
<211> LENGTH: 45
<212> TYPE: DNA
<213> ORGANISM: Adenovirus

<400> SEQUENCE: 72
agctttctta taaattttca gtgttagact agtaaattgc ttaag                      45

<210> SEQ ID NO 73
<211> LENGTH: 45
<212> TYPE: DNA
<213> ORGANISM: Adenovirus

<400> SEQUENCE: 73
agctcttaag caatttacta gtctaacact gaaaatttat aagaa                      45

<210> SEQ ID NO 74
<211> LENGTH: 37
<212> TYPE: DNA
<213> ORGANISM: Adenovirus

<400> SEQUENCE: 74
ccggagctcc atggcctaac tcgagtttac cactccc                               37
```

-continued

```
<210> SEQ ID NO 75
<211> LENGTH: 30
<212> TYPE: DNA
<213> ORGANISM: Adenovirus

<400> SEQUENCE: 75
cccaagctta gctcgacttt cactttttctc                                30

<210> SEQ ID NO 76
<211> LENGTH: 17
<212> TYPE: DNA
<213> ORGANISM: Adenovirus

<400> SEQUENCE: 76
gtgcctaggc cacgggg                                               17

<210> SEQ ID NO 77
<211> LENGTH: 13
<212> TYPE: DNA
<213> ORGANISM: Adenovirus

<400> SEQUENCE: 77
gtggcctagg cac                                                   13

<210> SEQ ID NO 78
<211> LENGTH: 20
<212> TYPE: DNA
<213> ORGANISM: Adenovirus

<400> SEQUENCE: 78
cacctctgcc taatcatctc                                            20

<210> SEQ ID NO 79
<211> LENGTH: 27
<212> TYPE: DNA
<213> ORGANISM: Adenovirus

<400> SEQUENCE: 79
gctctagaaa ttccactgcc ttccacc                                    27

<210> SEQ ID NO 80
<211> LENGTH: 35
<212> TYPE: DNA
<213> ORGANISM: Adenovirus

<400> SEQUENCE: 80
cgggatccgc caccatggcc agtcgggaag aggag                           35

<210> SEQ ID NO 81
<211> LENGTH: 33
<212> TYPE: DNA
<213> ORGANISM: Adenovirus

<400> SEQUENCE: 81
cggaattctt aaaaatcaaa ggggttctgc cgc                             33

<210> SEQ ID NO 82
<211> LENGTH: 34794
<212> TYPE: DNA
<213> ORGANISM: Adenovirus 35

<400> SEQUENCE: 82
catcatcaat aatatacctt atagatggaa tgtgccaat atgtaaatga ggtgatttta    60
```

-continued

| | | |
|---|---|---|
| aaaagtgtgg gccgtgtggt gattggctgt ggggttaacg gttaaaaggg gcggcgcggc | 120 |
| cgtgggaaaa tgacgtttta tgggggtgga gttttttgc aagttgtcgc gggaaatgtt | 180 |
| acgcataaaa aggcttcttt tctcacggaa ctacttagtt ttcccacggt atttaacagg | 240 |
| aaatgaggta gttttgaccg gatgcaagtg aaaattgctg attttcgcgc gaaaactgaa | 300 |
| tgaggaagtg ttttttctgaa taatgtggta tttatggcag ggtggagtat ttgttcaggg | 360 |
| ccaggtagac tttgacccat tacgtggagg tttcgattac cgtgttttttt acctgaattt | 420 |
| ccgcgtaccg tgtcaaagtc ttctgttttt acgtaggtgt cagctgatcg ctagggtatt | 480 |
| tatacctcag ggtttgtgtc aagaggccac tcttgagtgc cagcgagaag agttttctcc | 540 |
| tctgcgccgg cagtttaata ataaaaaaat gagagatttg cgatttctgc ctcaggaaat | 600 |
| aatctctgct gagactggaa atgaaatatt ggagcttgtg gtgcacgccc tgatgggaga | 660 |
| cgatccggag ccacctgtgc agcttttga gcctcctacg cttcaggaac tgtatgattt | 720 |
| agaggtagag ggatcggagg attctaatga ggaagctgtg aatggctttt ttaccgattc | 780 |
| tatgctttta gctgctaatg aaggattaga attagatccg cctttggaca ctttcaatac | 840 |
| tccaggggtg attgtggaaa gcggtacagg tgtaagaaaa ttacctgatt tgagttccgt | 900 |
| ggactgtgat ttgcactgct atgaagacgg gtttcctccg agtgatgagg aggaccatga | 960 |
| aaaggagcag tccatgcaga ctgcagcggg tgagggagtg aaggctgcca atgttggttt | 1020 |
| tcagttggat tgcccggagc ttcctggaca tggctgtaag tcttgtgaat tcacaggaa | 1080 |
| aaatactgga gtaaaggaac tgttatgttc gctttgttat atgagaacgc actgccactt | 1140 |
| tatttacagt aagtgtgttt aagttaaaat ttaaaggaat atgctgtttt tcacatgtat | 1200 |
| attgagtgtg agttttgtgc ttcttattat aggtcctgtg tctgatgctg atgaatcacc | 1260 |
| atctcctgat tctactacct cacctcctga tattcaagca cctgttcctg tggacgtgcg | 1320 |
| caagcccatt cctgtgaagc ttaagcctgg gaaacgtcca gcagtggaga aacttgagga | 1380 |
| cttgttacag ggtggggacg gacctttgga cttgagtaca cggaaacgtc caagacaata | 1440 |
| agtgttccat atccgtgttt acttaaggtg acgtcaatat ttgtgtgaga gtgcaatgta | 1500 |
| ataaaaatat gttaactgtt cactggtttt tattgctttt tgggcgggga ctcaggtata | 1560 |
| taagtagaag cagacctgtg tggttagctc ataggagctg gctttcatcc atggaggttt | 1620 |
| gggccatttt ggaagacctt aggaagacta ggcaactgtt agagagcgct tcggacggag | 1680 |
| tctccggttt ttggagattc tggttcgcta gtgaattagc tagggtagtt tttaggataa | 1740 |
| aacaggacta taaacaagaa tttgaaaagt tgttggtaga ttgcccagga ctttttgaag | 1800 |
| ctcttaattt gggccatcag gttcacttta aagaaaaagt tttatcagtt ttagactttt | 1860 |
| caaccccagg tagaactgct gctgctgtgg ctttttcttac ttttatatta gataaatgga | 1920 |
| tcccgcagac tcatttcagc aggggatacg ttttggatttt catagccaca gcattgtgga | 1980 |
| gaacatggaa ggttcgcaag atgaggacaa tcttaggtta ctggccagtg cagcctttgg | 2040 |
| gtgtagcggg aatcctgagg catccaccgg tcatgccagc ggttctggag gaggaacagc | 2100 |
| aagaggacaa cccgagagcc ggcctggacc ctccagtgga ggaggcggag tagctgactt | 2160 |
| gtctcctgaa ctgcaacggg tgcttactgg atctacgtcc actggacggg ataggggcgt | 2220 |
| taagagggag agggcatcca gtggtactga tgctagatct gagttggctt taagtttaat | 2280 |
| gagtcgcaga cgtcctgaaa ccatttggtg gcatgaggtt cagaaagagg gaagggatga | 2340 |
| agtttctgta ttgcaggaga aatattcact ggaacaggtg aaaacatgtt ggttggagcc | 2400 |

-continued

```
agaggatgat tgggcggtgg ccattaaaaa ttatgccaag atagctttga ggcctgataa    2460
acagtataag atcagtagac ggattaatat ccggaatgct tgttacatat ctggaaatgg    2520
ggctgaggtg gtaatagata ctcaagacaa gacagttatt agatgctgca tgatggatat    2580
gtggcctgga gtagtcggta tggaagcagt cacttttgta aatgttaagt ttaggggaga    2640
tggttataat ggaatagtgt ttatggccaa taccaaactt atattgcatg gttgtagctt    2700
ttttggtttc aacaatacct gtgtagatgc ctggggacag gttagtgtac gggggtgtag    2760
tttctatgcg tgttggattg ccacagctgg cagaaccaag agtcaattgt ctctgaagaa    2820
atgcatattc caaagatgta acctgggcat tctgaatgaa ggcgaagcaa gggtccgtca    2880
ctgcgcttct acagatactg gatgttttat tttaattaag ggaaatgcca gcgtaaagca    2940
taacatgatt tgtggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgttga ccaagtgcac catgcatgca gtgggcgta gaggaatgtt    3120 tatgccttac cagtgtaaca tgaatcatgt gaaagtgttg ttggaaccag atgcctttc    3180 cagaatgagc ctaacaggaa tctttgcat gaacacgcaa atctggaaga tcctgaggta    3240
tgatgatacg agatcgaggg tgcgcgcatg cgaatgcgga ggcaagcatg ccaggttcca    3300
gccggtgtgt gtagatgtga ccgaagatct cagaccggga catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gacatgagtg gaaatgcttc ttttaagggg ggagtcttca gcccttatct gacagggcgt    3540
ctcccatcct gggcaggagt tcgtcagaat gttatgggat ctactgtgga tggaagaccc    3600
gttcaacccg ccaattcttc aacgctgacc tatgctactt taagttcttc accttttgac    3660
gcagctgcag ccgctgccgc cgcctctgtc gccgctaaca ctgtgcttgg aatgggttac    3720
tatggaagca tcgtggctaa ttccacttcc tctaataacc cttctacact gactcaggac    3780
aagttacttg tccttttggc ccagctggag gctttgaccc aacgtctggg tgaactttct    3840
cagcaggtgg ccgagttgcg agtacaaact gagtctgctg tcggcacggc aaagtctaaa    3900
taaaaaaaat tccagaatca atgaataaat aaacgagctt gttgttgatt taaaatcaag    3960
tgtttttatt tcattttcg cgcacggtat gccctggacc accgatctcg atcattgaga    4020
actcggtgga ttttttccag aatcctatag aggtgggatt gaatgtttag atacatgggc    4080
attaggccgt ctttggggtg gagatagctc cattgaaggg attcatgctc cggggtagtg    4140
ttgtaaatca cccagtcata acaaggtcgc agtgcatggt gttgcacaat atctttaga    4200 agtaggctga ttgccacaga taagcccttg gtgtaggtgt ttacaaaccg gttgagctgg    4260
gaggggtgca ttcgaggtga aattatgtgc attttggatt ggattttaa gttggcaata    4320 ttgccgccaa gatcccgtct tgggttcatg ttatgaagga ctaccaagac ggtgtatccg    4380
gtacatttag gaaatttatc gtgcagcttg gatggaaaag cgtggaaaaa tttggagaca    4440
cccttgtgtc ctccgagatt ttccatgcac tcatccatga taatagcaat ggggccgtgg    4500
gcagcggcgc gggcaaacac gttccgtggg tctgacacat catagttatg ttcctgagtt    4560
aaatcatcat aagccatttt aatgaatttg gggcggagcg taccagattg gggtatgaat    4620
gttccttcgg gccccggagc atagttcccc tcacagattt gcatttccca agctttcagt    4680
tctgagggtg gaatcatgtc cacctggggg gctatgaaga acaccgtttc ggggcgggg    4740 gtgattagtt gggatgatag caagtttctg agcaattgag atttgccaca tccggtgggg    4800
```

```
ccataaataa ttccgattac aggttgcagg tggtagttta gggaacggca actgccgtct    4860
tctcgaagca aggggggccac ctcgttcatc atttcccttac catgcatatt ttcccgcacc   4920
aaatccatta ggaggcgctc tcctcctagt gatagaagtt cttgtagtga ggaaaagttt    4980
ttcagcggtt ttagaccgtc agccatgggc attttggaaa gagtttgctg caaaagttct    5040
agtctgttcc acagttcagt gatgtgttct atggcatctc gatccagcag acctcctcgt    5100
ttcgcgggtt tggacggctc ctggagtagg gtatgagacg atgggcgtcc agcgctgcca    5160
gggttcggtc cttccagggt ctcagtgttc gagtcagggt tgtttccgtc acagtgaagg    5220
ggtgtgcgcc tgcttgggcg cttgccaggg tgcgcttcag actcattctg ctggtggaga    5280
acttctgtcg cttggcgccc tgtatgtcgg ccaagtagca gtttaccatg agttcgtagt    5340
tgagcgcctc ggctgcgtgg cctttggcgc ggagcttacc tttggaagtt tccttgcata    5400
ccgggcagta taggcatttc agcgcataca gcttgggcgc aaggaaaatg gattctgggg    5460
agtatgcatc cgcgccgcag gaggcgcaaa cagtttcaca ttccaccagc caggttaaat    5520
ccggttcatt ggggtcaaaa acaagttttc cgccatattt tttgatgcgt ttcttacctt    5580
tggtctccat aagttcgtgt cctcgttgag tgacaaacag gctgtccgta tctccgtaga    5640
ctgattttac aggcctcttc tccagtggag tgcctcggtc ttcttcgtac aggaactctg    5700
accactctga tacaaaggcg cgcgtccagg ccagcacaaa ggaggctatg tgggaggggt    5760
agcgatcgtt gtcaaccagg gggtccacct tttccaaagt atgcaaacac atgtcaccct    5820
cttcaacatc caggaatgtg attggcttgt aggtgtattt cacgtgacct ggggtccccg    5880
ctgggggggt ataaaagggg gcggttcttt gctcttcctc actgtcttcc ggatcgctgt    5940
ccaggaacgt cagctgttgg ggtaggtatt ccctctcgaa ggcgggcatg acctctgcac    6000
tcaggttgtc agtttctaag aacgaggagg atttgatatt gacagtgccg gttgagatgc    6060 cttttcatgag gttttcgtcc atttggtcag aaaacacaat ttttttattg tcaagtttgg    6120
tggcaaatga tccatacagg gcgttggata aaagtttggc aatggatcgc atggtttggt    6180 tctttttcctt gtccgcgcgc tctttggcgg cgatgttgag ttggacatac tcgcgtgcca    6240
ggcacttcca ttcggggaag atagttgtta attcatctgg cacgattctc acttgccacc    6300
ctcgattatg caaggtaatt aaatccacac tggtggccac ctcgcctcga aggggttcat    6360
tggtccaaca gagcctacct cctttcctag aacagaaagg gggaagtggg tctagcataa    6420
gttcatcggg agggtctgca tccatggtaa agattcccgg aagtaaatcc ttatcaaaat    6480
agctgatggg agtggggtca tctaaggcca tttgccattc tcgagctgcc agtgcgcgct    6540
catatgggtt aaggggactg ccccagggca tgggatgggt gagagcagag gcatacatgc    6600
cacagatgtc atagacgtag atgggatcct caaagatgcc tatgtaggtt ggatagcatc    6660
gcccccctct gatacttgct cgcacatagt catatagttc atgtgatggc gctagcagcc    6720
ccggacccaa gttggtgcga ttgggttttt ctgttctgta gacgatctgg cgaaagatgg    6780
cgtgagaatt ggaagagatg gtgggtcttt gaaaaatgtt gaaatgggca tgaggtagac    6840
ctacagagtc tctgacaaag tgggcataag attcttgaag cttggttacc agttcggcgg    6900
tgacaagtac gtctagggcg cagtagtcaa gtgtttcttg aatgatgtca taacctggtt    6960 ggttttctt ttcccacagt tcgcggttga gaaggtattc ttcgcgatcc ttccagtact     7020
cttctagcgg aaaccgtct ttgtctgcac ggtaagatcc tagcatgtag aactgattaa     7080
ctgccttgta agggcagcag cccttctcta cgggtagaga gtatgcttga gcagctttc    7140
```

```
gtagcgaagc gtgagtaagg gcaaaggtgt ctctgaccat gactttgaga aattggtatt      7200
tgaagtccat gtcgtcacag gctccctgtt cccagagttg aagtctacc cgtttcttgt       7260 aggcggggtt gggcaaagcg aaagtaacat cattgaagag aatcttaccg gctctgggca      7320
taaaattgcg agtgatgcgg aaaggctgtg gtacttccgc tcgattgttg atcacctggg      7380
cagctaggac gatttcgtcg aaaccgttga tgttgtgtcc tacgatgtat aattctatga      7440
aacgcggcgt gcctctgacg tgaggtagct tactgagctc atcaaaggtt aggtctgtgg      7500
ggtcagataa ggcgtagtgt tcgagagccc attcgtgcag gtgaggattt gcatgtagga      7560
atgatgacca aagatctacc gccagtgctg tttgtaactg gtcccgatac tgacgaaaat      7620
gccggccaat tgccattttt tctggagtga cacagtagaa ggttctgggg tcttgttgcc      7680
atcgatccca cttgagttta atggctagat cgtgggccat gttgacgaga cgctcttctc      7740
ctgagagttt catgaccagc atgaaaggaa ctagttgttt gccaaaggat cccatccagg      7800
tgtaagtttc cacatcgtag gtcaggaaga gtctttctgt gcgaggatga gagccgatcg      7860
ggaagaactg gatttcctgc caccagttgg aggattggct gttgatgtga tggaagtaga      7920
agtttctgcg gcgcgccgag cattcgtgtt tgtgcttgta cagacggccg cagtagtcgc      7980
agcgttgcac gggttgtatc tcgtgaatga gctgtacctg gcttcccttg acgagaaatt      8040
tcagtgggaa gccgaggcct ggcgattgta tctcgtgctc ttctatattc gctgtatcgg      8100
cctgttcatc ttctgtttcg atggtggtca tgctgacgag cccccgcggg aggcaagtcc      8160
agacctcggc gcgggagggg cggagctgaa ggacgagagc gcgcaggctg gagctgtcca      8220
gagtcctgag acgctgcgga ctcaggttag taggtaggga cagaagatta acttgcatga      8280 tctttttccag ggcgtgcggg aggttcagat ggtacttgat ttccacaggt tcgtttgtag      8340
agacgtcaat ggcttgcagg gttccgtgtc ctttgggcgc cactaccgta cctttgtttt      8400
ttcttttgat cggtggtggc tctcttgctt cttgcatgct cagaagcggt gacggggacg      8460
cgcgccgggc ggcagcggtt gttccggacc cgggggcatg gctggtagtg gcacgtcggc      8520
gccgcgcacg ggcaggttct ggtattgcgc tctgagaaga cttgcgtgcg ccaccacgcg      8580
tcgattgacg tcttgtatct gacgtctctg ggtgaaagct accggccccg tgagcttgaa      8640
cctgaaagag agttcaacag aatcaatttc ggtatcgtta acggcagctt gtctcagtat      8700
ttcttgtacg tcaccagagt tgtcctggta ggcgatctcc gccatgaact gctcgatttc      8760
ttcctcctga agatctccgc gacccgctct ttcgacggtg gccgcgaggt cattggagat      8820
acggcccatg agttgggaga atgcattcat gcccgcctcg ttccagacgc ggctgtaaac      8880
cacggccccc tcggagtctc ttgcgcgcat caccacctga gcgaggttaa gctccacgtg      8940
tctggtgaag accgcatagt tgcataggcg ctgaaaaagg tagttgagtg tggtggcaat      9000
gtgttcggcg acgaagaaat acatgatcca tcgtctcagc ggcatttcgc taacatcgcc      9060
cagagcttcc aagcgctcca tggcctcgta gaagtccacg gcaaaattaa aaaactggga      9120
gtttcgcgcg gacacggtca attcctcctc gagaagacgg atgagttcgg ctatggtggc      9180
ccgtacttcg cgttcgaagg ctcccgggat ctcttcttcc tcttctatct cttcttccac      9240
taacatctct tcttcgtctt caggcggggg cggagggggc acgcggcgac gtcgacggcg      9300
cacgggcaaa cggtcgatga atcgttcaat gacctctccg cggcggcggc gcatggtttc      9360
agtgacggcg cggccgttct cgcgcggtcg cagagtaaaa acaccgccgc gcatctcctt      9420
aaagtggtga ctgggaggtt ctccgttttgg gaggagagg gcgctgatta tacatttat       9480 taattggccc gtagggactg cgcgcagaga tctgatcgtg tcaagatcca cgggatctga      9540
```

```
aaacctttcg acgaaagcgt ctaaccagtc acagtcacaa ggtaggctga gtacggcttc    9600
ttgtgggcgg gggtggttat gtgttcggtc tgggtcttct gtttcttctt catctcggga    9660
aggtgagacg atgctgctgg tgatgaaatt aaagtaggca gttctaagac ggcggatggt    9720
ggcgaggagc accaggtctt tgggtccggc ttgctggata cgcaggcgat tggccattcc    9780
ccaagcatta tcctgacatc tagcaagatc tttgtagtag tcttgcatga gccgttctac    9840
gggcacttct tcctcacccg ttctgccatg catacgtgtg agtccaaatc cgcgcattgg    9900
ttgtaccagt gccaagtcag ctacgactct ttcggcgagg atggcttgct gtacttgggt    9960
aagggtggct tgaaagtcat caaaatccac aaagcggtgg taagcccctg tattaatggt   10020
gtaagcacag ttggccatga ctgaccagtt aactgtctgg tgaccagggc gcacgagctc   10080
ggtgtattta aggcgcgaat aggcgcgggt gtcaaagatg taatcgttgc aggtgcgcac   10140
cagatactgg tacccrataa gaaaatgcgg cggtggttgg cggtagagag gccatcgttc   10200
tgtagctgga gcgccagggg cgaggtcttc aacataagg cggtgatagc cgtagatgta   10260
cctggacatc caggtgattc ctgcggcggt agtagaagcc cgaggaaact cgcgtacgcg   10320
gttccaaatg ttgcgtagcg gcatgaagta gttcattgta ggcacggttt gaccagtgag   10380
gcgcgcgcag tcattgatgc tctatagaca cggagaaaat gaaagcgttc agcgactcga   10440
ctccgtagcc tggaggaacg tgaacgggtt gggtcgcggt gtaccccggt tcgagacttg   10500
tactcgagcc ggccggagcc gcggctaacg tggtattggc actcccgtct cgacccagcc   10560
tacaaaaatc caggatacgg aatcgagtcg ttttgctggt ttccgaatgg cagggaagtg   10620
agtcctattt tttttttttt tttgccgctc agatgcatcc cgtgctgcga cagatgcgcc   10680
cccaacaaca gccccctcg cagcagcagc agcagcaacc acaaaaggct gtccctgcaa   10740
ctactgcaac tgccgccgtg agcggtgcgg gacagcccgc ctatgatctg gacttggaag   10800
agggcgaagg actggcacgt ctaggtgcgc cttcgcccga gcggcatccg cgagttcaac   10860
tgaaaaaaga ttctcgcgag gcgtatgtgc cccaacagaa cctatttaga gacagaagcg   10920
gcgaggagcc ggaggagatg cgagcttccc gctttaacgc gggtcgtgag ctgcgtcacg   10980
gtttggaccg aagacgagtg ttgcgagacg aggatttcga agttgatgaa gtgacaggga   11040
tcagtcctgc cagggcacac gtggctgcag ccaaccttgt atcggcttac gagcagacag   11100
taaaggaaga gcgtaacttc caaaagtctt ttaataatca tgtgcgaacc ctgattgccc   11160
gcgaagaagt taccettggt ttgatgcatt tgtgggattt gatggaagct atcattcaga   11220
accctactag caaacctctg accgcccagc tgtttctggt ggtgcaacac agcagagaca   11280
atgaggcttt cagagaggcg ctgctgaaca tcaccgaacc cgaggggaga tggttgtatg   11340
atcttatcaa cattctacag agtatcatag tgcaggagcg gagcctgggc ctggccgaga   11400
aggtagctgc catcaattac tcggttttga gcttgggaaa atattacgct cgcaaaatct   11460
acaagactcc atacgttccc atagacaagg aggtgaagat agatgggttc tacatgcgca   11520
tgacgctcaa ggtcttgacc ctgagcgatg atcttgggt gtatcgcaat gacagaatgc   11580
atcgcgcggt tagcgccagc aggaggcgcg agttaagcga cagggaactg atgcacagtt   11640
tgcaaagagc tctgactgga gctggaaccg agggtgagaa ttacttcgac atgggagctg   11700
acttgcagtg gcagcctagt cgcagggctc tgagcgccgc gacggcagga tgtgagcttc   11760
cttacataga agaggcggat gaaggcgagg aggaagaggg cgagtacttg gaagactgat   11820
ggcacaaccc gtgtttttg ctagatggaa cagcaagcac cggatcccgc aatgcgggcg   11880
```

```
gcgctgcaga gccagccgtc cggcattaac tcctcggacg attggaccca ggccatgcaa   11940
cgtatcatgg cgttgacgac tcgcaacccc gaagcccttta gacagcaacc ccaggccaac   12000
cgtctatcgg ccatcatgga agctgtagtg ccttcccgat ctaatcccac tcatgagaag   12060
gtcctggcca tcgtgaacgc gttggtggag aacaaagcta ttcgtccaga tgaggccgga   12120
ctggtataca acgctctctt agaacgcgtg gctcgctaca acagtagcaa tgtgcaaacc   12180
aatttggacc gtatgataac agatgtacgc gaagccgtgt ctcagcgcga aaggttccag   12240
cgtgatgcca acctgggttc gctggtggcg ttaaatgctt tcttgagtac tcagcctgct   12300
aatgtgccgc gtggtcaaca ggattatact aactttttaa gtgctttgag actgatggta   12360
tcagaagtac ctcagagcga agtgtatcag tccggtcctg attacttctt tcagactagc   12420
agacagggct tgcagacggt aaatctgagc caagctttta aaaaccttaa aggtttgtgg   12480
ggagtgcatg ccccggtagg agaaagagca accgtgtcta gcttgttaac tccgaactcc   12540
cgcctgttat tactgttggt agctcctttc accgacagcg gtagcatcga ccgtaattcc   12600
tatttgggtt acctactaaa cctgtatcgc gaagccatag ggcaaagtca ggtggacgag   12660
cagacctatc aagaaattac ccaagtcagt cgcgctttgg gacaggaaga cactggcagt   12720
ttggaagcca ctctgaactt cttgcttacc aatcggtctc aaaagatccc tcctcaatat   12780
gctcttactg cggaggagga gaggatcctt agatatgtgc agcagagcgt gggattgttt   12840
ctgatgcaag agggggcaac tccgactgca gcactggaca tgacagcgcg aaatatggag   12900
cccagcatgt atgccagtaa ccgacctttc attaacaaac tgctggacta cttgcacaga   12960
gctgccgcta tgaactctga ttatttcacc aatgccatct taaacccgca ctggctgccc   13020
ccacctggtt tctacacggg cgaatatgac atgcccgacc ctaatgacgg atttctgtgg   13080
gacgacgtgg acagcgatgt ttttcacct ctttctgatc atcgcacgtg gaaaaaggaa   13140
ggcggtgata gaatgcattc ttctgcatcg ctgtccgggg tcatgggtgc taccgcggct   13200
gagcccgagt ctgcaagtcc ttttcctagt ctacccttt ctctacacag tgtacgtagc   13260
agcgaagtgg gtagaataag tcgcccgagt ttaatgggcg aagaggagta cctaaacgat   13320
tccttgctca gaccggcaag agaaaaaaat ttcccaaaca atggaataga agtttggtg   13380
gataaaatga gtagatggaa gacttatgct caggatcaca gagacgagcc tgggatcatg   13440
gggactacaa gtagagcgag ccgtagacgc cagcgccatg acagacagag gggtcttgtg   13500
tgggacgatg aggattcggc cgatgatagc agcgtgttgg acttgggtgg gagaggaagg   13560
ggcaacccgt ttgctcattt gcgccctcgc ttgggtggta tgttgtgaaa aaaaataaaa   13620
aagaaaaact caccaaggcc atggcgacga gcgtacgttc gttcttcttt attatctgtg   13680
tctagtataa tgaggcgagt cgtgctaggc ggagcggtgt tgtatccgga gggtcctcct   13740
ccttcgtacg agagcgtgat gcagcagcag caggcgacgg cggtgatgca atccccactg   13800
gaggctccct ttgtgcctcc gcgatacctg gcacctacgg agggcagaaa cagcattcgt   13860
tactcggaac tggcacctca gtacgatacc accaggttgt atctggtgga caacaagtcg   13920
gcggacattg cttctctgaa ctatcagaat gaccacagca cttcttgac cacggtggtg   13980
cagaacaatg actttacccc tacggaagcc agcacccaga ccattaactt tgatgaacga   14040
tcgcggtggg gcggtcagct aaagaccatc atgcatacta acatgccaaa cgtgaacgag   14100
tatatgttta gtaacaagtt caaagcgcgt gtgatggtgt ccagaaaacc tcccgacggt   14160
gctgcagttg gggatactta tgatcacaag caggatattt tggaatatga gtggttcgag   14220
tttactttgc cagaaggcaa ctttttcagtt actatgacta ttgatttgat gaacaatgcc   14280
```

```
atcatagata attacttgaa agtgggtaga cagaatggag tgcttgaaag tgacattggt    14340
gttaagttcg acaccaggaa cttcaagctg ggatgggatc cgaaaccaa gttgatcatg     14400
cctggagtgt atacgtatga agccttccat cctgacattg tcttactgcc tggctgcgga    14460
gtggatttta ccgagagtcg tttgagcaac cttcttggta tcagaaaaaa acagccattt    14520
caagagggtt ttaagatttt gtatgaagat ttagaaggtg gtaatattcc ggccctcttg    14580
gatgtagatg cctatgagaa cagtaagaaa gaacaaaaag ccaaaataga agctgctaca    14640
gctgctgcag aagctaaggc aaacatagtt gccagcgact ctacaagggt tgctaacgct    14700
ggagaggtca gaggagacaa ttttgcgcca cacctgttc cgactgcaga atcattattg     14760
gccgatgtgt ctgaaggaac ggacgtgaaa ctcactattc aacctgtaga aaagatagt     14820
aagaatagaa gctataatgt gttggaagac aaaatcaaca cagcctatcg cagttggtat    14880
ctttcgtaca attatggcga tcccgaaaaa ggagtgcgtt cctggacatt gctcaccacc    14940
tcagatgtca cctgcggagc agagcaggtt tactggtcgc ttccagacat gatgaaggat    15000
cctgtcactt tccgctccac tagacaagtc agtaactacc ctgtggtggg tgcagagctt    15060
atgcccgtct tctcaaagag cttctacaac gaacaagctg tgtactccca gcagctccgc    15120
cagtccacct cgcttacgca cgtcttcaac cgctttcctg agaaccagat tttaatccgt    15180
ccgccggcgc ccaccattac caccgtcagt gaaaacgttc ctgctctcac agatcacggg    15240
accctgccgt tgcgcagcag tatccgggga gtccaacgtg tgaccgttac tgacgccaga    15300
cgccgcacct gtccctacgt gtacaaggca ctgggcatag tcgcaccgcg cgtcctttca    15360
agccgcactt tctaaaaaaa aaaaatgtcc attcttatct cgcccagtaa taacaccggt    15420
tggggtctgc gcgctccaag caagatgtac ggaggcgcac gcaaacgttc tacccaacat    15480
cccgtgcgtg ttcgcggaca ttttcgcgct ccatggggtg ccctcaaggg ccgcactcgc    15540
gttcgaacca ccgtcgatga tgtaatcgat caggtggttg ccgacgcccg taattatact    15600
cctactgcgc ctacatctac tgtggatgca gttattgaca gtgtagtggc tgacgctcgc    15660
aactatgctc gacgtaagag ccggcgaagg cgcattgcca gacgccaccg agctaccact    15720
gccatgcgag ccgcaagagc tctgctacga agagctagac gcgtggggcg aagagccatg    15780
cttaggcgg ccagacgtgc agcttcgggc gccagcgccg gcaggtcccg caggcaagca     15840
gccgctgtcg cagcggcgac tattgccgac atggcccaat cgcgaagagg caatgtatac    15900
tgggtgcgtg acgctgccac cggtcaacgt gtacccgtgc gcacccgtcc ccctcgcact    15960
tagaagatac tgagcagtct ccgatgttgt gtcccagcgg cgaggatgtc caagcgcaaa    16020
tacaaggaag aaatgctgca ggttatcgca cctgaagtct acggccaacc gttgaaggat    16080
gaaaaaaaac cccgcaaaat caagcgggtt aaaaaggaca aaaagaaga ggaagatggc     16140
gatgatgggc tggcggagtt tgtgcgcgag tttgccccac ggcgacgcgt gcaatggcgt    16200
gggcgcaaag ttcgacatgt gttgagacct ggaacttcgg tggtctttac acccggcgag    16260
cgttcaagcg ctacttttaa gcgttcctat gatgaggtgt acgggatga tgatattctt     16320
gagcaggcgg ctgaccgatt aggcgagttt gcttatggca agcgtagtag aataacttcc    16380
aaggatgaga cagtgtcaat acccttggat catggaaatc ccacccctag tcttaaaccg    16440
gtcactttgc agcaagtgtt acccgtaact ccgcgaacag gtgttaaacg cgaaggtgaa    16500
gatttgtatc ccactatgca actgatggta cccaaacgcc agaagttgga ggacgttttg    16560
gagaaagtaa aagtggatcc agatattcaa cctgaggtta aagtgagacc cattaagcag    16620
```

```
gtagcgcctg gtctgggggt acaaactgta gacattaaga ttcccactga aagtatggaa    16680
gtgcaaactg aacccgcaaa gcctactgcc acctccactg aagtgcaaac ggatccatgg    16740
atgcccatgc ctattacaac tgacgccgcc ggtcccactc gaagatcccg acgaaagtac    16800
ggtccagcaa gtctgttgat gcccaattat gttgtacacc catctattat tcctactcct    16860
ggttaccgag gcactcgcta ctatcgcagc cgaaacagta cctcccgccg tcgccgcaag    16920
acacctgcaa atcgcagtcg tcgccgtaga cgcacaagca aaccgactcc cggcgccctg    16980
gtgcggcaag tgtaccgcaa tggtagtgcg gaacctttga cactgccgcg tgcgcgttac    17040
catccgagta tcatcactta atcaatgttg ccgctgcctc cttgcagata tggccctcac    17100
ttgtcgcctt cgcgttccca tcactggtta ccgaggaaga aactcgcgcc gtagaagagg    17160
gatgttggga cgcggaatgc gacgctacag gcgacggcgt gctatccgca agcaattgcg    17220
gggtggtttt ttaccagcct taattccaat tatcgctgct gcaattggcg cgataccagg    17280
catagcttcc gtggcggttc aggcctcgca acgacattga cattggaaaa aaaacgtata    17340
aataaaaaaa aatacaatgg actctgacac tcctggtcct gtgactatgt tttcttagag    17400
atggaagaca tcaattttttc atccttggct ccgcgacacg gcacgaagcc gtacatgggc    17460
acctggagcg acatcggcac gagccaactg aacggggggcg ccttcaattg gagcagtatc    17520
tggagcgggc ttaaaaattt tggctcaacc ataaaaacat acgggaacaa agcttggaac    17580
agcagtacag gacaggcgct tagaaataaa cttaaagacc agaacttcca acaaaaagta    17640
gtcgatggga tagcttccgg catcaatgga gtggtagatt tggctaacca ggctgtgcag    17700
aaaaagataa acagtcgttt ggacccgccg ccagcaaccc caggtgaaat gcaagtggag    17760
gaagaaattc ctccgccaga aaaacgaggc gacaagcgtc cgcgtcccga tttggaagag    17820
acgctggtga cgcgcgtaga tgaaccgcct tcttatgagg aagcaacgaa gcttggaatg    17880
cccaccacta gaccgatagc cccaatggcc accggggtga tgaaaccttc tcagttgcat    17940
cgacccgtca ccttggattt gccccctccc cctgctgcta ctgctgtacc cgcttctaag    18000
cctgtcgctg ccccgaaacc agtcgccgta gccaggtcac gtcccggggg cgctcctcgt    18060
ccaaatgcgc actggcaaaa tactctgaac agcatcgtgg gtctaggcgt gcaaagtgta    18120
aaacgccgtc gctgcttttta attaaatatg gagtagcgct taacttgcct atctgtgtat    18180
atgtgtcatt acacgccgtc acagcagcag aggaaaaaag gaagaggtcg tgcgtcgacg    18240
ctgagttact ttcaagatgg ccaccccatc gatgctgccc caatgggcat acatgcacat    18300
cgccggacag gatgcttcgg agtacctgag tccgggtctg gtgcagttcg cccgcgccac    18360
agacacctac ttcaatctgg gaaataagtt tagaaatccc accgtagcgc cgacccacga    18420
tgtgaccacc gaccgtagcc agcggctcat gttgcgcttc gtgcccgttg accgggagga    18480
caatacatac tcttacaaag tgcggtacac cctggccgtg ggcgacaaca gagtgctgga    18540
tatgccagc acgttctttg acattagggg cgtgttggac agaggtccca gtttcaaacc    18600
ctattctggt acggcttaca actctctggc tcctaaaggc gctccaaatg catctcaatg    18660
gattgcaaaa ggcgtaccaa ctgcagcagc cgcaggcaat ggtgaagaag aacatgaaac    18720
agaggagaaa actgctactt acactttttgc caatgctcct gtaaaagccg aggctcaaat    18780
tacaaaagag ggcttaccaa taggtttgga gatttcagct gaaaacgaat ctaaacccat    18840
ctatgcagat aaactttatc agccagaacc tcaagtggga gatgaaactt ggactgacct    18900
agacggaaaa accgaagagt atggaggcag ggctctaaag cctactacta acatgaaacc    18960
ctgttacggg tcctatgcga agcctactaa tttaaaaggt ggtcaggcaa aaccgaaaaa    19020
```

```
ctcggaaccg tcgagtgaaa aaattgaata tgatattgac atggaatttt ttgataactc   19080
atcgcaaaga acaaacttca gtcctaaaat tgtcatgtat gcagaaaatg taggtttgga   19140
aacgccagac actcatgtag tgtacaaacc tggaacagaa gacacaagtt ccgaagctaa   19200
tttgggacaa cagtctatgc ccaacagacc caactacatt ggcttcagag ataactttat   19260
tggactcatg tactataaca gtactggtaa catgggggtg ctggctggtc aagcgtctca   19320
gttaaatgca gtggttgact tgcaggacag aaacacagaa cttcttacc aactcttgct    19380 tgactctctg ggcgacagaa ccagatactt tagcatgtgg aatcaggctg tggacagtta   19440
tgatcctgat gtacgtgtta ttgaaaatca tggtgtggaa gatgaacttc ccaactattg   19500
ttttccactg gacggcatag gtgttccaac aaccagttac aaatcaatag ttccaaatgg   19560
agaagataat aataattgga agaacctga agtaaatgga acaagtgaga tcggacaggg    19620
taatttgttt gccatggaaa ttaaccttca agccaatcta tggcgaagtt cctttattc    19680 caatgtggct ctgtatctcc cagactcgta caaatacacc ccgtccaatg tcactcttcc   19740
agaaaacaaa aacacctacg actacatgaa cgggcgggtg gtgccgccat ctctagtaga   19800
cacctatgtg aacattggtg ccaggtggtc tctggatgcc atggacaatg tcaacccatt   19860
caaccaccac cgtaacgctg gcttgcgtta ccgatctatg cttctgggta acggacgtta   19920
tgtgcctttc cacatacaag tgcctcaaaa attcttcgct gttaaaaacc tgctgcttct   19980
cccaggctcc tacacttatg agtggaactt taggaaggat gtgaacatgg ttctacagag   20040
ttccctcggt aacgacctgc gggtagatgg cgccagcatc agtttcacga gcatcaacct   20100
ctatgctact tttttcccca tggctcacaa caccgcttcc acccttgaag ccatgctgcg   20160
gaatgacacc aatgatcagt cattcaacga ctacctatct gcagctaaca tgctctaccc   20220
cattcctgcc aatgcaacca atattcccat ttccattcct tctcgcaact gggcggcttt   20280
cagaggctgg tcatttacca gactgaaaac caaagaaact ccctctttgg ggtctggatt   20340 tgaccctac tttgtctatt ctggttctat tccctacctg gatggtacct tctacctgaa    20400
ccacactttt aagaaggttt ccatcatgtt tgactcttca gtgagctggc ctggaaatga   20460
caggttacta tctcctaacg aatttgaaat aaagcgcact gtggatggcg aaggctacaa   20520
cgtagcccaa tgcaacatga ccaaagactg gttcttggta cagatgctcg ccaactacaa   20580
catcggctat cagggcttct acattccaga aggatacaaa gatcgcatgt attcattttt   20640
cagaaacttc cagcccatga gcaggcaggt ggttgatgag gtcaattaca aagacttcaa   20700
ggccgtcgcc ataccctacc aacacaacaa ctctggcttt gtgggttaca tggctccgac   20760
catgcgccaa ggtcaaccct atcccgctaa ctatccctat ccactcattg gaacaactgc   20820
cgtaaatagt gttacgcaga aaagttctt gtgtgacaga accatgtggc gcataccgtt    20880
ctcgagcaac ttcatgtcta tgggggccct tacagacttg ggacagaata tgctctatgc   20940
caactcagct catgctctgg acatgacctt tgaggtggat cccatggatg agcccaccct   21000
gctttatctt ctcttcgaag ttttcgacgt ggtcagagtg catcagccac accgcggcat   21060
catcgaggca gtctacctgc gtacaccgtt ctcggccggt aacgctacca cgtaagaagc   21120
ttcttgcttc ttgcaaatag cagctgcaac catggcctgc ggatcccaaa acggctccag   21180
cgagcaagag ctcagagcca ttgtccaaga cctgggttgc ggaccctatt ttttgggaac   21240
ctacgataag cgcttcccgg ggttcatggc ccccgataag ctcgcctgtg ccattgtaaa   21300 tacgccgga cgtgagacgg ggggagagca ctggttggct ttcggttgga acccacgttc    21360
```

```
taacacctgc tacctttttg atccttttgg attctcggat gatcgtctca aacagattta    21420
ccagtttgaa tatgagggtc tcctgcgccg cagcgctctt gctaccaagg accgctgtat    21480
tacgctggaa aaatctaccc agaccgtgca gggccccccgt tctgccgcct gcggactttt    21540
ctgctgcatg ttccttcacg cctttgtgca ctggcctgac cgtcccatgg acggaaaccc    21600
caccatgaaa ttgctaactg gagtgccaaa caacatgctt cattctccta aagtccagcc    21660
caccctgtgt gacaatcaaa aagcactcta ccatttcctt aatacccatt cgccttattt    21720
tcgctctcat cgtacacaca tcgaaagggc cactgcgttc gaccgtatgg atgttcaata    21780
atgactcatg taaacaacgt gttcaataaa catcacttta tttttttaca tgtatcaagg    21840
ctctggatta cttatttatt tacaagtcga atgggttctg acgagaatca gaatgacccg    21900
caggcagtga tacgttgcgg aactgatact tgggttgcca cttgaattcg ggaatcacca    21960
acttgggaac cggtatatcg ggcaggatgt cactccacag ctttctggtc agctgcaaag    22020
ctccaagcag gtcaggagcc gaaatcttga aatcacaatt aggaccagtg ctctgagcgc    22080
gagagttgcg gtacaccgga ttgcagcact gaaacaccat cagcgacgga tgtctcacgc    22140
ttgccagcac ggtgggatct gcaatcatgc ccacatccag atcttcagca ttggcaatgc    22200
tgaacggggt catcttgcag gtctgcctac ccatggcggg cacccaatta ggcttgtggt    22260
tgcaatcgca gtgcagggg atcagtatca tcttggcctg atcctgtctg attcctggat    22320
acacggctct catgaaagca tcatattgct tgaaagcctg ctgggcttta ctaccctcgg    22380
tataaaacat cccgcaggac ctgctcgaaa actggttagc tgcacagccg gcatcattca    22440
cacagcagcg ggcgtcattg ttggctattt gcaccacact tctgccccag cggttttggg    22500
tgattttggt tcgctcggga ttctccttta aggctcgttg tccgttctcg ctggccacat    22560
ccatctcgat aatctgctcc ttctgaatca taatattgcc atgcaggcac ttcagcttgc    22620
cctcataatc attgcagcca tgaggccaca acgcacagcc tgtacattcc caattatggt    22680
gggcgatctg agaaaagaa tgtatcattc cctgcagaaa tcttcccatc atcgtgctca    22740
gtgtcttgtg actagtgaaa gttaactgga tgcctcggtg ctcttcgttt acgtactggt    22800
gacagatgcg cttgtattgt tcgtgttgct caggcattag tttaaaacag gttctaagtt    22860
cgttatccag cctgtacttc tccatcagca gacacatcac ttccatgcct ttctcccaag    22920
cagacaccag gggcaagcta atcggattct taacagtgca ggcagcagct cctttagcca    22980
gagggtcatc tttagcgatc ttctcaatgc ttcttttgcc atccttctca acgatgcgca    23040
cgggcgggta gctgaaaccc actgctacaa gttgcgcctc ttctctttct tcttcgctgt    23100
cttgactgat gtcttgcatg gggatatgtt tggtcttcct tggcttcttt ttggggggta    23160
tcggaggagg aggactgtcg ctccgttccg gagacaggga ggattgtgac gtttcgctca    23220
ccattaccaa ctgactgtcg gtagaagaac ctgacccccac acggcgacag gtgttttttct    23280 tcgggggcag aggtggaggc gattgcgaag ggctgcggtc cgacctggaa ggcggatgac    23340
tggcagaacc ccttccgcgt tcggggtgt gctccctgtg gcggtcgctt aactgatttc    23400
cttcgcggct ggccattgtg ttctcctagg cagagaaaca acagacatgg aaactcagcc    23460
attgctgtca acatcgccac gagtgccatc acatctcgtc ctcagcgacg aggaaaagga    23520
gcagagctta agcattccac cgcccagtcc tgccaccacc tctaccctag aagataagga    23580
ggtcgacgca tctcatgaca tgcagaataa aaaagcgaaa gagtctgaga cagacatcga    23640
gcaagacccg ggctatgtga caccggtgga acacgaggaa gagttgaaac gctttctaga    23700
gagagaggat gaaaactgcc caaaacagcg agcagataac tatcaccaag atgctggaaa    23760
```

```
tagggatcag aacaccgact acctcatagg gcttgacggg gaagacgcgc tccttaaaca   23820
tctagcaaga cagtcgctca tagtcaagga tgcattattg gacagaactg aagtgcccat   23880
cagtgtggaa gagctcagct gcgcctacga gcttaacctt ttttcacctc gtactccccc   23940
caaacgtcag ccaaacggca cctgcgagcc aaatcctcgc ttaaactttt atccagcttt   24000
tgctgtgcca gaagtactgg ctacctatca catctttttt aaaaatcaaa aaattccagt   24060
ctcctgccgc gctaatcgca cccgcgccga tgccctactc aatctgggac ctggttcacg   24120
cttacctgat atagcttcct tggaagaggt tccaaagatc ttcgagggtc tgggcaataa   24180
tgagactcgg gccgcaaatg ctctgcaaaa gggagaaaat ggcatggatg agcatcacag   24240
cgttctggtg gaattggaag gcgataatgc cagactcgca gtactcaagc gaagcgtcga   24300
ggtcacacac ttcgcatatc ccgctgtcaa cctgccccct aaagtcatga cggcggtcat   24360
ggaccagtta ctcattaagc gcgcaagtcc cctttcagaa gacatgcatg acccagatgc   24420
ctgtgatgag ggtaaaccag tggtcagtga tgagcagcta acccgatggc tgggcaccga   24480
ctctccccgg gatttggaag agcgtcgcaa gcttatgatg gccgtggtgc tggttaccgt   24540
agaactagag tgtctccgac gtttctttac cgattcagaa accttgcgca aactcgaaga   24600
gaatctgcac tacacttttta gacacggctt tgtgcggcag gcatgcaaga tatctaacgt   24660
ggaactcacc aacctggttt cctacatggg tattctgcat gagaatcgcc taggacaaag   24720
cgtgctgcac agcacccctta aggggggaagc ccgccgtgat tacatccgcg attgtgtcta   24780
tctctacctg tgccacacgt ggcaaaccgg catgggtgta tggcagcaat gtttagaaga   24840
acagaacttg aaagagcttg acaagctctt acagaaatct cttaaggttc tgtggacagg   24900
gttcgacgag cgcaccgtcg cttccgacct ggcagacctc atcttcccag agcgtctcag   24960
ggttactttg cgaaacggat tgcctgactt tatgagccag agcatgctta acaattttcg   25020
ctctttcatc ctggaacgct ccggtatcct gcccgccacc tgctgcgcac tgccctccga   25080
ctttgtgcct ctcacctacc gcgagtgccc ccgccgcta tggagtcact gctacctgtt   25140
ccgtctggcc aactatctct cctaccactc ggatgtgatc gaggatgtga gcggagacgg   25200
cttgctggag tgccactgcc gctgcaatct gtgcacgccc caccggtccc tagcttgcaa   25260
cccccagttg atgagcgaaa cccagataat aggcaccttt gaattgcaag ccccagcag   25320 ccaaggcgat gggtcttctc ctgggcaaag tttaaaactg accccgggac tgtggacctc   25380
cgcctacttg cgcaagtttg ctccggaaga ttaccacccc tatgaaatca gttctatga   25440 ggaccaatca cagcctccaa aggccgaact ttcggcttgc gtcatcaccc aggggggcaat   25500 tctgccccaa ttgcaagcca tccaaaaatc ccgccaagaa tttctactga aaagggtaa   25560 gggggtctac cttgacccccc agaccggcga ggaactcaac acaaggttcc ctcaggatgt   25620
cccaacgacg agaaaacaag aagttgaagg tgcagccgcc gcccccagaa gatatggagg   25680
aagattggga cagtcaggca gaggaggcgg aggaggacag tctggaggac agtctggagg   25740
aagacagttt ggaggaggaa aacgaggagg cagaggaggt ggaagaagta accgccgaca   25800
aacagttatc ctcggctgcg gagacaagca acagcgctac catctccgct ccgagtcgag   25860
gaacccggcg gcgtcccagc agtagatggg acgagaccgg acgcttcccg aacccaacca   25920
gcgcttccaa gaccggtaag aaggatcggc agggatacaa gtcctggcgg gggcataaga   25980
atgccatcat ctcctgcttg catgagtgcg ggggcaacat atccttcacg cggcgctact   26040
tgctattcca ccatggggtg aactttccgc gcaatgtttt gcattactac cgtcacctcc   26100
```

```
acagcccta ctatagccag caaatcccga cagtctcgac agataaagac agcggcggcg   26160
acctccaaca gaaaccagc agcggcagtt agaaaataca caacaagtgc agcaacagga   26220
ggattaaaga ttacagccaa cgagccagcg caaacccgag agttaagaaa tcggatcttt   26280
ccaaccctgt atgccatctt ccagcagagt cggggtcaag agcaggaact gaaaataaaa   26340
aaccgatctc tgcgttcgct caccagaagt tgtttgtatc acaagagcga agatcaactt   26400
cagcgcactc tcgaggacgc cgaggctctc ttcaacaagt actgcgcgct gactcttaaa   26460
gagtaggcag cgaccgcgct tattcaaaaa aggcgggaat tacatcatcc tcgacatgag   26520
taaagaaatt cccacgcctt acatgtggag ttatcaaccc caaatgggat tggcagcagg   26580
cgcctcccag gactactcca cccgcatgaa ttggctcagc gccgggcctt ctatgatttc   26640
tcgagttaat gatatacgcg cctaccgaaa ccaaatactt ttggaacagt cagtccttac   26700
caccacgccc cgccaacacc ttaatcccag aaattggccc gccgccctag tgtaccagga   26760
aagtcccgct cccaccactg tattacttcc tcgagacgcc caggccgaag tccaaatgac   26820
taatgcaggt gcgcagttag ctggcggctc caccctatgt cgtcacaggc ctcggcataa   26880
tataaaacgc ctgatgatca gaggccgagg tatccagctc aacgacgagt cggtgagctc   26940
tccgcttggt ctacgaccag acggaatctt tcagattgcc ggctgcggga gatcttcctt   27000
caccctcgt caggctgttc tgactttgga agttcgtct tcgcaacccc gctcgggcgg   27060
aatcgggacc gttcaatttg tagaggagtt tactccctct gtctacttca ccccttctc   27120
cggatctcct gggcactacc cggacgagtt cataccgaac ttcgacgcga ttagcgagtc   27180
agtggacggc tacgattgat gtctggtgac gcggctgagc tatctcggct gcgacatcta   27240
gaccactgcc gccgctttcg ctgctttgcc cgggaactta ttgagttcat ctacttcgaa   27300
ctccccaagg atcacccta aggtccggcc cacggagtgc ggattactat cgaaggcaaa   27360
atagactctc gcctgcaacg aatttctcc cagcggcccg tgctgatcga gcgagaccag   27420
ggaaacacca cggtttccat ctactgcatt tgtaatcacc ccggattgca tgaaagcctt   27480
tgctgtctta tgtgtactga gtttaataaa aactgaatta agactctcct acggactgcc   27540
gcttcttcaa cccggatttt acaaccagaa gaacaaaact tttcctgtcg tccaggactc   27600
tgttaacttc acctttccta ctcacaaact agaagctcaa cgactacacc gcttttccag   27660
aagcattttc cctactaata ctactttcaa aaccggaggt gagctccacg gtctccctac   27720
agaaaaccct tgggtggaag cgggccttgt agtactagga attcttgcgg gtgggcttgt   27780
gattattctt tgctacctat acacaccttg cttcactttc ctagtggtgt tgtggtattg   27840
gtttaaaaaa tggggcccat actagtcttg cttgttttac tttcgctttt ggaaccgggt   27900
tctgccaatt acgatccatg tctagacttt gacccagaaa actgcacact tacttttgca   27960
cccgacacaa gccgcatctg tggagttctt attaagtgcg gatgggaatg caggtccgtt   28020
gaaattacac acaataacaa aacctggaac aataccttat ccaccacatg ggagccagga   28080
gttcccgagt ggtacactgt ctctgtccga ggtcctgacg gttccatccg cattagtaac   28140
aacactttca ttttttctga atgtgcgat ctggccatgt tcatgagcaa acagtattct   28200
ctatggcctc ctagcaagga caacatcgta acgttctcca ttgcttattg cttgtgcgct   28260
tgccttctta ctgctttact gtgcgtatgc atacacctgc ttgtaaccac tcgcatcaaa   28320
aacgccaata caaagaaaaa aatgccttaa cctctttctg tttacagaca tggcttctct   28380
tacatctctc atatttgtca gcattgtcac tgccgctcac ggacaaacag tcgtctctat   28440
cccactagga cataattaca ctctcatagg acccccaatc acttcagagg tcatctggac   28500
```

-continued

```
caaactggga agcgttgatt actttgatat aatctgtaac aaaacaaaac caataatagt    28560
aacttgcaac atacaaaatc ttacattgat taatgttagc aaagtttaca gcggttacta    28620
ttatggttat gacagataca gtagtcaata tagaaattac ttggttcgtg ttacccagtt    28680
gaaaaccacg aaaatgccaa atatggcaaa gattcgatcc gatgacaatt ctctagaaac    28740
ttttacatct cccaccacac ccgacgaaaa aaacatccca gattcaatga ttgcaattgt    28800
tgcagcggtg gcagtggtga tggcactaat aataatatgc atgcttttat atgcttgtcg    28860
ctacaaaaag tttcatccta aaaaacaaga tctcctacta aggcttaaca tttaatttct    28920
ttttatacag ccatggtttc cactaccaca ttccttatgc ttactagtct cgcaactctg    28980
acttctgctc gctcacacct cactgtaact ataggctcaa actgcacact aaaaggacct    29040
caaggtggtc atgtcttttg gtggagaata tatgacaatg gatggtttac aaaaccatgt    29100
gaccaacctg gtagattttt ctgcaacggc agagacctaa ccattatcaa cgtgacagca    29160
aatgacaaag gcttctatta tggaaccgac tataaaagta gtttagatta taacattatt    29220
gtactgccat ctaccactcc agcaccccgc acaactactt tctctagcag cagtgtcgct    29280
aacaatacaa tttccaatcc aacctttgcc gcgcttttaa aacgcactgt gaataattct    29340
acaacttcac atacaacaat ttccacttca acaatcagca tcatcgctgc agtgacaatt    29400
ggaatatcta ttcttgtttt taccataacc tactacgcct gctgctatag aaaagacaaa    29460
cataaaggtg atccattact tagatttgat atttaatttg ttctttttttt ttatttacag    29520
tatggtgaac accaatcatg gtacctagaa atttcttctt caccatactc atctgtgctt    29580
ttaatgtttg cgctactttc acagcagtag ccacagcaac cccagactgt ataggagcat    29640
ttgcttccta tgcactttttt gcttttgtta cttgcatctg cgtatgtagc atagtctgcc    29700
tggttattaa tttttttccaa cttctagact ggatccttgt gcgaattgcc tacctgcgcc    29760
accatcccga ataccgcaac caaaatatcg cggcacttct tagactcatc taaaaccatg    29820
caggctatac taccaatatt tttgcttcta ttgcttccct acgctgtctc aaccccagct    29880
gcctatagta ctccaccaga acaccttaga aaatgcaaat tccaacaacc gtggtcattt    29940
cttgcttgct atcgagaaaa atcagaaatc cccccaaatt taataatgat tgctggaata    30000
attaatataa tctgttgcac cataatttca ttttttgatat accccctatt tgattttggc    30060
tggaatgctc ccaatgcaca tgatcatcca caagacccag aggaacacat tccccacaa    30120
aacatgcaac atccaatagc gctaatagat tacgaaagtg aaccacaacc cccactactc    30180
cctgctatta gttacttcaa cctaaccggc ggagatgact gaaacactca ccacctccaa    30240
ttccgccgag gatctgctcg atatggacgg ccgcgtctca gaacaacgac ttgcccaact    30300
acgcatccgc cagcagcagg aacgcgtggc caaagagctc agagatgtca tccaaattca    30360
ccaatgcaaa aaaggcatat tctgtttggt aaaacaagcc aagatatcct acgagatcac    30420
cgctactgac catcgcctct cttacgaact tggcccccaa cgacaaaaat ttacctgcat    30480
ggtgggaatc aacccatag ttatcaccca acaaagtgga gatactaagg gttgcattca    30540
ctgctcctgc gattccatcg agtgcaccta caccctgctg aagaccctat gcggcctaag    30600
agacctgcta ccaatgaatt aaaaaaaaat gattaataaa aaatcactta cttgaaatca    30660
gcaataaggt ctctgttgaa attttctccc agcagcacct cacttccctc ttcccaactc    30720
tggtattcta aaccccgttc agcggcatac tttctccata ctttaaaggg gatgtcaaat    30780
tttagctcct ctcctgtacc cacaatcttc atgtctttct tcccagatga ccaagagagt    30840
```

```
ccggctcagt gactccttca accctgtcta ccccctatgaa gatgaaagca cctcccaaca    30900
cccctttata aacccagggt ttatttcccc aaatggcttc acacaaagcc cagacggagt    30960
tcttacttta aaatgtttaa ccccactaac aaccacaggc ggatctctac agctaaaagt    31020
gggaggggga cttacagtgg atgacactga tggtacctta caagaaaaca tacgtgctac    31080
agcacccatt actaaaaata atcactctgt agaactatcc attggaaatg gattagaaac    31140
tcaaaacaat aaactatgtg ccaaattggg aaatgggtta aaatttaaca acggtgacat    31200
ttgtataaag gatagtatta acaccttatg gactggaata aaccctccac ctaactgtca    31260
aattgtggaa aacactaata caaatgatgg caaacttact ttagtattag taaaaaatgg    31320
agggcttgtt aatggctacg tgtctctagt tggtgtatca gacactgtga accaaatgtt    31380
cacacaaaag acagcaaaca tccaattaag attatatttt gactcttctg gaaatctatt    31440
aactgaggaa tcagacttaa aaattccact taaaaataaa tcttctacag cgaccagtga    31500
aactgtagcc agcagcaaag cctttatgcc aagtactaca gcttatccct tcaacaccac    31560
tactagggat agtgaaaact acattcatgg aatatgttac tacatgacta gttatgatag    31620
aagtctattt cccttgaaca tttctataat gctaaacagc cgtatgattt cttccaatgt    31680
tgcctatgcc atacaatttg aatggaatct aaatgcaagt gaatctccag aaagcaacat    31740
agctacgctg accacatccc cctttttctt ttcttacatt acagaagacg acaactaaaa    31800
taaagtttaa gtgtttttat ttaaaatcac aaaattcgag tagttatttt gcctccacct    31860
tcccatttga cagaatacac caatctctcc ccacgcacag cttaaaacat ttggatacca    31920
ttagagatag acattgtttt agattccaca ttccaaacag tttcagagcg agccaatctg    31980
gggtcagtga tagataaaaa tccatcgcga tagtctttta aagcgctttc acagtccaac    32040
tgctgcggat gcgactccgg agtttggatc acggtcatct ggaagaagaa cgatgggaat    32100
cataatccga aaacggtatc ggacgattgt gtctcatcaa acccacaagc agccgctgtc    32160
tgcgtcgctc cgtgcgactg ctgtttatgg gatcagggtc cacagtttcc tgaagcatga    32220
ttttaatagc ccttaacatc aactttctgg tgcgatgcgc gcagcaacgc attctgattt    32280
cactcaaatc tttgcagtag gtacaacaca ttattacaat attgtttaat aaaccataat    32340
taaaagcgct ccagccaaaa ctcatatctg atataatcgc ccctgcatga ccatcatacc    32400
aaagtttaat ataaattaaa tgacgttccc tcaaaaacac actacccaca tacatgatct    32460
cttttggcat gtgcatatta acaatctgtc tgtaccatgg acaacgttgg ttaatcatgc    32520
aacccaatat aaccttccgg aaccacactg ccaacaccgc tcccccagcc atgcattgaa    32580
gtgaaccctg ctgattacaa tgacaatgaa gaacccaatt ctctcgaccg tgaatcactt    32640
gagaatgaaa aatatctata gtggcacaac atagacataa atgcatgcat cttctcataa    32700
tttttaactc ctcaggattt agaaacatat cccagggaat aggaagctct tgcagaacag    32760
taaagctggc agaacaagga agaccacgaa cacaacttac actatgcata gtcatagtat    32820
cacaatctgg caacagcggg tggtcttcag tcatagaagc tcgggtttca ttttcctcac    32880
aacgtggtaa ctgggctctg gtgtaagggt gatgtctggc gcatgatgtc gagcgtgcgc    32940
gcaaccttgt cataatggag ttgcttcctg acattctcgt attttgtata gcaaaacgcg    33000
gccctggcag aacacactct tcttcgcctt ctatcctgcc gcttagcgtg ttccgtgtga    33060
tagttcaagt acagccacac tcttaagttg gtcaaaagaa tgctggcttc agttgtaatc    33120
aaaactccat cgcatctaat tgttctgagg aaatcatcca cggtagcata tgcaaatccc    33180
aaccaagcaa tgcaactgga ttgcgtttca agcaggagag gagagggaag agacggaaga    33240
```

```
accatgttaa tttttattcc aaacgatctc gcagtacttc aaattgtaga tcgcgcagat    33300
ggcatctctc gcccccactg tgttggtgaa aaagcacagc taaatcaaaa gaaatgcgat    33360
tttcaaggtg ctcaacggtg gcttccaaca aagcctccac gcgcacatcc aagaacaaaa    33420
gaataccaaa agaaggagca ttttctaact cctcaatcat catattacat tcctgcacca    33480
ttcccagata atttcagct ttccagcctt gaattattcg tgtcagttct tgtggtaaat     33540
ccaatccaca cattacaaac aggtcccgga gggcgccctc caccaccatt cttaaacaca    33600
ccctcataat gacaaaatat cttgctcctg tgtcacctgt agcgaattga gaatggcaac    33660
atcaattgac atgcccttgg ctctaagttc ttctttaagt tctagttgta aaaactctct    33720
catattatca ccaaactgct tagccagaag cccccggga acaagagcag gggacgctac     33780
agtgcagtac aagcgcagac ctccccaatt ggctccagca aaaacaagat tggaataagc    33840
atattgggaa ccaccagtaa tatcatcgaa gttgctggaa atataatcag gcagagtttc    33900
ttgtagaaat tgaataaaag aaaaatttgc caaaaaaaca ttcaaaacct ctgggatgca    33960
aatgcaatag gttaccgcgc tgcgctccaa cattgttagt tttgaattag tctgcaaaaa    34020 taaaaaaaa acaagcgtca tatcatagta gcctgacgaa caggtggata aatcagtctt     34080
tccatcacaa gacaagccac agggtctcca gctcgaccct cgtaaaacct gtcatcgtga    34140
ttaaacaaca gcaccgaaag ttcctcgcgg tgaccagcat gaataagtct tgatgaagca    34200
tacaatccag acatgttagc atcagttaag gagaaaaaac agccaacata gcctttgggt    34260
ataattatgc ttaatcgtaa gtatagcaaa gccacccctc gcggatacaa agtaaaaggc    34320
acaggagaat aaaaaatata attatttctc tgctgctgtt taggcaacgt cgcccccggt    34380
ccctctaaat acacatacaa agcctcatca gccatggctt accagagaaa gtacagcggg    34440
cacacaaacc acaagctcta aagtcactct ccaacctstc cacaatatat atacacaagc    34500
cctaaactga cgtaatggga ctaaagtgta aaaaatcccg ccaaacccaa cacacacccc    34560
gaaactgcgt caccagggaa aagtacagtt tcacttccgc aatcccaaca agcgtcactt    34620
cctctttctc acggtacgtc acatcccatt aacttacaac gtcatttttcc cacggccgcg    34680 ccgccccttt taaccgttaa ccccacagcc aatcaccaca cggcccacac tttttaaaat    34740
cacctcattt acatattggc accattccat ctataaggta tattattgat gatg          34794
```

<210> SEQ ID NO 83
<211> LENGTH: 356
<212> TYPE: PRT
<213> ORGANISM: Artificial
<220> FEATURE:
<223> OTHER INFORMATION: Chimeric fiber protein dervied from adenovirus
      5 and adenovirus 16
<220> FEATURE:
<221> NAME/KEY: MISC_FEATURE
<222> LOCATION: (159)..(159)
<223> OTHER INFORMATION: Xaa at position 159 could indicate any amino
      acid

<400> SEQUENCE: 83

Met Leu Leu Gln Met Lys Arg Ala Arg Pro Ser Glu Asp Thr Phe Asn
1               5                   10                  15

Pro Val Tyr Pro Tyr Glu Asp Glu Ser Ser Ser Gln His Pro Phe Ile
            20                  25                  30

Asn Pro Gly Phe Ile Ser Ser Asn Gly Phe Ala Gln Ser Pro Asp Gly
        35                  40                  45

Val Leu Thr Leu Lys Cys Val Asn Pro Leu Thr Thr Ala Ser Gly Pro

```
                    50                  55                  60
Leu Gln Leu Lys Val Gly Ser Ser Leu Thr Val Asp Thr Ile Asp Gly
 65                  70                  75                  80

Ser Leu Glu Glu Asn Ile Thr Ala Ala Ala Pro Leu Thr Lys Thr Asn
                 85                  90                  95

His Ser Ile Gly Leu Leu Ile Gly Ser Gly Leu Gln Thr Lys Asp Asp
                100                 105                 110

Lys Leu Cys Leu Ser Leu Glu Asp Gly Leu Val Thr Lys Asp Asp Lys
                115                 120                 125

Leu Cys Leu Ser Leu Gly Asp Gly Leu Ile Thr Lys Asn Asp Val Leu
130                 135                 140

Cys Ala Lys Leu Gly His Gly Leu Val Phe Asp Ser Ser Asn Xaa Ile
145                 150                 155                 160

Thr Ile Glu Asn Asn Thr Leu Trp Thr Gly Ala Lys Pro Ser Ala Asn
                165                 170                 175

Cys Val Ile Lys Glu Gly Glu Asp Ser Pro Asp Cys Lys Leu Thr Leu
                180                 185                 190

Val Leu Val Lys Asn Gly Gly Leu Ile Asn Gly Tyr Ile Thr Leu Met
                195                 200                 205

Gly Ala Ser Glu Tyr Thr Asn Thr Leu Phe Lys Asn Asn Gln Val Thr
                210                 215                 220

Ile Asp Val Asn Leu Ala Phe Asp Asn Thr Gly Gln Ile Ile Thr Tyr
225                 230                 235                 240

Leu Ser Ser Leu Lys Ser Asn Leu Asn Phe Lys Asp Asn Gln Asn Met
                245                 250                 255

Ala Thr Gly Thr Ile Thr Ser Ala Lys Gly Phe Met Pro Ser Thr Thr
                260                 265                 270

Ala Tyr Pro Phe Ile Thr Tyr Ala Thr Glu Thr Leu Asn Glu Asp Tyr
                275                 280                 285

Ile Tyr Gly Glu Cys Tyr Tyr Lys Ser Thr Asn Gly Thr Leu Phe Pro
                290                 295                 300

Leu Lys Val Thr Val Thr Leu Asn Arg Arg Met Leu Ala Ser Gly Met
305                 310                 315                 320

Ala Tyr Ala Met Asn Phe Ser Trp Ser Leu Asn Ala Glu Glu Ala Pro
                325                 330                 335

Glu Thr Thr Glu Val Thr Leu Ile Thr Ser Pro Phe Phe Ser Tyr
                340                 345                 350

Ile Arg Glu Asp
        355

<210> SEQ ID NO 84
<211> LENGTH: 325
<212> TYPE: PRT
<213> ORGANISM: Artificial
<220> FEATURE:
<223> OTHER INFORMATION: Chimeric fiber protein dervied from adenovirus
      5 and adenovirus 35

<400> SEQUENCE: 84

Met Leu Leu Gln Met Lys Arg Ala Arg Pro Ser Glu Asp Thr Phe Asn
 1               5                  10                  15

Pro Val Tyr Pro Tyr Glu Asp Glu Ser Thr Ser Gln His Pro Phe Ile
                20                  25                  30

Asn Pro Gly Phe Ile Ser Pro Asn Gly Phe Thr Gln Ser Pro Asp Gly
                35                  40                  45
```

```
Val Leu Thr Leu Lys Cys Leu Thr Pro Leu Thr Thr Thr Gly Gly Ser
    50                  55                  60

Leu Gln Leu Lys Val Gly Gly Leu Thr Val Asp Asp Thr Asp Gly
65                  70                  75                  80

Thr Leu Gln Glu Asn Ile Arg Ala Thr Ala Pro Ile Thr Lys Asn Asn
                85                  90                  95

His Ser Val Glu Leu Ser Ile Gly Asn Gly Leu Glu Thr Gln Asn Asn
                100                 105                 110

Lys Leu Cys Ala Lys Leu Gly Asn Gly Leu Lys Phe Asn Asn Gly Asp
                115                 120                 125

Ile Cys Ile Lys Asp Ser Ile Asn Thr Leu Trp Thr Gly Ile Asn Pro
    130                 135                 140

Pro Pro Asn Cys Gln Ile Val Glu Asn Thr Asn Thr Asn Asp Gly Lys
145                 150                 155                 160

Leu Thr Leu Val Leu Val Lys Asn Gly Gly Leu Val Asn Gly Tyr Val
                165                 170                 175

Ser Leu Val Gly Val Ser Asp Thr Val Asn Gln Met Phe Thr Gln Lys
                180                 185                 190

Thr Ala Asn Ile Gln Leu Arg Leu Tyr Phe Asp Ser Ser Gly Asn Leu
    195                 200                 205

Leu Thr Glu Glu Ser Asp Leu Lys Ile Pro Leu Lys Asn Lys Ser Ser
    210                 215                 220

Thr Ala Thr Ser Glu Thr Val Ala Ser Ser Lys Ala Phe Met Pro Ser
225                 230                 235                 240

Thr Thr Ala Tyr Pro Phe Asn Thr Thr Thr Arg Asp Ser Glu Asn Tyr
                245                 250                 255

Ile His Gly Ile Cys Tyr Tyr Met Thr Ser Tyr Asp Arg Ser Leu Phe
                260                 265                 270

Pro Leu Asn Ile Ser Ile Met Leu Asn Ser Arg Met Ile Ser Ser Asn
    275                 280                 285

Val Ala Tyr Ala Ile Gln Phe Glu Trp Asn Leu Asn Ala Ser Glu Ser
    290                 295                 300

Pro Glu Ser Asn Ile Met Thr Leu Thr Thr Ser Pro Phe Phe Phe Ser
305                 310                 315                 320

Tyr Ile Thr Glu Asp
                325

<210> SEQ ID NO 85
<211> LENGTH: 325
<212> TYPE: PRT
<213> ORGANISM: Artificial
<220> FEATURE:
<223> OTHER INFORMATION: Chimeric fiber protein dervied from adenovirus
      5 and adenovirus 51

<400> SEQUENCE: 85

Met Leu Leu Gln Met Lys Arg Ala Arg Pro Ser Glu Asp Thr Phe Asn
1               5                   10                  15

Pro Val Tyr Pro Tyr Glu Asp Glu Ser Thr Ser Gln His Pro Phe Ile
                20                  25                  30

Asn Pro Gly Phe Ile Ser Pro Asn Gly Phe Thr Gln Ser Pro Asp Gly
            35                  40                  45

Val Leu Thr Leu Asn Cys Leu Thr Pro Leu Thr Thr Thr Gly Gly Pro
    50                  55                  60

Leu Gln Leu Lys Val Gly Gly Gly Leu Ile Val Asp Asp Thr Asp Gly
65                  70                  75                  80
```

-continued

```
Thr Leu Gln Glu Asn Ile Arg Val Thr Ala Pro Ile Thr Lys Asn Asn
                85                  90                  95

His Ser Val Glu Leu Ser Ile Gly Asn Gly Leu Glu Thr Gln Asn Asn
            100                 105                 110

Lys Leu Cys Ala Lys Leu Gly Asn Gly Leu Lys Phe Asn Asn Gly Asp
        115                 120                 125

Ile Cys Ile Lys Asp Ser Ile Asn Thr Leu Trp Thr Gly Ile Lys Pro
    130                 135                 140

Pro Pro Asn Cys Gln Ile Val Glu Asn Thr Asp Thr Asn Asp Gly Lys
145                 150                 155                 160

Leu Thr Leu Val Leu Val Lys Asn Gly Gly Leu Val Asn Gly Tyr Val
                165                 170                 175

Ser Leu Val Gly Val Ser Asp Thr Val Asn Gln Met Phe Thr Gln Lys
            180                 185                 190

Ser Ala Thr Ile Gln Leu Arg Leu Tyr Phe Asp Ser Ser Gly Asn Leu
        195                 200                 205

Leu Thr Asp Glu Ser Asn Leu Lys Ile Pro Leu Lys Asn Lys Ser Ser
    210                 215                 220

Thr Ala Thr Ser Glu Ala Ala Thr Ser Ser Lys Ala Phe Met Pro Ser
225                 230                 235                 240

Thr Thr Ala Tyr Pro Phe Asn Thr Thr Thr Arg Asp Ser Glu Asn Tyr
                245                 250                 255

Ile His Gly Ile Cys Tyr Tyr Met Thr Ser Tyr Asp Arg Ser Leu Val
            260                 265                 270

Pro Leu Asn Ile Ser Ile Met Leu Asn Ser Arg Thr Ile Ser Ser Asn
        275                 280                 285

Val Ala Tyr Ala Ile Gln Phe Glu Trp Asn Leu Asn Ala Lys Glu Ser
    290                 295                 300

Pro Glu Ser Asn Ile Ala Thr Leu Thr Thr Ser Pro Phe Phe Phe Ser
305                 310                 315                 320

Tyr Ile Ile Glu Asp
                325

<210> SEQ ID NO 86
<211> LENGTH: 585
<212> TYPE: PRT
<213> ORGANISM: Adenovirus serotype 5

<400> SEQUENCE: 86

Met Leu Leu Gln Met Lys Arg Ala Arg Pro Ser Glu Asp Thr Phe Asn
1               5                   10                  15

Pro Val Tyr Pro Tyr Asp Thr Glu Thr Gly Pro Pro Thr Val Pro Phe
            20                  25                  30

Leu Thr Pro Pro Phe Val Ser Pro Asn Gly Phe Gln Glu Ser Pro Pro
        35                  40                  45

Gly Val Leu Ser Leu Arg Leu Ser Glu Pro Leu Val Thr Ser Asn Gly
    50                  55                  60

Met Leu Ala Leu Lys Met Gly Asn Gly Leu Ser Leu Asp Glu Ala Gly
65                  70                  75                  80

Asn Leu Thr Ser Gln Asn Val Thr Thr Val Ser Pro Pro Leu Lys Lys
                85                  90                  95

Thr Lys Ser Asn Ile Asn Leu Glu Ile Ser Ala Pro Leu Thr Val Thr
            100                 105                 110

Ser Glu Ala Leu Thr Val Ala Ala Ala Ala Pro Leu Met Val Ala Gly
```

-continued

```
            115                 120                 125
Asn Thr Leu Thr Met Gln Ser Gln Ala Pro Leu Thr Val His Asp Ser
    130                 135                 140

Lys Leu Ser Ile Ala Thr Gln Gly Pro Leu Thr Val Ser Glu Gly Lys
145                 150                 155                 160

Leu Ala Leu Gln Thr Ser Gly Pro Leu Thr Thr Asp Ser Ser Thr
                165                 170                 175

Leu Thr Ile Thr Ala Ser Pro Pro Leu Thr Thr Ala Thr Gly Ser Leu
                180                 185                 190

Gly Ile Asp Leu Lys Glu Pro Ile Tyr Thr Gln Asn Gly Lys Leu Gly
                195                 200                 205

Leu Lys Tyr Gly Ala Pro Leu His Val Thr Asp Asp Leu Asn Thr Leu
    210                 215                 220

Thr Val Ala Thr Gly Pro Gly Val Thr Ile Asn Asn Thr Ser Leu Gln
225                 230                 235                 240

Thr Lys Val Thr Gly Ala Leu Gly Phe Asp Ser Gln Gly Asn Met Gln
                245                 250                 255

Leu Asn Val Ala Gly Gly Leu Arg Ile Asp Ser Gln Asn Arg Arg Leu
                260                 265                 270

Ile Leu Asp Val Ser Tyr Pro Phe Asp Ala Gln Asn Gln Leu Asn Leu
                275                 280                 285

Arg Leu Gly Gln Gly Pro Leu Phe Ile Asn Ser Ala His Asn Leu Asp
    290                 295                 300

Ile Asn Tyr Asn Lys Gly Leu Tyr Leu Phe Thr Ala Ser Asn Asn Ser
305                 310                 315                 320

Lys Lys Leu Glu Val Asn Leu Ser Thr Ala Lys Gly Leu Met Phe Asp
                325                 330                 335

Ala Thr Ala Ile Ala Ile Asn Ala Gly Asp Gly Leu Glu Phe Gly Ser
                340                 345                 350

Pro Asn Ala Pro Asn Thr Asn Pro Leu Lys Thr Lys Ile Gly His Gly
                355                 360                 365

Leu Glu Phe Asp Ser Asn Lys Ala Met Val Pro Lys Leu Gly Thr Gly
    370                 375                 380

Leu Ser Phe Asp Ser Thr Gly Ala Ile Thr Val Gly Asn Lys Asn Asn
385                 390                 395                 400

Asp Lys Leu Thr Leu Trp Thr Thr Pro Ala Pro Ser Pro Asn Cys Arg
                405                 410                 415

Leu Asn Ala Glu Lys Asp Ala Lys Leu Thr Leu Val Leu Thr Lys Cys
                420                 425                 430

Gly Ser Gln Ile Leu Ala Thr Val Ser Val Leu Ala Val Lys Gly Ser
                435                 440                 445

Leu Ala Pro Ile Ser Gly Thr Val Gln Ser Ala His Leu Ile Ile Arg
    450                 455                 460

Phe Asp Glu Asn Gly Val Leu Leu Asn Asn Ser Phe Leu Asp Pro Glu
465                 470                 475                 480

Tyr Trp Asn Phe Arg Asn Gly Asp Leu Thr Glu Gly Thr Ala Tyr Thr
                485                 490                 495

Asn Ala Val Gly Phe Met Pro Asn Leu Ser Ala Tyr Pro Lys Ser His
                500                 505                 510

Gly Lys Thr Ala Lys Ser Asn Ile Val Ser Gln Val Tyr Leu Asn Gly
                515                 520                 525

Asp Lys Thr Lys Pro Val Thr Leu Thr Ile Thr Leu Asn Gly Thr Gln
    530                 535                 540
```

-continued

```
Glu Thr Gly Asp Thr Thr Pro Ser Ala Tyr Ser Met Ser Phe Ser Trp
545                 550                 555                 560

Asp Trp Ser Gly His Asn Tyr Ile Asn Glu Ile Phe Ala Thr Ser Ser
            565                 570                 575

Tyr Thr Phe Ser Tyr Ile Ala Gln Glu
            580                 585
```

SEROTYPE OF ADENOVIRUS AND USES THEREOF

CROSS-REFERENCE TO RELATED APPLICATIONS

This application is a continuation of U.S. patent application Ser. No. 09/573,740, filed May 18, 2000, now U.S. Pat. No. 6,913,922, issued Jul. 5, 2005, which claims the benefit under 35 U.S.C. § 119(e) of U.S. Provisional Patent Application No. 60/134,764, filed May 18, 1999, now abandoned, the entirety of each of which is incorporated by reference.

TECHNICAL FIELD

The present invention relates generally to biotechnology and more particularly to the field of gene therapy, especially gene therapy involving elements derived from viruses, more in particular, elements of adenoviruses.

BACKGROUND

Adenoviruses have been proposed as suitable vehicles to deliver genes to a host. There are a number of features of adenoviruses that make them particularly useful for the development of gene-transfer vectors for human gene therapy. The adenovirus genome is well characterized. It consists of a linear double-stranded DNA molecule of approximately 36,000 base pairs ("bp"). The adenovirus DNA contains identical Inverted Terminal Repeats ("ITRs") of approximately 90-140 base pairs with the exact length depending on the serotype. The viral origins of replication are within the ITRs exactly at the genome ends.

The biology of the adenoviruses is characterized in detail. The adenovirus is not associated with severe human pathology in immuno-competent individuals. The virus is extremely efficient in introducing its DNA into a host cell; the virus can infect a wide variety of cells and has a broad host range. The virus can be produced at high virus titers in large quantities.

The virus can be rendered replication defective by deletion of the early-region 1 (E1) of the viral genome (Brody et al., 1994). Most adenoviral vectors currently used in gene therapy have a deletion in the E1 region, where desired genetic information can be substituted.

Based on these features, preferred methods for in vivo gene transfer into human target cells make use of adenoviral vectors as gene delivery vehicles. However, drawbacks associated with the therapeutic use of adenoviral vectors in humans still exist. A major drawback is the existence of widespread pre-existing immunity among the population against adenoviruses. Exposure to wild-type adenoviruses is very common in humans, as has been documented extensively (reviewed in Wadell, 1984). This exposure has resulted in immune responses against most types of adenoviruses, not alone against adenoviruses to which individuals have actually been exposed, but also against adenoviruses which have similar (neutralizing) epitopes. This phenomenon of pre-existing antibodies in humans, in combination with a strong secondary humoral and cellular immune response against the virus, can seriously affect gene transfer using recombinant adenoviral vectors.

To date, six different subgroups of human adenoviruses have been proposed which in total encompasses 51 distinct adenovirus serotypes (see Table 1). A serotype is defined on the basis of its immunological distinctiveness as determined by quantitative neutralization with animal antisera (horse, rabbit). If neutralization shows a certain degree of cross-reaction between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al., 1991). The nine serotypes identified last (42-51) were isolated for the first time from HIV-infected patients (Hierholzer et al. 1988; Schnurr et al. 1993). For reasons not well understood, most of such immune-compromised patients shed adenoviruses that were rarely or never isolated from immune-competent individuals (Hierholzer et al. 1988, 1992; Khoo et al., 1995; De Jong et al., 1998).

The vast majority of people have had previous exposure to adenoviruses, especially the well-investigated adenovirus serotypes 5 and type 2 ("Ad5" and "Ad2") or immunologically related serotypes. Importantly, these two serotypes are also the most extensively studied for use in human gene therapy.

As previously stated, the usefulness of these adenoviruses or cross-immunizing adenoviruses to prepare gene delivery vehicles may be seriously hampered, since the individual to whom the gene delivery vehicle is provided, will raise a neutralizing response to such a vehicle before long.

Thus, a need exists in the field of gene therapy to provide gene delivery vehicles, preferably based on adenoviruses, which do not encounter pre-existing immunity and/or which are capable of avoiding or diminishing neutralizing antibody responses.

SUMMARY OF THE INVENTION

Disclosed is a gene delivery vehicle comprising at least one Ad35 element or a functional equivalent thereof, responsible for avoiding or diminishing neutralizing activity against adenoviral elements by the host to which the gene is to be delivered and a gene of interest. A functional equivalent/homologue of an Ad35 (element) for the purposes of the present invention is an adenovirus (element) which, like adenovirus 35, encounters pre-existing immunity in less than about 10% of the hosts to which it is administered for the first time, or which is capable in more than about 90% of the hosts to which it is administered of avoiding or diminishing the immune response.

Throughout the world, populations of humans can have varying pre-existing immunity profiles. For the present invention, the gene delivery vehicle of choice is preferably matched with a pre-existing immunity profile for the particular population in a particular geographic area. Typical examples of such adenoviruses are adenovirus serotypes 34, 26, 48 and 49.

A gene delivery vehicle may be based on Ad35 or a functional homologue thereof, but it may also be based on another backbone, such as that of adenovirus 2 or 5, so long as it comprises at least one of the elements from Ad35 or a functional equivalent thereof, which leads to a diminishment of the immune response against such an Ad2- or Ad5-based gene delivery vehicle. Of course, the gene delivery vehicle may also comprise elements from other (adeno) viruses, so long as one replaces an element that could lead to immunity against such a gene delivery vehicle by an element of Ad35 or a functional homologue thereof, which has less of such a drawback and which, preferably, avoids such a drawback.

In the present invention, a "gene delivery vehicle" is any vehicle capable of delivering a nucleic acid of interest to a host cell. It must, according to the invention, comprise an element of Ad35 or a functional equivalent thereof, which must have a beneficial effect regarding the immune response against such a vehicle. Basically, all other elements making up the vehicle can be any elements known in the art or developed in the art, as long as together they are capable of delivering the nucleic acid of interest. In principle, the person skilled in the art can use and/or produce any adenoviral products or production systems that can or have been applied in the adenoviral field. Typically, the products of the invention can be made in the packaging cells useable with, for example, Ad5, typically the vectors based on Ad35 can be produced and/or used in the same manner as those of other adenoviruses, for example, Ad2 and/or Ad5.

A good overview of the possibilities of minimal vectors, packaging systems, intracellular amplification, vector and plasmid-based systems can be found in co-pending, co-owned International Patent Application PCT/NL99/00235, published as International Patent Publication WO 9955132 on Nov. 4, 1999, or U.S. Pat. No. 5,994,128 to Bout et al., the entirety of both of which are incorporated herein by reference. Non-viral delivery systems can also be provided with elements according to the invention, as can viral delivery systems. Both kinds of systems are well known in the art in many different set-ups and do therefore not need any further elaboration here. A review on the many different systems and their properties can be found in Robbins and Ghivizzani (1998) and in Prince (1998), also incorporated herein by reference.

Gene delivery vehicles typically contain a nucleic acid of interest. A nucleic acid of interest can be a gene or a functional part of a gene (wherein a gene is any nucleic acid which can be expressed) or a precursor of a gene or a transcribed gene on any nucleic acid level (DNA and/or RNA: double- or single-stranded). Genes of interest are well known in the art and typically include those encoding therapeutic proteins such as TPA, EPO, cytokines, antibodies or derivatives thereof, etc.

An overview of therapeutic proteins to be applied in gene therapy is listed hereinafter. They include: immune-stimulatory factors like tumor-specific antigens, cytokines, etc.; anti-angiogenic factors, non-limiting examples of which are endostatin, angiostatin, ATF-BPTI CDT-6, dominant-negative VEGF-mutants, etc.; angiogenic factors, non-limiting examples of which are VEGF, fibroblast growth factors, nitric oxide synthases, C-type natriuretic peptide, etc.; inflammation inhibiting proteins like soluble CD40, FasL, IL-12, IL-10, IL-4, IL-13 and excreted single chain antibodies to CD4, CD5, CD7, CD52, Il-2, IL-1, IL-6, TNF, etc., or excreted single chain antibodies to the T-cell receptor on the auto-reactive T-cells. Also, dominant-negative mutants of PML may be used to inhibit the immune response.

Furthermore, antagonists of inflammation promoting cytokines may be used, for example, IL-1RA (receptor antagonist) and soluble receptors like sIL-1RI, sIL-1RII, sTNFRI and sTNFRII. Growth and/or immune response inhibiting genes such as ceNOS, Bcl3, cactus and IκBα, β or γ and apoptosis inducing proteins like the VP3 protein of chicken anemia virus may also be used. Furthermore, suicide genes like HSV-TK, cytosine deaminase, nitroreductase and linamerase may be used.

A nucleic acid of interest may also be a nucleic acid that can hybridize with a nucleic acid sequence present in the host cell thereby inhibiting expression or transcription or translation of the nucleic acid. It may also block through co-suppression. In short, a "nucleic acid of interest" is any nucleic acid that one may wish to provide a cell with in order to induce a response by that cell, such as production of a protein, inhibition of such production, apoptosis, necrosis, proliferation, differentiation, etc.

The present invention is the first to disclose adenovirus 35 or a functional homologue thereof, for therapeutic use, therefore, the invention also provides an Ad35 or a functional homologue thereof, or a chimeric virus derived therefrom, or a gene delivery vehicle based on the virus, its homologue or its chimera for use as a pharmaceutical. The serotype of the present invention, adenovirus type 35, is in itself known in the art. It is an uncommon group B adenovirus that was isolated from patients with acquired immunodeficiency syndrome and other immunodeficiency disorders (Flomenberg et al., 1987; De Jong et al., 1983). Ad35 has been shown to differ from the more fully characterized subgroup C (including Ad2 and Ad5) with respect to pathogenic properties (Basler et al., 1996). It has been suggested that this difference may be correlated with differences in the E3 region of the Ad35 genome (Basler et al., 1996). The DNA of Ad35 has been partially cloned and mapped (Kang et al., 1989a and b; Valderrama-Leon et al., 1985).

B-type adenovirus serotypes such as 34 and 35 have a different E3 region than other serotypes. Typically, this region is involved in suppressing immune response to adenoviral products. Thus, the invention provides a gene delivery vehicle according to the invention whereby the elements involved in avoiding or diminishing immune response comprise Ad35 E3 expression products or the genes encoding them or functional equivalents of either or both.

Another part of adenoviruses involved in immune responses is the capsid, in particular the penton and/or the hexon proteins. Thus, the invention also provides a gene delivery vehicle according to the invention whereby the elements comprise at least one Ad35-capsid protein or functional part thereof, such as fiber, penton and/or hexon proteins or a gene encoding at least one of them. It is not necessary that a whole protein relevant for immune response be of Ad35 (or a functional homologue thereof) origin. It is very well possible to insert a part of an adenovirus fiber, penton or hexon protein into another fiber, penton or hexon. Thus, chimeric proteins are obtained.

It is also possible to have a penton of a certain adenovirus, a hexon from another and a fiber or an E3 region from yet another adenovirus. According to the invention, at least one of the proteins or genes encoding them should comprise an element from Ad35 or a functional homologue thereof, whereby the element has an effect on the immune response of the host. Thus, the invention provides a gene delivery vehicle according to the invention, which is a chimera of Ad35 with at least one other adenovirus. In this way one can also modify the resulting virus in other aspects than the immune response alone. One can enhance its efficiency of infection with elements responsible therefor; one can enhance its replication on a packaging cell, or one can change its tropism.

Adenovirus serotypes differ in their natural tropism. The adenovirus serotypes 2, 4, 5 and 7 all have a natural affiliation towards lung epithelia and other respiratory tissues. In contrast, serotypes 40 and 41 have a natural affiliation towards the gastrointestinal tract. The serotypes described differ in at least capsid proteins (penton-base, hexon), proteins responsible for cell binding (fiber protein), and proteins involved in adenovirus replication. This difference in tropism and capsid protein among serotypes has led to the many research efforts aimed at redirecting the adenovirus tropism by modification of the capsid proteins. Thus, the invention, for example, provides a gene delivery vehicle according to the invention that has a different tropism than Ad35. Of course, the tropism should be altered preferably such that the gene delivery vehicle is delivered preferentially to a subset of the host's cells, i.e., the target cells. Changes in tropism and other changes that can also be applied in the present invention of adenoviral or other gene delivery vehicles are disclosed in co-pending, co-owned European Patent applications Nos. 98204482.8, 99200624.7 and 98202297.2, incorporated herein by reference. Of course, the present application also provides any and all building blocks necessary and/or useful to get to the gene delivery vehicles and/or the chimeras, etc., of the present invention. This includes packaging cells such as PER.C6 (ECACC deposit number 96022940) or cells based thereon, but adapted for Ad35 or a functional homologue thereof; it also includes any nucleic acids encoding functional parts of Ad35 or a functional homologue thereof, such as helper constructs and packaging constructs, as well as vectors comprising genes of interest and, e.g., an ITR, etc. Typically, the previously incorporated U.S. Pat. No. 5,994,128 to Bout et al. (Nov. 30, 1999) discloses elements necessary and useful for arriving at the invented gene delivery vehicles. Thus, the invention also provides a nucleic acid encoding at least a functional part of a gene delivery vehicle according to the invention, or a virus, homologue or chimera thereof, according to the invention. According to the invention, such elements, which encode functions that will end up in the resulting gene delivery vehicle must comprise or be encoded by a nucleic acid encoding at least one of the Ad35 elements or a functional equivalent thereof, responsible for avoiding or diminishing neutralizing activity against adenoviral elements by the host to which the gene is to be delivered. Typically, the gene of interest would be present on the same nucleic acid that means that such a nucleic acid has such a gene or that it has a site for introducing a gene of interest therein.

Typically, such a nucleic acid also comprises at least one ITR and, if it is a nucleic acid to be packaged, also a packaging signal. However, as mentioned before all necessary and useful elements and/or building blocks for the present invention can be found in the incorporated U.S. Pat. No. 5,994,128 to Bout et al. A set of further improvements in the field of producing adenoviral gene delivery vehicles is applicant's plasmid system disclosed in PCT/NL99/00235 incorporated herein before. This system works (in one embodiment) as a homologous recombination of an adapter plasmid and a longer plasmid, together comprising all elements of the nucleic acid to be incorporated in the gene delivery vehicle. These methods can also be applied to the presently invented gene delivery vehicles and their building elements. Thus, the invention also provides a nucleic acid according to the invention further comprising a region of nucleotides designed or useable for homologous recombination, preferably as part of at least one set of two nucleic acids comprising a nucleic acid according to the invention, whereby the set of nucleic acids is capable of a single homologous recombination event with each other, which leads to a nucleic acid encoding a functional gene delivery vehicle.

Both empty packaging cells (in which the vector to be packaged to make a gene delivery vehicle according to the invention still has to be introduced or produced) as well as cells comprising a vector according to the invention to be packaged are provided. Thus, the invention also encompasses a cell comprising a nucleic acid according to the invention or a set of nucleic acids according to the invention, preferably a cell which complements the necessary elements for adenoviral replication which are absent from the nucleic acid to be packaged, or from a set of nucleic acids according to the invention. In the present invention, it has been found that E1-deleted Ad35 vectors are not capable of replication on cells that provide adenovirus 5 proteins in trans. The invention therefore further provides a cell capable of providing Ad35 E1 proteins in trans. Such a cell is typically a human cell derived from the retina or the kidney. Embryonic cells, such as amniocytes, have been shown to be particularly suited for the generation of an E1-complementing cell line. Such cells are therefore preferred in the present invention. Serotype-specific complementation by E1 proteins can be due to one or more protein(s) encoded by the E1 region. It is therefore essential that at least the serotype-specific protein be provided in trans in the complementing cell line. The non-serotype-specific E1 proteins essential for effective complementation of an E1-deleted adenovirus can be derived from other adenovirus serotypes. Preferably, at least an E1 protein from the E1B region of Ad35 is provided in trans to complement E1-deleted Ad35-based vectors. In one embodiment, nucleic acid encoding the one or more serotype-specific E1 proteins is introduced into the PER.C6 cell or a cell originating from a PER.C6 cell, or a similar packaging cell complementing with elements from Ad35 or a functional homologue thereof.

As already alluded to, the invention also encompasses a method for producing a gene delivery vehicle according to the invention, comprising expressing a nucleic acid according to the invention, in a cell according to the invention, and harvesting the resulting gene delivery vehicle. The above refers to the filling of the empty packaging cell with the relevant nucleic acids. The format of the filled cell is, of course, also part of the present invention, which provides a method for producing a gene delivery vehicle according to the invention, comprising culturing a filled packaging cell (producer cell) according to the invention in a suitable culture medium and harvesting the resulting gene delivery vehicle.

The resulting gene delivery vehicles obtainable by any method according to the invention are, of course, also part of the present invention, particularly also a gene delivery vehicle which is derived from a chimera of an adenovirus and an integrating virus.

Adenoviral gene delivery vehicles do not normally integrate into the host genome. For long-term expression of genes in a host cell, it is therefore preferred to prepare chimeras that do have that capability. Such chimeras have been disclosed in co-pending, co-owned International Patent Application PCT/NL98/00731, International Patent Publication WO 99/32647, published Jul. 1, 1999, incorporated herein by reference. A very good example of a chimera of an adenovirus and an integrating virus is where the integrating virus is an adeno-associated virus. As discussed hereinbefore, other useful chimeras, which can also be combined with the above, are chimeras (be it in swapping whole proteins or parts thereof or both) that have altered tropism. A very good example thereof is a chimera of Ad35 and Ad16, possibly with elements from, for instance, Ad2 or Ad5, wherein the tropism determining part of Ad16 or a functional equivalent thereof is used to direct the gene delivery vehicle to synoviocytes and/or smooth muscle cells (see European patent applications nos. 98204482.8 and 99200624.7, corresponding to European Patent Publication 1,016,726, published Jul. 5, 2000, and International Patent Publication WO 00/52186, published Sep. 8, 2000, the entirety of both of which are incorporated herein by reference). Dendritic cells ("DC") and hemopoietic stem cells ("HSC") are not easily transduced with Ad2- or Ad5-derived gene delivery vehicles. The present invention provides gene delivery vehicles that possess increased transduction capacity of DC and HSC cells. Such gene delivery vehicles at least comprise the tissue tropism determining part of an Ad35 adenovirus. The invention therefore further provides the use of a tissue tropism determining part of an Ad35 capsid for transducing dendritic cells and/or hemopoietic stem cells. Other B-type adenoviruses are also suited. A tissue tropism determining part comprises at least the knob and/or the shaft of a fiber protein. Of course, it is very well possible for a person skilled in the art to determine the amino acid sequences responsible for the tissue tropism in the fiber protein. Such knowledge can be used to devise chimeric proteins comprising such amino acid sequences. Such chimeric proteins are therefore also part of the invention.

DCs are very efficient antigen presenting cells. By introducing the gene delivery vehicle into such cells, the host's immune system can be triggered toward specific antigens. Such antigens can be encoded by nucleic acid delivered to the DC or by the proteins of the gene delivery vehicle itself. The present invention therefore also provides a gene delivery vehicle with the capacity to evade the host immune system as a vaccine. The vector being capable of evading the immune system long enough to efficiently find target cells and at the same time capable of delivering specific antigens to antigen presenting cells thereby allowing the induction and/or stimulation of efficient immune responses toward the specific antigen(s). To further modulate the immune response, the gene delivery vehicle may comprise proteins and/or nucleic acids encoding such proteins capable of modulating an immune response. Non-limiting examples of such proteins are found among the interleukins, adhesion molecules, co-stimulatory proteins, the interferons, etc. The invention therefore further provides a vaccine comprising a gene delivery vehicle of the invention. The invention further provides an adenovirus vector with the capacity to efficiently transduce DC and/or HSC, the vehicle comprising at least a tissue tropism determining part of Ad35. The invention further provides the use of such delivery vehicles for the transduction of HSC and/or DC cells. Similar tissue tropisms are found among other adenoviruses of serotype B, particularly in Ad11 and are also part of the invention. Of course, it is also possible to provide other gene delivery vehicles with the tissue tropism determining part thereby providing such delivery vehicles with an enhanced DC and/or HSC transduction capacity. Such gene delivery vehicles are therefore also part of the invention.

The gene delivery vehicles according to the invention can be used to deliver genes or nucleic acids of interest to host cells. Such use will typically be a pharmaceutical one. Such a use is included in the present invention. Compositions suitable for such a use are also part of the present invention. The amount of gene delivery vehicle that needs to be present per dose or per infection ("m.o.i.") will depend on the condition to be treated, the route of administration (typically parenteral) the subject and the efficiency of infection, etc. Dose finding studies are well known in the art and those already performed with other (adenoviral) gene delivery vehicles can typically be used as guides to find suitable doses of the gene delivery vehicles according to the invention. Typically, this is also where one can find suitable excipients, suitable means of administration, suitable means of preventing infection with the vehicle where it is not desired, etc. Thus, the invention also provides a pharmaceutical formulation comprising a gene delivery vehicle according to the invention and a suitable excipient, as well as a pharmaceutical formulation comprising an adenovirus, a chimera thereof, or a functional homologue thereof according to the invention and a suitable excipient.

BRIEF DESCRIPTION OF THE FIGURES

FIG. 3: Schematic representation of a partial restriction map of Ad35 (taken from Kang et al., 1989) and the clones generated to make recombinant Ad35-based viruses.

FIG. 4: Bar graph presenting the percentage sera samples that show neutralizing activity to a selection of adenovirus serotypes. Sera were derived from healthy volunteers from Belgium and the UK.

FIG. 5: Bar graph presenting the percentage sera samples that show neutralizing activity to adenovirus serotypes 5, 11, 26, 34, 35, 48 and 49. Sera were derived from five different locations in Europe and the United States.

FIG. 6: Sequence of human adenovirus type 35 (SEQ ID NO:82).

FIG. 23: Alignment of the chimeric fiber proteins of Ad5fib16, Ad5fib35 and Ad5fib51 with the Ad5 fiber sequence (from top to bottom, SEQ ID NOs:86, 83, 84, and 85).

FIG. 30: Temperature-dependent growth of PER.C6. PER.C6 cells were cultured in DMEM supplemented with 10% FBS (Gibco BRL) and 10 mM MgCl$_2$ in a 10% CO$_2$ atmosphere at 32° C., 37° C. or 39° C. At day 0, a total of 1×10$^6$ PER.C6 cells were seeded per 25 cm$^2$ tissue culture flask (Nunc) and the cells were cultured at 32° C., 37° C. or 39° C. At day 1-8, cells were counted. The growth rate and the final cell density of the PER.C6 culture at 39° C. are comparable to that at 37° C. The growth rate and final density of the PER.C6 culture at 32° C. were slightly reduced as compared to that at 37° C. or 39° C. PER.C6 cells were seeded at a density of 1×10$^6$ cells per 25 cm$^2$ tissue culture flask and cultured at 32°, 37° or 39° C. At the indicated time points, cells were counted in a Burker cell counter. PER.C6 grows well at 32°, 37° and 39° C.

FIG. 31: DBP levels in PER.C6 cells transfected with pcDNA3, pcDNA3wtE2A or pcDNA3ts125E2A. Equal amounts of whole-cell extract were fractionated by SDS-PAGE on 10% gels. Proteins were transferred onto Immobilon-P membranes and DBP protein was visualized using the αDBP monoclonal B6 in an ECL detection system. All of the cell lines derived from the pcDNA3ts125E2A transfection express the 72-kDa E2A-encoded DBP protein (left panel: lanes 4-14; middle panel: lanes 1-13; right panel: lanes 1-12). In contrast, the only cell line derived from the pcDNAwtE2A transfection did not express the DBP protein (left panel, lane 2). No DBP protein was detected in extract from a cell line derived from the pcDNA3 transfection (left panel, lane 1), which serves as a negative control. Extract from PER.C6 cells transiently transfected with pcDNA3ts125 (left panel, lane 3) served as a positive control for the Western blot procedure. These data confirm that constitutive expression of wtE2A is toxic for cells and that using the ts125 mutant of E2A can circumvent this toxicity.

FIG. 32: Suspension growth of PER.C6ts125E2A C5-9. The tsE2A-expressing cell line PER.C6tsE2A.c5-9 was cultured in suspension in serum-free Ex-cellä. At the indicated time points, cells were counted in a Burker cell counter. The results of 8 independent cultures are indicated. PER.C6tsE2A grows well in suspension in serum-free Ex-cellä medium.

FIG. 33: Growth curve PER.C6 and PER.C6tsE2A. PER.C6 cells or PER.C6ts125E2A (c8-4) cells were cultured at 37° C. or 39° C., respectively. At day 0, a total of 1×10$^6$ cells were seeded per 25 cm$^2$ tissue culture flask. At the indicated time points, cells were counted. The growth of PER.C6 cells at 37° C. is comparable to the growth of PER.C6ts125E2A c8-4 at 39° C. This shows that constitutive over-expression of ts125E2A has no adverse effect on the growth of cells at the non-permissive temperature of 39° C.

FIG. 34: Stability of PER.C6ts125E2A. For several passages, the PER.C6ts125E2A cell line clone 8-4 was cultured at 39° C. in medium without G418. Equal amounts of whole-cell extract from different passage numbers were fractionated by SDS-PAGE on 10% gels. Proteins were transferred onto Immobilon-P membranes and DBP protein was visualized using the αDBP monoclonal B6 in an ECL detection system. The expression of ts125E2A encoded DBP is stable for at least 16 passages, which is equivalent to approximately 40 cell doublings. No decrease in DBP levels was observed during this culture period, indicating that the expression of ts125E2A is stable, even in the absence of G418 selection pressure.

FIG. 35: tTA activity in hygromycin-resistant PER.C6/tTA (A) and PER/E2A/tTA (B) cells. Sixteen independent hygromycin-resistant PER.C6/tTA cell colonies and 23 independent hygromycin-resistant PER/E2A/tTA cell colonies were grown in 10 cm$^2$ wells to sub-confluency and transfected with 2 µg of pUHC 13-3 (a plasmid that contains the reporter gene luciferase under the control of the 7xtetO promoter). One half of the cultures were maintained in medium containing doxycycline to inhibit the activity of tTA. Cells were harvested at 48 hours after transfection and luciferase activity was measured. The luciferase activity is indicated in relative light units (RLU) per µg protein.

DETAILED DESCRIPTION OF THE INVENTION

Figure 1:
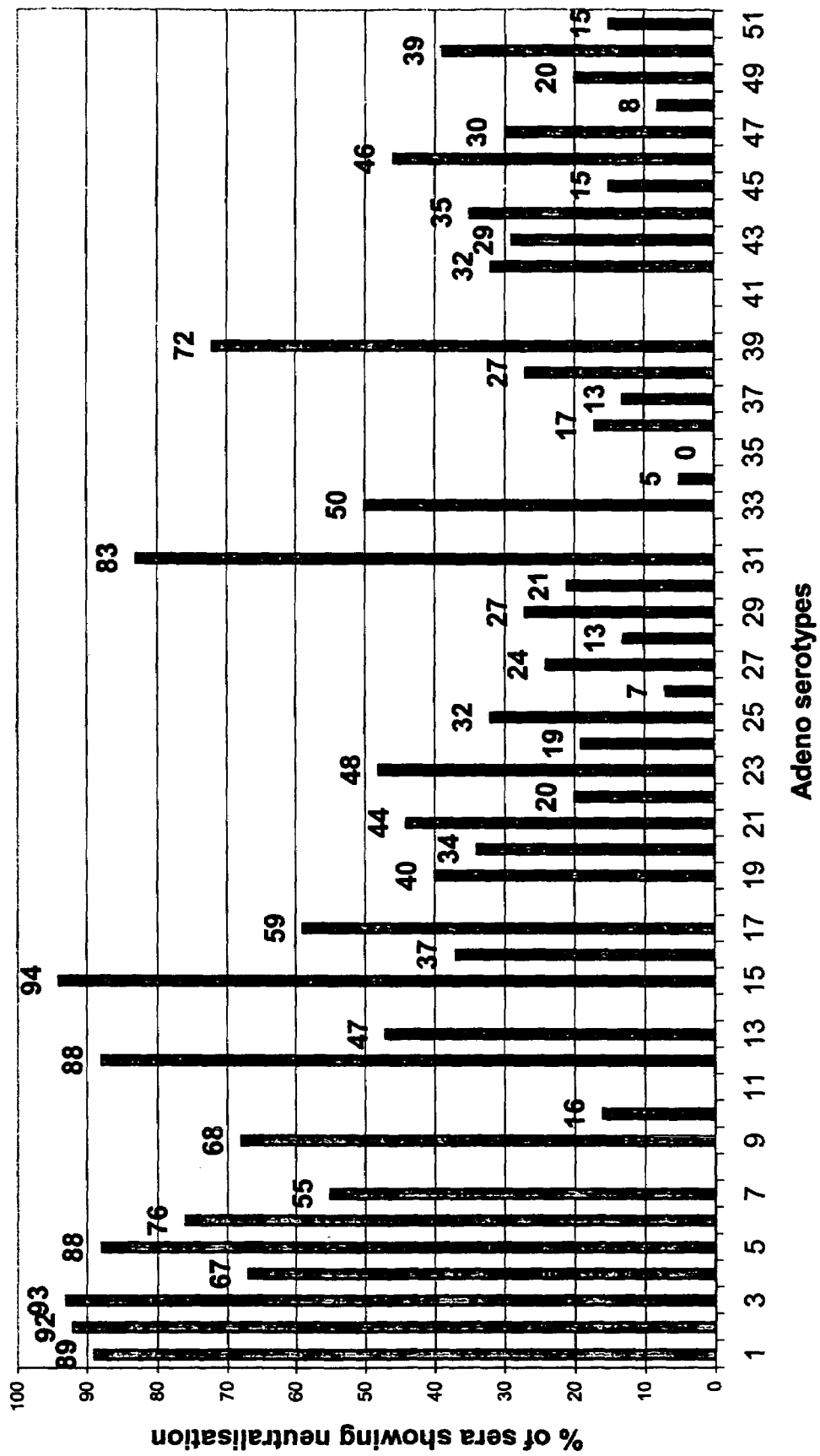
FIG. 1: Bar graph showing the percentage of serum samples positive for neutralization for each human wt adenovirus tested (see Example 1 for description of the neutralization assay).

As previously stated, the most extensively studied serotypes of adenovirus are not ideally suited for delivering additional genetic material to host cells. This fact is partially due to the pre-existing immunity among the population against these serotypes. This presence of pre-existing antibodies in humans, in combination with a strong secondary humoral and cellular immune response against the virus will affect adenoviral gene therapy.

The present invention provides the use of at least elements of a serotype and functional homologues thereof of adenovirus that are very suitable as gene therapy vectors. The present invention also discloses an automated high-throughput screening of all known adenovirus serotypes against sera from many individuals. Surprisingly, no neutralizing ability was found in any of the sera that were evaluated against one particular serotype, adenovirus 35 ("Ad35"). This makes the serotype of the present invention extremely useful as a vector system for gene therapy in man. Such a vector system is capable of efficiently transferring genetic material to a human cell without the inherent problem of pre-existing immunity.

Typically, a virus is produced using an adenoviral vector (typically a plasmid, cosmid, or baculovirus vector). Such vectors are, of course, also part of the present invention.

The invention also provides adenovirus-derived vectors that have been rendered replication defective by deletion or inactivation of the E1 region. Of course, a gene of interest can also be inserted at, for instance, the site of E1 of the original adenovirus from which the vector is derived.

In all aspects of the invention, the adenoviruses may contain deletions in the E1 region and insertions of heterologous genes either linked or not to a promoter. Furthermore, the adenoviruses may contain deletions in the E2, E3 or E4 regions and insertions of heterologous genes linked to a promoter. In these cases, E2- and/or E4-complementing cell lines are used to generate recombinant adenoviruses.

One may choose to use the Ad35 serotype itself for the preparation of recombinant adenoviruses to be used in gene therapy. Alternatively, one may choose to use elements derived from the serotype of the present invention in such recombinant adenoviruses. One may, for instance, develop a chimeric adenovirus that combines desirable properties from different serotypes. Some serotypes have a somewhat limited host range, but have the benefit of being less immunogenic; while others are the other way around. Some have a problem of being of a limited virulence, but have a broad host range and/or a reduced immunogenicity. Such chimeric adenoviruses are known in the art, and they are intended to be within the scope of the present invention. Thus, in one embodiment, the invention provides a chimeric adenovirus comprising at least a part of the adenovirus genome of the present serotype, providing it with absence of pre-existing immunity, and at least a part of the adenovirus genome from another adenovirus serotype resulting in a chimeric adenovirus. In this manner, the chimeric adenovirus produced is such that it combines the absence of pre-existing immunity of the serotype of the present invention, to other characteristics of another serotype. Such characteristics may be temperature stability, assembly, anchoring, redirected infection, production yield, redirected or improved infection, stability of the DNA in the target cell, etc.

A packaging cell will generally be needed in order to produce sufficient amount of adenoviruses. For the production of recombinant adenoviruses for gene therapy purposes, several cell lines are available. These include but are not limited to the known cell lines PER.C6, 911, 293, and E1 A549.

An important feature of the present invention is the means to produce the adenovirus. Typically, one does not want an adenovirus batch for clinical applications to contain replication competent adenovirus. In general, therefore, it is desired to omit a number of genes (but at least one) from the adenoviral genome on the adenoviral vector and to supply these genes in the genome of the cell in which the vector is brought to produce chimeric adenovirus. Such a cell is usually called a "packaging cell." The invention thus also provides a packaging cell for producing an adenovirus (a gene delivery vehicle) according to the invention, comprising in trans all elements necessary for adenovirus production not present on the adenoviral vector according to the invention. Typically, vectors and packaging cells have to be adapted to one another so that they have all the necessary elements, but do not have overlapping elements which lead to replication competent virus by recombination.

Thus, the invention also provides a kit of parts comprising a packaging cell according to the invention and a recombinant vector according to the invention wherein essentially no sequence overlap leading to recombination resulting in the production of replication competent adenovirus exists between the cell and the vector.

Thus, the invention provides methods for producing adenovirus, which, upon application, will escape pre-existing humoral immunity. Such methods include providing a vector with elements derived from an adenovirus serotype against which virtually no natural immunity exists and transfecting the vector in a packaging cell according to the invention and allowing for production of viral particles.

In one aspect, the invention includes the use of the adenovirus serotype of the present invention to overcome naturally existing or induced, neutralizing host activity towards adenoviruses administered in vivo for therapeutic applications. The need for a new serotype is stressed by observations that 1) repeated systemic delivery of recombinant Ad5 is unsuccessful due to the formation of high titers of neutralizing antibodies against recombinant Ad5 (Schulick et al., 1997), and 2) pre-existing or humoral immunity is already widespread in the population.

In another aspect, the invention provides the use of gene delivery vehicles of the invention or the use of Ad35 for vaccination purposes. Such use prevents, at least in part, undesired immune responses of the host. Non-limiting examples of undesired immune responses include evoking an immune response against the gene delivery vehicle or Ad35 and/or boosting an immune response against the gene delivery vehicle or Ad35.

In another aspect of the invention, alternating use is made of Ad vectors belonging to different subgroups. This aspect of the invention therefore circumvents the inability to repeat the administration of an adenovirus for gene therapy purposes.

The invention is further explained by the use of the following illustrative Examples.

EXAMPLES

Example 1

A High Throughput Assay for the Detection of Neutralizing Activity in Human Serum To enable screening of a large amount of human sera for the presence of neutralizing antibodies against all adenovirus serotypes, an automated 96-wells assay was developed.

Human Sera

A panel of 100 individuals was selected. Volunteers (50% male, 50% female) were healthy individuals between ages 20 and 60 years old with no restriction for race. All volunteers signed an informed consent form. People professionally involved in adenovirus research were excluded.

Approximately 60 ml of blood was drawn in dry tubes. Within two hours after sampling, the blood was centrifuged at 2500 rpm for 10 minutes. Approximately 30 ml serum was transferred to polypropylene tubes and stored frozen at −20° C. until further use.

Serum was thawed and heat-inactivated at 56° C. for 10 minutes and then aliquoted to prevent repeated cycles of freeze/thawing. Part was used to make five steps of twofold dilutions in medium (DMEM, Gibco BRL) in a quantity enough to fill out approximately 70 96-well plates. Aliquots of undiluted and diluted sera were pipetted in deep-well plates (96-well format) and, using a programmed platemate, dispensed in 100 μl aliquots into 96-well plates. This way the plates were loaded with eight different sera in duplo (100 μl/well) according to the scheme below:

| S1/2 | S1/4 | S1/8 | S1/16 | S1/32 | S5/2 | S5/4 | S5/8 | S5/16 | S5/32 | — | — |
|------|------|------|-------|-------|------|------|------|-------|-------|---|---|
| S1/2 | S1/4 | S1/8 | S1/16 | S1/32 | S5/2 | S5/4 | S5/8 | S5/16 | S5/32 | — | — |
| S2/2 | S2/4 | S2/8 | S2/16 | S2/32 | S6/2 | S6/4 | S6/8 | S6/16 | S6/32 | — | — |
| S2/2 | S2/4 | S2/8 | S2/16 | S2/32 | S6/2 | S6/4 | S6/8 | S6/16 | S6/32 | — | — |
| S3/2 | S3/4 | S3/8 | S3/16 | S3/32 | S7/2 | S7/4 | S7/8 | S7/16 | S7/32 | — | — |
| S3/2 | S3/4 | S3/8 | S3/16 | S3/32 | S7/2 | S7/4 | S7/8 | S7/16 | S7/32 | — | — |
| S4/2 | S4/4 | S3/8 | S3/16 | S3/32 | S8/2 | S8/4 | S8/8 | S8/16 | S8/32 | — | — |
| S4/2 | S4/4 | S3/8 | S3/16 | S3/32 | S8/2 | S8/4 | S8/8 | S8/16 | S8/32 | — | — |

Where S1/2 to S8/2 in columns 1 and 6 represent 1× diluted sera and Sx/4, Sx/8, Sx/16 and Sx/32 the twofold serial dilutions. The last plates also contained four wells filled with 100 μl fetal calf serum as a negative control.

Plates were kept at −20° C. until further use.

Preparation of Human Adenovirus Stocks

Prototypes of all known human adenoviruses were inoculated on T25 flasks seeded with PER.C6 cells (Fallaux et al., 1998) and harvested upon full CPE. After freeze/thawing, 1-2 ml of the crude lysates was used to inoculate a T80 flask with PER.C6 and virus was harvested at full CPE. The timeframe between inoculation and occurrence of CPE as well as the amount of virus needed to re-infect a new culture differed between serotypes. Adenovirus stocks were prepared by freeze/thawing and used to inoculate 3-4 T175 cm$^2$ three-layer flasks with PER.C6 cells. Upon occurrence of CPE, cells were harvested by tapping the flask, pelleted and virus was isolated and purified by a two-step CsCl gradient as follows. Cell pellets were dissolved in 50 ml 10 mM NaPO$_4$ buffer (pH 7.2) and frozen at −20° C. After thawing at 37° C., 5.6 ml sodium deoxycholate (5% w/v) was added. The solution was mixed gently and incubated for 5-15 minutes at 37° C. to completely lyse the cells. After homogenizing the solution, 1875 μl 1 M MgCl$_2$ was added. After the addition of 375 μl DNAse (10 mg/ml) the solution was incubated for 30 minutes at 37° C. Cell debris was removed by centrifugation at 1880×g for 30 minutes at RT without brake. The supernatant was subsequently purified from proteins by extraction with FREON (3×). The cleared supernatant was loaded on a 1 M Tris/HCl buffered cesium chloride block gradient (range: 1.2/1.4 g/ml) and centrifuged at 21,000 rpm for 2.5 hours at 10° C. The virus band was isolated after which a second purification using a 1 M Tris/HCl buffered continuous gradient of 1.33 g/ml of cesium chloride was performed. The virus was then centrifuged for 17 hours at 55,000 rpm at 10° C. The virus band was isolated and sucrose (50% w/v) was added to a final concentration of 1%. Excess cesium chloride was removed by dialysis (three times 1 hr at RT) in dialysis slides (Slide-a-lizer, cut off 10,000 kDa, Pierce, USA) against 1.5 liter PBS supplemented with CaCl$_2$ (0.9 mM), MgCl$_2$ (0.5 mM) and an increasing concentration of sucrose (1, 2, 5%). After dialysis, the virus was removed from the slide-a-lizer after which it was aliquoted in portions of 25 and 100 μl upon which the virus was stored at −85° C.

To determine the number of virus particles per milliliter, 50 μl of the virus batch was run on a high-pressure liquid chromatograph (HPLC) as described by Shabram et al. (1997). Viruses were eluted using a NaCl gradient ranging from 0 to 600 mM. As depicted in table I, the NaCl concentration by which the viruses were eluted differed significantly among serotypes.

Most human adenoviruses replicated well on PER.C6 cells with a few exceptions. Adenovirus type 8 and 40 were grown on 911-E4 cells (He et al., 1998). Purified stocks contained between $5 \times 10^{10}$ and $5 \times 10^{12}$ virus particles/ml (VP/ml; see Table I).

Titration of Purified Human Adenovirus Stocks

Adenoviruses were titrated on PER.C6 cells to determine the amount of virus necessary to obtain full CPE in five days, the length of the neutralization assay. Hereto, 100 μl medium was dispensed into each well of 96-well plates. 25 μl of adenovirus stocks pre-diluted $10^4$, $10^5$, $10^6$ or $10^7$ times were added to column 2 of a 96-well plate and mixed by pipetting up and down 10 times. Then 25 μl was brought from column 2 to column 3 and again mixed. This was repeated until column 11, after which, 25 μl from column 11 was discarded. This way, serial dilutions in steps of 5 were obtained starting off from a pre-diluted stock. Then $3 \times 10^4$ PER.C6 cells (ECACC deposit number 96022940) were added in a 100 μl volume and the plates were incubated at 37° C., 5% CO$_2$ for five or six days. CPE was monitored microscopically. The method of Reed and Muensch was used to calculate the cell culture-inhibiting dose 50% (CCID$_{50}$).

In parallel, identical plates were set up that were analyzed using the MTT assay (Promega). In this assay living cells are quantified by colorimetric staining. Hereto, 20 μl MTT (7.5 mgr/ml in PBS) was added to the wells and incubated at 37° C., 5% CO$_2$ for two hours. The supernatant was removed and 100 μl of a 20:1 isopropanol/triton-X100 solution was added to the wells. The plates were put on a 96-wells shaker for 3-5 minutes to solubilize the precipitated staining. Absorbance was measured at 540 nm and at 690 nm (background). By this assay, wells with proceeding CPE or full CPE can be distinguished.

Neutralization Assay 96-well plates with diluted human serum samples were thawed at 37° C., 5% CO$_2$. Adenovirus stocks diluted to 200 CCID$_{50}$ per 50 μl were prepared and 50 μl aliquots were added to columns 1-11 of the plates with serum. Plates were incubated for 1 hour at 37° C., 5% CO$_2$. Then 50 μl PER.C6 cells at $6 \times 10^5$/ml were dispensed in all wells and incubated for 1 day at 37° C., 5% CO$_2$. Supernatant was removed using fresh pipette tips for each row and 200 μl fresh medium was added to all wells to avoid toxic effects of the serum. Plates were incubated for another 4 days at 37° C., 5% CO$_2$. In addition, parallel control plates were set up in duplo with diluted positive control sera generated in rabbits and specific for each serotype to be tested in rows A and B and with negative control serum (FCS) in rows C and D. Also, in each of the rows E-H a titration was performed as described above with steps of five times dilutions starting with 200 CCID$_{50}$ of each virus to be tested. On day 5, one of the control plates was analyzed microscopically and with the MTT assay. The experimental titer was calculated from the control titration plate observed microscopically. If CPE was found to be complete, i.e., the first dilution in the control titration experiment analyzed by MTT shows clear cell death, all assay plates were processed. If not, the assay was allowed to proceed for one or more days until full CPE was apparent after which all plates were processed. In most cases, the assay was terminated at day 5. For Ad1, 5, 33, 39, 42 and 43 the assay was left for six days and for Ad2 for eight days.

A serum sample is regarded as "non-neutralizing" when, at the highest serum concentration, a maximum protection of 40% is seen compared to controls without serum.

The results of the analysis of 44 prototype adenoviruses against serum from 100 healthy volunteers are shown in FIG. 1. As expected, the percentage of serum samples that contained neutralizing antibodies to Ad2 and Ad5 was very high. This was also true for most of the lower numbered adenoviruses. Surprisingly, none of the serum samples contained neutralizing antibodies to Ad35. Also, the number of individuals with neutralizing antibody titers to the serotypes 26, 34 and 48 was very low. Therefore, recombinant E1-deleted adenoviruses based on Ad35 or one of the other above mentioned serotypes have an important advantage compared to recombinant vectors based on Ad5 with respect to clearance of the viruses by neutralizing antibodies.

Also, Ad5-based vectors that have (parts of) the capsid proteins involved in immunogenic response of the host replaced by the corresponding (parts of) the capsid proteins of Ad35 or one of the other serotypes will be less, or even not, neutralized by the vast majority of human sera.

Figure 2:
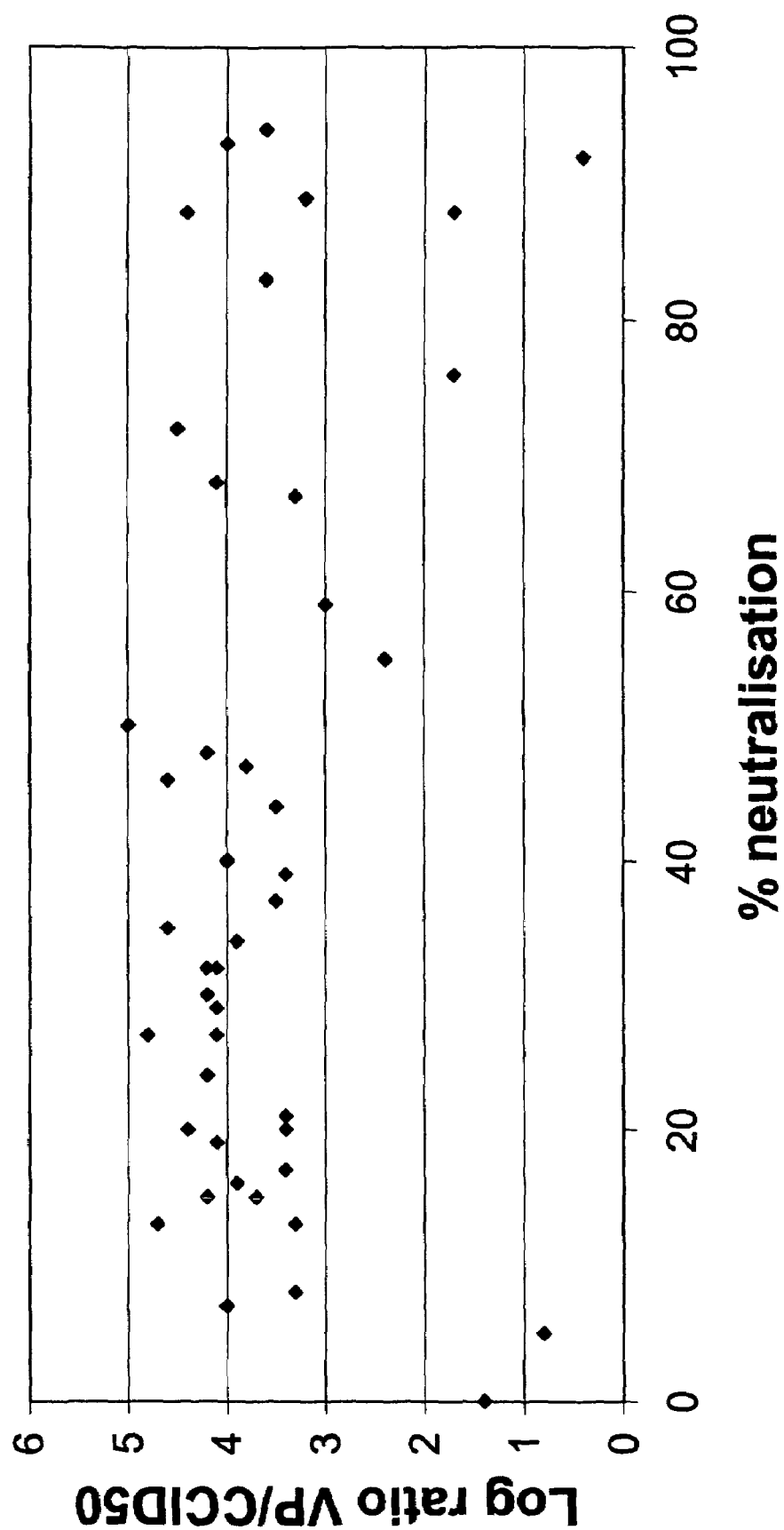
FIG. 2: Graph showing absence of correlation between the $VP/CCID_{50}$ ratio and the percentage of neutralization.

As can be seen in Table I, the $VP/CCID_{50}$ ratio calculated from the virus particles per ml and the $CCID_{50}$ obtained for each virus in the experiments was highly variable, and ranged from 0.4 to 5 per log. This is probably caused by different infection efficiencies of PER.C6 cells and by differences in replication efficiency of the viruses. Furthermore, differences in batch qualities may play a role. A high $VP/CCID_{50}$ ratio means that more viruses were put in the wells to obtain CPE in 5 days. As a consequence, the outcome of the neutralization study might be biased since more (inactive) virus particles could shield the antibodies. To check whether this phenomenon had taken place, the $VP/CCID_{50}$ ratio was plotted against the percentage of serum samples found positive in the assay (FIG. 2). The graph clearly shows that there is no negative correlation between the amount of viruses in the assay and neutralization in serum.

Example 2

Generation of Ad5 Plasmid Vectors for the Production of Recombinant Viruses and Easy Manipulation of Adenoviral Genes pBr/Ad.Bam-rITR (ECACC Deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322-derived vector DNA prepared as follows: pBr322 DNA was digested with EcoRV and BamHI, dephosphorylated by treatment with TSAP enzyme (Life Technologies) and purified on LMP agarose gel (SeaPlaque GTG). After transformation into competent *E. coli* DH5α (Life Techn.) and analysis of ampicillin-resistant colonies, one clone was selected that showed a digestion pattern as expected for an insert extending from the BamHI site in Ad5 to the right ITR.

Sequence analysis of the cloning border at the right ITR revealed that the most 3' G residue of the ITR was missing, the remainder of the ITR was found to be correct. The missing G residue is complemented by the other ITR during replication.

pBr/Ad.Sal-rITR (ECACC Deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt Ad5 DNA and purified with the GENECLEAN II kit (Bio101, Inc.). One clone was chosen and the integrity of the Ad5 sequences was determined by restriction enzyme analysis. Clone pBr/Ad.Sal-rITR contains Ad5 sequences from the SalI site at bp 16746 up to and including the rITR (missing the most 3' G residue).

pBr/Ad.Cla-Bam (ECACC Deposit P97082117)

Wild-type ("wt") Ad5 DNA was digested with ClaI and BamHI, and the 20.6 kb fragment was isolated from gel by electro-elution. pBr322 was digested with the same enzymes and purified from agarose gel by GENECLEAN. Both fragments were ligated and transformed into competent DH5α. The resulting clone pBr/Ad.Cla-Bam was analyzed by restriction enzyme digestion and shown to contain an insert with adenovirus sequences from bp 919 to 21566.

pBr/Ad.AflII-Bam (ECACC Deposit P97082114)

Clone pBr/Ad.Cla-Bam was linearized with EcoRI (in pBr322) and partially digested with AflII. After heat inactivation of AflII for 20 minutes at 65° C., the fragment ends were filled in with Klenow enzyme. The DNA was then ligated to a blunt double-stranded oligo linker containing a PacI site (5'-AATTGTCTTAATTAACCGCTTA 3'(SEQ ID NO:1)). This linker was made by annealing the following two oligonucleotides: 5'-AATTGTCTTAATTAACCGC 3'(SEQ ID NO:2) and 5'-AATTGCGGTTAATTAAGAC 3'(SEQ ID NO:3), followed by blunting with Klenow enzyme. After precipitation of the ligated DNA to change buffer, the ligations were digested with an excess PacI enzyme to remove concatameres of the oligo. The 22016 bp partial fragment containing Ad5 sequences from bp 3534 up to 21566 and the vector sequences, was isolated in LMP agarose (SeaPlaque GTG), re-ligated and transformed into competent DH5α. One clone that was found to contain the PacI site and that had retained the large adeno fragment was selected and sequenced at the 5' end to verify correct insertion of the PacI linker in the (lost) AflII site.

pBr/Ad.Bam-rITRpac#2 (ECACC Deposit P97082120) and pBr/Ad.Bam-rITRpac#8 (ECACC Deposit P97082121)

To allow insertion of a PacI site near the ITR of Ad5 in clone pBr/Ad.Bam-rITr, about 190 nucleotides were removed between the ClaI site in the pBr322 backbone and the start of the ITR sequences. This was done as follows: pBr/Ad.Bam-rITR was digested with ClaI and treated with nuclease Bal3 for varying lengths of time (2 minutes, 5 minutes, 10 minutes and 15 minutes). The extent of nucleotide removal was followed by separate reactions on pBr322 DNA (also digested at the ClaI site), using identical buffers and conditions. Bal31 enzyme was inactivated by incubation at 75° C. for 10 minutes, the DNA was precipitated and re-suspended in a smaller volume TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10 minutes or 15 minutes. The 10 minute- or 15 minute-treated pBr/Ad.Bam-rITR samples were then ligated to the above described blunted PacI linkers (see pBr/Ad.AflII-Bam). Ligations were purified by precipitation, digested with excess PacI and separated from the linkers on an LMP agarose gel. After re-ligation, DNAs were transformed into competent DH5α and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

pWE/Ad.AflII-rITR (ECACC Deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double-stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using λ1 phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

pBr/Ad.lITR-Sal(9.4) (ECACC Deposit P97082115)

Adeno 5 wt DNA was treated with Klenow enzyme in the presence of excess dNTPs and subsequently digested with SalI. Two of the resulting fragments, designated left ITR-Sal(9.4) and Sal(16.7)-right ITR, respectively, were isolated in LMP agarose (SeaPlaque GTG). pBr322 DNA was digested with EcoRV and SalI and treated with phosphatase (Life Technologies). The vector fragment was isolated using the GENECLEAN method (Bio101, Inc.) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9462.

pBr/Ad.lITR-Sal(16.7) (ECACC Deposit P97082118)

pBr/Ad.lITR-Sal(9.4) is digested with SalI and dephosphorylated (TSAP, Life Technologies). To extend this clone up to the third SalI site in Ad5, pBr/Ad.Cla-Bam was linearized with BamHI and partially digested with SalI. A 7.3 kb SalI fragment containing adenovirus sequences from 9462-16746 was isolated in LMP agarose gel and ligated to the SalI-digested pBr/Ad.lITR-Sal(9.4) vector fragment.

pWE/Ad.AflII-EcoRI pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534-27336.

Generation of pWE/Ad.AflII-rITRsp

The 3' ITR in the vector pWE/Ad.AflII-rITR does not include the terminal G-nucleotide. Furthermore, the PacI site is located almost 30 bp from the right ITR. Both these characteristics may decrease the efficiency of virus generation due to inefficient initiation of replication at the 3' ITR. Note that during virus generation, the left ITR in the adapter plasmid is intact and enables replication of the virus DNA after homologous recombination.

To improve the efficiency of initiation of replication at the 3' ITR, the pWE/Ad.AflII-rITR was modified as follows: construct pBr/Ad.Bam-rITRpac#2 was first digested with PacI and then partially digested with AvrII and the 17.8 kb vector containing fragment was isolated and dephosphorylated using SAP enzyme (Boehringer Mannheim). This fragment lacks the adenovirus sequences from nucleotide 35464 to the 3'ITR. Using DNA from pWE/Ad.AflII-rITR as template and the primers: ITR-EPH: 5'-CGG AAT TCT TAA TTA AGT TAA CAT CAT CAA TAA TAT ACC-3' (SEQ ID NO:4) and Ad101: 5'-TGA TTC ACA TCG GTC AGT GC-3'(SEQ ID NO:5).

A 630 bp PCR fragment was generated corresponding to the 3' Ad5 sequences. This PCR fragment was subsequently cloned in the vector pCR2.1 (Invitrogen) and clones containing the PCR fragment were isolated and sequenced to check correct DNA amplification. The PCR clone was then digested with PacI and AvrII and the 0.5 kb adeno insert was ligated to the PacI/partial AvrII-digested pBr/Ad.Bam-rITRpac#2 fragment generating pBr/Ad.Bam-rITRsp. Next, this construct was used to generate a cosmid clone (as previously described herein) that has an insert corresponding to the adenovirus sequences 3534 to 35938. This clone was designated pWE/AflII-rITRsp.

Generation of pWE/Ad.AflII-rITRΔE2A:

Deletion of the E2A coding sequences from pWE/Ad.AflII-rITR (ECACC deposit P97082116) has been accomplished as follows. The adenoviral sequences flanking the E2A coding region at the left and the right site were amplified from the plasmid pBr/Ad.Sal.rITR (ECACC Deposit P97082119) in a PCR reaction with the Expand PCR system (Boehringer) according to the manufacturer's protocol. The following primers were used:

Right flanking sequences (corresponding Ad5 nucleotides 24033 to 25180): ΔE2A.SnaBI: 5'-GGC GTA CGT AGC CCT GTC GAA AG-3' (SEQ ID NO:6) and ΔE2A.DBP-start: 5'-CCA ATGCAT TCG AAG TAC TTC CTT CTC CTA TAG GC-3' (SEQ ID NO:7). The amplified DNA fragment was digested with SnaBI and NsiI (NsiI site is generated in the primer ΔE2A.DBP-start, underlined).

Left flanking sequences (corresponding Ad5 nucleotides 21557 to 22442): ΔE2A.DBP-stop: 5'-CCA ATGCAT ACG GCG CAG ACG G-3' (SEQ ID NO:8) and ΔE2A.BamHI: 5'-GAG GTG GAT CCC ATG GAC GAG-3' (SEQ ID NO:9).

The amplified DNA was digested with BamHI and NsiI (NsiI site is generated in the primer ΔE2A.DBP-stop, underlined). Subsequently, the digested DNA fragments were ligated into SnaBI/BamHI-digested pBr/Ad.Sal-rITR. Sequencing confirmed the exact replacement of the DBP coding region with a unique NsiI site in plasmid pBr/Ad.Sal-rITRΔE2A. The unique NsiI site can be used to introduce an expression cassette for a gene to be transduced by the recombinant vector.

The deletion of the E2A coding sequences was performed such that the splice acceptor sites of the 100K encoding L4-gene at position 24048 in the top strand was left intact. In addition, the poly-adenylation signals of the original E2A-RNA and L3-RNAs at the left hand site of the E2A coding sequences were left intact. This ensures proper expression of the L3-genes and the gene encoding the 100K L4-protein during the adenovirus life cycle.

Next, the plasmid pWE/Ad.AflII-rITRΔE2A was generated. The plasmid pBr/Ad.Sal-rITRΔE2A was digested with BamHI and SpeI. The 3.9 Kb fragment in which the unique NsiI site replaced the E2A coding region was isolated. The pWE/Ad.AflII-rITR was digested with BamHI and SpeI. The 35 Kb DNA fragment, from which the BamHI/SpeI fragment containing the E2A coding sequence was removed, was isolated. The fragments were ligated and packaged using λ1 phage-packaging extracts according to the manufacturer protocol (Stratagene), yielding the plasmid pWE/Ad.AflII-rITRΔE2A.

This cosmid clone can be used to generate adenoviral vectors that are deleted for E2A by co-transfection of PacI-digested DNA together with digested adapter plasmids onto packaging cells that express functional E2A gene product.

Construction of Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK (described in U.S. Pat. No. 5,994,128 to Bout et al.) is an example of an adapter plasmid designed for use according to the invention in combination with the improved packaging cell lines of the invention. This plasmid was used as the starting material to make a new vector in which nucleic acid molecules comprising specific promoter and gene sequences can be easily exchanged.

First, a PCR fragment was generated from pZipΔMo+PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ ID NO:10) and LTR-2: 5'-GCG GAT CCT TCG AAC CAT GGT AAG CTT GGT ACC GCT AGC GTT AAC CGG GCG ACT CAG TCA ATC G-3'(SEQ ID NO:11). Pwo DNA polymerase (Boehringer Mannheim) was used according to manufacturer's protocol with the following temperature cycles: once 5 minutes at 95° C.; 3 minutes at 55° C.; and 1 minute at 72° C., and 30 cycles of 1 minute at 95° C., 1 minute at 60° C., 1 minute at 72° C., followed by once 10 minutes at 72° C. The PCR product was then digested with BamHI and ligated into pMLP10 (Levrero et al., 1991) vector digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990) using the following primers: HSA1, 5'-GCG CCA CCA TGG GCA GAG CGA TGG TGG C-3' (SEQ ID NO:12) and HSA2, 5'-GTT AGA TCT AAG CTT GTC GAC ATC GAT CTA CTA ACA GTA GAG ATG TAG AA-3' (SEQ ID NO:13). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI(sticky)-SalI (blunt) fragment and cloned into the 3.5 kb NcoI(sticky)/BstBI(blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd/L420-HSA that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Replacing the promoter, gene and poly-A sequences in pAd/L420-HSA with the CMV promoter, a multiple cloning site, an intron and a poly-A signal made another adapter plasmid that was designed to allow easy exchange of nucleic acid molecules. For this purpose, pAd/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was designated pAd5/CLIP.

To enable removal of vector sequences from the left ITR in pAd5/Clip, this plasmid was partially digested with EcoRI and the linear fragment was isolated. An oligo of the sequence 5'-TTAAGTCGAC-3' (SEQ ID NO:14) was annealed to itself resulting in a linker with a SalI site and EcoRI overhang. The linker was ligated to the partially digested pAd5/Clip vector and clones were selected that had the linker inserted in the EcoRI site 23 bp upstream of the left adenovirus ITR in pAd5/Clip resulting in pAd5/Clipsal. Likewise, the EcoRI site in pAd5/Clip has been changed to a PacI site by insertion of a linker of the sequence 5'-AATTGTCTTAATTAACCGCAATT-3' (SEQ ID NO:15). The pAd5/Clip vector was partially digested with EcoRI, dephosphorylated and ligated to the PacI linker with EcoRI overhang. The ligation mixture was digested with PacI to remove concatamers, isolated from agarose gel and re-ligated. The resulting vector was designated pAd5/Clippac. These changes enable more flexibility to liberate the left ITR from the plasmid vector sequences.

The vector pAd5/L420-HSA was also modified to create a SalI or PacI site upstream of the left ITR. Hereto pAd5/L420-HSA was digested with EcoRI and ligated to the previously herein described PacI linker. The ligation mixture was digested with PacI and religated after isolation of the linear DNA from agarose gel to remove concatamerized linkers. This resulted in adapter plasmid pAd5/L420-HSA-pac. This construct was used to generate pAd5/L420-HSAsal as follows: pAd5/L420-HSApac was digested with ScaI and BsrGI and the vector fragment was ligated to the 0.3 kb fragment isolated after digestion of pAd5/Clipsal with the same enzymes.

Generation of Adapter Plasmids pAdMire and pAdApt

To create an adapter plasmid that only contains a polylinker sequence and no promoter or polyA sequences, pAd5/L420-HSApac was digested with AvrII and BglII. The vector fragment was ligated to a linker oligonucleotide digested with the same restriction enzymes. Annealing oligos of the following sequence made the linker: PLL-1: 5'-GCC ATC CCT AGG AAG CTT GGT ACC GGT GAA TTC GCT AGC GTT AAC GGA TCC TCT AGA CGA GAT CTG G-3' (SEQ ID NO:16) and PLL-2: 5'-CCA GAT CTC GTC TAG AGG ATC CGT TAA CGC TAG CGA ATT CAC CGG TAC CAA GCT TCC TAG GGA TGG C-3' (SEQ ID NO:17). The annealed linkers were digested with AvrII and BglII and separated from small ends by column purification (Qiaquick nucleotide removal kit) according to manufacturer's recommendations. The linker was then ligated to the AvrII/BglII-digested pAd5/L420-HSApac fragment. A clone, designated AdMire, was selected that had the linker incorporated and was sequenced to check the integrity of the insert.

Adapter Plasmid AdMire Enables Easy Insertion of Complete Expression Cassettes

An adapter plasmid containing the human CMV promoter that mediates high expression levels in human cells was constructed as follows: pAd5/L420-HSApac was digested with AvrII and 5' protruding ends were filled in using Klenow enzyme. A second digestion with HindIII resulted in removal of the L420 promoter sequences. The vector fragment was isolated and ligated to a PCR fragment containing the CMV promoter sequence. This PCR fragment was obtained after amplification of CMV sequences from pCMVLacI (Stratagene) with the following primers: CMVplus: 5'-GATCGGTACTGCAGTGGTCAATATTGGC-CATTAGCC-3' (SEQ ID NO:18) and CMVminA: 5'-GAT-CAAGCTTCCAATGCACCGTTCCCGGC-3' (SEQ ID NO: 19).

The PCR fragment was first digested with PstI (underlined in CMVplus) after which the 3'-protruding ends were removed by treatment with T4 DNA polymerase. Then the DNA was digested with HindIII (underlined in CMVminA) and ligated into the herein described pAd5/L420-HSApac vector fragment digested with AvrII and HindIII. The resulting plasmid was designated pAd5/CMV-HSApac. This plasmid was then digested with HindIII and BamHI and the vector fragment was isolated and ligated to the polylinker sequence obtained after digestion of AdMire with HindIII and BglII. The resulting plasmid was designated pAdApt. Adapter plasmid pAdApt contains nucleotides −735 to +95 of the human CMV promoter (Boshart et al., 1985). A second version of this adapter plasmid containing a SalI site in place of the PacI site upstream of the left ITR was made by inserting the 0.7 kb ScaI-BsrGI fragment from pAd5/Clipsal into pAdApt digested with ScaI and partially digested with BsrGI. This clone was designated pAdApt.sal.

Generation of Recombinant Adenoviruses Based on Ad5

RCA-free recombinant adenoviruses can be generated very efficiently using the herein described adapter plasmids and the pWe/Ad.AflII-rITR or pWE/Ad.AflII-rITrsp constructs. Generally, the adapter plasmid containing the desired transgene in the desired expression cassette is digested with suitable enzymes to liberate the insert from vector sequences at the 3' and/or at the 5' end. The adenoviral complementation plasmids pWE/Ad.AflII-rITR or pWE/Ad.AflII-rITRsp are digested with PacI to liberate the adeno sequences from the vector plasmids. As a non-limiting example, the generation of AdApt-LacZ is described. Adapter plasmid pAdApt-LacZ was generated as follows. The *E. coli* LacZ gene was amplified from the plasmid pMLP.nlsLacZ (EP 95-202 213) by PCR with the primers 5'-GGGGTGGCCAGGGTACCTCTAGGCTTTTGCAA-3' (SEQ ID NO:20) and 5'-GGGGGGATCCATAAACAAGT-TCAGAATCC-3' (SEQ ID NO:21). The PCR reaction was performed with Ex Taq (Takara) according to the supplier's protocol at the following amplification program: 5 minutes at 94° C., 1 cycle; 45 seconds at 94° C. and 30 seconds at 60° C. and 2 minutes at 72° C., 5 cycles; 45 seconds at 94° C. and 30 at seconds at 65° C. and 2 minutes at 72° C., 25 cycles; 10 minutes at 72° C.; 45 seconds at 94° C. and 30 seconds at 60° C. and 2 minutes at 72° C., 5 cycles, I cycle. The PCR product was subsequently digested with KpnI and BamHI and the digested DNA fragment was ligated into KpnI/BamHI-digested pcDNA3 (Invitrogen), giving rise to pcDNA3.nlsLacZ. Construct pcDNA3.nlsLacZ was then digested with KpnI and BamHI and the 3 kb LacZ fragment was isolated from gel using the GENECLEAN spin kit (Bio101, Inc.). pAdApt was also digested with KpnI and BamHI and the linear vector fragment was isolated from gel as above. Both isolated fragments were ligated and one clone containing the LacZ insert was selected. Construct pAdApt-LacZ was digested with SalI, purified by the GENECLEAN spin kit and subsequently digested with PacI. pWE/Ad.AflII-rITRsp was digested with PacI. Both digestion mixtures were treated for 30 minutes at 65° C. to inactivate the enzymes. Samples were put on gel to estimate the concentration. 2.5×10$^6$ PER.C6 cells were seeded in T25 flasks in DMEM with 10% FCS and 10 mM MgCl. The next day, four microgram of each plasmid was transfected into PER.C6 cells using lipofectamine transfection reagents (Life Technologies Inc.) according to instructions of the manufacturer. The next day, the medium was replaced by fresh culture medium and cells were further cultured at 37° C., 10% $CO_2$. Again, one day later, cells were trypsinized, seeded into T80 flasks and cultured at 37° C., 10% $CO_2$. Full CPE was obtained 6 days after seeding in the T80 flask. Cells were harvested in the medium and subjected to one freeze/thaw cycle. The crude lysate obtained this way was used to plaque-purify the mixture of viruses. Ten plaques were picked, expanded in a 24-well plate and tested for LacZ expression following infection of A549 cells. Viruses from all ten plaques expressed LacZ.

Example 3

Generation of Chimeric Recombinant Adenoviruses

Generation of Hexon Chimeric Ad5-Based Adenoviruses

Neutralizing antibodies in human serum are mainly directed to the hexon protein and to a lesser extent to the penton protein. Hexon proteins from different serotypes show highly variable regions present in loops that are predicted to be exposed at the outside of the virus (Athappilly et al., 1994; *J. Mol. Biol.* 242, 430-455). Most type-specific epitopes have been mapped to these highly variable regions (Toogood et al., 1989; *J. Gen Virol.* 70, 3203-3214). Thus, replacement of (or replacement of part of) the hexon sequences with corresponding sequences from a different serotype is an effective strategy to circumvent (pre-existing) neutralizing antibodies to Ad5. Hexon coding sequences of Ad5 are located between nucleotides 18841 and 21697.

To facilitate easy exchange of hexon coding sequences from alternative adenovirus serotypes into the Ad5 backbone, first a shuttle vector was generated. This sub-clone, coded pBr/Ad.Eco-PmeI, was generated by first digesting plasmid pBr322 with EcoRI and EcoRV and inserting the 14 kb PmeI-EcoRI fragment from pWE/Ad.AflII-Eco. In this shuttle vector a deletion was made of a 1430 bp SanDI fragment by digestion with SanDI and re-ligation to give pBr/Ad.Eco-PmeIΔSanDI. The removed fragment contains unique SpeI and MunI sites. From pBr/Ad.Eco-PmeIΔDSanDI the Ad5 DNA encoding hexon was deleted. Hereto, the hexon flanking sequences were PCR amplified and linked together thereby generating unique restriction sites replacing the hexon coding region. For these PCR reactions four different oligonucleotides were required: Δhex1-Δhex4:

ΔDhex1:  (SEQ ID NO:22)
5'- CCT GGT GCT GCC AAC AGC-3',

ΔDhex2:  (SEQ ID NO:23)
5'- CCG GAT CCA CTA GTG GAA AGC GGG CGC GCG-3',

ΔDhex3:  (SEQ ID NO:24)
5'- CCG GAT CCA ATT GAG AAG CAA GCA ACA TCA ACA
                                                    AC-3'
and ΔDhex4:  (SEQ ID NO:25)
5'- GAG AAG GGC ATG GAG GCT G-3'.

The amplified DNA product of ±1100 bp obtained with oligonucleotides Δhex1 and Δhex2 was digested with BamHI and FseI. The amplified DNA product of ±1600 bp obtained with oligonucleotides Δhex3 and Δhex4 was digested with BamHI and SbfI. These digested PCR fragments were subsequently purified from agarose gel and in a tri-part ligation reaction using T4 ligase enzyme linked to pBr/Ad.Eco-PmeI ΔSanDI digested with FseI and SbfI. The resulting construct was coded pBr/Ad.Eco-PmeΔHexon. This construct was sequenced in part to confirm the correct nucleotide sequence and the presence of unique restriction sites MunI and SpeI.

pBr/Ad.Eco-PmeΔHexon serves as a shuttle vector to introduce heterologous hexon sequences amplified from virus DNA from different serotypes using primers that introduce the unique restriction sites MunI and SpeI at the 5' and 3' ends of the hexon sequences respectively. To generate Ad5-based vectors that contain hexon sequences from the serotypes to which healthy individuals have no, or very low, titers of NAB the hexon sequences of Ad35, Ad34, Ad26 and Ad48 were amplified using the following primers: Hex-up2: 5'-GACTAGTCAAGATGGCYACCCCHTCGATGATG-3' (SEQ ID NO:26) (where Y can be a C or T and H can be an A, T or C as both are degenerate oligo nucleotides) and Hex-down2: 5'-GCTGGCCAATTGTATGTKGTKGCGT-TRCCGGC-3' (SEQ ID NO:27) (where K can be a T or G and R can be an A or G as both are degenerate oligo nucleotides).

These primers were designed using the sequences of published hexon coding regions (for example hexon sequences of Ad2, Ad3, Ad4, Ad5, Ad7, Ad16, Ad40 and Ad41 can be obtained at Genbank). Degenerated nucleotides were incorporated at positions that show variation between serotypes.

PCR products were digested with SpeI and MunI and cloned into the pBr/Ad.Eco-PmeΔHexon construct digested with the same enzymes.

The hexon modified sequences were subsequently introduced in the construct pWE/Ad.AflII-rITR by exchange of the AscI fragment generating pWE/Ad.AflII-rITRHexXX where XX stands for the serotype used to amplify hexon sequences.

The pWE/Ad.AflII-rITRHexXX constructs were then used to make viruses in the same manner as previously described herein for Ad5 recombinant viruses.

Generation of Penton Chimeric Ad5-Based Recombinant Viruses

The adenovirus type 5 penton gene is located between sequences 14156 and 15869. Penton base is the adenovirus capsid protein that mediates internalization of the virus into the target cell. At least some serotypes (type C and B) have been shown to achieve this by interaction of an RGD sequence in penton with integrins on the cell surface. However, type F adenoviruses do not have an RGD sequence and for most viruses of the A and D group the penton sequence is not known. Therefore, the penton may be involved in target cell specificity. Furthermore, as a capsid protein, the penton protein is involved in the immunogenicity of the adenovirus (Gahery-Segard et al., 1998). Therefore, replacement of Ad5 penton sequences with penton sequences from serotypes to which no or low titers of NAB exist in addition to replacement of the hexon sequences will prevent clearance of the adenoviral vector more efficiently than replacement of hexon alone. Replacement of penton sequences may also affect infection specificity.

To be able to introduce heterologous penton sequences in Ad5 we made use of the plasmid-based system described above. First, a shuttle vector for penton sequences was made by insertion of the 7.2 kb NheI-EcoRV fragment from construct pWE/Ad.AflII-EcoRI into pBr322 digested with the same enzymes. The resulting vector was designated pBr/XN. From this plasmid, Ad5 penton sequences were deleted and replaced by unique restriction sites that were then used to introduce new penton sequences from other serotypes. Hereto, the left flanking sequences of penton in pBr/XN were PCR amplified using the following primers: DP5-F: 5'-CTG TTG CTG CTG CTA ATA GC-3' (SEQ ID NO:28) and DP5-R: 5'-CGC GGA TCC TGT ACA ACT AAG GGG AAT ACA AG-3' (SEQ ID NO:29).

DP5-R has a BamHI site (underlined) for ligation to the right flanking sequence and also introduces a unique BsrGI site (bold face) at the 5'-end of the former Ad5 penton region. The right flanking sequence was amplified using: DP3-F: 5'-CGC GGA TCC CTT AAG GCA AGC ATG TCC ATC CTT-3' (SEQ ID NO:30) and DP3-3R: 5'-AAA ACA CGT TTT ACG CGT CGA CCT TTC-3' (SEQ ID NO:31). DP3-F has a BamHI site (underlined) for ligation to the left flanking sequence and also introduces a unique AflII site (bold face) at the 3' end of the former Ad5 penton region.

The two resulting PCR fragments were digested with BamHI and ligated together. Then this ligation mixture was digested with AvrII and BglII. pBr/XN was also digested with AvrII and BglII and the vector fragment was ligated to the digested ligated PCR fragments. The resulting clone was designated pBr/Ad.Δpenton. Penton coding sequences from Ad35, Ad34, Ad26 and Ad48 were PCR amplified such that the 5' and 3' ends contained the BsrGI and AflII sites respectively. Hereto, the following primers were used:

For Ad34 and Ad35:
 (SEQ ID NO:32)
P3-for:
5'-GCT CGA TGT ACA ATG AGG AGA CGA GCC GTG CTA-3'
and
 (SEQ ID NO:33)
P3-rev:
5'-GCT CGA CTT AAG TTA GAA AGT GCG GCT TGA AAG-3'.

For Ad26 and Ad48:
 (SEQ ID NO:34)
P17F:
5'-GCT CGA TGT ACA ATG AGG CGT GCG GTG GTG TCT
                                                    TC-3'
and
 (SEQ ID NO:35)
P17R:
5'-GCT CGA CTT AAG TTA GAA GGT GCG ACT GGA AAG
                                                    C-3'.

Amplified PCR products were digested with BfrI and BsrGI and cloned into pBr/Ad.Δpenton digested with the same enzymes. Introduction of these heterologous penton sequences into the pBr/Ad.Δpenton generated constructs designated pBr/Ad.pentonXX, wherein XX represents the number of the serotype corresponding to the serotype used to amplify the inserted penton sequences. Subsequently, the new penton sequences were introduced in the pWE/Ad.AflIII-rITR vector having a modified hexon. For example, penton sequences from Ad35 were introduced in the construct pWE/Ad.AflII-rITRHex35 by exchange of the common FseI fragment. Other combinations of penton and hexon sequences were also made. Viruses with modified hexon and penton sequences were made as described above using cotransfection with an adapter plasmid on PER.C6 cells. In addition, penton sequences were introduced in the pWE/Ad.AflII-rITR construct. The latter constructs contain only a modified penton, and viruses generated from these constructs will be used to study the contribution of penton sequences to the neutralization of adenoviruses and also for analysis of possible changes in infection efficiency and specificity.

Generation of Fiber Chimeric Ad5-Based Viruses

Adenovirus infection is mediated by two capsid proteins fiber and penton. Binding of the virus to the cells is achieved by interaction of the protruding fiber protein with a receptor on the cell surface. Internalization then takes place after interaction of the penton protein with integrins on the cell surface. At least some adenovirus from subgroups C and B have been shown to use a different receptor for cell binding and, therefore, have different infection efficiencies on different cell types. Thus, it is possible to change the infection spectrum of adenoviruses by changing the fiber in the capsid. The fiber coding sequence of Ad5 is located between nucleotides 31042 and 32787. To remove the Ad5 DNA encoding fiber, we started with construct pBr/Ad.Bam-rITR. First, an NdeI site was removed from this construct. For this purpose, pBr322 plasmid DNA was digested with NdeI. After which, protruding ends were filled using Klenow enzyme. This pBr322 plasmid was then re-ligated, digested with NdeI, and transformed into *E. coli* DH5α. The obtained pBr/ΔNdeI plasmid was digested with ScaI and SalI and the resulting 3198 bp vector fragment was ligated to the 15349 bp ScaI-SalI fragment derived from pBr/Ad.BamrITR, resulting in plasmid pBr/Ad.Bam-rITRΔNdeI which hence contained a unique NdeI site. Next, a PCR was performed with oligonucleotides NY-up: 5'-CGA CAT ATG TAG ATG CAT TAG TTT GTG TTA TGT TTC AAC GTG-3' (SEQ ID NO:36) and NY-down: 5'-GGA GAC CAC TGC CAT GTT-3' (SEQ ID NO:37).

During amplification, both an NdeI (bold face) and an NsiI restriction site (underlined) were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM MgCl$_2$, and 1 unit of Elongase heat stable polymerase (Gibco, The Netherlands). One-tenth of the PCR product was run on an agarose gel that demonstrated that the expected DNA fragment of ±2200 bp was amplified. This PCR fragment was subsequently purified using GENECLEAN kit system (Bio101, Inc.). Then, both the construct pBr/Ad.Bam-rITRΔNdeI, as well as the PCR product, were digested with restriction enzymes NdeI and SbfI. The PCR fragment was subsequently cloned using T4 ligase enzyme into the NdeI- and SbfI-digested pBr/Ad-.Bam-rITRΔNdeI, generating pBr/Ad.BamRΔFib.

This plasmid allows insertion of any PCR-amplified fiber sequence through the unique NdeI and NsiI sites that are inserted in place of the removed fiber sequence. Viruses can be generated by a double homologous recombination in packaging cells described in U.S. Pat. No. 5,994,128 to Bout et al. using an adapter plasmid, construct pBr/Ad.AflII-EcoRI digested with PacI and EcoRI and a pBr/Ad.BamRΔFib construct in which heterologous fiber sequences have been inserted. To increase the efficiency of virus generation, the construct pBr/Ad.BamRΔFib was modified to generate a PacI site flanking the right ITR. Hereto, pBr/Ad.BamRΔFib was digested with AvrII and the 5 kb adenovirus fragment was isolated and introduced into the vector pBr/Ad.Bam-rITR.pac#8 described above replacing the corresponding AvrII fragment. The resulting construct was designated pBr/Ad.BamRΔFib.pac.

Once a heterologous fiber sequence is introduced in pBr/Ad.BamRΔFib.pac, the fiber-modified right hand adenovirus clone is introduced into a large cosmid clone as previously described herein for pWE/Ad.AflII-rITR. Such a large cosmid clone allows generation of adenovirus by only one homologous recombination. Ad5-based viruses with modified fibers have been made and described (see, European Patent Appln. Nos. 98204482.8 and 99200624.7). In addition, hexon and penton sequences from serotypes from this invention are combined with the desired fiber sequences to generate viruses that infect the target cell of choice very efficiently. For example, smooth muscle cells, endothelial cells or synoviocytes (all from human origin) are very well infected with Ad5-based viruses with a fiber from subgroup B viruses, especially Ad16.

The foregoing examples in which specific sequences can be deleted from the Ad5 backbone in the plasmids and replaced by corresponding sequences from other serotypes demonstrate the flexibility of the system. It is evident that by the methods described herein, any combination of capsid gene from different serotypes can be made. Thus, chimeric recombinant Ad5-based adenoviruses are designed with desired hexon and penton sequences making the virus less sensitive for neutralization and with desired fiber sequences allowing efficient infection in specific target tissues.

Example 4

Construction of a Plasmid-Based System to Generate Ad35 Recombinant Viruses

Partial restriction maps of Ad35 have been published previously (Valderrama-Leon et al., 1985; Kang et al., 1989; Li et al. 1991). An example of a functional plasmid-based system to generate recombinant adenoviruses based on Ad35 consists of the following elements:

1. An adapter plasmid comprising a left ITR and packaging sequences derived from Ad35 and at least one restriction site for insertion of an heterologous expression cassette and lacking E1 sequences. Furthermore, the adapter plasmid contains Ad35 sequences 3' from the E1B coding region including the pIX promoter and coding sequences sufficient to mediate homologous recombination of the adapter plasmid with a second nucleotide.

2. A second nucleotide comprising sequences homologous to the adapter plasmid and Ad35 sequences necessary for the replication and packaging of the recombinant virus, that is, early, intermediate and late genes that are not present in the packaging cell.

3. A packaging cell providing at least functional E1 proteins and proteins capable of complementing the E1 function of Ad35.

Ad35 DNA was isolated from a purified virus batch as follows. To 100 μl of virus stock (Ad35: 3.26×10$^{12}$ VP/ml), 10 μl 10× DNAse buffer (130 mM Tris-HCl pH7.5; 1.2 M CaCl$_2$; 50 mM MgCl$_2$) was added. After addition of 10 μl 10 mgr/ml DNAse I (Roche Diagnostics), the mixture was incubated for 1 hr at 37° C. Following addition of 2.5 µl 0.5M EDTA, 3.2 µl 20% SDS and 1.5 µl ProteinaseK (Roche Diagnostics; 20 mgr/ml), samples were incubated at 50° C. for 1 hr. Next, the viral DNA was isolated using the GENECLEAN spin kit (Bio101, Inc.) according to the manufacturer's instructions. DNA was eluted from the spin column with 25 µl sterile MilliQ water.

In the following, sizes of DNA fragments and fragment numbering will be used according to Kang et al. (1989). Ad35 DNA was digested with EcoRI and the three fragments (approximately 22.3 (A), 7.3 (B) and 6 kb (C)) were isolated from gel using the GENECLEAN kit (Bio101, Inc.). pBr322 was digested with EcoRI or with EcoRI and EcoRV and digested fragments were isolated from gel and dephosphorylated with TSAP enzyme (Gibco BRL). Next, the 6 kb Ad35 C fragment was ligated to the pBr322xEcoRI fragment and the ITR-containing Ad35 fragment (EcoRI-B) was ligated to the pBr322xEcoRI/EcoRV fragment. Ligations were incubated at 16° C. overnight and transformed into DH5α competent bacteria (Life Techn.). Minipreps of obtained colonies were analyzed for correct insertion of the Ad35 fragments by restriction analysis. Both the 6 kb and the 7.3 kb Ad35 fragments were found to be correctly inserted in pBr322. The 6 kb fragment was isolated in both orientations pBr/Ad35-Eco6.0$^+$ and pBr/Ad35-Eco6.0$^-$, whereby the + stands for 5' to 3' orientation relative to pBr322. The clone with the 7.3 kb Ad35 B insert, designated pBr/Ad35-Eco7.3 was partially sequenced to check correct ligation of the 3' ITR. It was found that the ITR had at least the sequence 5'-CATCATCAAT . . . -3' found in SEQ ID NO:40 in the lower strand. Then pBr/Ad35-Eco7.3 was extended to the 5' end by insertion of the 6 kb Ad35 fragment. Hereto, pBr/Ad35-Eco7.3 was digested with EcoRI and dephosphorylated. The fragment was isolated from gel and ligated to the 6 kb Ad35 EcoRI fragment. After transformation clones were tested for correct orientation of the insert and one clone was selected, designated pBr/Ad35-Eco13.3.

This clone was then extended with the ~5.4 kb SalI D fragment obtained after digestion of wt Ad35 with SalI. Hereto, the SalI site in the pBr322 backbone was removed by partial digestion of pBr/Ad35-Eco13.3 with SalI, filling in of the sticky ends by Klenow treatment and re-ligation. One clone was selected that contains a single SalI site in the adenoviral insert. This clone, designated pBrΔsal/Ad35-Eco13.3 was then linearized with AatII which is present in the pBr322 backbone and ligated to a SalI linker with AatII complementary ends. The DNA was then digested with excess SalI and the linear fragment was isolated and ligated to the 5.4 kb SalI-D fragment from Ad35. One clone was selected that contained the SalI fragment inserted in the correct orientation in pBr/Ad35-Eco13.3. The resulting clone, pBr/Ad35.Sal2-rITR contains the 3' ~17 kb of Ad35 including the right ITR. To enable liberation of the right ITR from the vector sequences at the time of virus generation, a NotI site flanking the right ITR was introduced by PCR.

The Ad35 EcoRI-A fragment of 22.3 kb was also cloned in pBr322xEcoRI/EcoRV. One clone, designated pBr/Ad35-EcoA3', was selected that apparently had a deletion of approximately 7 kb of the 5' end. It did contain the SalI site at 9.4 kb in Ad35 wt DNA and approximately 1.5 kb of sequences upstream. Using this SalI site and the unique NdeI site in the pBr322 backbone, this clone is extended to the 5' end by insertion of an approximately 5 kb Ad35 fragment 5' from the first SalI in Ad35 in such a way that a NotI restriction site was created at the 5' end of the Ad35 by insertion of a linker. This clone, designated pBr/Ad35.pIX-EcoA, does not contain the left end sequences (ITR, packaging sequences and E1) and at the 3' end it has approximately 3.5 kb overlap with clone pBr/Ad35.Sal2-rITR.

To create an adapter plasmid, Ad35 was digested with SalI and the left end B fragment of ~9.4 kb was isolated. pBr322 was digested with EcoRV and SalI, isolated from gel and dephosphorylated with TSAP enzyme. Both fragments were ligated and clones with correct insertion and correct sequence of the left ITR were selected. To enable liberation of the left ITR from the vector sequences at the time of virus generation, a NotI site flanking the left ITR is introduced by PCR. From this clone, the E1 sequences were deleted and replaced by a polylinker sequence using PCR. The polylinker sequence is used to introduce an expression cassette for a gene of choice.

Recombinant Ad35 clones are generated by transfection of PER.C6 cells with the adapter plasmid, pBr/Ad35.pIX-EcoA and pBr/Ad35.Sal2-rITR as shown in FIG. 3. Homologous recombination gives rise to recombinant viruses.

Example 5

The Prevalence of Neutralizing Activity (NA) to Ad35 is Low in Human Sera from Different Geographic Locations In Example 1, the analysis of neutralizing activity ("NA") in human sera from one location in Belgium was described. Strikingly, of a panel of 44 adenovirus serotypes tested, one serotype, Ad35, was not neutralized in any of the 100 sera assayed. In addition, a few serotypes, Ad26, Ad34 and Ad48 were found to be neutralized in 8%, or less, of the sera tested. This analysis was further extended to other serotypes of adenovirus not previously tested and, using a selection of serotypes from the first screen, was also extended to sera from different geographic locations.

Hereto, adenoviruses were propagated, purified and tested for neutralization in the CPE-inhibition assay as described in Example 1. Using the sera from the same batch as in Example 1, adenovirus serotypes 7B, 11, 14, 18 and 44/1876 were tested for neutralization. These viruses were found to be neutralized in, respectively, 59, 13, 30, 98 and 54% of the sera. Thus, of this series, Ad11 is neutralized with a relatively low frequency.

Since it is known that the frequency of isolation of adenovirus serotypes from human tissue as well as the prevalence of NA to adenovirus serotypes may differ on different geographic locations, we further tested a selection of the adenovirus serotypes against sera from different places. Human sera were obtained from two additional places in Europe (Bristol, UK and Leiden, NL) and from two places in the United States (Stanford, Calif. and Great Neck, N.Y.). Adenoviruses that were found to be neutralized in 20% or less of the sera in the first screen, as well as Ad2, Ad5, Ad27, Ad30, Ad38, Ad43, were tested for neutralization in sera from the UK. The results of these experiments are presented in FIG. 4.

Adenovirus serotypes 2 and 5 were again neutralized in a high percentage of human sera. Furthermore, some of the serotypes that were neutralized in a low percentage of sera in the first screen are neutralized in a higher percentage of sera from the UK, e.g., Ad26 (7% vs. 30%), Ad28 (13% vs. 50%), Ad34 (5% vs. 27%) and Ad48 (8% vs. 32%). Neutralizing activity against Ad11 and Ad49 that were found in a relatively low percentage of sera in the first screen, were found in an even lower percentage of sera in this second screen (13% vs. 5% and 20% vs. 11%, respectively). Serotype Ad35 that was not neutralized in any of the sera in the first screen, was now found to be neutralized in a low percentage (8%) of sera from the UK. The prevalence of NA in human sera from the UK is the lowest to serotypes Ad11 and Ad35.

For further analysis, sera obtained from two locations in the U.S. (Stanford, Calif. and Great Neck, N.Y.) and from The Netherlands (Leiden). FIG. 5 presents an overview of data obtained with these sera and the previous data. Not all viruses were tested in all sera, except for Ad5, Ad11 and Ad35. The overall conclusion from this comprehensive screen of human sera is that the prevalence of neutralizing activity to Ad35 is the lowest of all serotypes throughout the western countries: on average 7% of the human sera contain neutralizing activity (5 different locations). Another B-group adenovirus, Ad11 is also neutralized in a low percentage of human sera (average 11% in sera from 5 different locations). Adenovirus type 5 is neutralized in 56% of the human sera obtained from 5 different locations. Although not tested in all sera, D-group serotype 49 is also neutralized with relatively low frequency in samples from Europe and from one location of the U.S. (average 14%).

In the herein described neutralization experiments, a serum is judged non-neutralizing when, in the well with the highest serum concentration, the maximum protection of CPE is 40% compared to the controls without serum. The protection is calculated as follows:

$$\% \text{ protection} = \frac{OD \text{ corresponding well} - OD \text{ virus control}}{OD \text{ non-infected control} - OD \text{ virus control}} \times 100\%$$

As described in Example 1, the serum is plated in five different dilutions ranging from 4× to 64× diluted. Therefore, it is possible to distinguish between low titers (i.e., neutralization only in the highest serum concentrations) and high titers of NA (i.e., also neutralization in wells with the lowest serum concentration). Of the human sera used in our screen that were found to contain neutralizing activity to Ad5, 70% turned out to have high titers, whereas of the sera that contained NA to Ad35, only 15% had high titers. Of the sera that were positive for NA to Ad11 only 8% had high titers. For Ad49, this was 5%. Therefore, not only is the frequency of NA to Ad35, Ad11 and Ad49 much lower as compared to Ad5, but of the sera that do contain NA to these viruses, the vast majority have low titers. Adenoviral vectors based on Ad11, Ad35 or Ad49 have, therefore, a clear advantage over Ad5-based vectors when used as gene therapy vehicles or vaccination vectors in vivo or in any application where infection efficiency is hampered by neutralizing activity.

In the following examples, the construction of a vector system for the generation of safe, RCA-free Ad35-based vectors is described.

Example 6

Sequence of the Human Adenovirus Type 35

Ad35 viruses were propagated on PER.C6 cells and DNA was isolated as described in Example 4. The total sequence was generated by Qiagen Sequence Services (Qiagen GmbH, Germany). Total viral DNA was sheared by sonification and the ends of the DNA were made blunt by T4 DNA polymerase. Sheared blunt fragments were size fractionated on agarose gels and gel slices corresponding to DNA fragments of 1.8 to 2.2 kb were obtained. DNA was purified from the gel slices by the QIAquick gel extraction protocol and subcloned into a shotgun library of pUC19 plasmid cloning vectors. An array of clones in 96-wells plates covering the target DNA 8 (+/−2) times was used to generate the total sequence. Sequencing was performed on Perkin-Elmer 9700 thermocyclers using Big Dye Terminator chemistry and AmpliTaq FS DNA polymerase followed by purification of sequencing reactions using QIAGEN DyeEx 96 technology. Sequencing reaction products were then subjected to automated separation and detection of fragments on ABI 377 XL 96 lane sequencers. Initial sequence results were used to generate a contig sequence and gaps were filled in by primer walking reads on the target DNA or by direct sequencing of PCR products. The ends of the virus turned out to be absent in the shotgun library, most probably due to cloning difficulties resulting from the amino acids of pTP that remain bound to the ITR sequences after proteinase K digestion of the viral DNA. Additional sequence runs on viral DNA solved most of the sequence in those regions, however it was difficult to obtain a clear sequence of the most terminal nucleotides. At the 5' end the sequence portion obtained was 5'-CCAATAATATACCT-3' (SEQ ID NO:38) while at the 3' end, the obtained sequence portion was 5'-AGGTATATTATTGATGATGGG-3' (SEQ ID NO:39). Most human adenoviruses have a terminal sequence 5'-CATCATCAATAATATACC-3'(SEQ ID NO:40). In addition, a clone representing the 3' end of the Ad35 DNA obtained after cloning the terminal 7 kb Ad35 EcoRI fragment into pBr322 (see Example 4) also turned out to have the typical CATCATCAATAAT... sequence as seen in SEQ ID NO:40. Therefore, Ad35 may have the typical end sequence and the differences obtained in sequencing directly on the viral DNA are due to artifacts correlated with run-off sequence runs and the presence of residual amino acids of pTP.

The total sequence of Ad35 with corrected terminal sequences is given in FIG. 6. Based upon sequence homology with Ad5 (Genbank #M72360) and Ad7 (partial sequence Genbank #X03000) and on the location of open reading frames, the organization of the virus is identical to the general organization of most human adenoviruses, especially the subgroup B viruses. The total length of the genome is 34,794 basepairs.

Example 7

Construction of a Plasmid-Based Vector System to Generate Recombinant Ad35-Based Viruses A functional plasmid-based vector system to generate recombinant adenoviral vectors comprises the following components:

1. An adapter plasmid comprising a left ITR and packaging sequences derived from Ad35 and at least one restriction site for insertion of an heterologous expression cassette and lacking E1 sequences. Furthermore, the adapter plasmid contains Ad35 sequences 3' from the E1B coding region including the pIX promoter and coding sequences enough to mediate homologous recombination of the adapter plasmid with a second nucleic acid molecule.

2. A second nucleic acid molecule, comprising sequences homologous to the adapter plasmid, and Ad35 sequences necessary for the replication and packaging of the recombinant virus, that is, early, intermediate and late genes that are not present in the packaging cell.

3. A packaging cell providing at least functional E1 proteins capable of complementing the E1 function of Ad35.

Other methods for the generation of recombinant adenoviruses on complementing packaging cells are known in the art, and may be applied to Ad35 viruses without departing from the invention. As an example, the construction of a plasmid-based system, as outlined above, is described in detail below.

1) Construction of Ad35 Adapter Plasmids

Figure 7:
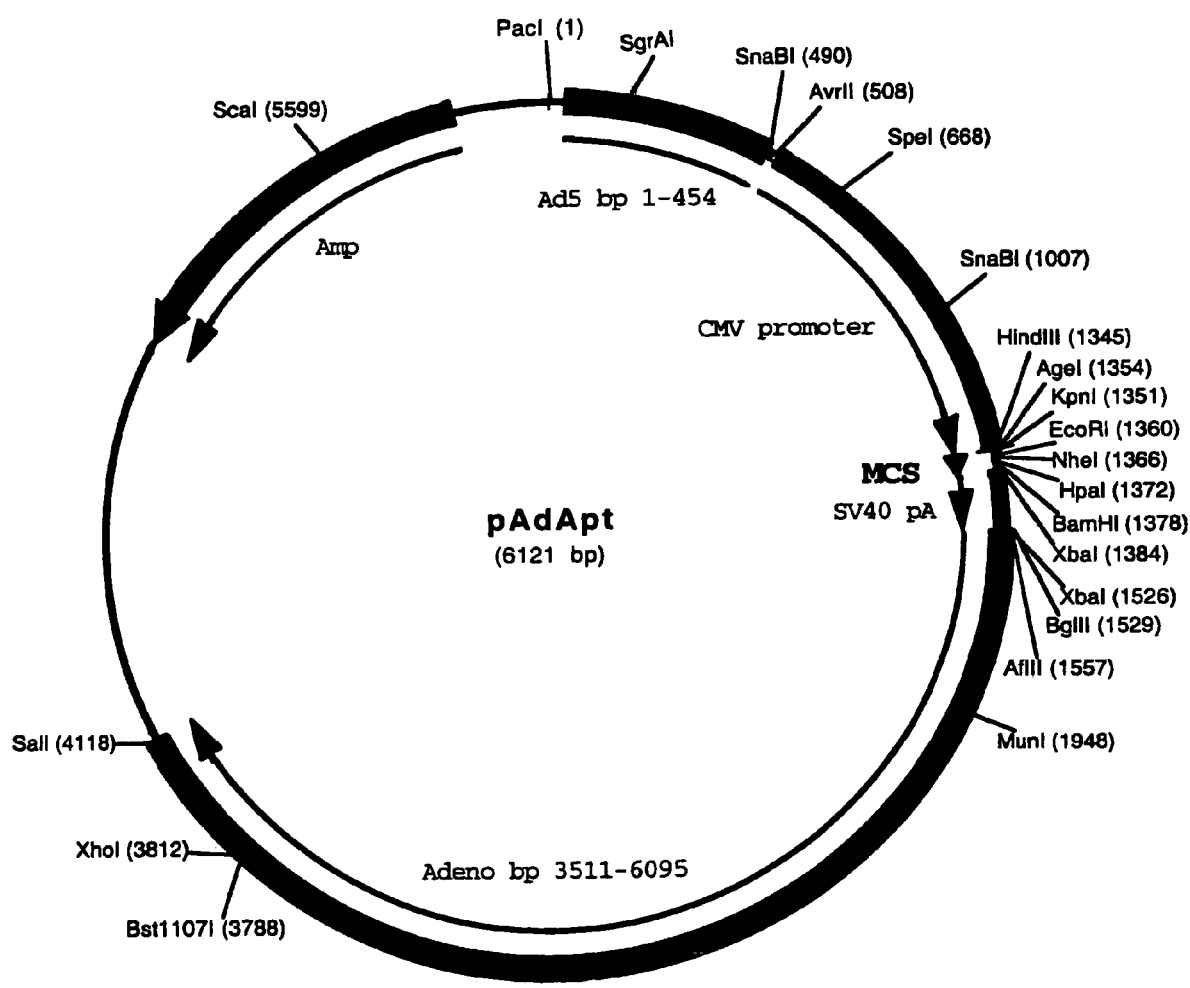
FIG. 7: Map of pAdApt.
Figure 8:
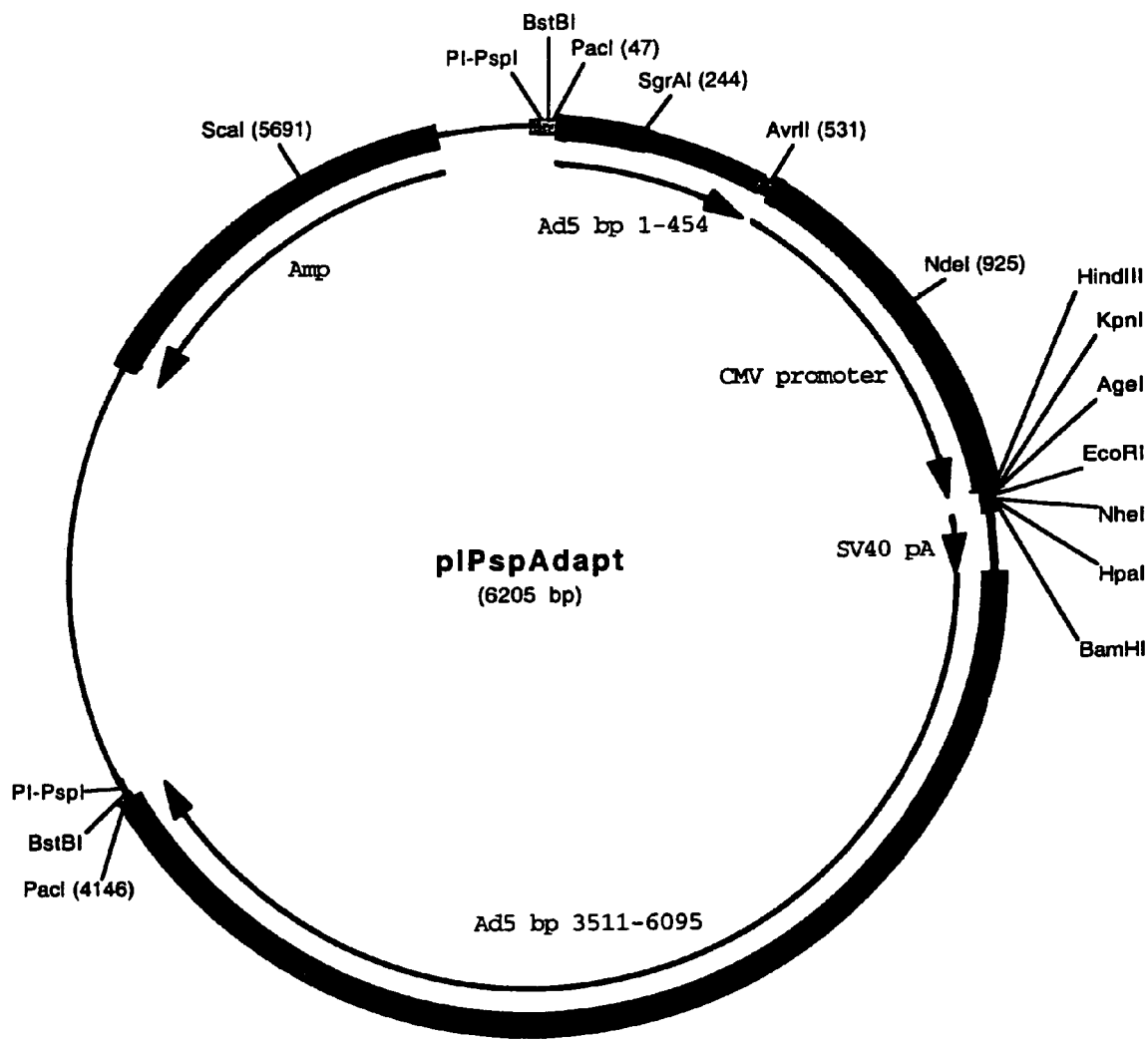
FIG. 8: Map of pIPspAdapt.

Hereto, the adapter plasmid pAdApt (FIG. 7; described in Example 2) was first modified to obtain adapter plasmids that contain extended polylinkers and that have convenient unique restriction sites flanking the left ITR and the adenovirus sequence at the 3' end to enable liberation of the adenovirus insert from plasmid vector sequences. Construction of these plasmids is described below in detail:

Adapter plasmid pAdApt (Example 2) was digested with SalI and treated with Shrimp Alkaline Phosphatase to reduce re-ligation. A linker, composed of the following two phosphorylated and annealed oligos: ExSalPacF 5'-TCG ATG GCA AAC AGC TAT TAT GGG TAT TAT GGG TTC GAA TTA ATT AA-3' (SEQ ID NO:41); and ExSalPacR 5'-TCG ATT AAT TAA TTC GAA CCC ATA ATA CCC ATA ATA GCT GTT TGC CA-3' (SEQ ID NO:42); was directly ligated into the digested construct, thereby replacing the SalI restriction site by Pi-PspI, SwaI and PacI. This construct was designated pADAPT+ExSalPac linker. Furthermore, part of the left ITR of pAdApt was amplified by PCR using the following primers: PCLIPMSF: 5'-CCC CAA TTG GTC GAC CAT CAT CAA TAA TAT ACC TTA TTT TGG-3' (SEQ ID NO:43) and pCLIPBSRGI: 5'-GCG AAA ATT GTC ACT TCC TGT G-3' (SEQ ID NO:44). The amplified fragment was digested with MunI and BsrGI and cloned into pAd5/Clip (see, Example 2), which was partially digested with EcoRI and, after purification, digested with BsrGI, thereby re-inserting the left ITR and packaging signal. After restriction enzyme analysis, the construct was digested with ScaI and SgrAI and an 800 bp fragment was isolated from gel and ligated into ScaI/SgrAI-digested pADAPT+ExSalPac linker. The resulting construct, designated pIPspSalAdapt, was digested with SalI, dephosphorylated, and ligated to the phosphorylated ExSalPacF/ExSalPacR double-stranded linker previously mentioned. A clone in which the PacI site was closest to the ITR was identified by restriction analysis and sequences were confirmed by sequence analysis. This novel pAdApt construct, termed pIPspAdapt (FIG. 8) thus harbors two ExSalPac linkers containing recognition sequences for PacI, PI-PspI and BstBI, which surround the adenoviral part of the adenoviral adapter construct, and which can be used to linearize the plasmid DNA prior to cotransfection with adenoviral helper fragments.

Figure 9:
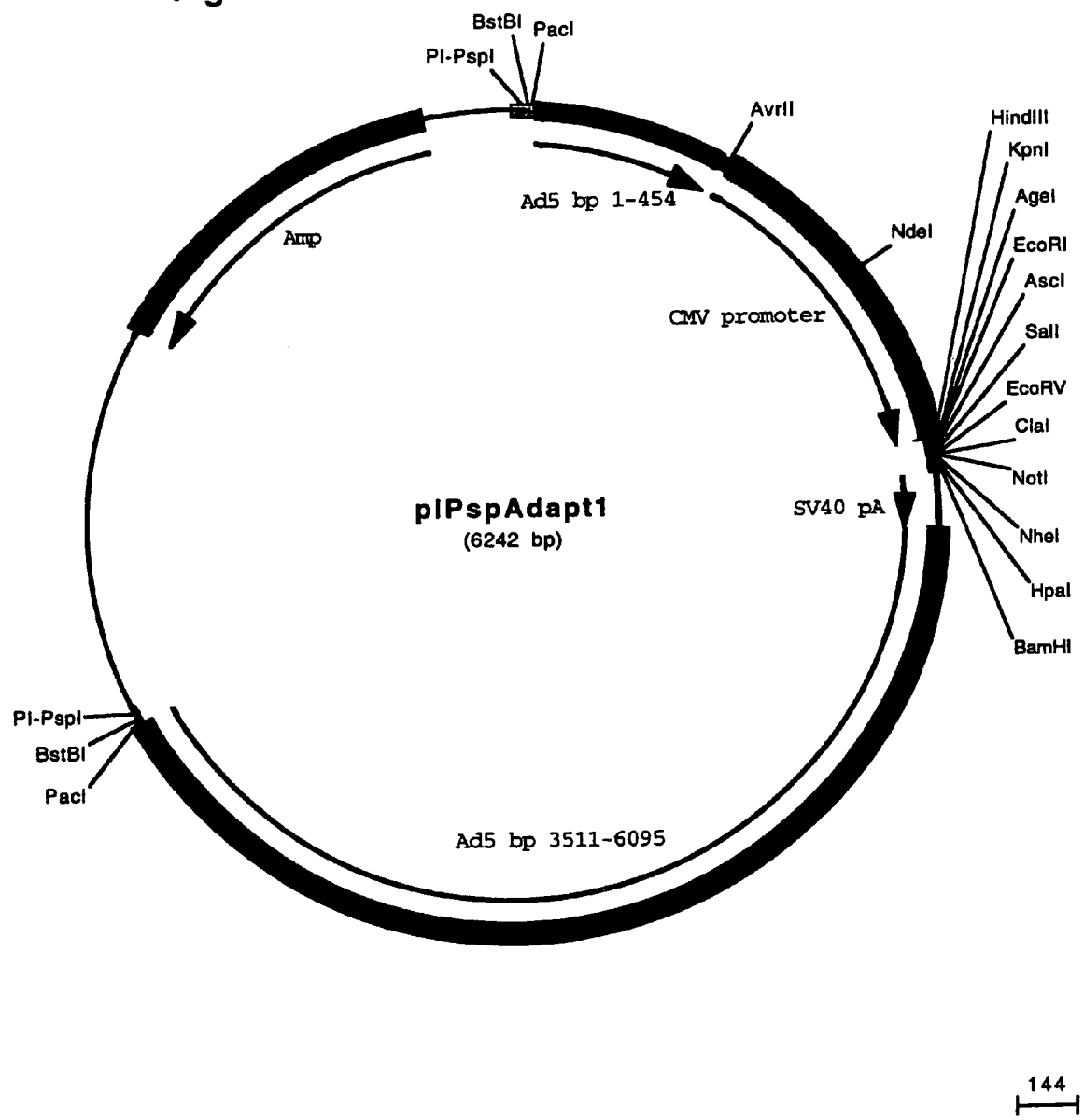
FIG. 9: Map of pIPspAdapt1.

In order to further increase transgene cloning permutations, a number of polylinker variants were constructed based on pIPspAdapt. For this purpose, pIPspAdapt was first digested with EcoRI and dephosphorylated. A linker composed of the following two phosphorylated and annealed oligos: Ecolinker+: 5'-AAT TCG GCG CGC CGT CGA CGA TAT CGA TAG CGG CCG C-3' (SEQ ID NO:45) and Ecolinker–: 5'-AAT TGC GGC CGC TAT CGA TAT CGT CGA CGG CGC GCC G-3' (SEQ ID NO:46) was ligated into this construct, thereby creating restriction sites for AscI, SalI, EcoRV, ClaI and NotI. Both orientations of this linker were obtained, and sequences were confirmed by restriction analysis and sequence analysis. The plasmid containing the polylinker in the order 5' HindIII, KpnI, AgeI, EcoRI, AscI, SalI, EcoRV, ClaI, NotI, NheI, HpaI, BamHI and XbaI was termed pIPspAdapt1 (FIG. 9), while the plasmid containing the polylinker in the order HindIII, KpnI, AgeI, NotI, ClaI, EcoRV, SalI, AscI, EcoRI, NheI, HpaI, BamHI and XbaI was termed pIPspAdapt2.

Figure 10:
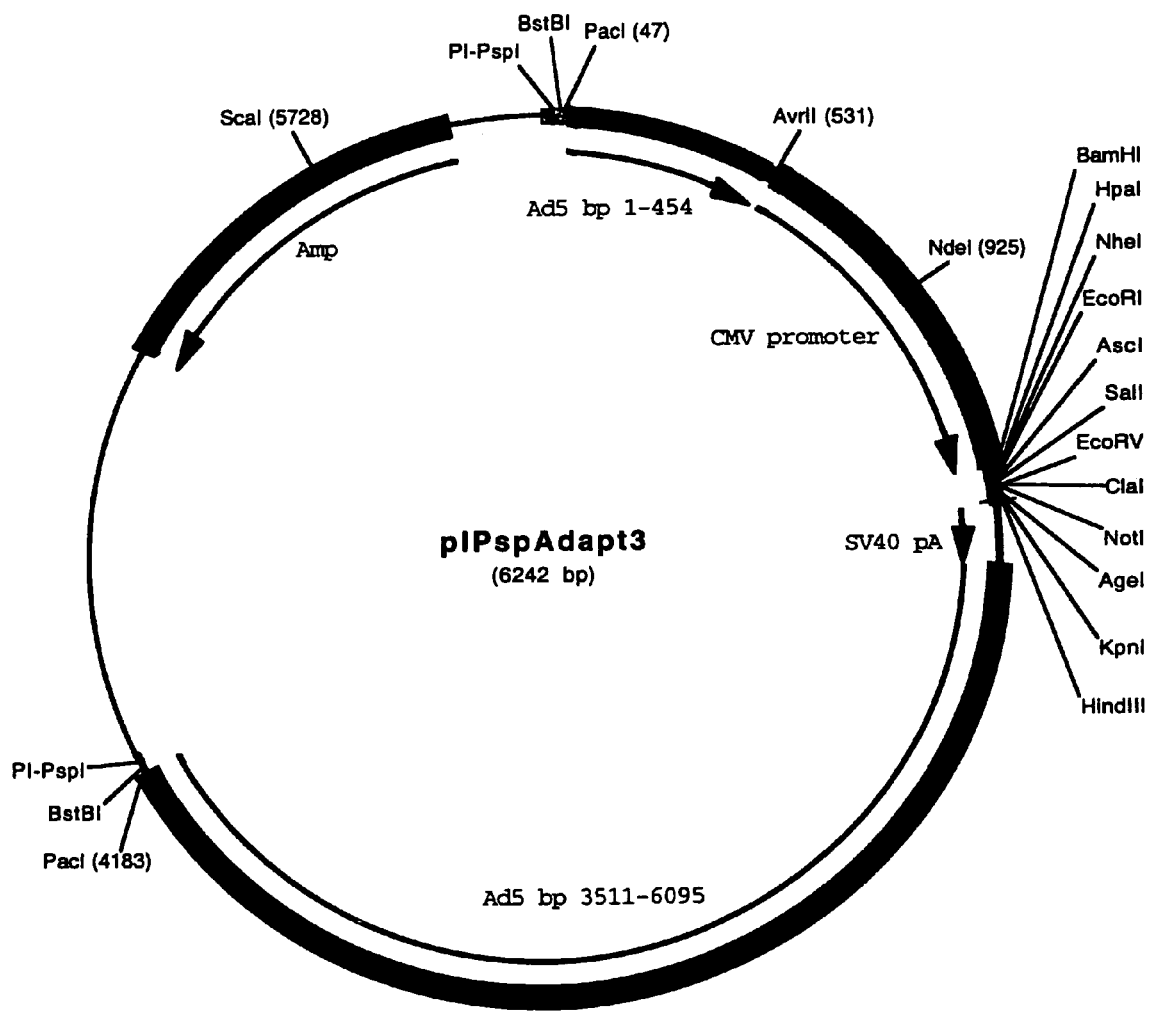
FIG. 10: Map of pIPspAdapt3.

To facilitate the cloning of other sense or antisense constructs, a linker composed of the following two oligonucleotides was designed, to reverse the polylinker of pIPspAdapt: HindXba+ 5'-AGC TCT AGA GGA TCC GTT AAC GCT AGC GAA TTC ACC GGT ACC AAG CTT A-3' (SEQ ID NO:47); HindXba– 5'-CTA GTA AGC TTG GTA CCG GTG AAT TCG CTA GCG TTA ACG GAT CCT CTA G-3' (SEQ ID NO:48). This linker was ligated into HindIII/XbaI-digested pIPspAdapt and the correct construct was isolated. Confirmation was done by restriction enzyme analysis and sequencing. This new construct, pIPspAdaptA, was digested with EcoRI and the previously mentioned Ecolinker was ligated into this construct. Both orientations of this linker were obtained, resulting in pIPspAdapt3 (FIG. 10), which contains the polylinker in the order XbaI, BamHI, HpaI, NheI, EcoRI, AscI, SalI, EcoRV, ClaI, NotI, AgeI, KpnI and HindIII. All sequences were confirmed by restriction enzyme analysis and sequencing.

Adapter plasmids based on Ad35 were then constructed as follows:

The left ITR and packaging sequence corresponding to Ad35 wt sequences nucleotides 1 to 464 (FIG. 6) were amplified by PCR on wtAd35 DNA using the following primers: Primer 35F1: 5'-CGG AAT TCT TAA TTA ATC GAC ATC ATC AAT AAT ATA CCT TAT AG-3' (SEQ ID NO:49) and Primer 35R2: 5'-GGT GGT CCT AGG CTG ACA CCT ACG TAA AAA CAG-3' (SEQ ID NO:50). Amplification introduces a PacI site at the 5' end and an AvrII site at the 3' end of the sequence.

For the amplification, Platinum Pfx DNA polymerase enzyme (LTI) was used according to manufacturer's instructions, but with primers at 0.6 μM and with DMSO added to a final concentration of 3%. Amplification program was as follows: 2 min. at 94° C. (30 sec. at 94° C., 30 sec. at 56° C., 1 min. at 68° C.) for 30 cycles, followed by 10 min. at 68° C.

The PCR product was purified using a PVR purification kit (LTI) according to the manufacturer's instructions, and digested with PacI and AvrII. The digested fragment was then purified from gel using the GENECLEAN kit (Bio101, Inc.). The Ad5-based adapter plasmid pIPspAdApt-3 (FIG. 10) was digested with AvrII and then partially with PacI and the 5762 bp fragment was isolated in an LMP agarose gel slice and ligated with the above-mentioned PCR fragment digested with the same enzymes and transformed into electrocompetent DH10B cells (LTI). The resulting clone is designated pIPspAdApt3-Ad35lITR.

In parallel, a second piece of Ad35 DNA was amplified using the following primers: 35F3: 5'-TGG TGG AGA TCT GGT GAG TAT TGG GAA AAC-3' (SEQ ID NO:51) and 35R4: 5'-CGG AAT TCT TAA TTA AGG GAA ATG CAA ATC TGT GAG G-3' (SEQ ID NO:52).

Figure 11:
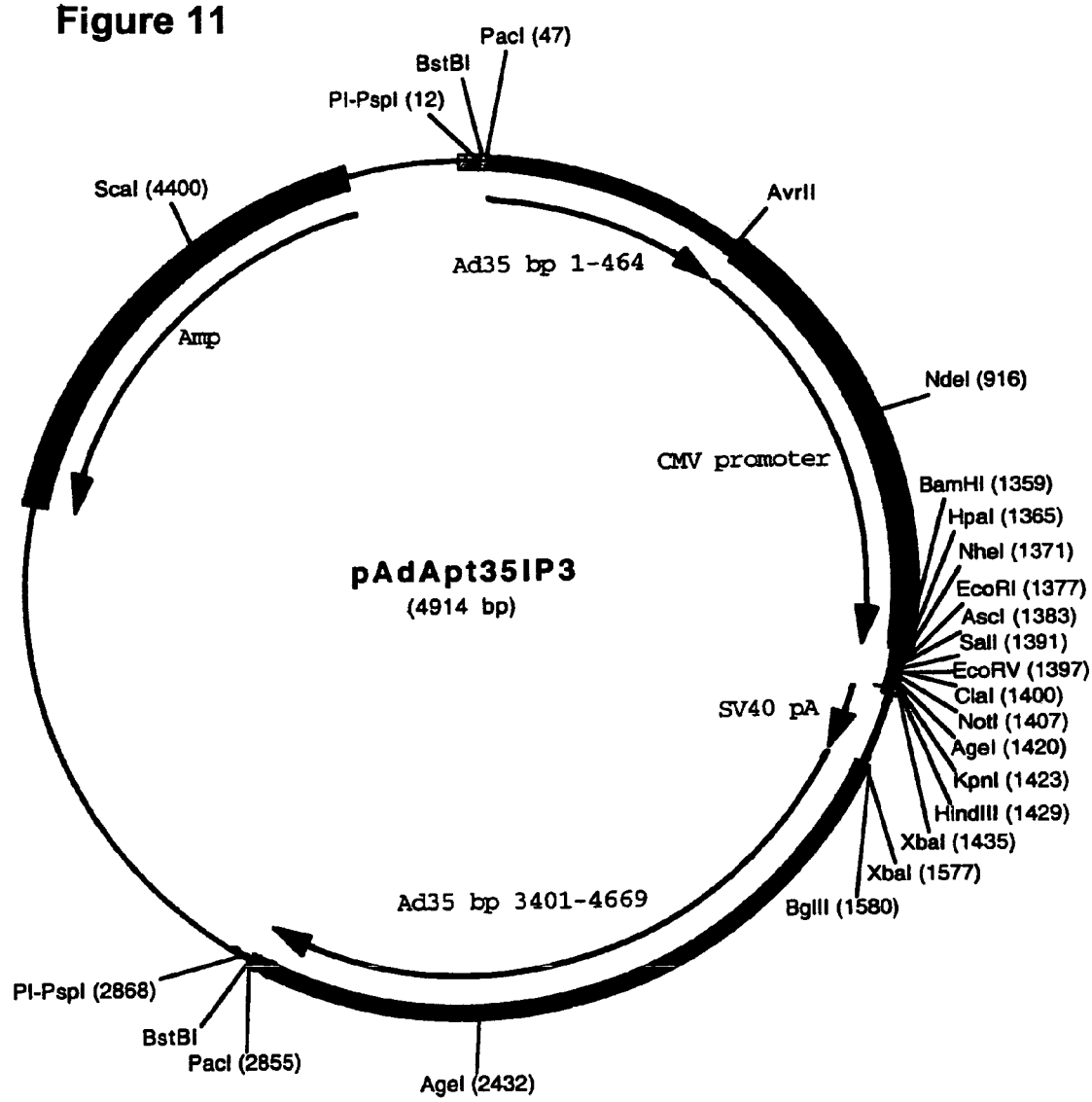
FIG. 11: Map of pAdApt35IP3.
Figure 12:
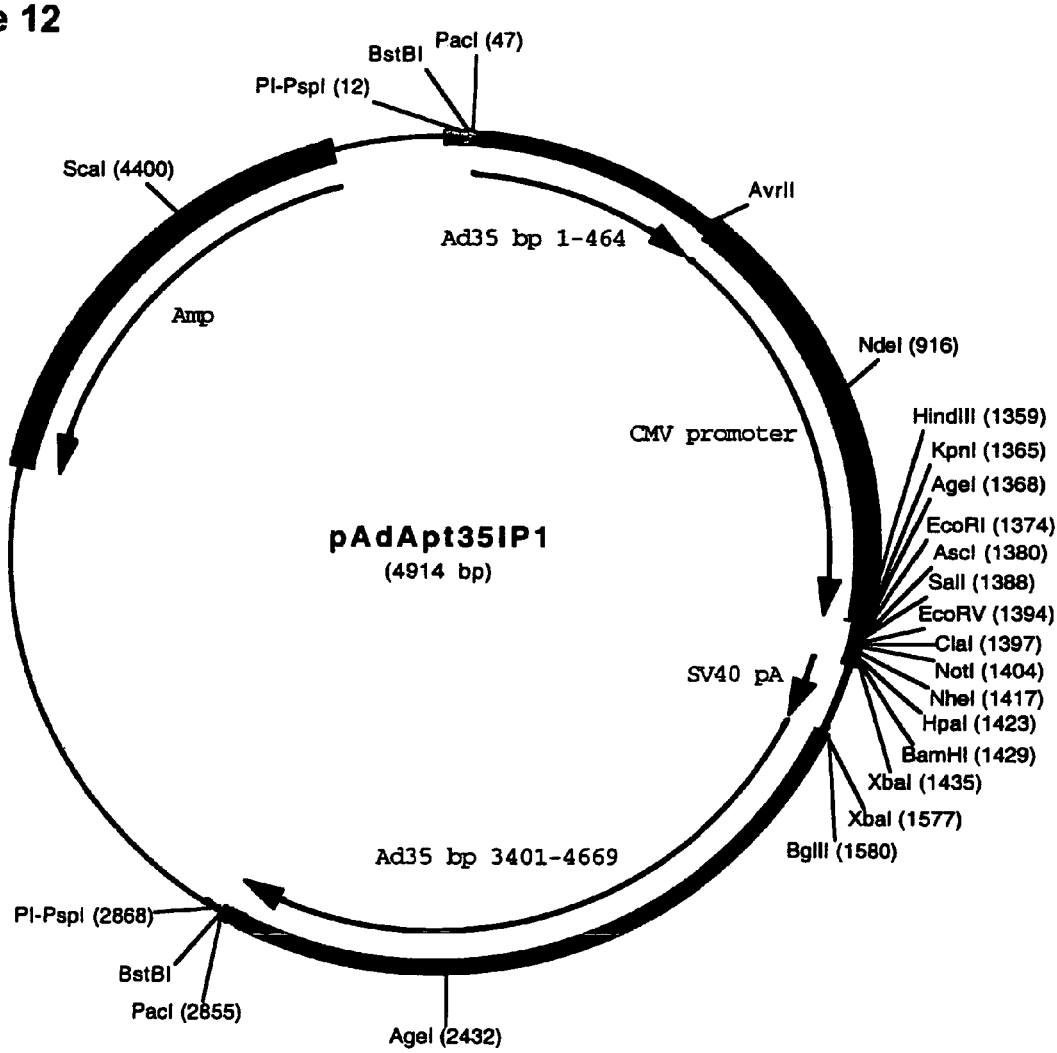
FIG. 12: Map of pAdApt35IP1.

The sequence of this fragment corresponds to nucleotides 3401 to 4669 of wtAd35 (FIG. 6) and contains 1.3 kb of sequences starting directly 3' from the E1B 55 k coding sequence. Amplification and purification were done as previously described herein for the fragment containing the left ITR and packaging sequence. The PCR fragment was then digested with PacI and subcloned into pNEB193 vector (New England Biolabs) digested with SmaI and PacI. The integrity of the sequence of the resulting clone was checked by sequence analysis. pNEB/Ad35pF3R4 was then digested with BglII and PacI and the Ad35 insert was isolated from gel using the QIAExII kit (Qiagen). pIPspAdApt3-Ad35lITR was digested with BglII and then partially with PacI. The 3624 bp fragment (containing vector sequences, the Ad35 ITR and packaging sequences as well as the CMV promoter, multiple cloning region and polyA signal) was also isolated using the QIAExII kit (Qiagen). Both fragments were ligated and transformed into competent DH10B cells (LTI). The resulting clone, pAdApt35IP3 (FIG. 11), has the expression cassette from pIPspAdApt3 but contains the Ad35 left ITR and packaging sequences and a second fragment corresponding to nucleotides 3401 to 4669 from Ad35. A second version of the Ad35 adapter plasmid having the multiple cloning site in the opposite orientation was made as follows:

pIPspAdapt1 (FIG. 9) was digested with NdeI and BglII and the 0.7 kbp band containing part of the CMV promoter, the MCS and SV40 polyA was isolated and inserted in the corresponding sites of pAdApt35IP3 generating pAdApt35IP1 (FIG. 12).

pAdApt35.LacZ and pAdApt35.Luc adapter plasmids were then generated by inserting the transgenes from pcDNA.LacZ (digested with KpnI and BamHI) and pAdApt.Luc (digested with HindIII and BamHI) into the corresponding sites in pAdApt35IP1. The generation of pcDNA.LacZ and pAdApt.Luc is described in International Patent Application WO99/55132.

2) Construction of Cosmid pWE.Ad35.pXI-rITR

Figure 13:
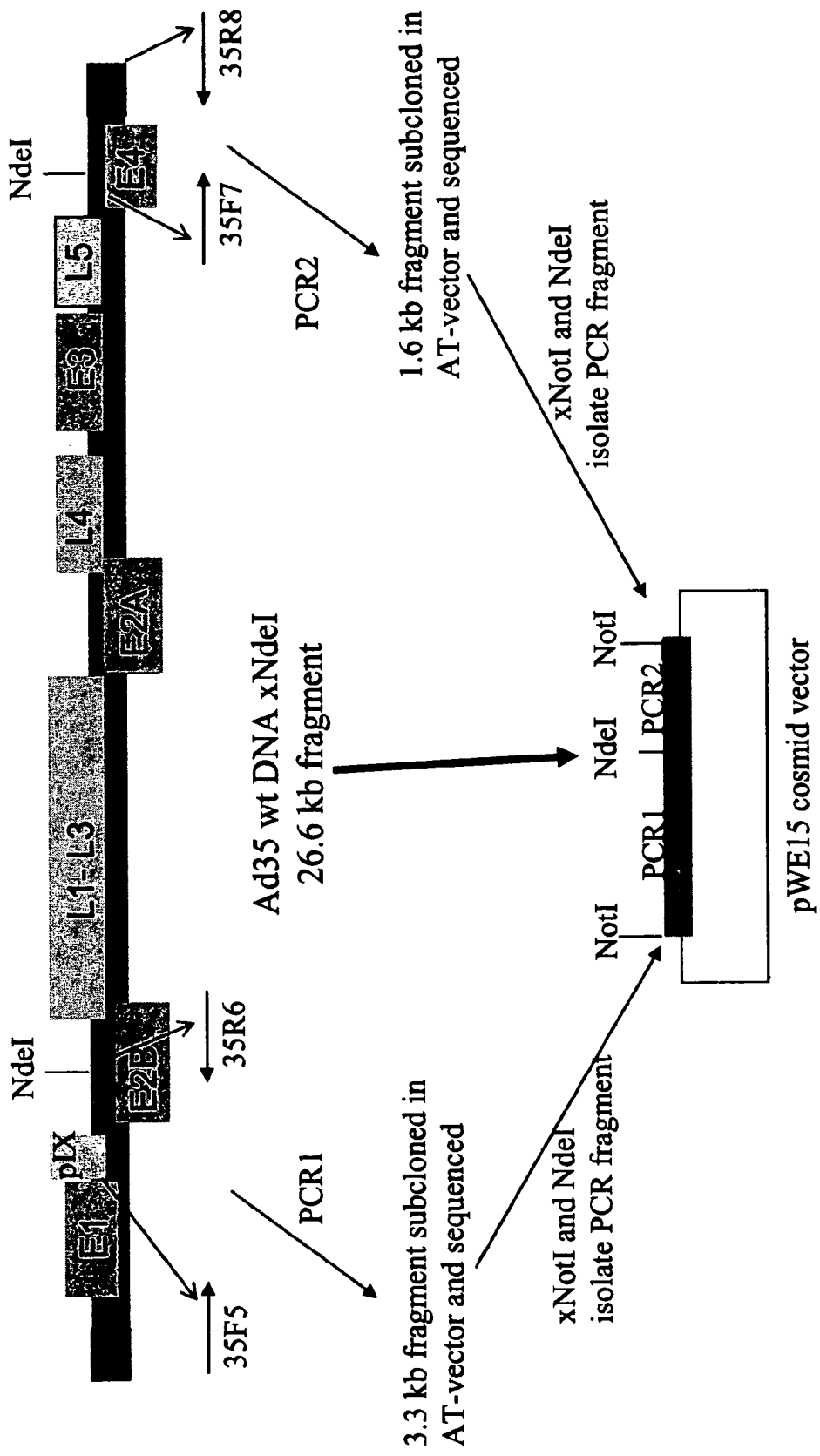
FIG. 13: Schematic representation of the steps undertaken to construct pWE.Ad35.pIX-rITR.

FIG. 13 presents the various steps undertaken to construct the cosmid clone containing Ad35 sequences from bp 3401 to 34794 (end of the right ITR) that are described in detail below.

A first PCR fragment (pIX-NdeI) was generated using the following primer set: 35F5: 5'-CGG AAT TCG CGG CCG CGG TGA GTA TTG GGA AAA C-3' (SEQ ID NO:53) and 35R6: 5'-CGC CAG ATC GTC TAC AGA ACA G-3' (SEQ ID NO:54).

DNA polymerase Pwo (Roche) was used according to manufacturer's instructions, however, with an end concentration of 0.6 µM of both primers and using 50 ngr wt Ad35 DNA as template. Amplification was done as follows: 2 min. at 94° C., 30 cycles of 30 sec. at 94° C., 30 sec. at 65° C. and 1 min. 45 sec. at 72° C., followed by 8 min. at 68° C. To enable cloning in the TA cloning vector PCR2.1, a last incubation with 1 unit superTaq polymerase (HT Biotechnology LTD) for 10 min. at 72° C. was performed.

The 3370 bp amplified fragment contains Ad35 sequences from bp 3401 to 6772 with a NotI site added to the 5' end. Fragments were purified using the PCR purification kit (LTI).

A second PCR fragment (NdeI-rITR) was generated using the following primers: 35F7: 5'-GAA TGC TGG CTT CAG TTG TAA TC-3' (SEQ ID NO:55) and 35R8: 5'-CGG AAT TCG CGG CCG CAT TTA AAT CAT CAT CAA TAA TAT ACC-3' (SEQ ID NO:56).

Amplification was done with pfx DNA polymerase (LTI) according to manufacturer's instructions but with 0.6 µM of both primers and 3% DMSO using 10 ngr. of wtAd35 DNA as template. The program was as follows: 3 min. at 94° C. and 5 cycles of 30 sec. at 94° C., 45 sec. at 40° C., 2 min. 45 sec. at 68° C. followed by 25 cycles of 30 sec. at 94° C., 30 sec. at 60° C., 2 min. 45 sec. at 68° C. To enable cloning in the TA-cloning vector PCR2.1, a last incubation with 1 unit superTaq polymerase for 10 min. at 72° C. was performed. The 1.6 kb amplified fragment ranging from nucleotides 33178 to the end of the right ITR of Ad35, was purified using the PCR purification kit (LTI).

Figure 14:
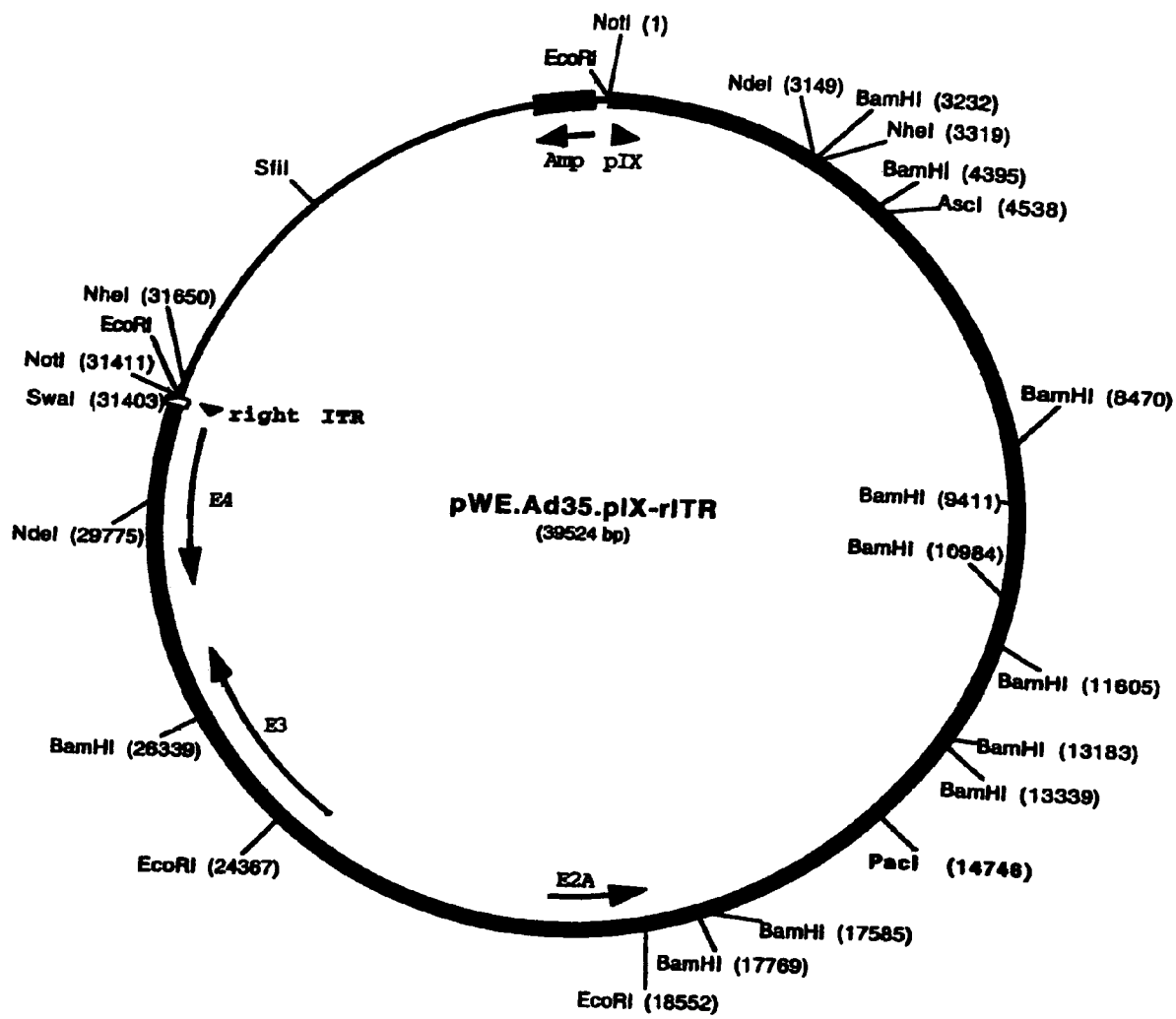
FIG. 14: Map of pWE.Ad35.pIX-rITR.

Both purified PCR fragments were ligated into the PCR2.1 vector of the TA-cloning kit (Invitrogen) and transformed into STBL-2 competent cells (LTI). Clones containing the expected insert were sequenced to confirm correct amplification. Next, both fragments were excised from the vector by digestion with NotI and NdeI and purified from gel using the GENECLEAN kit (Bio101, Inc.). Cosmid vector pWE15 (Clontech) was digested with NotI, dephosphorylated and also purified from gel. These three fragments were ligated and transformed into STBL2 competent cells (LTI). One of the correct clones that contained both PCR fragments was then digested with NdeI, and the linear fragment was purified from gel using the GENECLEAN kit. Ad35 wt DNA was digested with NdeI and the 26.6 kb fragment was purified from LMP gel using agarase enzyme (Roche) according to the manufacturer's instructions. These fragments were ligated together and packaged using λ1 phage packaging extracts (Stratagene) according to the manufacturer's protocol. After infection into STBL-2 cells, colonies were grown on plates and analyzed for presence of the complete insert. One clone with the large fragment inserted in the correct orientation and having the correct restriction patterns after independent digestions with three enzymes (NcoI, PvuII and ScaI) was selected. This clone is designated pWE.Ad35.pIX-rITR. It contains the Ad35 sequences from bp 3401 to the end and is flanked by NotI sites (FIG. 14).

3) Generation of Ad35-Based Recombinant Viruses on PER.C6

Wild-type Ad35 virus can be grown on PER.C6 packaging cells to very high titers. However, whether the Ad5-E1 region that is present in PER.C6 is able to complement E1-deleted Ad35 recombinant viruses is unknown. To test this, PER.C6 cells were cotransfected with the above described adapter plasmid pAdApt35.LacZ and the large backbone fragment pWE.Ad35.pIX-rITR. First, pAdApt35.LacZ was digested with PacI and pWE.Ad35.pIX-rITR was digested with NotI. Without further purification, 4 µgr of each construct was mixed with DMEM (LTI) and transfected into PER.C6 cells, seeded at a density of $5 \times 10^6$ cells in a T25 flask the day before, using Lipofectamin (LTI) according to the manufacturer's instructions. As a positive control, 6 µgr of PacI-digested pWE.Ad35.pIX-rITR DNA was cotransfected with a 6.7 kb NheI fragment isolated from Ad35 wt DNA containing the left end of the viral genome including the E1 region. The next day, medium (DMEM with 10% FBS and 10 mM $MgCl_2$) was refreshed and cells were further incubated. At day 2 following the transfection, cells were trypsinized and transferred to T80 flasks. The positive control flask showed CPE at five days following transfection, showing that the pWE.Ad35.pIX-rITR construct is functional at least in the presence of Ad35-E1 proteins. The transfection with the Ad35 LacZ adapter plasmid and pWE.Ad35.pIX-rITR did not give rise to CPE. These cells were harvested in the medium at day 10 and freeze/thawed once to release virus from the cells. 4 ml of the harvested material was added to a T80 flask with PER.C6 cells (at 80% confluency) and incubated for another five days. This harvest/re-infection was repeated for two times but there was no evidence for virus-associated CPE.

From this experiment, it seems that the Ad5-E1 proteins are not, or not well enough, capable of complementing Ad35 recombinant viruses, however, it may be that the sequence overlap of the adapter plasmid and the pWE.Ad35.pIX-rITR backbone plasmid is not large enough to efficiently recombine and give rise to a recombinant virus genome. The positive control transfection was done with a 6.7 kb left end fragment and therefore the sequence overlap was about 3.5 kb. The adapter plasmid and the pWE.Ad35.pIX-rITR fragment have a sequence overlap of 1.3 kb. To check whether the sequence overlap of 1.3 kb is too small for efficient homologous recombination, a cotransfection was done with PacI-digested pWE.Ad35.pIX-rITR and a PCR fragment of Ad35 wt DNA generated with the above mentioned 35F1 and 35R4 using the same procedures as previously described herein. The PCR fragment thus contains left end sequences up to bp 4669 and, therefore, has the same overlap sequences with pWE.Ad35.pIX-rITR as the adapter plasmid pAdApt35.LacZ, but has Ad35 E1 sequences. Following PCR column purification, the DNA was digested with SalI to remove possible intact template sequences. A transfection with the digested PCR product alone served as a negative control. Four days after the transfection, CPE occurred in the cells transfected with the PCR product and the Ad35 pIX-rITR fragment, and not in the negative control. This result shows that a 1.3 kb overlapping sequence is sufficient to generate viruses in the presence of Ad35 E1 proteins. From these experiments, we conclude that the presence of at least one of the Ad35.E1 proteins is necessary to generate recombinant Ad35-based vectors from plasmid DNA on Ad5-complementing cell lines.

Example 8

1) Construction of Ad35.E1 Expression Plasmids

Since Ad5-E1 proteins in PER.C6 are incapable of complementing Ad35 recombinant viruses efficiently, Ad35 E1 proteins have to be expressed in Ad5-complementing cells (e.g., PER.C6). Otherwise, a new packaging cell line expressing Ad35 E1 proteins has to be made, starting from either diploid primary human cells or established cell lines not expressing adenovirus E1 proteins. To address the first possibility, the Ad35 E1 region was cloned in expression plasmids as described below.

First, the Ad35 E1 region from bp 468 to bp 3400 was amplified from wtAd35 DNA using the following primer set: 35F11: 5'-GGG GTA CCG AAT TCT CGC TAG GGT ATT TAT ACC-3' (SEQ ID NO:57) and 35F10: 5'-GCT CTA GAC CTG CAG GTT AGT CAG TTT CTT CTC CAC TG-3' (SEQ ID NO:58). This PCR introduces a KpnI and EcoRI site at the 5' end and an SbfI and XbaI site at the 3' end.

Amplification on 5 ngr. template DNA was done with Pwo DNA polymerase (Roche) using the manufacturer's instructions, however, with both primers at a final concentration of 0.6 µM. The program was as follows: 2 min. at 94° C., 5 cycles of 30 sec. at 94° C., 30 sec. at 56° C. and 2 min. at 72° C., followed by 25 cycles of 30 sec. at 94° C., 30 sec. at 60° C. and 2 min. at 72° C., followed by 10 min. at 72° C. PCR product was purified by a PCR purification kit (LTI) and digested with KpnI and XbaI. The digested PCR fragment was then ligated to the expression vector pRSVhbvNeo (see below) also digested with KpnI and XbaI. Ligations were transformed into competent STBL-2 cells (LTI) according to manufacturer's instructions and colonies were analyzed for the correct insertion of Ad35E1 sequences into the polylinker in between the RSV promoter and HBV polyA.

Figure 15:
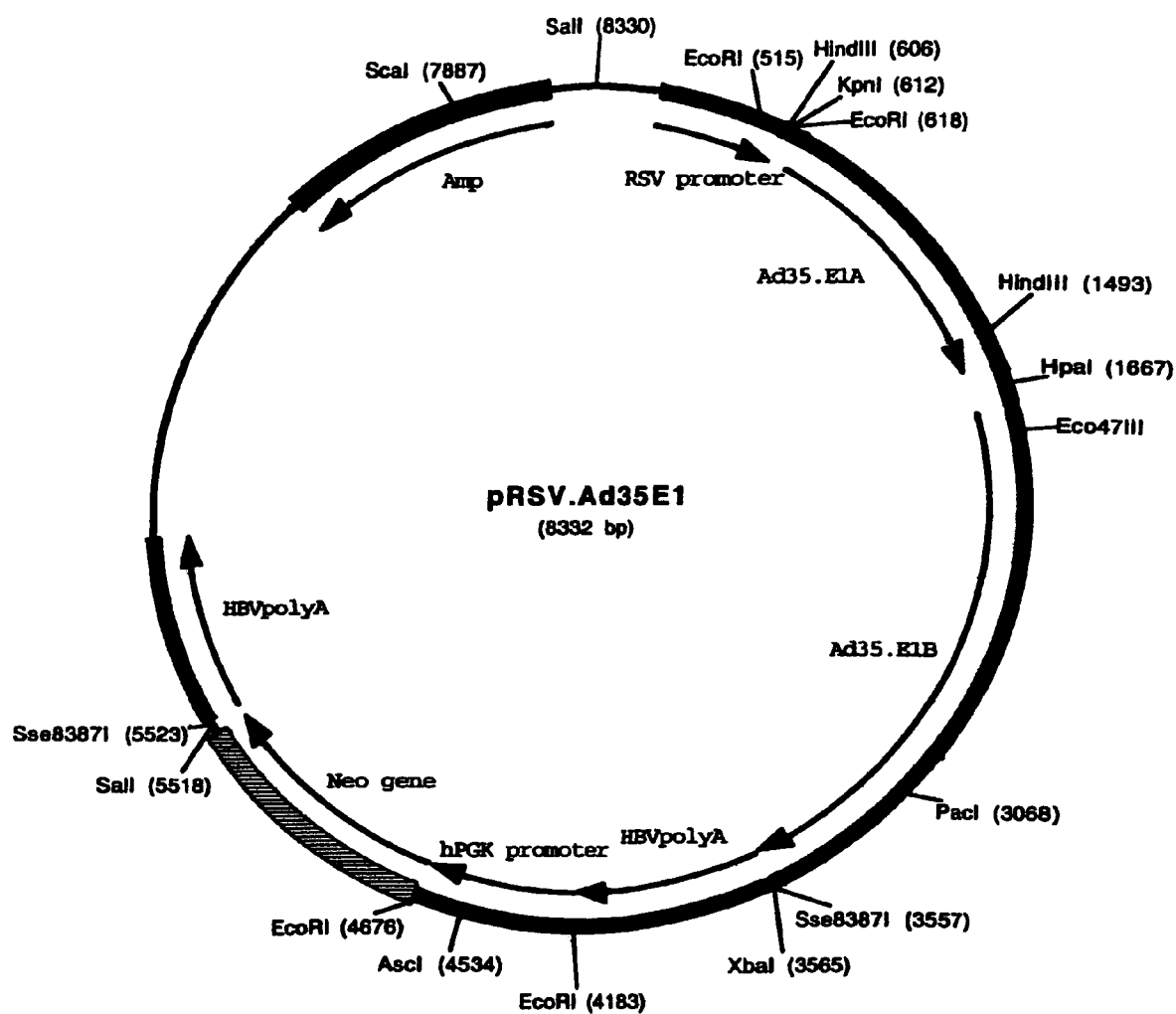
FIG. 15: Map of pRSV.Ad35-E1.
Figure 16:
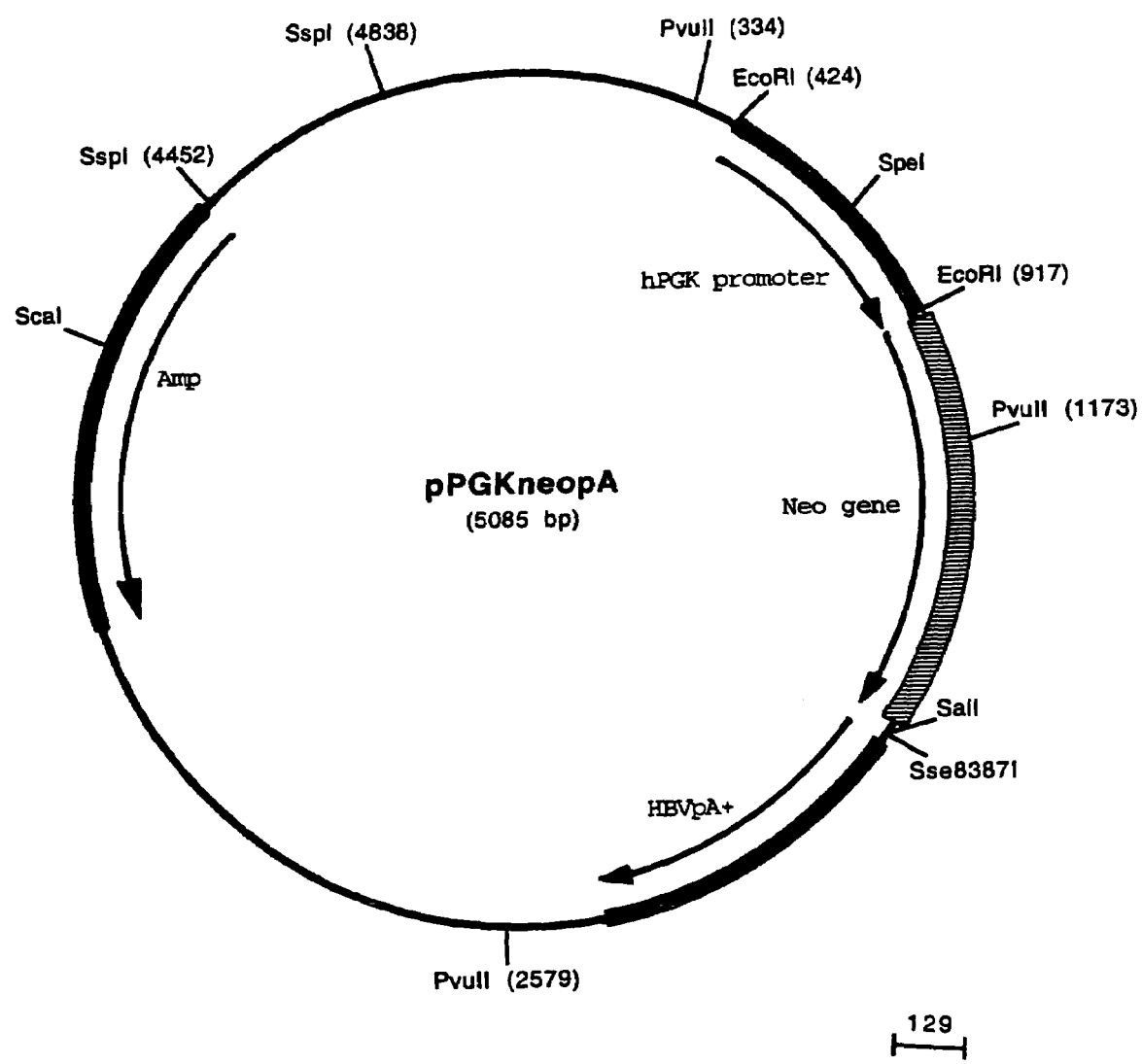
FIG. 16: Map of pGKneopA.
Figure 17:
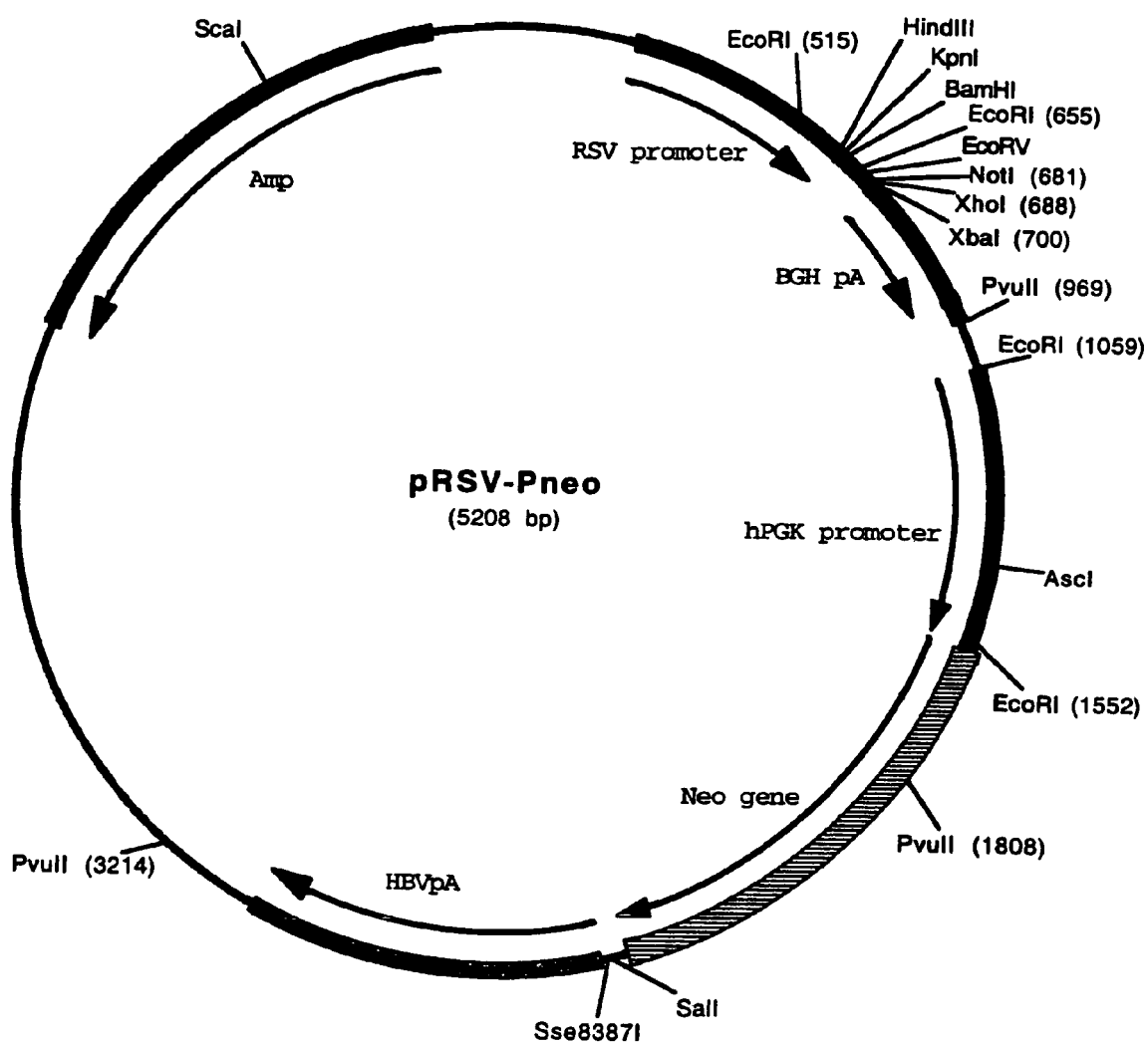
FIG. 17: Map of pRSVpNeo.

The resulting clone was designated pRSV.Ad35-E1 (FIG. 15). The Ad35 sequences in pRSV.Ad35-E1 were checked by sequence analysis.

pRSVhbvNeo was generated as follows: pRc-RSV (Invitrogen) was digested with PvuII, dephosphorylated with TSAP enzyme (LTI), and the 3 kb vector fragment was isolated in low melting point agarose (LMP). Plasmid pPGKneopA (FIG. 16; described in International Patent Application WO96/35798) was digested with SspI completely to linearize the plasmid and facilitate partial digestion with PvuII. Following the partial digestion with PvuII, the resulting fragments were separated on a LMP agarose gel and the 2245 bp PvuII fragment, containing the PGK promoter, neomycin-resistance gene and HBVpolyA, was isolated. Both isolated fragments were ligated to give the expression vector pRSV-pNeo that now has the original SV40prom-neo-SV40polyA expression cassette replaced by a PGKprom-neo-HBVpolyA cassette (FIG. 17). This plasmid was further modified to replace the BGHpA with the HBVpA as follows: pRSVpNeo was linearized with ScaI and further digested with XbaI. The 1145 bp fragment, containing part of the Amp gene and the RSV promoter sequences and polylinker sequence, was isolated from gel using the GeneClean kit (Bio101, Inc.). Next, pRSVpNeo was linearized with ScaI and further digested with EcoRI partially and the 3704 bp fragment containing the PGKneo cassette and the vector sequences were isolated from gel as above. A third fragment, containing the HBV polyA sequence flanked by XbaI and EcoRI at the 5' and 3' end respectively, was then generated by PCR amplification on pRSVpNeo using the following primer set: HBV-F: 5'-GGC TCT AGA GAT CCT TCG CGG GAC GTC-3' (SEQ ID NO:59) and HBV-R: 5'-GGC GAA TTC ACT GCC TTC CAC CAA GC-3' (SEQ ID NO:60).

Figure 18:
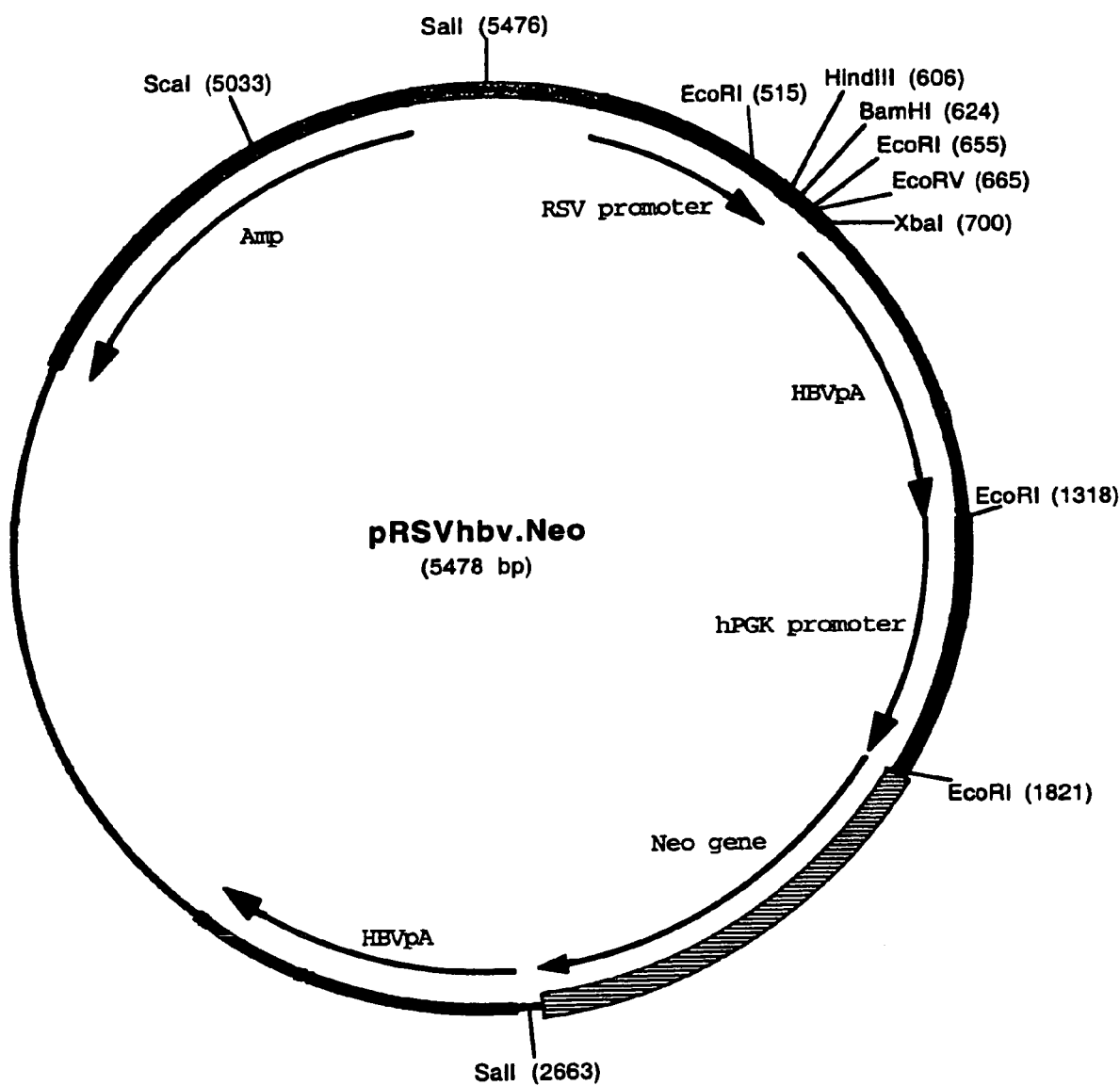
FIG. 18: Map of pRSVhbvNeo.

Amplification was done with Elongase enzyme (LTI) according to the manufacturer's instructions with the following conditions: 30 seconds at 94° C., then 5 cycles of 45 seconds at 94° C., 1 minute at 42° C. and 1 minute at 68° C., followed by 30 cycles of 45 seconds at 94° C., 1 minute at 65° C. and 1 minute at 68° C., followed by 10 minutes at 68° C. The 625 bp PCR fragment was then purified using the Qiaquick PCR purification kit, digested with EcoRI and XbaI and purified from gel using the GENECLEAN kit. The three isolated fragments were ligated and transformed into DH5α competent cells (LTI) to give the construct pRSVhbvNeo (FIG. 18). In this construct, the transcription regulatory regions of the RSV expression cassette and the neomycin selection marker are modified to reduce overlap with adenoviral vectors that often contain CMV and SV40 transcription regulatory sequences.

2) Generation of Ad35 Recombinant Viruses on PER.C6 Cells Cotransfected with an Ad35-E1 Expression Construct PER.C6 cells were seeded at a density of $5 \times 10^6$ cells in a T25 flask and, the next day, transfected with a DNA mixture containing:

1 µg pAdApt35.LacZ digested with PacI
5 µg pRSV.Ad35E1 undigested
2 µg pWE.Ad35.pfX-rITR digested with NotI Transfection was done using Lipofectamine according to the manufacturer's instructions. Five hours after addition of the transfection mixture to the cells, medium was removed and replaced by fresh medium. After two days, cells were transferred to T80 flasks and further cultured. One week post-transfection, 1 ml of the medium was added to A549 cells and, the following day, cells were stained for LacZ expression. Blue cells were clearly visible after two hours of staining indicating that recombinant LacZ-expressing viruses were produced. The cells were further cultured, but no clear appearance of CPE was noted. However, after 12 days, clumps of cells appeared in the monolayer and 18 days following transfection, cells were detached. Cells and medium were then harvested, freeze-thawed once, and 1 ml of the crude lysate was used to infect PER.C6 cells in a 6-well plate. Two days after infection, cells were stained for LacZ activity. After two hours, 15% of the cells were stained blue. To test for the presence of wt and/or replicating competent viruses, A549 cells were infected with these viruses and further cultured. No signs of CPE were found indicating the absence of replication competent viruses. These experiments show that recombinant AdApt35.LacZ viruses were made on PER.C6 cells cotransfected with an Ad35-E1 expression construct.

3) Ad35 Recombinant Viruses Escape Neutralization in Human Serum Containing Neutralizing Activity to Ad5 Viruses The AdApt35.LacZ viruses were then used to investigate infection in the presence of serum that contains neutralizing activity to Ad5 viruses. Purified Ad5-based LacZ virus served as a positive control for NA. Hereto, PER.C6 cells were seeded in a 24-wells plate at a density of $2\times10^5$ cells/well. The next day, a human serum sample with high neutralizing activity to Ad5 was diluted in culture medium in five steps of five times dilutions. 0.5 ml of diluted serum was then mixed with $4\times10^6$ virus particles AdApt5.LacZ virus in 0.5 ml medium and, after 30 minutes of incubation at 37° C., 0.5 ml of the mixture was added to PER.C6 cells in duplicate. For the AdApt35.LacZ viruses, 0.5 ml of the diluted serum samples were mixed with 0.5 ml crude lysate containing AdApt35.LacZ virus and, after incubation, 0.5 ml of this mixture was added to PER.C6 cells in duplo. Virus samples incubated in medium without serum were used as positive controls for infection. After two hours of infection at 37° C., medium was added to reach a final volume of 1 ml and cells were further incubated. Two days after infection, cells were stained for LacZ activity. The results are shown in Table II. From these results, it is clear that whereas AdApt5.LacZ viruses are efficiently neutralized, AdApt35.LacZ viruses remain infectious irrespective of the presence of human serum. This proves that recombinant Ad35-based viruses escape neutralization in human sera that contain NA to Ad5-based viruses.

Example 9

An Ad5/Fiber35 Chimeric Vector with Cell Type Specificity for Hemopoietic CD34$^+$ Lin$^-$ Stem Cells In Example 3, we described the generation of a library of Ad5-based adenoviruses harboring fiber proteins of other serotypes. As a non-limiting example for the use of this library, we here describe the identification of fiber-modified adenoviruses that show improved infection of hemopoietic stem cells.

Cells isolated from human bone marrow, umbilical cord blood, or mobilized peripheral blood carrying the flow cytometric phenotype of being positive for the CD34 antigen and negative for the early differentiation markers CD33, CD38, and CD71 (lin$^-$) are commonly referred to as hemopoietic stem cells (HSC). Genetic modification of these cells is of major interest since all hemopoietic lineages are derived from these cells and therefore the HSC is a target cell for the treatment of many acquired or congenital human hemopoietic disorders. Examples of diseases that are possibly amenable for genetic modification of HSC include, but are not limited to, Hurlers disease, Hunter's disease, Sanfilippos disease, Morquios disease, Gaucher disease, Farbers disease, Niemann-Pick disease, Krabbe disease, Metachromatic Leucodistrophy, I-cell disease, severe immunodeficiency syndrome, Jak-3 deficiency, Fucosidose deficiency, thallasemia, and erythropoietic porphyria. Besides these hemopoietic disorders, also strategies to prevent or treat acquired immunodeficiency syndrome ("AIDS") and hemopoietic cancers are based on the genetic modification of HSCs (or cells derived from HSCs such as CD4-positive T lymphocytes in case of AIDS). The examples listed herein thus aim at introducing DNA into the HSC in order to complement on a genetic level for a gene and protein deficiency. In case of strategies for AIDS or cancer, the DNA to be introduced into the HSC can be anti-viral genes or silicide genes.

Besides the examples listed herein, several other areas exist in which efficient transduction of HSCs using adenoviral vectors can play an important role, for instance, in the field of tissue engineering. In this area, it is important to drive differentiation of HSCs to specific lineages. Some, non-limiting, examples are ex vivo bone formation, cartilage formation, skin formation, as well as the generation of T-cell precursors or endothelial cell precursors. The generation of bone, cartilage or skin in bioreactors can be used for transplantation after bone fractures or spinal cord lesions or severe burn injuries. Naturally, transduced cells can also directly be re-infused into a patient. The formation of large numbers of endothelial cell precursor from HSCs is of interest since these endothelial precursor cells can home, after re-infusion, to sites of cardiovascular injury such as ischemia. Likewise, the formation of large numbers of T-cells from HSCs is of interest since these T-cell precursors can be primed, ex vivo, to eradicate certain targets in the human body after re-infusion of the primed T-cells. Preferred targets in the human body can be tumors or virus-infected cells.

Figure 19:
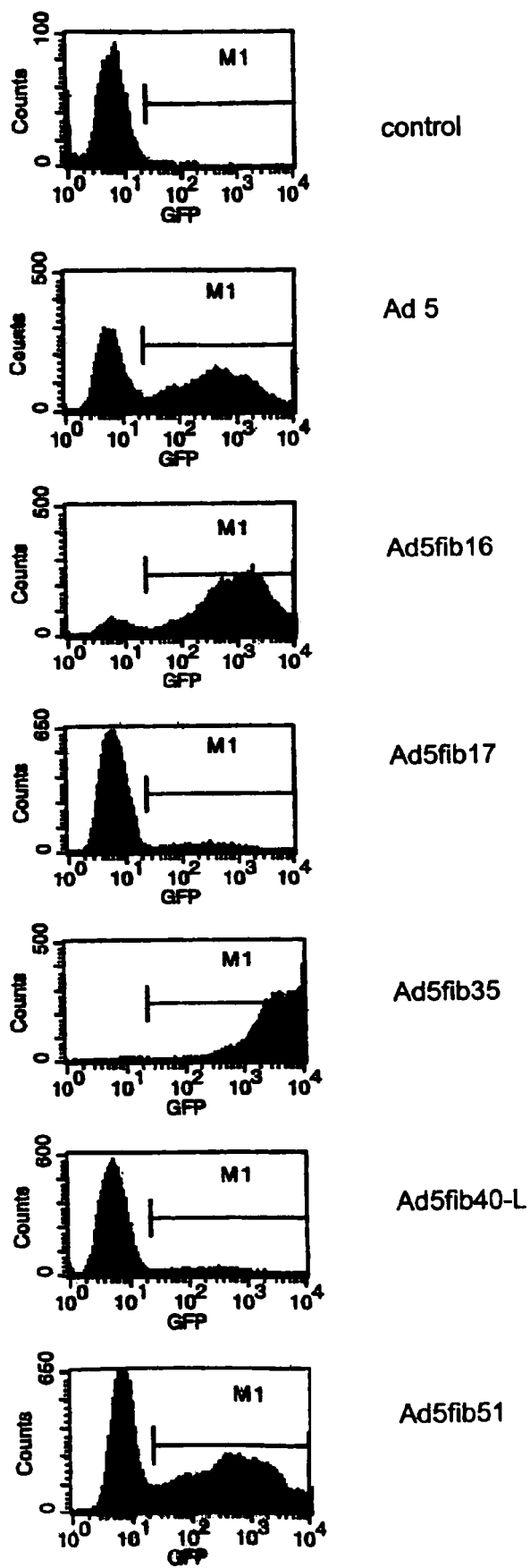
FIG. 19: Flow cytometric analyses on GFP expression in human TF-1 cells. Non-transduced TF-1 cells were used to set a background level of 1%. GFP expression in cells transduced with Ad5, Ad5.Fib16, Ad5.Fib17, Ad5.Fib40-L, Ad5.Fib35, and Ad5.Fib51 is shown.
Figure 20:
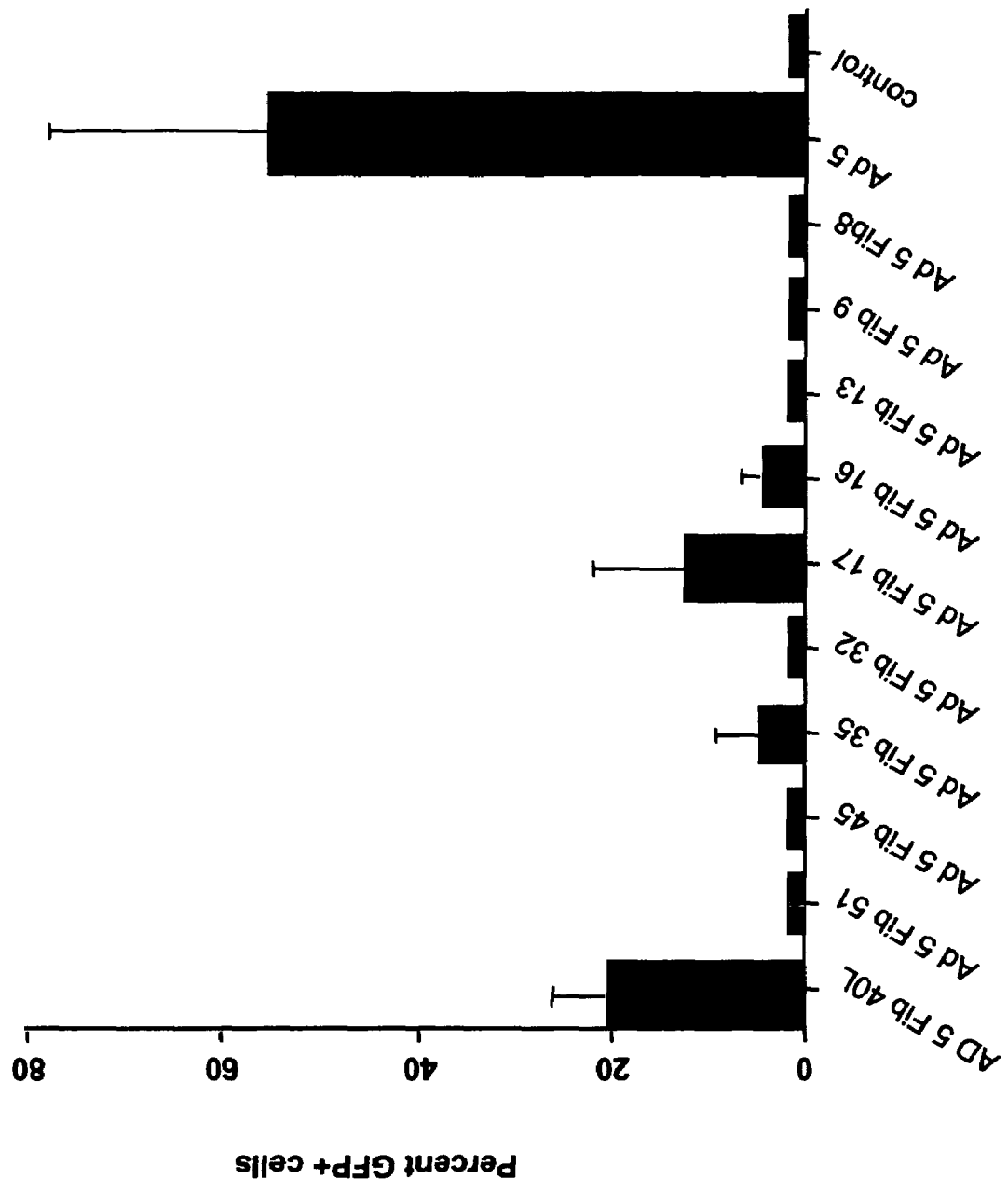
FIG. 20: Transduction of primary human fibroblast-like stroma. Cells were analyzed 48 hours after a two-hour exposure to the different chimeric fiber viruses. Shown is percentage of cells found positive for the transgene: GFP using a flow cytometer. Non-transduced stroma cells were used to set a background at 1%. Results of different experiments (n=3) are shown ± standard deviation.

From the herein-described examples, it can be concluded that efficient gene delivery to HSCs is a major interest for the field of gene therapy. Therefore, alteration of the Ad5 host cell range to be able to target HSCs in vitro as well as in vivo is a major interest of the invention. To identify a chimeric adenovirus with preferred infection characteristics for human HSCs, we generated a library of Ad5-based viruses carrying the fiber molecule from alternative adenoviral serotypes (serotypes 8, 9, 13, 16, 17, 32, 35, 45, 40-L, 51). The generation of this fiber-modified library is described in Example 3 hereof. Ad5 was included as a reference. A small panel of this library was tested on human TF-1 (erythroid leukemia, ATCC CRL-2003) whereas all chimeric viruses generated were tested on human primary stroma cells and human HSCs. Human TF-1 cells were routinely maintained in DMEM supplemented with 10% FCS and 50 ng/ml IL-3 (Sandoz, Basel, Switzerland). Human primary fibroblast-like stroma, isolated from a bone marrow aspirate, is routinely maintained in DMEM/10% FCS. Stroma was seeded at a concentration of $1\times10^5$ cells per well of 24-well plates. 24 hours after seeding cells were exposed for 2 hours to 1,000 virus particles per cell of Ad5, Ad5.Fib16, Ad5.Fib17, Ad5.Fib35, Ad5.Fib40-L, or Ad5.Fib51 all carrying GFP as a marker. After 2 hours, cells were washed with PBS and reseeded in medium without addition of virus. TF-1 cells were seeded at a concentration of $2\times10^5$ cells per well of 24-well plates and were also exposed for 2 hours to 1,000 virus particles of the different chimeric adenoviruses. Virus was removed by washing the cells after the 2 hours exposure. Both cell types were harvested 48 hours after virus exposure and analyzed for GFP expression using a flow cytometer. The results on TF-1 cells, shown in FIG. 19, demonstrate that chimeric adenoviruses carrying a fiber from serotypes 16, 35, or 51 (all derived from adenovirus subgroup B) have preferred infection characteristics as compared to Ad5 (subgroup C), Ad5.Fib17 (subgroup D), or Ad5.Fib40-L (subgroup F). Primary human stroma was tested since these cells are commonly used as "feeder" cells to allow proliferation and maintenance of HSCs under ex vivo culture conditions. In contrast to the transduction of TF-1 cells, none of the fiber chimeric adenoviruses were able to efficiently transduce human primary stroma (FIG. 20). Reasonable infection of human fibroblast-like primary stroma was observed only with Ad5 despite the observation that none of the known receptor molecules are expressed on these cells (see Table III). The absence of infection of human stroma using the chimeric viruses is advantageous since, in a co-culture setting, the chimeric adenovirus will not be absorbed primarily by the stroma "feeder" cells.

To test the transduction capacity of the fiber chimeric viruses, a pool of umbilical cord blood (3 individuals) was used for the isolation of stem cells. $CD34^+$ cells were isolated from mononuclear cell preparation using a MACS laboratory separation system (Miltenyi Biotec) using the protocol supplied by the manufacturer. Of the $CD34^+$ cells, $2\times10^5$ were seeded in a volume of 150 μl DMEM (no serum; Gibco, Gaithersburg, Md.) and 10 μl of chimeric adenovirus (to give a final virus particles/cell ratio of 1,000) was added. The chimeric adenoviruses tested were Ad5, Ad5.Fib16, Ad5.Fib35, Ad5Fib17, Ad5.Fib51 all containing GFP as a marker. Cells were incubated for 2 hours in a humidified atmosphere of 10% $CO_2$ at 37° C. Thereafter, cells were washed once with 500 μl DMEM and re-suspended in 500 μl of StemPro-34 SF medium (Life Technologies, Grand Island, N.Y.).

Figure 21:
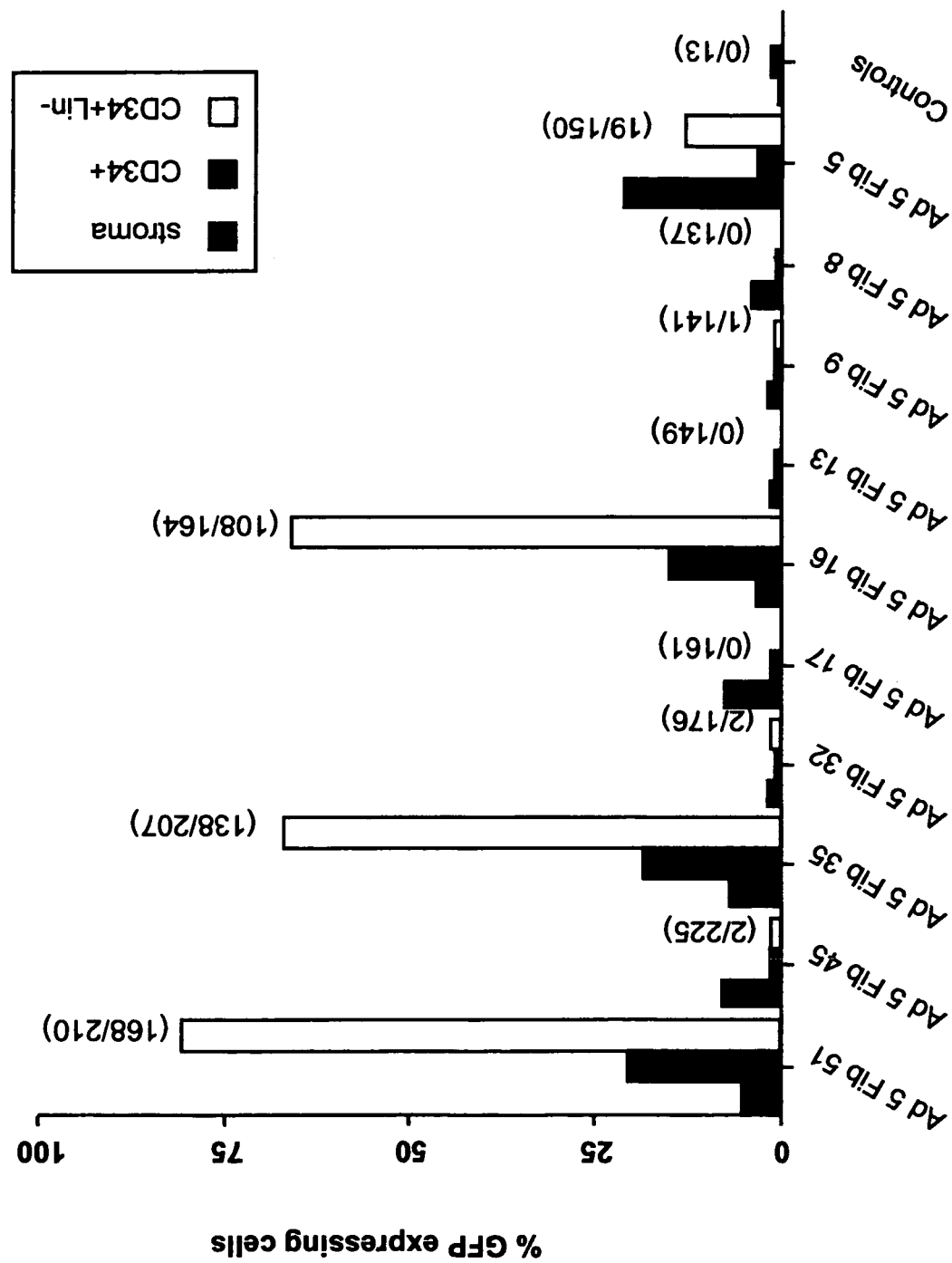
FIG. 21: Transduction of primary human fibroblast-like stroma, $CD34^+$ cells and $CD34^+Lin^-$ cells. Cells were analyzed 5 days after a two-hour exposure to the different chimeric fiber viruses. Shown is percentage of cells found positive for the transgene: GFP using a flow cytometer. Non-transduced cells were used to set a background at 1%. Also shown is the number of GFP-positive events divided by the total number of events analyzed (between brackets).
Figure 22A:
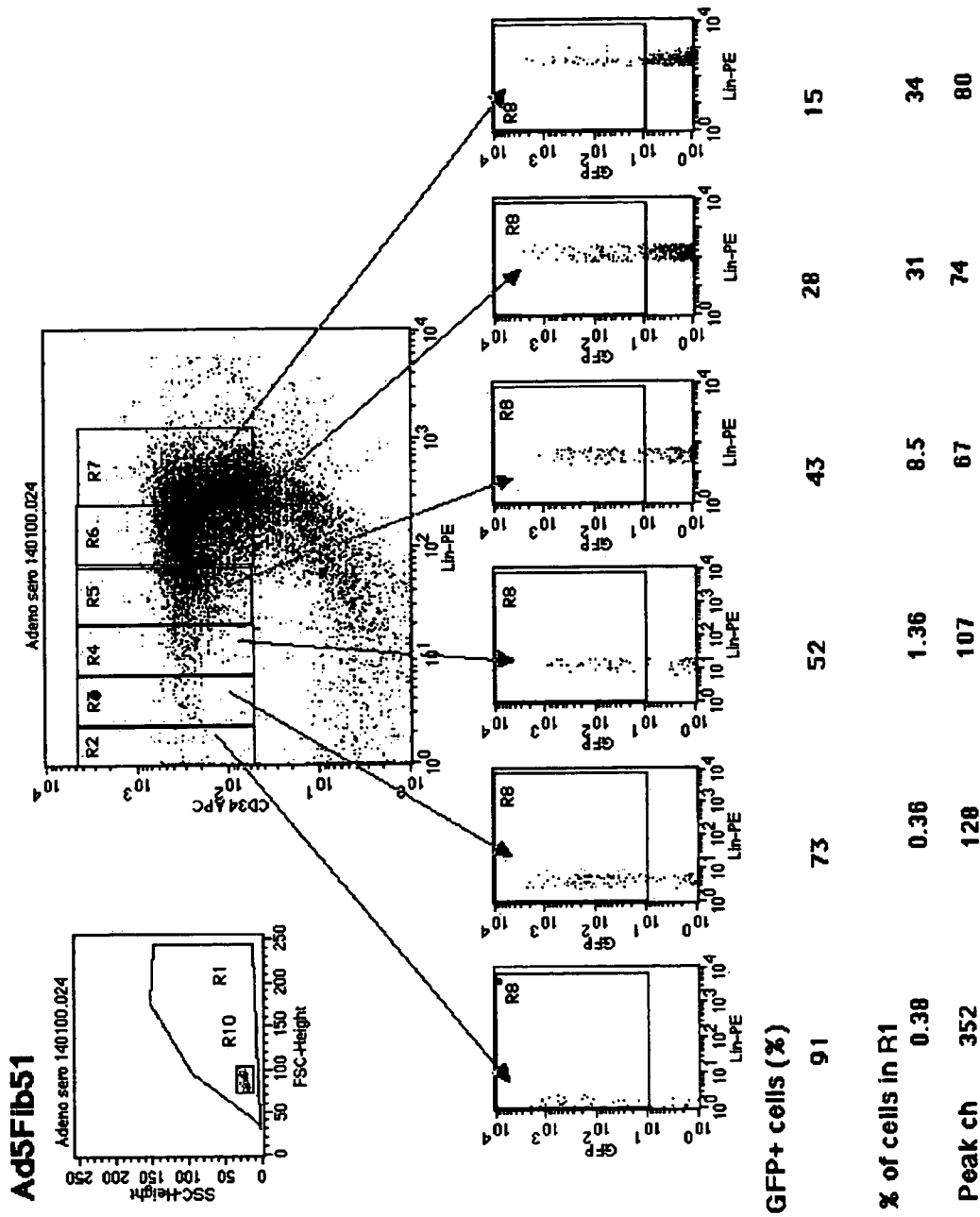
FIG. 22A: Flow cytometric analysis of GFP-positive cells after transduction of $CD34^+$ cells with Ad5.Fib51. All cells gated in R2-R7 are positive for CD34 but differ in their expression of early differentiation markers CD33, CD38, and CD71 (Lin). Cells in R2 are negative for CD33, CD38, and CD71 whereas cells in R7 are positive for these markers. To demonstrate specificity of Ad5.Fib51 the percentage of GFP-positive cells was determined in R2-R7 that proofed to decline from 91% (R2) to 15% (R7).
Figure 22B:
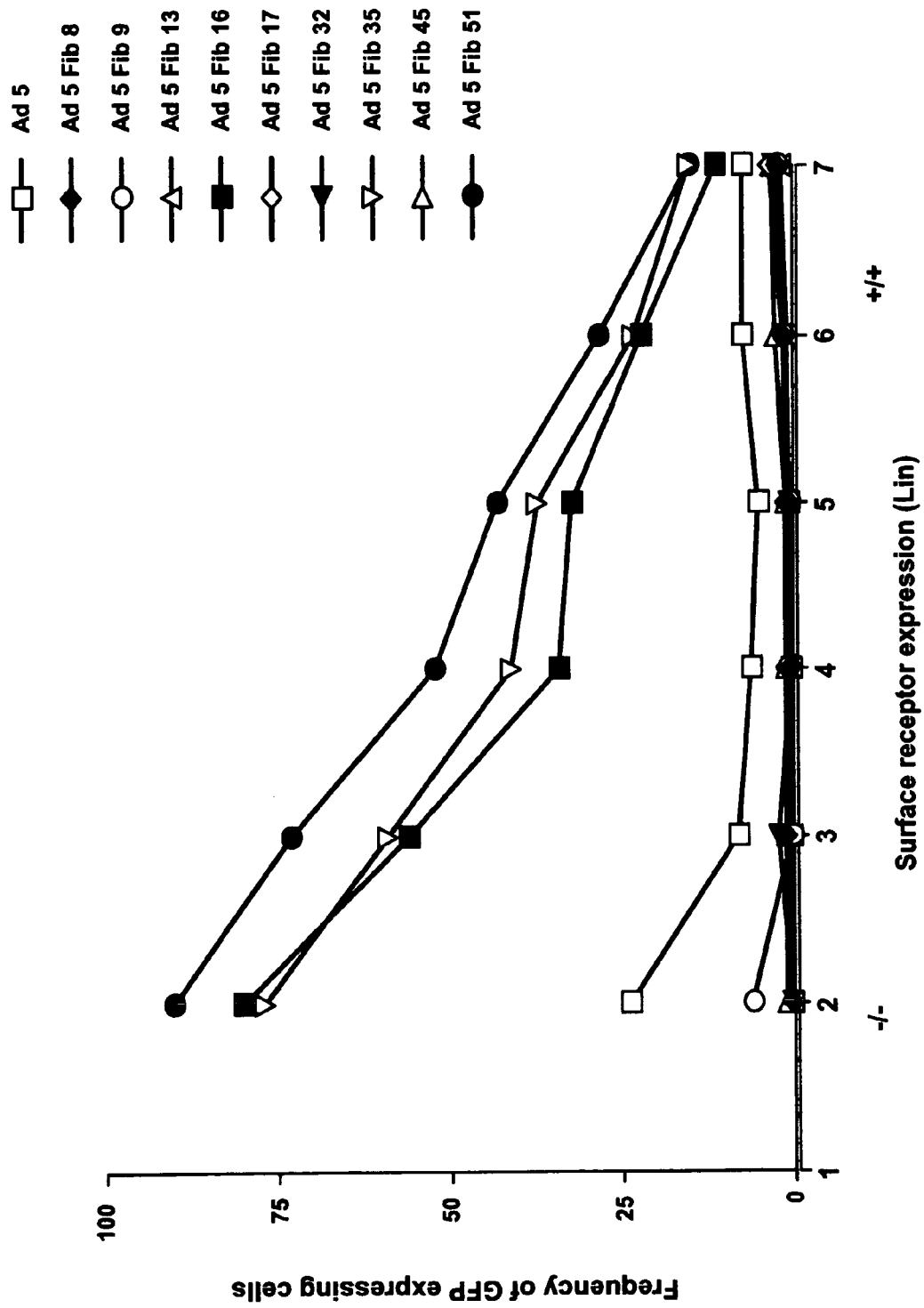
FIG. 22B: Identical experiment as shown under FIG. 22A (X-axes is R2-R7) but for the other Ad fiber chimeric viruses showing that Ad5.Fib35, and Ad5.Fib16 behave similar as Ad5.Fib51.

Cells were then cultured for 5 days in 24-well plates (Greiner, Frickenhausen, Germany) on irradiated (20 Gy) pre-established human bone marrow stroma (ref 1), in a humidified atmosphere of 10% $CO_2$ at 37° C. After 5 days, the entire cell population was collected by trypsinization with 100 μl 0.25% Trypsin-EDTA (Gibco). The number of cells before and after 5 days of culture was determined using a hematocytometer. The number of $CD34^+$ and $CD34^{++}$ $CD33,38,71^-$ cells in each sample was calculated from the total number of cells recovered and the frequency of the $CD34^{++}CD33,38,71^-$ cells in the whole population as determined by FACS analysis. The transduction efficiency was determined by FACS analysis while monitoring, in distinct sub-populations, the frequency of GFP-expressing cells as well as the intensity of GFP per individual cell. The results of this experiment, shown in FIG. 21, demonstrate that Ad5 or the chimeric adenovirus Ad5.Fib17 does not infect $CD34^+$ $Lin^-$ cells as witnessed by the absence of GFP expression. In contrast, with the chimeric viruses carrying the fiber molecule of serotypes 16, 51, or 35, high percentages of GFP-positive cells are scored in this cell population. Specificity for $CD34^+Lin^-$ is demonstrated since little GFP expression is observed in $CD34^+$ cells that are also expressing CD33, CD38, and CD71. Sub-fractioning of the $CD34^+$ $Lin^-$ cells (FIG. 22) showed that the percentage of cells positive for GFP declines using Ad5.Fib16, Ad5.Fib35, or Ad5.Fib51 when the cells become more and more positive for the early differentiation markers CD33 (myeloid), CD71 (erythroid), and CD38 (common early differentiation marker). These results thus demonstrate the specificity of the chimeric adenoviruses Ad5.Fib16, Ad5.Fib35, and Ad5.Fib51 for HSCs.

Figure 23:
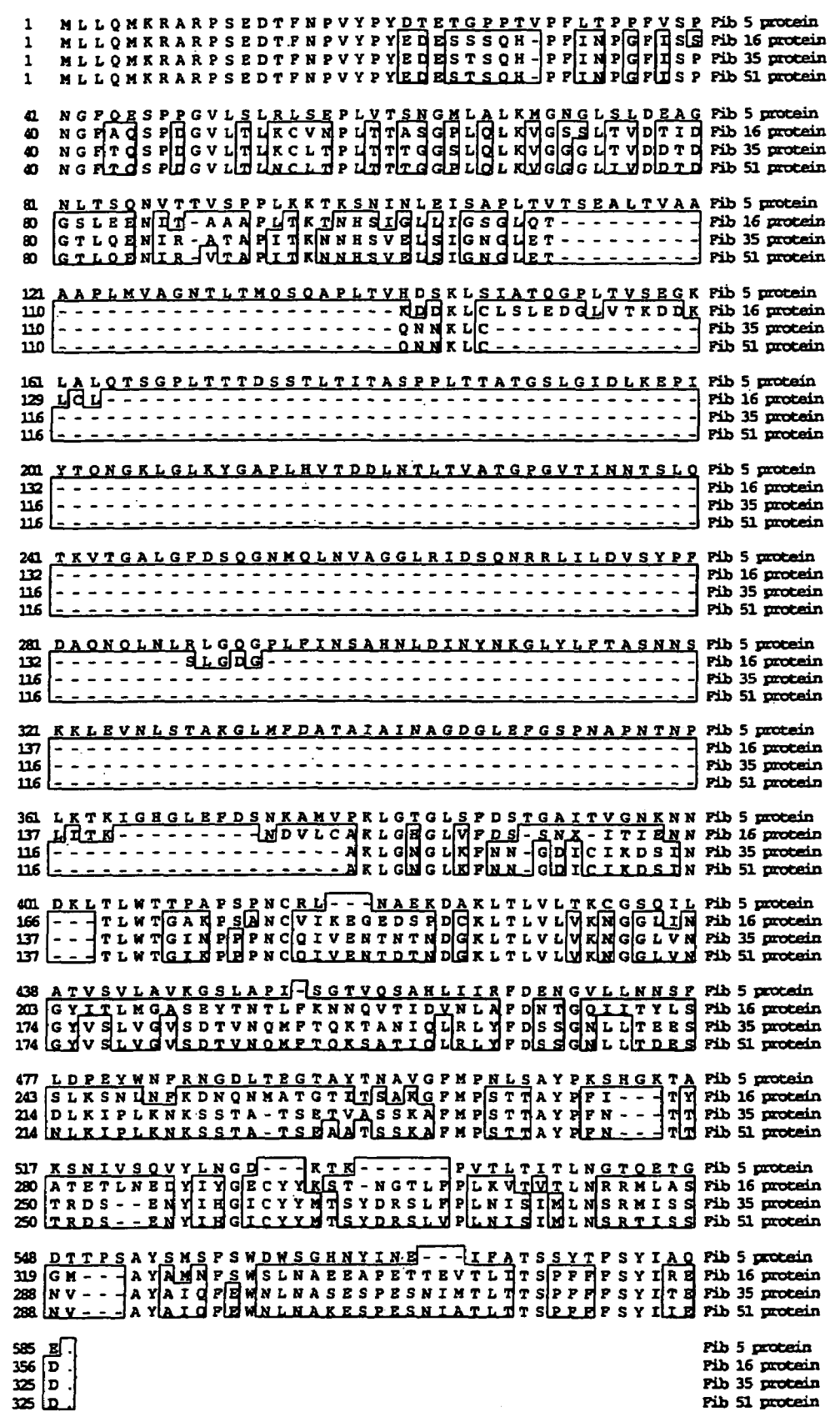
Figure 24:
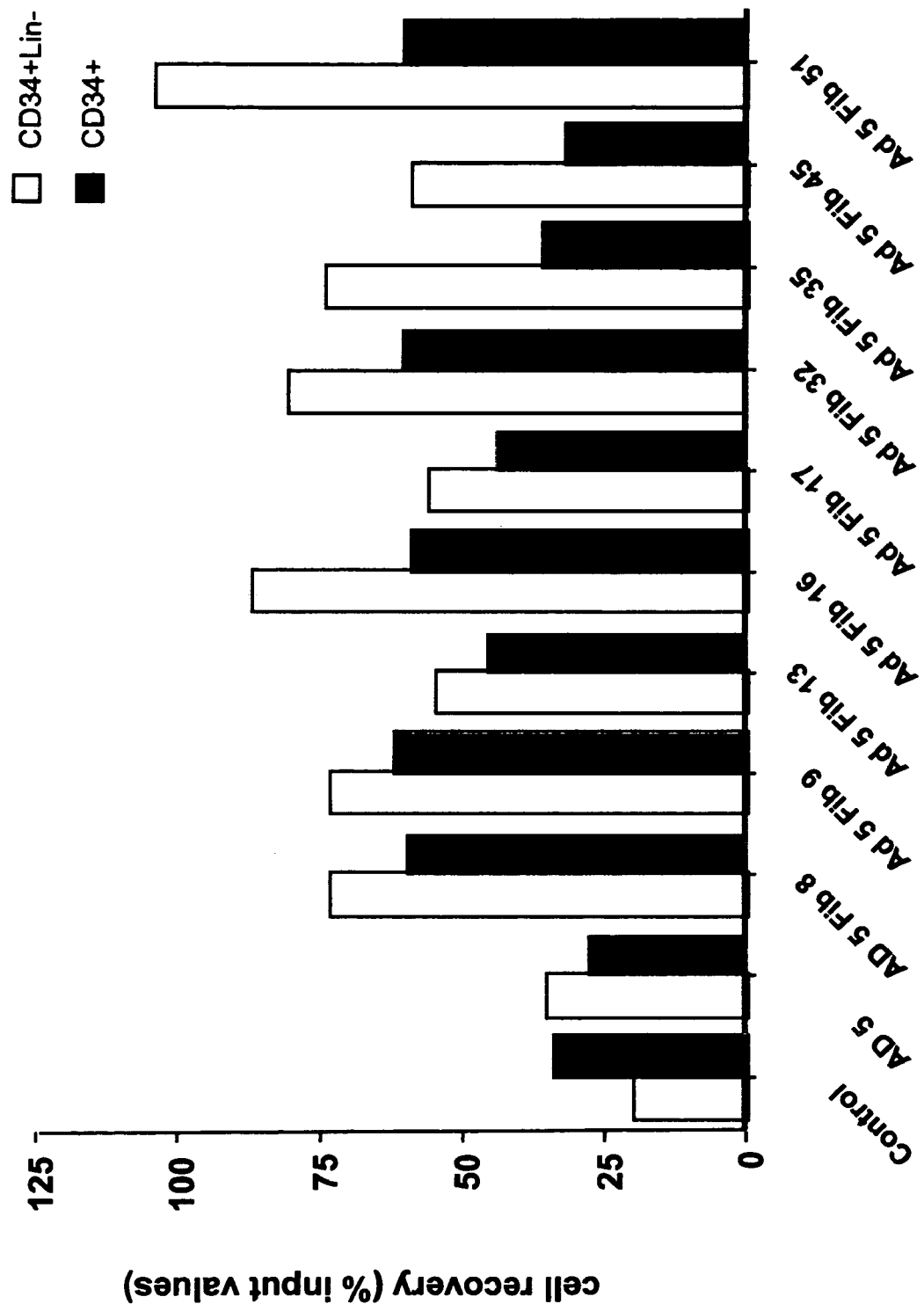
FIG. 24: Toxicity of Adenovirus exposure to primitive human bone marrow cells and stem cells. Cell cultures were counted just before and 5 days after adenovirus transduction. Shown is the percentage of primitive human bone marrow cells (CD34$^+$) and HSCs (CD34$^+$Lin$^-$) recovered as compared to day 0.

FIG. 23 shows an alignment of the Ad5 fiber with the chimeric B-group fiber proteins derived from Ad16, 35 and 51. By determining the number of cells recovered after the transduction procedure, the toxicity of adenovirus can be determined. The recovery of the amount of CD34+ cells as well as the amount of $CD34^+Lin^-$ (FIG. 24) demonstrates that a 2 hour exposure to 1,000 adenovirus particles did not have an effect on the number of cells recovered.

Example 10

An Ad5/fiber35 Chimeric Vector with Cell Type Specificity for Dendritic Cells

Dendritic cells are antigen presenting cells ("APC"), specialized to initiate a primary immune response, and able to boost a memory type of immune response. Dependent on their stage of development, DC display different functions: immature DC are very efficient in the uptake and processing of antigens for presentation by Major Histocompatibility Complex ("MHC") class I and class II molecules, whereas mature DC, being less effective in antigen capture and processing, perform much better at stimulating naive and memory $CD4^+$ and $CD8^+$ T cells, due to the high expression of MHC molecules and co-stimulatory molecules at their cell surface. The immature DCs mature in vivo after uptake of antigen, travel to the T-cell areas in the lymphoid organs, and prime T-cell activation.

Since DCs are the cells responsible for triggering an immune response, there has been a long standing interest in loading DCs with immunostimulatory proteins, peptides, or the genes encoding these proteins, to trigger the immune system. The applications for this strategy are in the field of cancer treatment as well as in the field of vaccination. So far, anti-cancer strategies have focused primarily on ex vivo loading of DCs with antigen (protein or peptide). These studies have revealed that this procedure resulted in induction of cytotoxic T cell activity. The antigens used to load the cells are generally identified as being tumor specific. Some, non-limiting, examples of such antigens are GP100, mage, or Mart-1 for melanoma.

Besides treatment of cancer, many other potential human diseases are currently being prevented through vaccination. In the vaccination strategy, a "crippled" pathogen is presented to the immune system via the action of the antigen presenting cells, i.e., the immature DCs. Well-known examples of disease prevention via vaccination strategies include Hepatitis A, B, and C, influenza, rabies, yellow fever, and measles. Besides these well-known vaccination programs, research programs for treatment of malaria, ebola, river blindness, HIV and many other diseases are being developed. Many of the identified pathogens are considered too dangerous for the generation of "crippled" pathogen vaccines. This latter thus calls for the isolation and characterization of proteins of each pathogen to which a "full blown" immune response is mounted, thus resulting in complete protection upon challenge with wild-type pathogen.

For the strategy of loading DCs with immunostimulatory proteins or peptides to become therapeutically feasible, at least two distinct criteria have to be met. First, the isolation of large numbers of DCs that can be isolated, manipulated, and re-infused into a patient, making the procedure autologous. To date, it is possible to obtain such large quantities of immature DCs from cultured peripheral blood monocytes from any given donor. Second, a vector that can transduce DCs efficiently such that the DNA encoding for an immunostimulatory protein can be delivered. The latter is extremely important since it has become clear that the time required for DCs to travel to the lymphoid organs is such that most proteins or peptides are already released from the DCs, resulting in incomplete immune priming. Because DCs are terminally differentiated and thus non-dividing cells, recombinant adenoviral vectors are being considered for delivering the DNA encoding for antigens to DCs. Ideally, this adenovirus should have a high affinity for dendritic cells, but should also not be recognized by neutralizing antibodies of the host such that in vivo transduction of DCs can be accomplished. The latter would obviate the need for ex vivo manipulations of DCs but would result in a medical procedure identical to the vaccination programs that are currently in place, i.e., intramuscular or subcutaneous injection predominantly. Thus, DC transduced by adenoviral vectors encoding an immunogenic protein may be ideally suited to serve as natural adjuvants for immunotherapy and vaccination.

From the described examples, it can be concluded that efficient gene delivery to DCs is a major interest in the field of gene therapy. Therefore, alteration of the Ad5 host cell range to be able to target DCs in vitro as well as in vivo is a major interest of the invention. To identify a chimeric adenovirus with preferred infection characteristics for human DCs, we generated a library of Ad5-based viruses carrying the fiber molecule from alternative serotypes (serotypes 8, 9, 13, 16, 17, 32, 35, 45, 40-L, 51). Ad5 was included as a reference.

We evaluated the susceptibility of human monocyte-derived immature and mature DC to recombinant chimeric adenoviruses expressing different fibers.

Human PBMC from healthy donors were isolated through Ficoll-Hypaque density centrifugation. Monocytes were isolated from PBMC by enrichment for $CD14^+$ cells using staining with FITC-labeled anti-human CD 14 monoclonal antibody (Becton Dickinson), anti-FITC microbeads and MACS separation columns (Miltenyi Biotec).

This procedure usually results in a population of cells that are <90% $CD14^+$ as analyzed by FACS. Cells were placed in culture using RPMI-1640 medium (Gibco) containing 10% Fetal Bovine Serum ("FBS") (Gibco), 200 ng/ml rhu GM-CSF (R&D/ITK diagnostics, 100 ng/ml rhu IL-4 (R&D/ITK diagnostics) and cultured for 7 days with feeding of the cultures with fresh medium containing cytokines on alternate days. After 7 days, the immature DC resulting from this procedure express a phenotype $CD83^-$, $CD14^{low}$ or $CD14^-$, $HLA-DR^+$, as was demonstrated by FACS analysis. Immature DCs are matured by culturing the cells in a medium containing 100 ng/ml TNF-α for 3 days, after which, they expressed CD83 on their cell surface.

Figure 25:
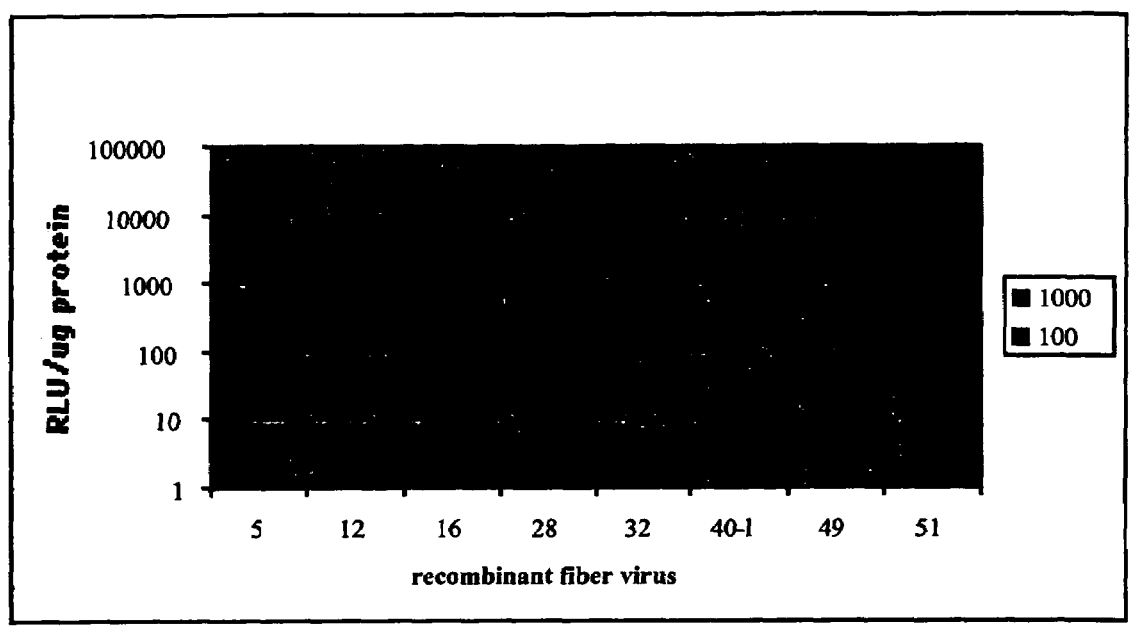
FIG. 25: Transduction of immature DCs at a virus dose of 100 or 1,000 virus particles per cell. Virus tested is Ad5 and Ad5-based vectors carrying the fiber of serotype 12 (Ad5.Fib12), 16 (Ad5.Fib16), 28 (Ad5.Fib28), 32 (Ad5.Fib32), the long fiber of 40 (Ad5.Fib40-L, 49 (Ad5.Fib49), 51 (Ad5.Fib51). Luciferase transgene expression is expressed as relative light units per microgram of protein.

In a pilot experiment, $5\times10^5$ immature DCs were seeded in wells of 24-well plates and exposed for 24 hours to 100 and 1,000 virus particles per cell of each fiber recombinant virus. Virus tested was Ad5, and the fiber chimeric viruses based on Ad5: Ad5.Fib12, Ad5.Fib16, Ad5.Fib28, Ad5.Fib32, Ad5.Fib40-L (long fiber of serotype 40), Ad5.Fib49, and Ad5.Fib51 (where Fibxx stands for the serotype from which the fiber molecule is derived). These viruses are derived from subgroup C, A, B, D, D, F, D, and B, respectively. After 24-hours, cells were lysed (1% Triton X-100/PBS) and luciferase activity was determined using a protocol supplied by the manufacturer (Promega, Madison, Wis., USA). The results of this experiment, shown in FIG. 25, demonstrate that Ad5 poorly infects immature DCs as witnessed by the low level of transgene expression. In contrast, Ad5.Fib16 and Ad5.Fib51 (both a B-group fiber chimeric virus) and also Ad5.Fib40-L (Subgroup F) show efficient infection of immature DCs based on luciferase transgene expression.

Figure 26:
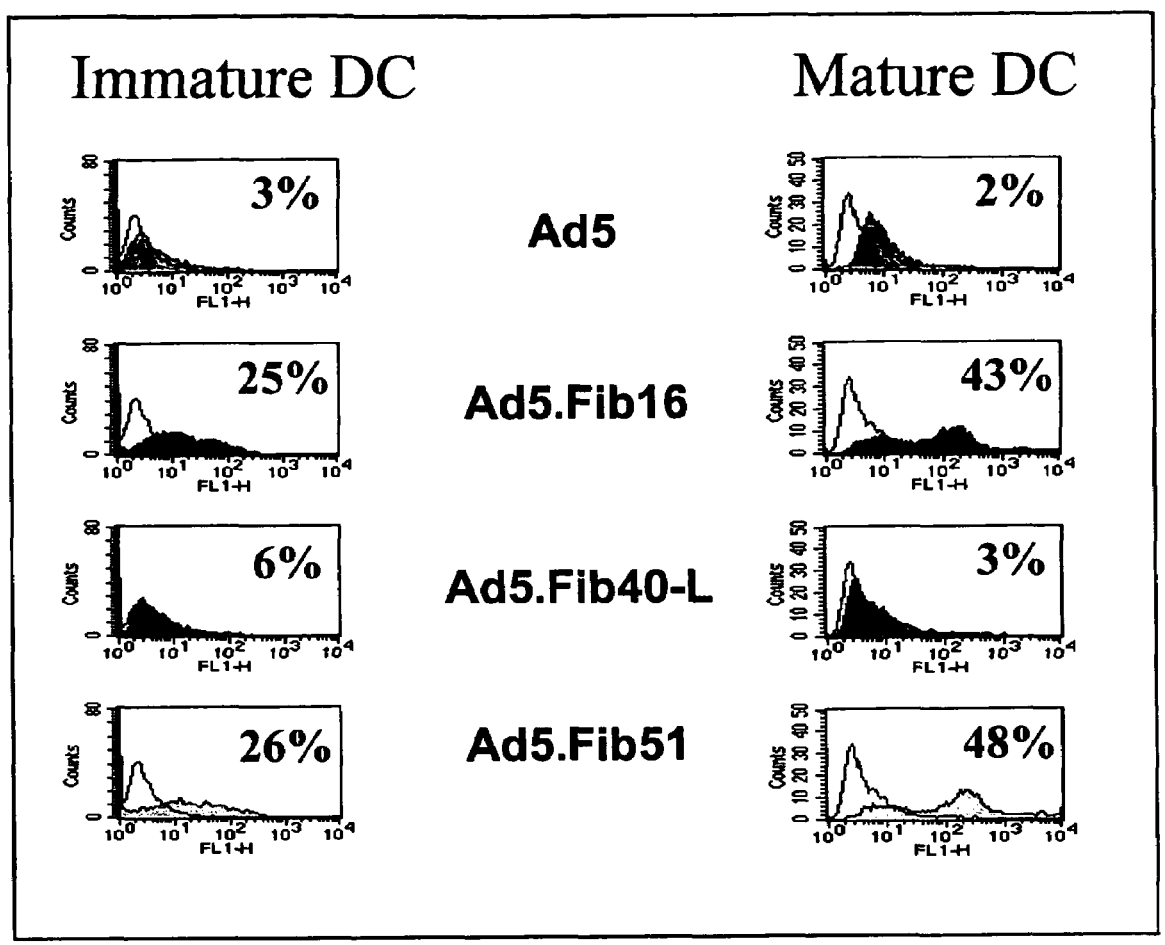
FIG. 26: Flow cytometric analyses of LacZ expression on immature and mature DCs transduced with 10,000 virus particles per cell of Ad5 or the fiber chimeric vectors Ad5.Fib16, Ad5.Fib40-L, or Ad5.Fib51. Percentages of cells scored positive are shown in the upper left corner of each histogram.

In a second experiment, $5\times10^5$ immature and mature DC were infected with 10,000 virus particles per cell of Ad5, Ad5.Fib16, Ad5.Fib40-L, and Ad5.Fib51 all carrying the LacZ gene as a marker. LacZ expression was monitored by flow cytometric analysis using a CM-FDG kit system and the instructions supplied by the manufacturer (Molecular Probes, Leiden, NL). The results of this experiment, shown in FIG. 26, correlate with the previous experiment in that Ad5.Fib16 and Ad5.Fib51 are superior to Ad5 in transducing mature and immature human DCs. Also, this experiment shows that Ad5.Fib40-L is not as good as Ad5.Fib16 and Ad5.Fib51, but is better than Ad5.

Figure 27:
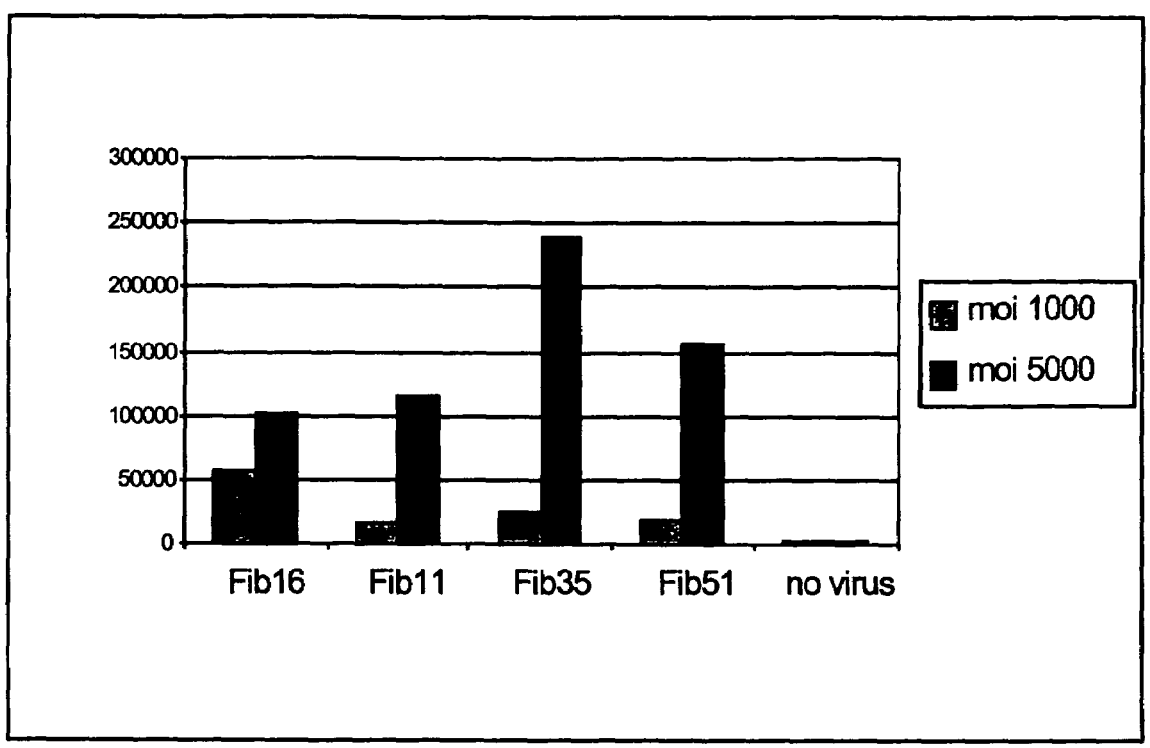
FIG. 27: Luciferase transgene expression in human immature DCs measured 48 hours after transduction with 1,000 or 5,000 virus particles per cell. Viruses tested were fiber chimeric viruses carrying the fiber of subgroup B members (serotypes 11, 16, 35, and 51).
Figure 28:
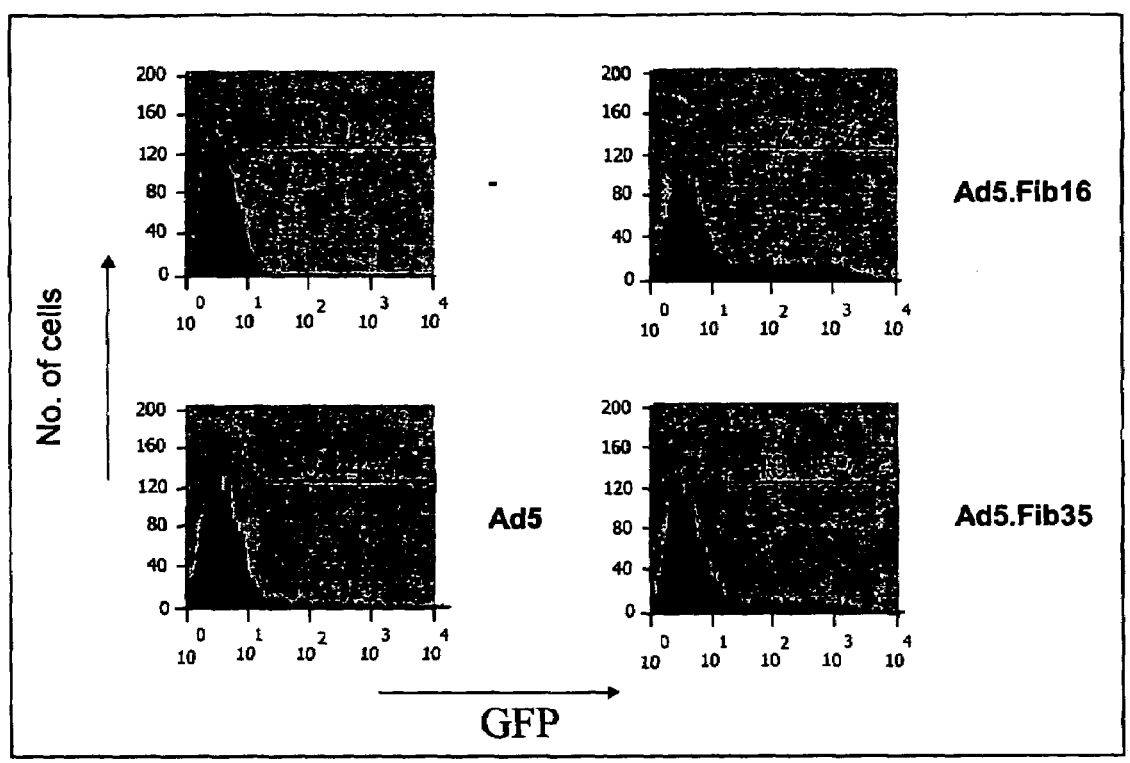
FIG. 28: GFP expression in immature human DCs 48 hours after transduction with 1,000 virus particles per cell of Ad5, Ad5.Fib16, and Ad5.Fib35. Non-transduced cells were used to set a background level of approximately 1% (−).

Based on these results, we tested other chimeric adenoviruses containing fibers of B group viruses, for example, Ad5.Fib11 and Ad5.Fib35 for their capacity to infect DCs. We focused on immature DCs, since these are the cells that process an expressed transgene product into MHC class I and II presentable peptides. Immature DCs were seeded at a cell density of $5\times10^5$ cells/well in 24 well plates (Costar) and infected with 1,000 and 5,000 virus particles per cell, after which the cells were cultured for 48 hours under conditions for immature DCs prior to cell lysis and Luciferase activity measurements. The result of this experiment, shown in FIG. 27, demonstrate that Ad5-based chimeric adenoviruses containing fibers of group-B viruses efficiently infect immature DCs. In a fourth experiment, we again infected immature DCs identically as described in the former experiments but this time Ad5, Ad5.Fib16, and Ad5.Fib35 were used carrying GFP as a marker gene. The results on GFP expression measured with a flow cytometer 48 hours after virus exposure is shown in FIG. 28, and correlates with the data obtained so far. Thus, the results so far are consistent in that Ad5-based vectors carrying a fiber from an alternative adenovirus derived from subgroup B, predominantly fiber of 35, 51, 16, and 11, are superior to Ad5 for transducing human DCs.

Figure 29:
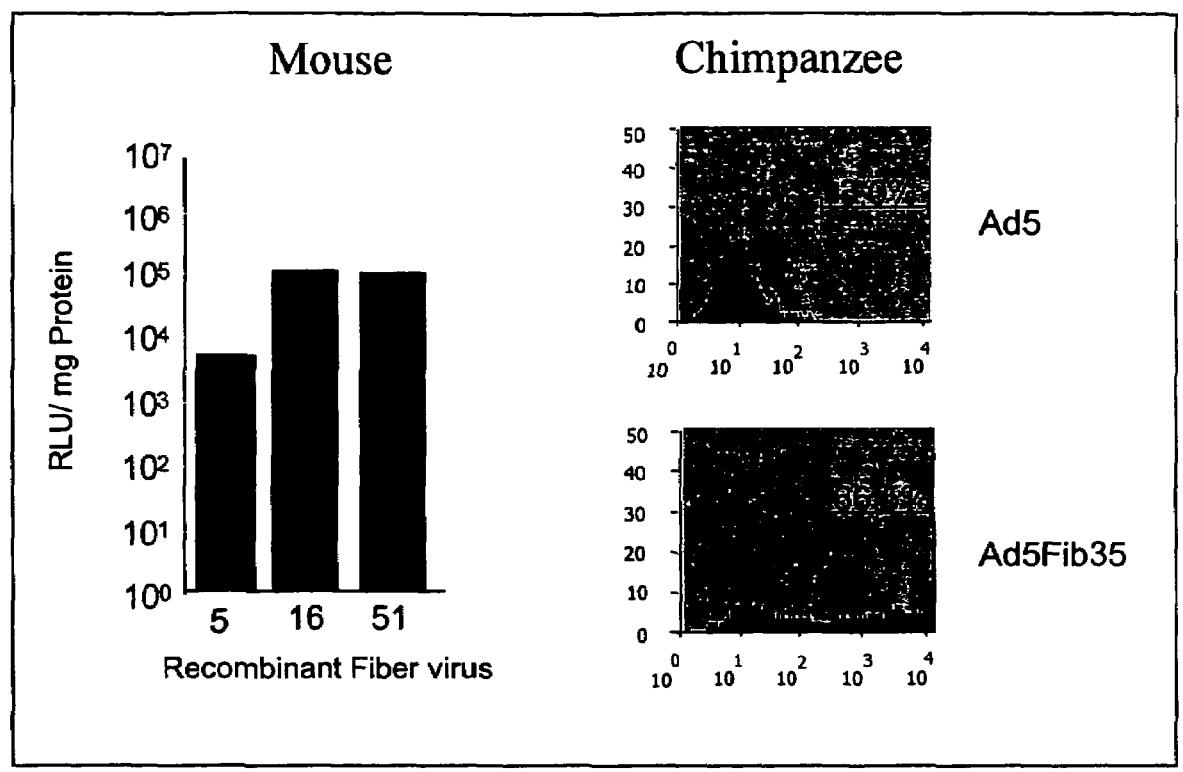
FIG. 29: Transduction of mouse and chimpanzee DCs. Luciferase transgene expression measured in mouse DCs 48 hours after transduction is expressed as relative light units per microgram of protein. Chimpanzee DCs were measured 48 hours after transduction using a flow cytometer. GFP expression demonstrates the poor transduction of Ad (35) in contrast to Ad5.Fib35 (66%).

The adenoviruses disclosed herein are also very suitable for vaccinating animals. To illustrate this, we tested DCs derived from mice and chimpanzees to identify whether these viruses could be used in these animal models. The latter, in particular, since the receptor for human adenovirus derived from subgroup B is unknown to date and therefore it is unknown whether this protein is conserved among species. For both species, immature DCs were seeded at a density of $10^5$ cells per well of 24-well plates. Cells were subsequently exposed for 48 hours to 1,000 virus particles per cell of Ad5, Ad5Fib16, and Ad5.Fib51 in case of mouse DC and Ad5, and Ad.Fib35 in case of chimpanzee DCs (see FIG. 29). The mouse experiment was performed with viruses carrying luciferase as a marker, and demonstrated approximately 10-50-fold increased luciferase activity as compared to Ad5.

The chimpanzee DCs were infected with the GFP viruses, and were analyzed using a flow cytometer. These results (also shown in FIG. 29) demonstrate that Ad5 (3%) transduces chimpanzee DCs very poorly as compared to Ad5.Fib35 (66.5%).

Example 11

Construction of a Plasmid-Based Vector System to Generate Ad11-Based Recombinant Viruses The results of the neutralization experiments described in Example 5 show that Ad11, like Ad35, was also not neutralized in the vast majority of human serum samples. Therefore, recombinant adenoviruses based on Ad11 are preferred above the commonly used Ad2 and Ad5-based vectors as vectors for gene therapy treatment and vaccination. Both Ad35 and Ad11 are B-group viruses and are classified as viruses belonging to DNA homology cluster 2 (Wadell, 1984). Therefore, the genomes of Ad35 and Ad11 are very similar.

To generate a plasmid-based system for the production of Ad11-based recombinant viruses; the adapter plasmid pAdApt35IP1 generated in Example 7 is modified as follows. Construct pAdApt35IP1 is digested with AvrII and then partially with PacI. The digestion mixture is separated on gel, and the 4.4 kb fragment containing the expression cassette and the vector backbone is isolated using the GENECLEAN kit (Bio101, Inc.). Then a PCR amplification is performed on wtAd11 DNA using the primers 35F1 and 35R2 (see Example 7) using Pwo DNA polymerase according to the manufacturer's instructions. The obtained PCR fragment of 0.5 kb is purified using the PCR purification kit (LTI), and ligated to the previously prepared fragment of pAdApt35IP1. This gives construct pAdApt11-35IP1, in which the 5' adenovirus fragment is exchanged for the corresponding sequence of Ad11. Next, pAdApt11-35IP1 is digested with BglII and partially with PacI. The obtained fragments are separated on gel, and the 3.6 kb fragment containing the vector sequences, the 5' adenovirus fragment, and the expression cassette is purified from gel as previously described. Next, a PCR fragment is generated using primers 35F3 and 35R4 (see Example 7) on wtAd11 DNA. Amplification is done as above and the obtained 1.3 kb fragment is purified and digested with BglII and PacI. The isolated fragments are then ligated to give construct pAdApt11IP1. This adapter plasmid now contains Ad11 sequences instead of Ad35 sequences. Correct amplification of PCR amplified Ad11 sequences is verified by comparison of the sequence in this clone with the corresponding sequence of Ad11 DNA. The latter is obtained by direct sequencing on Ad11 DNA using the indicated PCR primers. The large cosmid clone containing the Ad11 backbone is generated as follows. First, a PCR fragment is amplified on Ad11 DNA using the primers 35F5 and 35R6 with Pwo DNA polymerase as described in Example 7 for Ad35 DNA. The PCR fragment is then purified using the PCR purification kit (LTI) and digested with NotI and NdeI. The resulting 3.1 kb fragment is isolated from gel using the GENECLEAN kit (Bio101, Inc.). A second PCR fragment is then generated on Ad11 DNA using the primers 35F7 and 35R8 (see Example 7) with Pwo DNA polymerase according to the manufacturer's instructions and purified using the PCR purification kit (LTI). This amplified fragment is also digested with NdeI and NotI and the resulting 1.6 kb fragment is purified from gel as previously described. The two digested PCR fragments are then ligated together with cosmid vector pWE15 previously digested with NotI and dephosphorylated using TSAP enzyme (LTI) according to manufacturer's instructions. One clone is selected that has one copy of both fragments inserted. Correct clones are selected by analytical NotI digestion that gives a fragment of 4.7 kb. Confirmation is obtained by a PCR reaction using primers 35F5 and 35R8 that gives a fragment of the same size. The correct clone is then linearized with NdeI and isolated from gel. Next, wtAd11 DNA is digested with NdeI and the large 27 kb fragment is isolated from low melting point agarose gel using agarase enzyme (Roche) according to the manufacturer's instructions. Both fragments are then ligated and packaged using λ1 phage packaging extracts (Stratagene) according to the manufacturer's protocol. After infection into STBL-2 cells (LTI), colonies are grown on plates, and analyzed for the presence of the complete insert. The functionality of selected clones is then tested by cotransfection on PER.C6. Hereto, the DNA is digested with NotI and 6 μgr is cotransfected with 2 μgr of a PCR fragment generated on Ad11 DNA with primers 35F1 and 35R4 (see Example 7). Correct clones give CPE within one week following transfection. The correct clone is designated pWE.Ad11.pIX-rITR.

Using the previously described procedure, a plasmid-based system consisting of an adapter plasmid suitable for insertion of foreign genes and a large helper fragment containing the viral backbone is generated. Recombinant Ad11-based viruses are made using the methods described herein for Ad35-based recombinant viruses.

Example 12

Neutralization of Adenoviruses in Samples Derived from Patients

In the neutralization experiments described in Examples 1 and 5, all samples were derived from healthy volunteers. Since one of the applications of non-neutralized vectors is in the field of gene therapy, it is interesting to investigate whether Ad35 is also neutralized with a low frequency and with low titers in groups of patients that are candidates for treatment with gene therapy.

Cardio-Vascular Disease Patients 26 paired serum and pericardial fluid (PF) samples were obtained from patients with heart failure. These were tested against Ad5 and Ad35 using the neutralization assay described in Example 1. The results confirmed the previous data with samples from healthy volunteers. 70% of the serum samples contained NA to Ad5 and 4% to Ad35. In the pericardial fluid samples the titers were lower resulting in a total of 40% with NA to Ad5 and none to Ad35. There was a good correlation between NA in PF and serum, i.e., there were no positive PF samples without NA in the paired serum sample. These results show that non-neutralized vectors based on Ad35 are preferred over Ad5 vectors for treatment of cardio-vascular diseases. As is true for all forms of non-neutralized vectors in this application, the vector may be based on the genome of the non-neutralized serotype or may be based on Ad5 (or another serotype) though displaying at least the major capsid proteins (hexon, penton and optionally fiber) of the non-neutralized serotype.

Rheumatoid Arthritis Patients

The molecular determinant underlying arthritis is presently not known, but both T-cell dysfunction and imbalanced growth factor production in joints is known to cause inflammation and hyperplasia of synovial tissue. The synoviocytes start to proliferate and invade the cartilage and bone that leads to destruction of these tissues. Current treatment starts (when in an early stage) with administration of anti-inflammatory drugs (anti-TNF, IL1-RA, IL-10) and/or conventional drugs (e.g., MTX, sulfasalazine). In late stage RA, synovectomy is performed which is based on surgery, radiation, or chemical intervention. An alternative or additional option is treatment via gene therapy where an adenoviral vector is delivered directly into the joints of patients and expresses an anti-inflammatory drug or a silicide gene. Previous studies performed in rhesus monkeys suffering from collagen-induced arthritis have shown that Ad5-based vectors carrying a marker gene can transduce synoviocytes. Whether in the human situation adenoviral delivery is hampered by the presence of NA is not known. To investigate the presence of NA in the synovial fluid ("SF") of RA patients, SF samples were obtained from a panel of 53 randomly selected patients suffering from RA. These were tested against several wt adenoviruses using the neutralization assay described in Example 1. Results of this screen are presented in Table III. Adenovirus type 5 was found to be neutralized in 72% of the SF samples. Most of these samples contain high titers of NA since the highest dilution of the SF sample that was tested (64×) neutralized Ad5 viruses. This means that adenoviral vector delivery to the synoviocytes in the joints of RA patients will be very inefficient. Moreover, since the titers in the SF are so high it is doubtful whether lavage of the joints prior to vector injection will remove enough of the NA. Of the other serotypes that were tested, Ad35 was shown to be neutralized in only 4% of the samples. Therefore, these data confirm the results obtained in serum samples from healthy patients and show that, for treatment of RA, Ad35-based vectors or chimeric vectors displaying at least some of the capsid proteins from Ad35 are preferred vectors.

Example 13

Modifications in the Backbone of Ad35-Based Viruses

1) Generation of pBr/Ad35.Pac-rITR and pBr/Ad35.PRn

Example 4 describes the generation of the Ad35 subclone pBr/Ad35.Eco13.3. This clone contains Ad35 sequences from bp 21943 to the end of the right ITR cloned into the EcoRI and EcoRV sites of pBr322. To extend these sequences to the PacI site located at bp 18137 in Ad35, pBr/Ad35.Eco13.3 (see Example 4) was digested with AatII and SnaBI and the large vector-containing fragment was isolated from gel using the QIAExII gel extraction kit (Qiagen). Ad35 wt DNA was digested with PacI and SnaBI and the 4.6 kb fragment was isolated as above. This fragment was then ligated to a double-stranded ("ds") linker containing a PacI and an AatII overhang. This linker was obtained after annealing the following oligonucleotides:
A-P1: 5'-CTG GTG GTT AAT-3' (SEQ ID NO:61) and
A-P2: 5'-TAA CCA CCA GAC GT-3' (SEQ ID NO:62).

The ligation mix containing the double-stranded linker and the PacI-SnaBI Ad35 fragment was separated from unligated linker on a LMP gel. The 4.6 kb band was cut out of the gel, molten at 65° C., and then ligated to the purified pBr/Ad35.Eco13.3 vector fragment digested with AatII and SnaBI. Ligations were transformed into electrocompetent DH10B cells (Life Technologies Inc.). The resulting clone, pBr/Ad35.Pac-rITR, contained Ad35 sequences from the PacI site at bp 18137 up to the right ITR.

Next, a unique restriction site was introduced at the 3' end of the right ITR to be able to free the ITR from vector sequences. Hereto, a PCR fragment was used that covers Ad35 sequences from the NdeI site at bp 33165 to the right ITR having the restriction sites SwaI, NotI and EcoRI attached to the rITR. The PCR fragment was generated using primers 35F7 and 35R8 (described in Example 7). After purification, the PCR fragment was cloned into the AT cloning vector (Invitrogen) and sequenced to verify correct amplification. The correct amplified clone was then digested with EcoRI, blunted with Klenow enzyme and subsequently digested with NdeI and the PCR fragment was isolated. In parallel, the NdeI in the pBr vector in pBr/Ad35.Pac-rITR was removed as follows: A pBr322 vector from which the NdeI site was removed by digestion with NdeI, Klenow treatment and re-ligation, was digested with AatII and NheI. The vector fragment was isolated in LMP gel and ligated to the 16.7 kb Ad35 AatII-NheI fragment from pBr/Ad35.Pac-rITR that was also isolated in an LMP gel. This generated pBr/Ad35.Pac-rITR.ΔNdeI. Next, pBr/Ad35.Pac-rITR.ΔNdeI was digested with NheI, the ends were filled in using Klenow enzyme, and the DNA was then digested with NdeI. The large fragment containing the vector and Ad35 sequences was isolated. Ligation of this vector fragment and the PCR fragment resulted in pBr/Ad35.PRn. In this clone, specific sequences coding for fiber E2A, E3, E4 or hexon can be manipulated. In addition, promoter sequences that drive, for instance, the E4 proteins or the E2 can be mutated or deleted and exchanged for heterologous promoters.

2) Generation of Ad35-Based Viruses with Fiber Proteins from Different Serotypes Adenoviruses infect human cells with different efficiencies. Infection is accomplished by a two-step process involving both the fiber proteins that mediate binding of the virus to specific receptors on the cells, and the penton proteins that mediate internalization by interaction of, for example, the RGD sequence to integrins present on the cell surface. For subgroup B viruses, of which Ad35 is a member, the cellular receptor for the fiber protein is not known. Striking differences exist in infection efficiency of human cells of subgroup B viruses compared to subgroup C viruses like Ad5 (see International Patent Application WO 00/03029 and European Patent Application EP 99200624.7). Even within one subgroup, infection efficiencies of certain human cells may differ between various serotypes. For example, the fiber of Ad16, when present on an Ad5-based recombinant virus infects primary endothelial cells, smooth muscle cells and synoviocytes of human and rhesus monkey origin better than Ad5 chimeric viruses carrying the fiber of Ad35 or Ad51. Thus, to obtain high infection efficiencies of Ad35-based viruses, it may be necessary to change the fiber protein for a fiber protein of a different serotype. The technology for such fiber chimeras is described for Ad5-based viruses in Example 3, and is below exemplified for Ad35 viruses.

First, most fiber sequences are deleted from the Ad35 backbone in construct pBr/Ad35.PRn as follows:

The left flanking sequences and part of the fiber protein in Ad35 ranging from bp 30225 upstream of a unique MluI site up to bp 30872 (numbers according to wt Ad35 sequence as disclosed in FIG. 6) in the tail of fiber are amplified using primers DF35-1: 5'-CAC TCA CCA CCT CCA ATT CC-3' (SEQ ID NO:63) and DF35-2: 5'-CGG GAT CCC GTA CGG GTA GAC AGG GTT GAA GG-3' (SEQ ID NO:64).

This PCR amplification introduces a unique BsiWI site in the tail of the fiber gene. The right flanking sequences ranging from the end of the fiber protein at bp 31798 to bp 33199 (numbering according to wtAd35 sequence, FIG. 6), 3' from the unique NdeI site is amplified using primers DF35-3: 5'-CGG GAT CCG CTA GCT GAA ATA AAG TTT AAG TGT TTT TAT TTA AAA TCA C-3' (SEQ ID NO:65) and DF35-4: 5'-CCA GTT GCA TTG CTT GGT TGG-3' (SEQ ID NO:66).

This PCR introduces a unique NheI site in the place of the fiber sequences. PCR amplification is done with Pwo DNA polymerase (Roche) according to the manufacturer's instructions. After amplification, the PCR products are purified using a PCR purification kit and the fragments are digested with BamHI and ligated together. The 2 kb ligated fragments are purified from gel, and cloned in the PCR Script Amp vector (Stratagene). Correct amplification is checked by sequencing. The PCR fragment is then excised as an MluI/NdeI fragment and cloned in pBr/Ad35.PRn digested with the same enzymes. This generates pBr/Ad35.PRΔfib, a shuttle vector suitable to introduce fiber sequences of alternative serotypes. This strategy is analogous to the fiber modification strategy for Ad5-based viruses as disclosed in International Patent Application WO00/03029. Primers that are listed in Table I of that application were used to amplify fiber sequences of various subgroups of adenovirus. For amplification of fibers that are cloned in the pBr/Ad35.PRΔfib, the same (degenerate) primer sequences can be used, however, the NdeI site in the forward primers (tail oligonucleotides A to E) should be changed to a BsiWI site and the NsiI site in the reverse oligo (knob oligonucleotide 1 to 8) should be changed in an NheI site. Thus, fiber 16 sequences are amplified using the following degenerate primers: 5'-CCK GTS TAC CCG TAC GAA GAT GAA AGC-3' (SEQ ID NO:67) (where K can be a T or G and S can be a C or G as both are degenerate oligo nucleotides) and 5'-CCG GCT AGC TCA GTC ATC TTC TCT GAT ATA-3' (SEQ ID NO:68). Amplified sequences are then digested with BsiWI and NheI and cloned into pBr/Ad35.PRΔfib digested with the same enzymes to generate pBr/Ad35.PRfib16. The latter construct is then digested with PacI and SwaI and the insert is isolated from gel. The PacI/SwaI Ad35 fragment with modified fiber is then cloned into the corresponding sites of pWE/Ad35.pIX-rITR to give pWE/Ad35.pIX-rITR.fib16. This cosmid backbone can then be used with an Ad35-based adapter plasmid to generate Ad35 recombinant viruses that display the fiber of Ad16. Other fiber sequences can be amplified with (degenerate) primers as mentioned above. If one of the fibers sequences turns out to have an internal BsiWI or NheI site, the PCR fragment has to be digested partially with that enzyme.

3) Generation of Ad35-Based Viruses with Inducible, E1-Independent, E4 Expression The adenovirus E4 promoter is activated by expression of E1 proteins. It is unknown whether the Ad5 E1 proteins are capable of mediating activation of the Ad35 E4 promoter. Therefore, to enable production of Ad35 recombinant viruses on PER.C6 cells, it may be advantageous to make E4 expression independent of E1. This can be achieved by replacing the Ad35-E4 promoter by heterologous promoter sequences like, but not limited to, the 7xTetO promoter.

Recombinant E1-deleted Ad5-based vectors are shown to have residual expression of viral genes from the vector backbone in target cells, despite the absence of E1 expression. Viral gene expression increases the toxicity and may trigger a host immune response to the infected cell. For most applications of adenoviral vectors in the field of gene therapy and vaccination, it is desired to reduce or diminish the expression of viral genes from the backbone. One way to achieve this is to delete all, or as much as possible, sequences from the viral backbone. By deleting E2A, E2B or E4 genes and/or the late gene functions, one has to complement for these functions during production. This complementation can either be by means of a helper virus or through stable addition of these functions, with or without inducible transcription regulation, to the producer cell. Methods to achieve this have been described for Ad5 and are known in the art. One specific method is replacement of the E4 promoter by promoter sequences that are not active in the target cells. E4 proteins play a role in, for example, replication of adenoviruses through activation of the E2 promoter and in late gene expression through regulation of splicing and nuclear export of late gene transcripts. In addition, at least some of the E4 proteins are toxic to cells. Therefore, reduction or elimination of E4 expression in target cells will further improve Ad35-based vectors. One way to achieve this is to replace the E4 promoter by a heterologous promoter that is inactive in the target cells. An example of a heterologous promoter/activator system that is inactive in target cells is the tetracycline-inducible TetO system (Gossen and Bujard, 1992). Other prokaryotic or synthetic promoter/activator systems may be used. In this example, the E4 promoter in the backbone of the viral vector is replaced by a DNA fragment containing 7 repeats of the tetracycline responsive element from the tet operon (7xTetO). A strong transactivator for this promoter is a fusion protein containing the DNA binding domain of the tet repressor and the activation domain of VP16 (tet transactivator protein, tTa). Strong E4 expression, independent of E1 expression, can be accomplished in PER.C6 cells expressing tTa. tTa-expressing PER.C6 cells have been generated and described (see Example 15). Ad5-derived E1-deleted viruses with E4 under control of 7xTetO can be generated and propagated on these cells. Following infection in cells of human or animal origin (that do not express the tTa transactivator), E4 expression was found to be greatly diminished compared to E1-deleted viruses with the normal E4 promoter.

What follows is the construction of pWE/Ad35.pIX-rITR.TetO-E4, a cosmid helper vector to produce viruses with the E4 promoter replacement.

First, a fragment was generated by PCR amplification on pBr/Ad35.PRn DNA using the following primers: 35SITR: 5'-GAT CCG GAG CTC ACA ACG TCA TTT TCC CAC G-3' (SEQ ID NO:69) and 353ITR: 5'-CGG AAT TCG CGG CCG CAT TTA AAT C-3' (SEQ ID NO:70).

This fragment contains sequences between bp 34656 (numbering according to wtAd35) and the NotI site 3' of the right ITR in pBr/Ad35.PRn and introduces an SstI site 5' of the right ITR sequence.

A second PCR fragment was generated on pBr/Ad35.PRn DNA using primers: 35DE4: 5'-CCC AAG CTT GCT TGT GTA TAT ATA TTG TGG-3' (SEQ ID NO:71) and 35F7: see Example 7.

This PCR amplifies Ad35 sequences between bp 33098 and 34500 (numbering according to wtAd35) and introduces a HindIII site upstream of the E4 Tata-box. With these two PCR reactions the right- and left-flanking sequences of the E4 promoter are amplified. For amplification, Pwo DNA polymerase was used according to manufacturer's instructions.

A third fragment containing the 7xTetO promoter was isolated from construct pAAO-E-TATA-7xTetO by digestion with SstI and HindIII. The generation of pAAO-E-TATA-7xTetO is described below. The first PCR fragment (35S/353) was then digested with SstI and NotI and ligated to the 7xTetO fragment. The ligation mixture was then digested with HindIII and NotI and the 0.5 kb fragment is isolated from gel. The second PCR fragment (35DE4/35F7) was digested with NdeI and HindIII and gel purified. These two fragments were then ligated into pBr/Ad35.PRn digested with NdeI and NotI to give pBr/Ad35.PR.TetOE4. The modification of the E4 promoter was then transferred to the Ad35 helper cosmid clone by exchanging the PacI/SwaI fragment of the latter with the one from pBr/Ad35.PR.TetOE4 to give pWE/Ad35.pIX-rITR.TetOE4.

pAAO-E-TATA.7xTetO was generated as follows. Two oligonucleotides were synthesized: TATAplus: 5'-AGC TTT CTT ATA AAT TTT CAG TGT TAG ACT AGT AAA TTG CTT AAG-3' (SEQ ID NO:72) and TATAmin: 5'-AGC TCT TAA GCA ATT TAC TAG TCT AAC ACT GAA AAT TTA TAA GAA-3' (SEQ ID NO:73).

The oligonucleotides were annealed to yield a double-stranded DNA fragment with 5' overhangs that are compatible with HindIII-digested DNA. The product of the annealing reaction was ligated into HindIII-digested pGL3-Enhancer Vector (Promega) to yield pAAO-E-TATA. The clone that had the HindIII site at the 5' end of the insert restored was selected for further cloning.

Next, the heptamerized tet-operator sequence was amplified from the plasmid pUHC-13-3 (Gossen and Bujard, 1992) in a PCR reaction using the Expand PCR system (Roche) according to the manufacturer's protocol. The following primers were used: Tet3: 5'-CCG GAG CTC CAT GGC CTA ACT CGA GTT TAC CAC TCC C-3' (SEQ ID NO:74) and Tet5: 5'-CCC AAG CTT AGC TCG ACT TTC ACT TTT CTC-3' (SEQ ID NO:75).

The amplified fragment was digested with SstI and HindIII (these sites are present in tet3 and tet5, respectively) and cloned into SstI/HindIII-digested pAAO-E-TATA giving rise to pAAO-E-TATA-7xtetO.

To test the functionality of the generated pWE/Ad35.pIX-rITR.TetOE4 cosmid clone, the DNA was digested with NotI. The left end of wtAd35 DNA was then amplified using primers 35F1 and 35R4 (see Example 7). Following amplification, the PCR mixture was purified and digested with SalI to remove intact viral DNA. Then 4 gr of both the digested pWE/Ad35.pIX-rITR.TetOE4 and the PCR fragment was cotransfected into PER.C6-tTa cells that were seeded in T25 flasks the day before. Transfected cells were transferred to T80 flasks after two days and another two days later CPE was obtained, showing that the cosmid backbone is functional.

Example 14

Generation of Cell Lines Capable of Complementing E1-Deleted Ad35 Viruses

Generation of pIG135 and pIG270

Construct pIG.E1A.E1B contains E1 region sequences of Ad5 corresponding to nucleotides 459 to 3510 of the wt Ad5 sequence (Genbank accession number M72360) operatively linked to the human phosphoglycerate kinase promoter ("PGK") and the Hepatitis B Virus polyA sequences. The generation of this construct is described in International Patent Application No. WO97/00326. The E1 sequences of Ad5 were replaced by corresponding sequences of Ad35 as follows. pRSV.Ad35-E1 (described in Example 8) was digested with EcoRI and Sse8387I and the 3 kb fragment corresponding to the Ad35 E1 sequences was isolated from gel. Construct pIG.E1A.E1B was digested with Sse8387I completely and partially with EcoRI. The 4.2 kb fragment corresponding to vector sequences without the Ad5 E1 region but retaining the PGK promoter were separated from other fragments on LMP agarose gel and the correct band was excised from gel. Both obtained fragments were ligated resulting in pIG.Ad35-E1.

This vector was further modified to remove the LacZ sequences present in the pUC119 vector backbone. Hereto, the vector was digested with BsaAI and BstXI and the large fragment was isolated from gel. A double-stranded oligo was prepared by annealing the following two oligos: BB1: 5'-GTG CCT AGG CCA CGG GG-3' (SEQ ID NO:76) and BB2: 5'-GTG GCC TAG GCA C-3' (SEQ ID NO:77).

Ligation of the oligo and the vector fragment resulted in construct pIG135. Correct insertion of the oligo restores the BsaAI and BstXI sites and introduces a unique AvrII site. Next, we introduced a unique site at the 3' end of the Ad35-E1 expression cassette in pIG135. Hereto, the construct was digested with SapI and the 3' protruding ends were made blunt by treatment with T4 DNA polymerase. The thus treated linear plasmid was further digested with BsrGI and the large vector-containing fragment was isolated from gel. To restore the 3' end of the HBVpolyA sequence and to introduce a unique site, a PCR fragment was generated using the following primers: 270F: 5'-CAC CTC TGC CTA ATC ATC TC-3' (SEQ ID NO:78) and 270R: 5'-GCT CTA GAA ATT CCA CTG CCT TCC ACC-3' (SEQ ID NO:79).

The PCR was performed on pIG.Ad35.E1 DNA using Pwo polymerase (Roche) according to the manufacturer's instructions. The obtained PCR product was digested with BsrGI and dephosphorylated using TSAP enzyme (LTI), the latter to prevent insert dimerization on the BsrGI site. The PCR fragment and the vector fragment were ligated to yield construct pIG270.

Ad35 E1 Sequences are Capable of Transforming Rat Primary Cells

New born WAG/RIJ rats were sacrificed at 1 week of gestation and kidneys were isolated. After careful removal of the capsule, kidneys were disintegrated into a single cell suspension by multiple rounds of incubation in trypsin/EDTA (LTI) at 37° C. and collection of floating cells in cold PBS containing 1% FBS. When most of the kidney was trypsinized, all cells were re-suspended in DMEM supplemented with 10% FBS and filtered through a sterile cheesecloth. Baby Rat Kidney (BRK) cells obtained from one kidney were plated in 5 dishes (Greiner, 6 cm). When a confluency of 70-80% was reached, the cells were transfected with 1 or 5 µgr DNA/dish using the $CaPO_4$ precipitation kit (LTI) according to the manufacturer's instructions. The following constructs were used in separate transfections: pIG.E1A.E1B (expressing the Ad5-E1 region), pRSV.Ad35-E1, pIG.Ad35-E1 and pIG270 (the latter expressing the Ad35-E1). Cells were incubated at 37° C., 5% $CO_2$ until foci of transformed cells appeared. Table IV shows the number of foci that resulted from several transfection experiments using circular or linear DNA. As expected, the Ad5-E1 region efficiently transformed BRK cells. Foci also appeared in the Ad35-E1 transfected cell layer although with lower efficiency. The Ad35 transformed foci appeared at a later time point: ~2 weeks post transfection compared with 7-10 days for Ad5-E1. These experiments clearly show that the E1 genes of the B group virus Ad35 are capable of transforming primary rodent cells. This proves the functionality of the Ad35-E1 expression constructs and confirms earlier findings of the transforming capacity of the B-group viruses Ad3 and Ad7 (Dijkema, 1979). To test whether the cells in the foci were really transformed a few foci were picked and expanded. From the seven picked foci, at least five turned out to grow as established cell lines.

Generation of New Packaging Cells Derived from Primary Human Amniocytes

Amniotic fluid obtained after amniocentesis was centrifuged and cells were re-suspended in AmnioMax medium (LTI) and cultured in tissue culture flasks at 37° C. and 10% $CO_2$. When cells were growing nicely (approximately one cell division/24 hrs.), the medium was replaced with a 1:1 mixture of AmnioMax complete medium and DMEM low glucose medium (LTI) supplemented with Glutamax I (end concentration 4 mM, LTI) and glucose (end concentration 4.5 gr/L, LTI) and 10% FBS (LTI). For transfection ~5×10$^5$ cells were plated in 10 cm tissue culture dishes. The day after, cells were transfected with 20 µgr of circular pIG270/dish using the $CaPO_4$ transfection kit (LTI) according to manufacturer's instructions and cells were incubated overnight with the DNA precipitate. The following day, cells were washed 4 times with PBS to remove the precipitate and further incubated for over three weeks until foci of transformed cells appeared. Once a week, the medium was replaced by fresh medium. Other transfection agents like, but not limited to, LipofectAmine (LTI) or PEI (Polyethylenimine, high molecular weight, water-free, Aldrich) were used. Of these three agents PEI reached the best transfection efficiency on primary human amniocytes: ~1% blue cells 48 hrs. following transfection of pAdApt35.LacZ.

Foci are isolated as follows: The medium is removed and replaced by PBS after which foci are isolated by gently scraping the cells using a 50-200 µl Gilson pipette with a disposable filter tip. Cells contained in ~10 μl PBS were brought in a 96-well plate containing 15 μl trypsin/EDTA (LTI) and a single cell suspension was obtained by pipetting up and down and a short incubation at room temperature. After addition of 200 μl of the above described 1:1 mixture of AmnioMax complete medium and DMEM with supplements and 10% FBS, cells were further incubated. Clones that continued to grow were expanded and their ability to complement growth of E1-deleted adenoviral vectors of different sub-groups was analyzed, specifically ones derived from B-group viruses, specifically from Ad35 or Ad11.

Generation of New Packaging Cell Lines from HER Cells

HER cells were isolated and cultured in DMEM medium supplemented with 10% FBS (LTI). The day before transfection, ~$5 \times 10^5$ cells were plated in 6 cm dishes and cultured overnight at 37° C. and 10% $CO_2$. Transfection was done using the $CaPO_4$ precipitation kit (LTI) according to the manufacturer's instructions. Each dish was transfected with 8-10 μgr pIG270 DNA, either as a circular plasmid or as a purified fragment. To obtain the purified fragment, pIG270 was digested with AvrII and XbaI and the 4 kb fragment corresponding to the Ad35 E1 expression cassette was isolated from gel by agarase treatment (Roche). The following day, the precipitate was washed away carefully by four washes with sterile PBS. Then; fresh medium was added and transfected cells were further cultured until foci of transformed cells appear. When large enough (>100 cells) foci were picked and brought into 96-wells as described above. Clones of transformed HER cells that continue to grow, were expanded and tested for their ability to complement growth of E1-deleted adenoviral vectors of different sub-groups specifically ones derived from B-group viruses specifically from Ad35 or Ad11.

New Packaging Cell Lines Derived from PER.C6

As described in Example 8, it is possible to generate and grow Ad35 E1-deleted viruses on PER.C6 cells with cotransfection of an Ad35-E1 expression construct, e.g., pRSV.Ad35.E1. However, large-scale production of recombinant adenoviruses using this method is cumbersome because, for each amplification step, a transfection of the Ad35-E1 construct is needed. In addition, this method increases the risk of non-homologous recombination between the plasmid and the virus genome with high chances of generation of recombinant viruses that incorporate E1 sequences resulting in replication competent viruses. To avoid this, the expression of Ad35-E1 proteins in PER.C6 has to be mediated by integrated copies of the expression plasmid in the genome. Since PER.C6 cells are already transformed and express Ad5-E1 proteins, addition of extra Ad35-E1 expression may be toxic for the cells, however, it is not impossible to stably transfect transformed cells with E1 proteins since Ad5-E1-expressing A549 cells have been generated.

In an attempt to generate recombinant adenoviruses derived from subgroup B virus Ad7, Abrahamsen et al. (1997) were not able to generate E1-deleted viruses on 293 cells without contamination of wt Ad7. Viruses that were picked after plaque purification on 293-ORF6 cells (Brough et al., 1996) were shown to have incorporated Ad7 E1B sequences by non-homologous recombination. Thus, efficient propagation of Ad7 recombinant viruses proved possible only in the presence of Ad7-E1B expression and Ad5-E4-ORF6 expression. The E1B proteins are known to interact with cellular as well as viral proteins (Bridge et al., 1993; White, 1995). Possibly, the complex formed between the E1B 55K protein and E4-ORF6 which is necessary to increase mRNA export of viral proteins and to inhibit export of most cellular mRNAs, is critical and in some way serotype specific. The above experiments suggest that the E1A proteins of Ad5 are capable of complementing an Ad7-E1A deletion and that Ad7-E1B expression in adenovirus packaging cells on itself is not enough to generate a stable complementing cell line. To test whether one or both of the Ad35-E1B proteins is/are the limiting factor in efficient Ad35 vector propagation on PER.C6 cells, we have generated an Ad35 adapter plasmid that does contain the E1B promoter and E1B sequences but lacks the promoter and the coding region for E1A. Hereto, the left end of wtAd35 DNA was amplified using the primers 35F1 and 35R4 (both described in Example 7) with Pwo DNA polymerase (Roche) according to the manufacturer's instructions. The 4.6 kb PCR product was purified using the PCR purification kit (LTI) and digested with SnaBI and ApaI enzymes. The resulting 4.2 kb fragment was then purified from gel using the QIAExII kit (Qiagen). Next, pAdApt35IP1 (Example 7) was digested with SnaBI and ApaI and the 2.6 kb vector-containing fragment was isolated from gel using the GENECLEAN kit (Bio101, Inc). Both isolated fragments were ligated to give pBr/Ad35.leftITR-pIX. Correct amplification during PCR was verified by a functionality test as follows: The DNA was digested with BstBI to liberate the Ad35 insert from vector sequences and 4 μgr of this DNA was cotransfected with 4 μgr of NotI-digested pWE/Ad35.pIX-rITR (Example 7) into PER.C6 cells. The transfected cells were passaged to T80 flasks at day 2 and again two days later CPE had formed showing that the new pBr/Ad35.leftITR-pIX construct contains functional E1 sequences. The pBr/Ad35.leftITR-pIX construct was then further modified as follows: The DNA was digested with SnaBI and HindIII and the 5' HindII overhang was filled in using Klenow enzyme. Religation of the digested DNA and transformation into competent cells (LTI) gave construct pBr/Ad35leftITR-pIXΔDE1A. This latter construct contains the left end 4.6 kb of Ad35 except for E1A sequences between bp 450 and 1341 (numbering according to wtAd35, FIG. 6) and thus lacks the E1A promoter and most of the E1A coding sequences. pBr/Ad35.leftITR-pIXΔDE1A was then digested with BstBI and 2 μgr of this construct was cotransfected with 6 μgr of NotI-digested pWE/Ad35.pIX-rITR (Example 7) into PER.C6 cells. One week following transfection full CPE had formed in the transfected flasks.

This experiment shows that the Ad35-E1A proteins are functionally complemented by Ad5-e1A expression in PER.C6 cells and that at least one of the Ad35-E1B proteins cannot be complemented by Ad5-E1 expression in PER.C6. It further shows that it is possible to make a complementing cell line for Ad35 E1-deleted viruses by expressing Ad35-E1B proteins in PER.C6. Stable expression of Ad35-E1B sequences from integrated copies in the genome of PER.C6 cells may be driven by the E1B promoter and terminated by a heterologous poly-adenylation signal like, but not limited to, the HBVpA. The heterologous pA signal is necessary to avoid overlap between the E1B insert and the recombinant vector, since the natural E1B termination is located in the pIX transcription unit that has to be present on the adenoviral vector. Alternatively, the E1B sequences may be driven by a heterologous promoter like, but not limited to, the human PGK promoter or by an inducible promoter like, but not limited to, the 7xtetO promoter (Gossen and Bujard, 1992). Also in these cases the transcription termination is mediated by a heterologous pA sequence, e.g., the HBV pA. The Ad35-E1B sequences at least comprise one of the coding regions of the E1B 21K and the E1B 55K proteins located between nucleotides 1611 and 3400 of the wt Ad35 sequence. The insert may also include (part of the) Ad35-E1B sequences between nucleotides 1550 and 1611 of the wt Ad35 sequence.

Example 15

Generation of Producer Cell Lines for the Production of Recombinant Adenoviral Vectors Deleted in Early Region 1 and Early Region 2A Generation of PER.C6-tTA Cells Here is described the generation of cell lines for the production of recombinant adenoviral vectors that are deleted in early region 1 (E1) and early region 2A (E2A). The producer cell lines complement for the E1 and E2A deletion from recombinant adenoviral vectors in trans by constitutive expression of both E1 and E2A genes. The pre-established Ad5-E1 transformed human embryo retinoblast ("HER") cell line PER.C6 (International Patent Appln. WO 97/00326) was further equipped with E2A expression cassettes.

The adenoviral E2A gene encodes a 72 kDa DNA Binding Protein which has a high affinity for single-stranded DNA. Because of its function, constitutive expression of DBP is toxic for cells. The ts125E2A mutant encodes a DBP that has a Pro→Ser substitution of amino acid 413. Due to this mutation, the ts125E2A encoded DBP is fully active at the permissive temperature of 32° C., but does not bind to ssDNA at the non-permissive temperature of 39° C. This allows the generation of cell lines that constitutively express E2A, which is not functional and is not toxic at the non-permissive temperature of 39° C. Temperature-sensitive E2A gradually becomes functional upon temperature decrease and becomes fully functional at a temperature of 32° C., the permissive temperature.

A. Generation of Plasmids Expressing the Wild-Type E2A- or Temperature-Sensitive ts125E2A Gene pcDNA3wtE2A: The complete wild-type early region 2A (E2A) coding region was amplified from the plasmid pBR/Ad.Bam-rITR (ECACC Deposit P97082122) with the primers DBPpcr1 and DBPpcr2 using the Expand™ Long Template PCR system according to the standard protocol of the supplier (Boehringer Mannheim). The PCR was performed on a Biometra Trio Thermoblock, using the following amplification program: 94° C. for 2 minutes, 1 cycle; 94° C. for 10 seconds, 51° C. for 30 seconds, and 68° C. for 2 minutes, 1 cycle; 94° C. for 10 seconds, 58° C. for 30 seconds, and 68° C. for 2 minutes, 10 cycles; 94° C. for 10 seconds, 58° C. for 30 seconds, and 68° C. for 2 minutes with 10 seconds extension per cycle, 20 cycles; 68° C. for 5 minutes, 1 cycle. The primer DBPpcr1: CGG GAT CCG CCA CCA TGG CCA GTC GGG AAG AGG AG (5' to 3') (SEQ ID NO:80) contains a unique BamHI restriction site (underlined) 5' of the Kozak sequence (italic) and start codon of the E2A coding sequence. The primer DBPpcr2: CGG AAT TCT TAA AAA TCA AAG GGG TTC TGC CGC (5' to 3') (SEQ ID NO:81) contains a unique EcoRI restriction site (underlined) 3' of the stop codon of the E2A coding sequence. The bold characters refer to sequences derived from the E2A coding region. The PCR fragment was digested with BamHI/EcoRI and cloned into BamHI/EcoRI-digested pcDNA3 (Invitrogen), giving rise to pcDNA3wtE2A.

pcDNA3tsE2A: The complete ts125E2A-coding region was amplified from DNA isolated from the temperature-sensitive adenovirus mutant H5ts125. The PCR amplification procedure was identical to that for the amplification of wtE2A. The PCR fragment was digested with BamHI/EcoRI and cloned into BamHI/EcoRI-digested pcDNA3 (Invitrogen), giving rise to pcDNA3tsE2A. The integrity of the coding sequence of wtE2A and tsE2A was confirmed by sequencing.

B. Growth Characteristics of Producer Cells for the Production of Recombinant Adenoviral Vectors Cultured at 32°, 37° and 39° C.

PER.C6 cells were cultured in DMEM (Gibco BRL) supplemented with 10% FBS (Gibco BRL) and 10 mM $MgCl_2$ in a 10% $CO_2$ atmosphere at 32° C., 37° C. or 39° C. At day 0, a total of $1 \times 10^6$ PER.C6 cells were seeded per 25 $cm^2$ tissue culture flask (Nunc) and the cells were cultured at 32° C., 37° C. or 39° C. At day 1-8, cells were counted. FIG. 30 shows that the growth rate and the final cell density of the PER.C6 culture at 39° C. are comparable to that at 37° C. The growth rate and final density of the PER.C6 culture at 32° C. were slightly reduced as compared to that at 37° C. or 39° C. No significant cell death was observed at any of the incubation temperatures. Thus, PER.C6 performs very well both at 32° C. and 39° C., the permissive and non-permissive temperature for ts125E2A, respectively.

C. Transfection of PER.C6 with E2A Expression Vectors; Colony Formation and Generation of Cell Lines One day prior to transfection, $2 \times 10^6$ PER.C6 cells were seeded per 6 cm tissue culture dish (Greiner) in DMEM, supplemented with 10% FBS and 10 mM $MgCl_2$ and incubated at 37° C. in a 10% $CO_2$ atmosphere. The next day, the cells were transfected with 3, 5 or 8 µg of either pcDNA3, pcDNA3wtE2A or pcDNA3tsE2A plasmid DNA per dish, using the LipofectAMINE PLUSä Reagent Kit according to the standard protocol of the supplier (Gibco BRL), except that the cells were transfected at 39° C. in a 10% $CO_2$ atmosphere. After the transfection, the cells were constantly kept at 39° C., the non-permissive temperature for ts125E2A. Three days later, the cells were put in DMEM supplemented with 10% FBS, 10 mM $MgCl_2$ and 0.25 mg/ml G418 (Gibco BRL), and the first G418-resistant colonies appeared at 10 days post transfection. As shown in Table 1, there was a dramatic difference between the total number of colonies obtained after transfection of pcDNA3 (~200 colonies) or pcDNA3tsE2A (~100 colonies) and pcDNA3wtE2A (only 4 colonies). These results indicate that the toxicity of constitutively expressed E2A can be overcome by using a temperature-sensitive mutant of E2A (ts125E2A) and culturing of the cells at the non-permissive temperature of 39° C.

From each transfection, a number of colonies were picked by scraping the cells from the dish with a pipette. The detached cells were subsequently put into 24-well tissue culture dishes (Greiner) and cultured further at 39° C. in a 10% $CO_2$ atmosphere in DMEM, supplemented with 10% FBS, 10 mM $MgCl_2$ and 0.25 mg/ml G418. As shown in Table 1, 100% of the pcDNA3 transfected colonies (4/4) and 82% of the pcDNA3tsE2A transfected colonies (37/45) were established to stable cell lines (the remaining 8 pcDNA3tsE2A transfected colonies grew slowly and were discarded). In contrast, only 1 pcDNA3wtE2A-transfected colony could be established. The other 3 died directly after picking.

Next, the E2A expression levels in the different cell lines were determined by Western blotting. The cell lines were seeded on 6-well tissue culture dishes and sub-confluent cultures were washed twice with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the Bio-Rad protein assay, according to standard procedures of the supplier (BioRad). Equal amounts of whole-cell extract were fractionated by SDS-PAGE on 10% gels. Proteins were transferred onto Immobilon-P membranes (Millipore) and incubated with the αDBP monoclonal antibody B6. The secondary antibody was a horseradish-peroxidase-conjugated goat anti mouse antibody (BioRad). The Western blotting procedure and incubations were performed according to the protocol provided by Millipore. The complexes were visualized with the ECL detection system according to the manufacturer's protocol (Amersham). FIG. 31 shows that all of the cell lines derived from the pcDNA3tsE2A transfection expressed the 72-kDa E2A protein (left panel, lanes 4-14; middle panel, lanes 1-13; right panel, lanes 1-12). In contrast, the only cell line derived from the pcDNAwtE2A transfection did not express the E2A protein (left panel, lane 2). No E2A protein was detected in extract from a cell line derived from the pcDNA3 transfection (left panel, lane 1), which served as a negative control. Extract from PER.C6 cells transiently transfected with pcDNA3ts125 (left panel, lane 3) served as a positive control for the Western blot procedure. These data confirmed that constitutive expression of wtE2A is toxic for cells and that using the ts125 mutant of E2A could circumvent this toxicity.

D. Complementation of E2A Deletion in Adenoviral Vectors on PER.C6 Cells Constitutively Expressing Full-Length ts125E2A The adenovirus Ad5.dl802 is an Ad5-derived vector deleted for the major part of the E2A coding region and does not produce functional DBP. Ad5.dl802 was used to test the E2A trans-complementing activity of PER.C6 cells constitutively expressing ts125E2A. Parental PER.C6 cells or PER.C6tsE2A clone 3-9 were cultured in DMEM, supplemented with 10% FBS and 10 mM $MgCl_2$ at 39° C. and 10% $CO_2$ in 25 $cm^2$ flasks and either mock-infected or infected with Ad5.dl802 at an m.o.i. of 5. Subsequently, the infected cells were cultured at 32° C. and cells were screened for the appearance of a cytopathic effect ("CPE") as determined by changes in cell morphology and detachment of the cells from the flask. Full CPE appeared in the Ad5.dl802-infected PER.C6tsE2A clone 3-9 within 2 days. No CPE appeared in the Ad5.dl802-infected PER.C6 cells or the mock-infected cells. These data showed that PER.C6 cells constitutively expressing ts125E2A complemented in trans for the E2A deletion in the Ad5.dl802 vector at the permissive temperature of 32° C.

E. Serum-Free Suspension Culture of PER.C6tsE2A Cell Lines

Large-scale production of recombinant adenoviral vectors for human gene therapy requires an easy and scaleable culturing method for the producer cell line, preferably a suspension culture in medium devoid of any human or animal constituents. To that end, the cell line PER.C6tsE2A c5-9 (designated c5-9) was cultured at 39° C. and 10% $CO_2$ in a 175 $cm^2$ tissue culture flask (Nunc) in DMEM, supplemented with 10% FBS and 10 mM $MgCl_2$. At sub-confluency (70-80% confluent), the cells were washed with PBS (NPBI) and the medium was replaced by 25 ml serum-free suspension medium Ex-cell™ 525 (JRH) supplemented with 1×L-Glutamine (Gibco BRL), hereafter designated SFM. Two days later, cells were detached from the flask by flicking and the cells were centrifuged at 1,000 rpm for 5 minutes. The cell pellet was re-suspended in 5 ml SFM and 0.5 ml cell suspension was transferred to a 80 $cm^2$ tissue culture flask (Nunc), together with 12 ml fresh SFM. After 2 days, cells were harvested (all cells are in suspension) and counted in a Burker cell counter. Next, cells were seeded in a 125 ml tissue culture Erlenmeyer (Corning) at a seeding density of $3\times10^5$ cells per ml in a total volume of 20 ml SFM. Cells were further cultured at 125 RPM on an orbital shaker (GFL) at 39° C. in a 10% $CO_2$ atmosphere. Cells were counted at day 1-6 in a Burker cell counter. In FIG. 4, the mean growth curve from 8 cultures is shown. PER.C6tsE2A c5-9 performed well in serum-free suspension culture. The maximum cell density of approximately $2\times10^6$ cells per ml is reached within 5 days of culture.

F. Growth Characteristics of PER.C6 and PER.C6/E2A at 37° C. and 39° C.

PER.C6 cells or PER.C6ts125E2A (c8-4) cells were cultured in DMEM (Gibco BRL) supplemented with 10% FBS (Gibco BRL) and 10 mM $MgCl_2$ in a 10% $CO_2$ atmosphere at either 37° C. (PER.C6) or 39° C. (PER.C6ts125E2A c8-4). At day 0, a total of $1\times10^6$ cells were seeded per 25 $cm^2$ tissue culture flask (Nunc) and the cells were cultured at the respective temperatures. At the indicated time points, cells were counted. The growth of PER.C6 cells at 37° C. was comparable to the growth of PER.C6ts125E2A c8-4 at 39° C. (FIG. 33). This shows that constitutive expression of ts125E2A encoded DBP had no adverse effect on the growth of cells at the non-permissive temperature of 39° C.

G. Stability of PER.C6ts125E2A

For several passages, the PER.C6tsl25E2A cell line clone 8-4 was cultured at 39° C. and 10% $CO_2$ in a 25 $cm^2$ tissue culture flask (Nunc) in DMEM, supplemented with 10% FBS and 10 mM $MgCl_2$ in the absence of selection pressure (G418). At sub-confluency (70-80% confluent), the cells were washed with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the BioRad protein assay, according to standard procedures of the supplier (BioRad). Equal amounts of whole-cell extract were fractionated by SDS-PAGE in 10% gels. Proteins were transferred onto Immobilon-P membranes (Millipore) and incubated with the αaDBP monoclonal antibody B6. The secondary antibody was a horseradish-peroxidase-conjugated goat anti-mouse antibody (BioRad). The Western blotting procedure and incubations were performed according to the protocol provided by Millipore. The complexes were visualized with the ECL detection system according to the manufacturer's protocol (Amersham). The expression of ts125E2A encoded DBP was stable for at least 16 passages, which is equivalent to approximately 40 cell doublings (FIG. 34). No decrease in DBP levels was observed during this culture period, indicating that the expression of ts125E2A was stable, even in the absence of G418 selection pressure.

Example 16

Generation of tTA-Expressing Packaging Cell Lines

A. Generation of a Plasmid from which the tTA Gene is Expressed pcDNA3.1-tTA: The tTA gene, a fusion of the tetR and VP16 genes, was removed from the plasmid pUHD 15-1 (Gossen and Bujard, 1992) by digestion using the restriction enzymes BamHI and EcoRI. First, pUHD15-1 was digested with EcoRI. The linearized plasmid was treated with Klenow enzyme in the presence of dNTPs to fill in the EcoRI sticky ends. Then, the plasmid was digested with BamHI. The resulting fragment, 1025 bp in length, was purified from agarose. Subsequently, the fragment was used in a ligation reaction with BamHI/EcoRV-digested pcDNA 3.1 HYGRO (−) (Invitrogen) giving rise to pcDNA3.1-tTa. After transformation into competent *E. Coli* DH5αa (Life Techn.) and analysis of ampicillin-resistant colonies, one clone was selected that showed a digestion pattern as expected for pcDNA3.1-tTA.

B. Transfection of PER.C6 and PER.C6/E2A with the tTA Expression Vector; Colony Formation and Generation of Cell Lines One day prior to transfection, $2 \times 10^6$ PER.C6 or PER.C6/E2A cells were seeded per 60 mm tissue culture dish (Greiner) in Dulbecco's modified essential medium (DMEM, Gibco BRL) supplemented with 10% FBS (JRH) and 10 mM $MgCl_2$ and incubated at 37° C. in a 10% $CO_2$ atmosphere. The next day, cells were transfected with 4-8 µg of pcDNA3.1-tTa plasmid DNA using the LipofectAMINE PLUS™ Reagent Kit according to the standard protocol of the supplier (Gibco BRL). The cells were incubated with the LipofectAMINE PLUS™-DNA mixture for four hours at 37° C. and 10% $CO_2$. Then, 2 ml of DMEM supplemented with 20% FBS and 10 mM $MgCl_2$ was added and cells were further incubated at 37° C. and 10% $CO_2$. The next day, cells were washed with PBS and incubated in fresh DMEM supplemented with 10% FBS, 10 mM $MgCl_2$ at either 37° C. (PER.C6) or 39° C. (Per.C6/E2A) in a 10% $CO_2$ atmosphere for three days. Then, the media were exchanged for selection media; PER.C6 cells were incubated with DMEM supplemented with 10% FBS, 10 mM $MgCl_2$ and 50 µg/ml hygromycin B (GIBCO) while PER.C6/E2A cells were maintained in DMEM supplemented with 10% FBS, 10 mM $MgCl_2$ and 100 µg/ml hygromycin B. Colonies of cells that resisted the selection appeared within three weeks while nonresistant cells died during this period.

From each transfection, a number of independent, hygromycin-resistant cell colonies were picked by scraping the cells from the dish with a pipette and put into 2.5 $cm^2$ dishes (Greiner) for further growth in DMEM containing 10% FBS, 10 mM $MgCl_2$ and supplemented with 50 µg/ml (PER.C6 cells) or 100 µg/ml (PER.C6/E2A cells) hygromycin in a 10% $CO_2$ atmosphere and at 37° C. or 39° C., respectively.

Next, it was determined whether these hygromycin-resistant cell colonies expressed functional tTA protein. Therefore, cultures of PER.C6/tTA or PER/E2A/tTA cells were transfected with the plasmid pUHC 13-3 that contains the reporter gene luciferase under the control of the 7xtetO promoter (Gossen and Bujard, 1992). To demonstrate that the expression of luciferase was mediated by tTA, one half of the cultures were maintained in medium without doxycycline. The other half was maintained in medium with 8 µg/ml doxycycline (Sigma). The latter drug is an analogue of tetracycline and binds to tTA and inhibits its activity. All PER.C6/tTA and PER/E2A/tTA cell lines yielded high levels of luciferase, indicating that all cell lines expressed the tTA protein (FIG. 35). In addition, the expression of luciferase was greatly suppressed when the cells were treated with doxycycline. Collectively, the data showed that the isolated and established hygromycin-resistant PER.C6 and PER/E2A cell clones all expressed functional tTA.

TABLE I

| Serotype | Elution [NaCl] mM | VP/ml | $CCID_{50}$ | $log_{10}$ VP/$CCID_{50}$ ratio |
|---|---|---|---|---|
| 1 | 597 | $8.66 \times 10^{10}$ | $5.00 \times 10^7$ | 3.2 |
| 2 | 574 | $1.04 \times 10^{12}$ | $3.66 \times 10^{11}$ | 0.4 |
| 3 | 131 | $1.19 \times 10^{11}$ | $1.28 \times 10^7$ | 4.0 |
| 4 | 260 | $4.84 \times 10^{11}$ | $2.50 \times 10^8$ | 3.3 |
| 5 | 533 | $5.40 \times 10^{11}$ | $1.12 \times 10^{10}$ | 1.7 |
| 6 | 477 | $1.05 \times 10^{12}$ | $2.14 \times 10^{10}$ | 1.7 |
| 7 | 328 | $1.68 \times 10^{12}$ | $2.73 \times 10^9$ | 2.4 |
| 9 | 379 | $4.99 \times 10^{11}$ | $3.75 \times 10^7$ | 4.1 |
| 10 | 387 | $8.32 \times 10^{12}$ | $1.12 \times 10^9$ | 3.9 |

TABLE I-continued

| Serotype | Elution [NaCl] mM | VP/ml | $CCID_{50}$ | $log_{10}$ VP/$CCID_{50}$ ratio |
|---|---|---|---|---|
| 12 | 305 | $3.64 \times 10^{11}$ | $1.46 \times 10^7$ | 4.4 |
| 13 | 231 | $4.37 \times 10^{12}$ | $7.31 \times 10^8$ | 3.8 |
| 15 | 443 | $5.33 \times 10^{12}$ | $1.25 \times 10^9$ | 3.6 |
| 16 | 312 | $1.75 \times 10^{12}$ | $5.59 \times 10^8$ | 3.5 |
| 17 | 478 | $1.39 \times 10^{12}$ | $1.45 \times 10^9$ | 3.0 |
| 19 | 430 | $8.44 \times 10^{11}$ | $8.55 \times 10^7$ | 4.0 |
| 20 | 156 | $1.41 \times 10^{11}$ | $1.68 \times 10^7$ | 3.9 |
| 21 | 437 | $3.21 \times 10^{11}$ | $1.12 \times 10^8$ | 3.5 |
| 22 | 365 | $1.43 \times 10^{12}$ | $5.59 \times 10^7$ | 3.4 |
| 23 | 132 | $2.33 \times 10^{11}$ | $1.57 \times 10^7$ | 4.2 |
| 24 | 405 | $5.12 \times 10^{12}$ | $4.27 \times 10^8$ | 4.1 |
| 25 | 405 | $7.24 \times 10^{11}$ | $5.59 \times 10^7$ | 4.1 |
| 26 | 356 | $1.13 \times 10^{12}$ | $1.12 \times 10^8$ | 4.0 |
| 27 | 342 | $2.00 \times 10^{12}$ | $1.28 \times 10^8$ | 4.2 |
| 28 | 347 | $2.77 \times 10^{12}$ | $5.00 \times 10^7$ | 4.7 |
| 29 | 386 | $2.78 \times 10^{11}$ | $2.00 \times 10^7$ | 4.1 |
| 30 | 409 | $1.33 \times 10^{12}$ | $5.59 \times 10^8$ | 3.4 |
| 31 | 303 | $8.48 \times 10^{10}$ | $2.19 \times 10^7$ | 3.6 |
| 33 | 302 | $1.02 \times 10^{12}$ | $1.12 \times 10^7$ | 5.0 |
| 34 | 425 | $1.08 \times 10^{12}$ | $1.63 \times 10^{11}$ | 0.8 |
| 35 | 446 | $3.26 \times 10^{12}$ | $1.25 \times 10^{11}$ | 1.4 |
| 36 | 325 | $9.26 \times 10^{12}$ | $3.62 \times 10^9$ | 3.4 |
| 37 | 257 | $5.86 \times 10^{12}$ | $2.8 \times 10^9$ | 3.3 |
| 38 | 337 | $3.61 \times 10^{12}$ | $5.59 \times 10^7$ | 4.8 |
| 39 | 241 | $3.34 \times 10^{11}$ | $1.17 \times 10^7$ | 4.5 |
| 42 | 370 | $1.95 \times 10^{12}$ | $1.12 \times 10^8$ | 4.2 |
| 43 | 284 | $2.42 \times 10^{12}$ | $1.81 \times 10^8$ | 4.1 |
| 44 | 295 | $8.45 \times 10^{11}$ | $2.00 \times 10^7$ | 4.6 |
| 45 | 283 | $5.20 \times 10^{11}$ | $2.99 \times 10^7$ | 4.2 |
| 46 | 282 | $9.73 \times 10^{12}$ | $2.50 \times 10^8$ | 4.6 |
| 47 | 271 | $5.69 \times 10^{11}$ | $3.42 \times 10^7$ | 4.2 |
| 48 | 264 | $1.68 \times 10^{12}$ | $9.56 \times 10^8$ | 3.3 |
| 49 | 332 | $2.20 \times 10^{12}$ | $8.55 \times 10^7$ | 4.4 |
| 50 | 459 | $7.38 \times 10^{12}$ | $2.80 \times 10^9$ | 3.4 |
| 51 | 450 | $8.41 \times 10^{11}$ | $1.88 \times 10^8$ | 3.7 |

Legend to Table I:

All human adenoviruses used in the neutralization experiments were produced on PER.C6 cells (Fallaux et al., 1998) and purified on CsCl as described in Example 1. The NaCl concentration at which the different serotypes eluted from the HPLC column is shown. Virus particles/ml (VP/ml) were calculated from an Ad5 standard. The titer in the experiment ($CCID_{50}$) was determined on PER.C6 cells as described in Example 1 by titrations performed in parallel with the neutralization experiment. The $CCID_{50}$ is shown for the 44 viruses used in this study and reflects the dilution of the virus needed to obtain CPE in 50% of the wells after 5 days. The ratio of VP/$CCID_{50}$ is depicted in $log_{10}$ and is a measurement of the infectivity of the rent batches on PER.C6 cells.

TABLE II

AdApt35.LacZ viruses escape neutralization by human serum.

| Virus | no serum | Human serum dilution | | | | |
|---|---|---|---|---|---|---|
| | | 10x | 50x | 250x | 1250x | 6250x |
| AdApt5.LacZ moi: 5 VP/cell | 100% | 0% | 0% | 1% | 40% | 80% |
| AdApt35.LacZ 250 µl crude lysate | 100% | 100% | 100% | 100% | 100% | 100% |

TABLE III

Percentage of synovial fluid samples containing neutralizing activity (NA) to wt adenoviruses of different serotypes.

|  | % of SF samples with NA (all positives) | % of SF samples with NA (positives at ≧64x dilution) |
| --- | --- | --- |
| Ad5 | 72 | 59 |
| Ad26 | 66 | 34 |
| Ad34 | 45 | 19 |
| Ad35 | 4 | 0 |
| Ad48 | 42 | 4 |

TABLE IV

The numbers of foci obtained with the different E1 expression constructs in BRK transformation experiments.
Average # of foci/dish:

|  | Construct | 1 μgr | 5 μgr |
| --- | --- | --- | --- |
| Experiment 1 | pIG.E1A.E1B | nd | 60 |
|  | pIG.E1A.E1B | nd | 35 |
|  | pRSVAd35E1 | 0 | 3 |
|  | pIG.Ad35.E1 | 3 | 7 |
| Experiment 2 | pIG.E1A.E1B | 37 | nd |
|  | pIG.Ad35.E1 | nd | 2 |
| Experiment 3 | pIG.E1A.E1B | nd | 140 |
|  | pIG.Ad35.E1 | nd | 20 |
|  | pIG270 | nd | 30 |

REFERENCES

Abrahamsen, K., Kong, H-L., Mastrangeli, A., Brough, D., Lizonova, A., Crystal, R. and Falck-Pedersen, E. (1997). Construction of an adenovirus type 7a E1A hu – vector. *J. Virol*. 71, no. 11, pp. 8946-8951.

Athappilly, F. K., Murali, R., Rux, J. J., Cai, Z. and Burnett, R. M. (1994). The refined crystal structure of hexon, the major coat protein of adenovirus type 2, at 2.9 Å resolution. *J. Mol. Biol*. 242, 430-455.

Basler, C. F., Droguett, G., Horwitz, M. S. (1996). Sequence of the immunoregulatory early region 3 and flanking sequences of adenovirus type 35. *Gene* 170:249-54.

Bridge, E., Medghalchi, S., Ubol, S., Leesong, M. and Ketner, G. (1993). Adenovirus early region 4 and viral DNA synthesis. *Virology* 193, 794-801.

Brody, S. L. and Crystal, R. G. (1994). Adenovirus-mediated in vivo gene transfer. *Ann. N. Y. Acad. Sci*. 716: 90-101.

Boshart, M., Weber, F., Jahn, G., Dorsch-Hasler, K., Fleckenstein B. and Schaffner W. (1985). A very strong enhancer is located upstream of an immediate early gene of human cytomegalovirus. *Cell* 41, 521-530.

Dijkema, R., Dekker, B. M. M., van der Feltz, M. J. M. and van der Eb, A. J. (1979). Transformation of primary rat kidney cells by DNA fragments of weakly oncogenic adenoviruses. *J. Virol*. 32, No. 3, 943-950.

Fallaux, F. J., Bout, A., van der Velde, I., van den Wollenberg, D. J., Hehir, K. M., Keegan, J., Auger, C., Cramer, S. J., van Ormondt, H., van der Eb, A. J., Valerio, D. and Hoeben, R. C. (1998). New helper cells and matched early region 1-deleted adenovirus vectors prevent generation of replication competent adenoviruses. *Hum. Gene Ther.* 9, 1909-1917.

Gossen, M., and H. Bujard (1992). Tight control of gene expression in mammalian cells by tetracycline-responsive promoters. *Proc. Natl. Acad. Sci. USA* 89; 5547-5551.

Flomenberg, P. R., Chen, M., Munk, G., Horwitz, M. S. (1987). Molecular epidemiology of adenovirus type 35 infections in immunocompromised hosts. *J. Infect Dis.* 155(6): 1127-34.

Francki, R. I. B., Fauquet, C. M., Knudson, D. L. and Brown, F. (1991). Classification and nomenclature of viruses. Fifth report of the international Committee on taxonomy of viruses. *Arch. Virol. Suppl.* 2: 140-144.

Gahery-Segard, H., Farace, F., Godfrin, D., Gaston, J., Lengagne, R., Tursz, P., Boulanger, P. and Guillet, J.-G. (1998). Immune response to recombinant capsid proteins of adenovirus in humans: Antifiber and anti-penton base antibodies have a synergistic effect on neutralizing activity. *J. Virol.* 72, 2388-2397.

He, T-C., Zhou, S., Da Costa, L. T., Yu, J., Kinzler, K. W., Vogelstein, B. (1998). A simplified system for generating recombinant adenoviruses. *Proc. Natl. Acad. Sci. USA* 95, 2509-2514.

Hierholzer, J. C., Wigand, R., Anderson, L. J., Adrian, T., and Gold, J. W. M. (1988). Adenoviruses from patients with AIDS: a plethora of serotypes and a description of five new serotypes of subgenus D (types 43-47). *J. Infect. Dis.* 158, 804-813.

De Jong, P. J., Valderrama, G., Spigland, I. and Horwitz, M. S. (1983). Adenovirus isolates from urine of patients with acquired immunodeficiency syndrome. *Lancet* 1(8337): 1293-1296.

Kay, R., Takei, F., and Humphries, R. K. (1990). Expression cloning of a cDNA encoding M1/69. *J. Immunol.* 145, 1952-1959.

Kang, W. G., Berencsi, G., Takacs, M., Ascher, Z., Fejer, G., Nasz, I. (1989a). Molecular cloning and physical mapping of the DNA of human adenovirus type 35. *Acta. Microbiol. Hung.* 36(1): 67-75.

Kang, W. G., Berencsi, G., Banrevi, A., Ascher, Z., Fejer, G., Takacs, M., Kiss, A., Nasz, I. (1989b). Relationship of E1 and E3 regions of human Ad35 to those of human adenovirus subgroups A, C and D. *Acta. Microbiol. Hung.* 36(4): 445-57.

Levrero, M., Barban, V., Manteca, S., Ballay, A., Balsamo, C., Avantaggiati, M. L., Natoli, G., Skellekens, H., Tiollais, P., and Perricaudet, M. (1991). Defective and nondefective adenovirus vectors for expressing foreign genes in vitro and in vivo. *Gene* 101, 195-202.

Li, Q. G., Hambraeus, J. and Wadell, G. (1991). Genetic relationship between thirteen genomes of types of adenovirus 11, 34, and 35 with different tropisms. *Intervirol.* 32, 338-350.

Prince, H. M. (1998). Gene transfer: a review of methods and applications. *Pathology* 30(4), 335-347.

Robbins, P. D. and Ghivizzani, S. C. (1998). Viral vectors for gene therapy. *Pharmacol. Ther.* 80, 35-47.

Schnurr, D and Dondero, M. E. (1993). Two new candidate adenovirus serotypes. *Intervirol.* 36, 79-83.

Schulick, A. H., Vassalli, G., Dunn, P. F., Dong, G., Rade, J. J., Zamarron, C. and Dichek, D. A. (1997). Established immunity precludes adenovirus-mediated gene transfer in rat carotid arteries. Potential for immunosuppression and vector engineering to overcome barriers of immunity. *J. Clin. Invest.* 99(2), 209-19.

Shabram, P. W., Giroux, D. D., Goudreau, A. M., Gregory, R. J., Horn, M. T., Huyghe, B. G., Liu, X., Nunnally, M. H., Sugarman, B. J. and Sutjipto, S. (1997). Analytical anion-exchange HPLC of recombinant type-5 adenoviral particles. *Hum. Gene Ther.* 8(4): 453-465.

Toogood et al. (1989). *J. Gen. Virol.* 70, 3203-3214.

Toogood, C. I., Murali, R., Burnett, R. M., Hay, R.T. (1989). The adenovirus type 40 hexon: sequence, predicted structure and relationship to other adenovirus hexons. *J. Gen. Virol.* 70, 3203-14.

Valderrama-Leon, G., Flomenberg, P., Horwitz, M. S. (1985). Restriction endonuclease mapping of adenovirus 35, a type isolated from immunocompromised hosts. *J. Virol.* 56(2):647-50.

Wadell, G. (1984). Molecular epidemiology of adenoviruses. *Curr. Top. Microbiol. Immunol.* 110, 191-220.

White, E. (1995). Regulation of p53-dependent apoptosis by E1a and E1b. *Curr. Top. Microbiol. Immunol.* 199, 34-58.

What is claimed is:

1. A recombinant adenovirus comprising a heterologous gene of interest, wherein said adenovirus is selected from the group consisting of: adenovirus serotype 11 and 35.

2. A recombinant adenovirus comprising an adenoviral nucleic acid comprising a deletion in the E1 region, said deletion rendering the recombinant adenovirus replication-defective, and wherein said adenovirus is selected from the group consisting of: adenovirus serotype 11 and 35.

3. The recombinant adenovirus of claim 2, further comprising a gene of interest.

4. The recombinant adenovirus of claim 3, wherein said gene of interest is inserted in the E1 region of said adenoviral nucleic acid.

5. The recombinant adenovirus of claim 1, wherein said adenovirus is a chimera of an adenovirus selected from the group consisting of: adenovirus serotype 11 and 35, with at least one other adenovirus serotype.

6. The recombinant adenovirus of claim 5, wherein said other adenovirus is adenovirus serotype 16.

7. A pharmaceutical formulation comprising a recombinant adenovirus of claim 1, and a suitable excipient.

8. An adenoviral nucleic acid comprising a deletion in the E1 region, said adenoviral nucleic acid further encoding a recombinant adenovirus selected from the group consisting of: adenovirus serotype 1 and 35, and wherein said deletion renders the encoded recombinant adenovirus replication-defective.

9. The adenoviral nucleic acid of claim 8, further comprising a gene of interest.

10. The adenoviral nucleic acid of claim 9, wherein said gene of interest is inserted in the E1 region of said adenoviral nucleic acid.

11. The adenoviral nucleic acid of claim 8 further comprising a sequence encoding a tissue tropism determining part of adenovirus serotype 16.

12. A cell comprising the adenoviral nucleic acid of claim 8.

13. The cell of claim 12, which complements the functional deletion in the E1 region of said adenoviral nucleic acid.

14. An adenoviral nucleic acid comprising:
   a recombinant adenoviral nucleic acid based on an adenoviral serotype selected from the group consisting of Ad11, and Ad35; and
   a nucleotide sequence of interest present in the recombinant adenoviral nucleic acid;
   where the recombinant adenoviral nucleic acid has a deletion in the E1 region that renders the recombinant adenoviral nucleic acid replication-defective.

15. The adenoviral nucleic acid of claim 14, wherein the nucleotide sequence of interest is inserted in the E1 region of the adenoviral nucleic acid.

16. The adenoviral nucleic acid of claim 14, comprising a sequence encoding a fiber protein of adenovirus serotype 16.

17. A method of avoiding pre-existing adenoviral neutralizing antibodies in a subject in need of gene therapy, the method comprising:
   administering a replication defective adenoviral vector to the subject in need of gene therapy
   wherein the replication defective adenoviral vector is the recombinant adenovirus of claim 1.

* * * * *

UNITED STATES PATENT AND TRADEMARK OFFICE
CERTIFICATE OF CORRECTION

| | | |
|---|---|---|
| PATENT NO. | : 7,270,811 B2 | Page 1 of 2 |
| APPLICATION NO. | : 10/951102 | |
| DATED | : September 18, 2007 | |
| INVENTOR(S) | : Abraham Bout, Menzo Havenga and Ronald Vogels | |

It is certified that error appears in the above-identified patent and that said Letters Patent is hereby corrected as shown below:

On the title page:
In ITEM (56) References Cited,
OTHER PUBLICATIONS,

| | |
|---|---|
| Page 2, 2nd Column, 7th entry, 1st line, | in Abrahamsen, change "Tpe 7a" to --Type 7a-- |
| Page 3, 2nd Column, 2nd entry, 1st line, | in Green et al., change "cross: sheet" to --cross-sheet-- |
| Page 4, 1st Column, 18th entry, 3rd line, | in Ragot et al., change "Journals of Ltd." to --Journals Ltd.-- |

In the specification:

| | | |
|---|---|---|
| COLUMN 16, | LINE 30, | change "(5'-AATTGTCTTAATTAACCGCTTA 3' (SEQ" to --(5'-AATTGTC<u>TT</u>AATTAACCGCTTA 3' (SEQ-- |
| COLUMN 16, | LINE 52, | change "BAl3 for" to --Bal31 for-- |
| COLUMN 24, | LINE 24, | change "5'-CGC GGA TCC TGT ACA ACT" to --5'-CGC <u>GGA</u> <u>TCC</u> TGT ACA ACT-- |
| COLUMN 24, | LINE 30, | change "5'-CGC GGA TCC CTT AAG GCA AGC ATG TCC" to --5'-CGC <u>GGA</u> <u>TCC</u> CTT AAG GCA AGC ATG TCC-- |
| COLUMN 25, | LINE 43, | change "5'-CGA CAT ATG TAG ATG" to --5'-CGA CAT ATG TAG <u>ATG</u>-- |
| COLUMN 25, | LINE 44, | change "CAT TAG TTT GTG TTA TGT TTC AAC GTG-3'" to --<u>CAT</u> TAG TTT GTG TTA TGT TTC AAC GTG-3'-- |
| COLUMN 30, | LINE 22, | change "5'-CCAATAATATACCT-3'" to --5'-CCAATAATATACCT-3'-- |
| COLUMN 30, | LINE 24, | change "5'-AGGTATATTATTGATGATGGG-3'" to --5'-AGGTATATTATTGATGATGGG-3'-- |
| COLUMN 36, | LINE 48, | change "pWE.Ad35.pfX-rITR" to --pWE.Ad35.pIX-rIRT-- |
| COLUMN 51, | LINE 25, | change "Then;" to --Then-- |
| COLUMN 53, | LINE 51, | change "CGG GAT CCG CCA CCA TGG" to --CG<u>G</u> <u>GAT</u> <u>CC</u>*G* *CCA* *CC*A TGG-- |
| COLUMN 53, | LINE 52, | change "CCA GTC GGG AAG AGG AG" to --CCA GTC GGG AAG AGG AG-- |
| COLUMN 53, | LINE 55, | change "CGG AAT TCT" to --CG<u>G</u> <u>AAT</u> <u>TCT</u>-- |

UNITED STATES PATENT AND TRADEMARK OFFICE
CERTIFICATE OF CORRECTION

PATENT NO. : 7,270,811 B2  
APPLICATION NO. : 10/951102  
DATED : September 18, 2007  
INVENTOR(S) : Abraham Bout, Menzo Havenga and Ronald Vogels It is certified that error appears in the above-identified patent and that said Letters Patent is hereby corrected as shown below:

| | | |
|---|---|---|
| COLUMN 53, | LINE 56, | change "TAA AAA TCA AAG GGG TTC TGC CGC" to --TAA AAA TCA AAG GGG TTC TGC CGC-- |
| COLUMN 58, | LINE 54, | change "rent batches" to --different batches-- |
| COLUMN 59, | LINE 35, | change "E1A hu – vector." to --E1A⁻ vector.-- |

In the claims:  
CLAIM 5, COLUMN 121, LINE 28, change "is a chimera" to --is a chimaera--

Signed and Sealed this

Thirtieth Day of September, 2008

JON W. DUDAS  
*Director of the United States Patent and Trademark Office*